(12) United States Patent
Bell et al.

(10) Patent No.: US 12,281,124 B2
(45) Date of Patent: *Apr. 22, 2025

(54) HETEROCYCLIC COMPOUNDS AS MONOACYLGLYCEROL LIPASE INHIBITORS

(71) Applicant: Hoffmann-La Roche Inc., Little Falls, NJ (US)

(72) Inventors: Charles Bell, Cheshire (GB); Joerg Benz, Rheinfelden (DE); Luca Gobbi, Buus (CH); Uwe Grether, Efringen-Kirchen (DE); Katrin Groebke Zbinden, Liestal (CH); Benoit Hornsperger, Altkirch (FR); Buelent Kocer, Maulburg (DE); Carsten Kroll, Basel (CH); Bernd Kuhn, Reinach (CH); Marius Daniel Rinaldo Lutz, Zurich (CH); Fionn O'Hara, Basel (CH); Hans Richter, Grenzach-Wyhlen (DE); Martin Ritter, Mumpf (CH); Didier Rombach, Mulhouse (FR); Martin Kuratli, Birsfelden (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 29 days.

This patent is subject to a terminal disclaimer.

(21) Appl. No.: 18/475,065

(22) Filed: Sep. 26, 2023

(65) Prior Publication Data
US 2024/0150373 A1 May 9, 2024

Related U.S. Application Data

(63) Continuation of application No. 17/749,496, filed on May 20, 2022, now Pat. No. 11,802,133, which is a continuation of application No. 16/844,262, filed on Apr. 9, 2020, now abandoned, which is a continuation of application No. PCT/EP2019/071520, filed on Aug. 12, 2019.

(30) Foreign Application Priority Data

Aug. 13, 2018 (EP) .................... 18188681

(51) Int. Cl.
C07D 498/04 (2006.01)
C07D 519/00 (2006.01)

(52) U.S. Cl.
CPC ......... C07D 498/04 (2013.01); C07D 519/00 (2013.01)

(58) Field of Classification Search
CPC ................ C07D 498/04; C07D 519/00; A61K 31/5365
See application file for complete search history.

(56) References Cited

U.S. PATENT DOCUMENTS

| 5,214,038 | A | 5/1993 | Effland et al. |
| 8,431,695 | B2 | 4/2013 | O'Connor et al. |
| 10,106,556 | B2 | 10/2018 | Ikeda et al. |
| 10,610,520 | B2 | 4/2020 | Ikeda et al. |
| 11,390,610 | B2 | 7/2022 | Benz et al. |
| 11,420,961 | B2 | 8/2022 | Benz et al. |
| 11,608,347 | B2 | 3/2023 | Petersen et al. |
| 11,802,133 | B2 | 10/2023 | Bell et al. |
| 11,814,375 | B2 | 11/2023 | Benz et al. |
| 11,981,661 | B2 | 5/2024 | Benz et al. |
| 2010/0035893 | A1 | 2/2010 | Hoornaert et al. |
| 2010/0280240 | A1 | 11/2010 | Allison et al. |
| 2011/0059118 | A1 | 3/2011 | Fidalgo et al. |
| 2011/0251169 | A1 | 10/2011 | Green et al. |
| 2013/0046097 | A1 | 2/2013 | Tomesch et al. |
| 2014/0275015 | A1 | 9/2014 | Vaca et al. |
| 2014/0309218 | A1 | 10/2014 | Hubschwerlen et al. |
| 2015/0018335 | A1 | 1/2015 | Cisar et al. |
| 2017/0029390 | A1 | 2/2017 | Butler et al. |
| 2018/0079756 | A1 | 3/2018 | Ikeda et al. |
| 2018/0327410 | A1 | 11/2018 | Grice et al. |
| 2020/0255439 | A1 | 8/2020 | Kamata et al. |

(Continued)

FOREIGN PATENT DOCUMENTS

| EA | 009645 B1 | 2/2008 |
| EA | 018521 B1 | 8/2013 |

(Continued)

OTHER PUBLICATIONS

Alpar, A., et al., "Endocannabinoids modulate cortical development by configuring Slit2/Robo 1 signaling" Nat Commun 5(4421):1-13 (Jul. 17, 2014).
Anderson, A.C., "The Process of Structure-Based Drug Design" Chem Biol 10(9):787-797 (Sep. 1, 2003).
Ashton, K., et al., "Design and synthesis of novel amide AKT1 inhibitors with selectivity over CDK2" Bioorg Med Chem Lett 21(18):5191-5196 (Sep. 15, 2011).

(Continued)

Primary Examiner — Mark L Shibuya
Assistant Examiner — Rilla Marie Samsell
(74) Attorney, Agent, or Firm — Katherine J. Mackenzie

(57) ABSTRACT

The invention provides new heterocyclic compounds having the general formula (I)

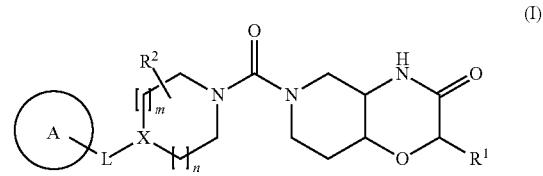

wherein A, L, X, m, n, $R^1$ and $R^2$ are as described herein, compositions including the compounds, processes of manufacturing the compounds and methods of using the compounds.

20 Claims, No Drawings

(56) References Cited

U.S. PATENT DOCUMENTS

| | | |
|---|---|---|
| 2020/0299277 A1 | 9/2020 | Benz et al. |
| 2020/0308158 A1 | 10/2020 | Bell et al. |
| 2020/0308190 A1 | 10/2020 | Bell et al. |
| 2020/0392125 A1 | 12/2020 | Benz et al. |
| 2021/0024546 A1 | 1/2021 | Petersen et al. |
| 2021/0094971 A1 | 1/2021 | Grether et al. |
| 2021/0094972 A1 | 1/2021 | Benz et al. |
| 2021/0094973 A1 | 1/2021 | Gobbi et al. |
| 2021/0107920 A1 | 4/2021 | Bell et al. |
| 2021/0107921 A1 | 4/2021 | Benz et al. |
| 2021/0277020 A1 | 9/2021 | Anselm et al. |
| 2021/0387999 A1 | 12/2021 | Kuhn et al. |
| 2022/0275005 A1 | 1/2022 | Grether et al. |
| 2022/0098176 A1 | 3/2022 | Benz et al. |
| 2022/0242876 A1 | 4/2022 | Kroll et al. |
| 2022/0135591 A1 | 5/2022 | Benz et al. |
| 2022/0202963 A1 | 6/2022 | Collin et al. |
| 2022/0106328 A1 | 7/2022 | Benz et al. |
| 2022/0213093 A1 | 7/2022 | Benz et al. |
| 2022/0220373 A1 | 7/2022 | Benz et al. |
| 2022/0267349 A1 | 8/2022 | Benz et al. |
| 2023/0117324 A1 | 4/2023 | Bell et al. |
| 2023/0183224 A1 | 6/2023 | Bell et al. |
| 2023/0203056 A1 | 6/2023 | Benz et al. |
| 2024/0199587 A1 | 6/2024 | Amoussa et al. |

FOREIGN PATENT DOCUMENTS

| | | |
|---|---|---|
| EP | 3279191 A1 | 2/2018 |
| JP | 2008-534497 | 8/2008 |
| JP | 2010-524907 A | 7/2010 |
| RU | 2042680 C1 | 8/1995 |
| WO | 2005/019215 A1 | 3/2005 |
| WO | 2005/066187 A1 | 7/2005 |
| WO | 2006/101496 | 9/2006 |
| WO | 2007/002057 A1 | 4/2007 |
| WO | 2007/098418 A1 | 8/2007 |
| WO | 2007/117557 A2 | 10/2007 |
| WO | 2009/145456 | 3/2009 |
| WO | 2009/097287 A1 | 6/2009 |
| WO | 2010/049302 | 6/2010 |
| WO | 2011/058766 A1 | 5/2011 |
| WO | 2011/059118 A1 | 5/2011 |
| WO | 2012/155199 A1 | 11/2012 |
| WO | 2013/059118 A1 | 4/2013 |
| WO | 2013/179024 A1 | 5/2013 |
| WO | 2013/093849 A1 | 6/2013 |
| WO | 2014/102630 A1 | 3/2014 |
| WO | 2014/170821 A1 | 10/2014 |
| WO | 2016/109501 A1 | 7/2016 |
| WO | 2016/180536 A1 | 11/2016 |
| WO | 2016/185279 A1 | 11/2016 |
| WO | 2016/205590 A1 | 12/2016 |
| WO | 2017/087858 A1 | 5/2017 |
| WO | 2017/087863 A1 | 5/2017 |
| WO | 2017/170830 A1 | 5/2017 |
| WO | 2017/171100 A1 | 5/2017 |
| WO | 2017/021805 | 9/2017 |
| WO | 2018/002220 | 4/2018 |
| WO | 2018/093949 | 5/2018 |
| WO | 2018/093953 | 5/2018 |
| WO | 2018/228934 A1 | 12/2018 |
| WO | 2019/105915 A1 | 4/2019 |
| WO | 2019/115660 A1 | 6/2019 |
| WO | 2019/134985 A1 | 7/2019 |
| WO | 2019/180185 A1 | 9/2019 |
| WO | 2019/180185 A2 | 9/2019 |
| WO | 2019/180185 A3 | 9/2019 |
| WO | 2019/180185 A4 | 9/2019 |
| WO | 2019/180185 A5 | 9/2019 |
| WO | 2019/180185 A6 | 9/2019 |
| WO | 2019/180185 A7 | 9/2019 |
| WO | 2019/180185 A8 | 9/2019 |
| WO | 2020/035424 A1 | 2/2020 |
| WO | 2020/035425 A1 | 2/2020 |
| WO | 2020/103815 | 5/2020 |
| WO | 2020/104494 A1 | 5/2020 |
| WO | 2021/058445 A1 | 4/2021 |

OTHER PUBLICATIONS

Barney, C., et al., "A convenient synthesis of hindered amines and α-trifluoromethylamines from ketones" Tetrahedron Lett 31(39):5547-5550 ( 1990).

Belikov, V.G. Pharmaceutical Chemistry—Tutorial "Part I: General Pharmaceutical Chemistry" (Eng. Translation), Fourth, Revised edition, Moscow-RU:MEDPress-Inform,:27-29 ( 2007).

Bernal-Chico, A., et al., "Blockade of Monoacylglycerol Lipase Inhibits Oligodendrocyte Excitotoxicity and Prevents Demyelination In Vivo" GLIA 63(1):163-176 (Jan. 1, 2015).

Chanda, P.K., et al., "Monoacylglycerol Lipase Activity Is a Critical Modulator of the Tone and Integrity of the Endocannabinoid System" Mol Pharmacol 78(6):996-1003 (Dec. 1, 2010).

Chang, J. et al., "Highly Selective Inhibitors of Monoacylglycerol Lipase Bearing a Reactive Group that is Bio-isosteric with Endocannabinoid Substrates" Chem Biol 19(5):579-588 (May 1, 2012).

Cisar, J., et al., "Identification of ABX-1431, a Selective Inhibitor of Monoacylglycerol Lipase and Clinical Candidate for Treatment of Neurological Disorders" Acs J Med Chem 61(20):9062-9084 (Aug. 1, 2018).

Damasio, A., "Alzheimer's Disease and Related Dementias" Cecil Textbook of Medicine 20(2):1992-1996 (Jan. 1, 1996).

Dugar, S. et al., "A Concise and Efficient Synthesis of Substituted Morpholines" Synthesis 47(5):712-720 (Mar. 1, 2015).

Duncan, M., et al., "Review article: endocannabinoids and their receptors in the enteric nervous system" Aliment Pharmacol Ther 22(8):667-683 (Oct. 15, 2005).

Durnov and Goldbenko, "Children's Oncology" Medicine (English machine translation),:139 ( 2002).

Evano, G., et al., "Copper-Mediated Coupling Reactions and Their Applications in Natural Products and Designed Biomolecules Synthesis" Chem Rev 108(8):3054-3131 (Aug. 13, 2008).

Feliu, A., et al., "2-Arachidonoylglycerol Reduces Proteoglycans and Enhances Remyelination in a Progressive Model of Demyelination" J Neurosci 37(35):8385-8398 (Aug. 30, 2017).

Fray, M., et al., "Second generation N-(1,2-diphenylethyl)piperazines as dual serotonin and noradrenaline reuptake inhibitors: improving metabolic stability and reducing ion channel activity" Bioorg Med Chem Lett 20(12):3788-3792 (Jun. 15, 2010).

Fray, M., et al., "Structure-activity relationships of N-substituted piperazine amine reuptake inhibitors" Bioorg Med Chem Lett 16(16):4349-4353 (Aug. 15, 2006).

Gavryushin, A., et al., "Efficient Cross-Coupling of Functionalized Arylzinc Halides Catalyzed by a Nickel Chloride-Diethyl Phosphite System" Org Lett 7(22):4871-4874 (Oct. 7, 2005).

Grill, M., et al., "Members of the endocannabinoid system are distinctly regulated in inflammatory bowel disease and colorectal cancer" Sci Rep 9(2358):1-13 (Feb. 20, 2019).

Gura, T., "Systems for Identifying New Drugs Are Often Faulty" Science 278(5340): 041-1042 (Nov. 7, 1997).

Haas, D., et al., "Recent Developments in Negishi Cross-Coupling Reactions" ACS CATAL 6(3):1540-1552 (Feb. 3, 2016).

He, S., et al., "High-Affinity Small-Molecule Inhibitors of the Menin-Mixed Lineage Leukemia (MLL) Interaction Closely Mimic a Natural Protein-Protein Interaction" J Med Chem 57(4):1543-1556 (Feb. 27, 2014).

Heravi, M., et al., "Buchwald-Hartwig reaction: An overview" J Organometallic Chem 861:17-104 (Apr. 15, 2018).

Hutchings, K., et al., "Synthesis and antibacterial activity of the C-7 side chain of 3-aminoquinazolinediones" Bioorg Med Chem Lett 18(18):5087-5090 (Sep. 15, 2008).

Iannotti, F. A., et al., "Endocannabinoids and endocannabinoid-related mediators: Targets, metabolism and role in neurological disorders" Prog Lipid Res 62:107-128 (Apr. 1, 2016).

Ignatowska-Jankowska, B., et al., "Selective Monoacylglycerol Lipase Inhibitors: Antinociceptive versus Cannabimimetic Effects in Mice" J Pharmacol Exp Ther 353(2):424-432 (May 1, 2015).

(56) References Cited

OTHER PUBLICATIONS

"International Preliminary Report on Patentability—PCT/EP2019/071520" (Report Issuance Date: Feb. 16, 2021, Chapter I),:pp. 1-8 (Feb. 25, 2021).
"International Preliminary Report on Patentability—PCT/EP2019/071522" (Report Issuance Date: Feb. 16, 2021, Chapter I),:pp. 1-9 (Feb. 25, 2021).
"International Preliminary Report on Patentability—PCT/EP2019/081870" (Report Issuance Date: May 25, 2021; Chapter I),:pp. 1-8 (Jun. 3, 2021).
"International Preliminary Report on Patentability—PCT/EP2019/057174" (Report Issuance Date: Sep. 22, 2020—Chapter I),:pp. 1-9 (Oct. 1, 2020).
"International Preliminary Report on Patentability—PCT/EP2020/074897" (Report Issuance Date: Mar. 9, 2022; Chapter I),:pp. 1-8 (Mar. 17, 2022).
"International Preliminary Report on Patentability—PCT/EP2020/076346" (Report Issuance Date: Mar. 15, 2022; Chapter I),:pp. 1-9 (Apr. 7, 2022).
"International Preliminary Report on Patentability—PCT/EP2020/076228" (Report Issuance Date: Mar. 15, 2022; Chapter I),:pp. 1-9 (Apr. 7, 2022).
"International Search Report—PCT/EP2019/057174" (w/Written Opinion),:pp. 1-14 (Jul. 3, 2019).
"International Search Report—PCT/EP2019/071520" (w/Written Opinion),:pp. 1-14 (Sep. 17, 2019).
"International Search Report—PCT/EP2019/071522" (w/Written Opinion),:pp. 1-15 (Sep. 17, 2019).
"International Search Report—PCT/EP2019/081870" (w/Written Opinion),:pp. 1-12 (Jan. 14, 2020).
"International Search Report—PCT/EP2020/074897" (w/Written Opinion),:pp. 1-15 (Nov. 18, 2020).
"International Search Report—PCT/EP2020/075260" (w/Written Opinion),:pp. 1-14 (Nov. 18, 2020).
"International Search Report—PCT/EP2020/076228" (w/Written Opinion),:pp. 1-14 (Nov. 12, 2020).
"International Search Report—PCT/EP2020/076346" (w/Written Opinion),:pp. 1-16 (Nov. 13, 2020).
"International Search Report—PCT/EP2020/076347" (w/Written Opinion),:pp. 1-16 (Nov. 30, 2020).
Ishichi, Y., et al., "Novel triple reuptake inhibitors with low risk of CAD associated liabilities: design, synthesis and biological activities of 4-[(1S)-1-(3,4-dichlorophenyl)-2-methoxyethyl]piperidine and related compounds" Bioorg Med Chem 21(15):4600-4613 (Aug. 1, 2013).
Janssen, F., et al., "Inhibitors of diacylglycerol lipases in neurodegenerative and metabolic disorders" Bioorg Med Chem Lett 26(16):3831-3837 (Aug. 15, 2016).
Johnson, J.I., et al., "Relationships between drug activity in NCI preclinical in vitro and in vivo models and early clinical trials" Brit J Cancer 84(10):1424-1431 (May 1, 2001).
Kayacelebi, A., et al., "Cross-validated stable-isotope dilution GC-MS and LC-MS/MS assays for monoacylglycerol lipase (MAGL) activity by measuring arachidonic acid released from the endocannabinoid 2-arachidonoyl glycerol" J Chromatogr B Analyt Technol Biomed Life Sci (Epub: Aug. 3, 2016), 1047:151-159 (Mar. 15, 2017).
Keenan, M., et al., "Design, structure-activity relationship and in vivo efficacy of piperazine analogues of fenarimol as inhibitors of Trypanosoma cruzi" Bioorg Med Chem 21(7):1756-1763 (Apr. 1, 2013).
Kitbunnadaj, R., et al., "Synthesis and structure-activity relationships of conformationally constrained histamine H(3) receptor agonists" J Med Chem 46(25):5445-5457 (Dec. 4, 2003).
Korhonen, J., et al., "Piperazine and piperidine carboxamides and carbamates as inhibitors of fatty acid amide hydrolase (FAAH) and monoacylglycerol lipase (MAGL)" Bioorg Med Chem 22(23):6694-6705 (Dec. 1, 2014).
Kummerer, K., "Pharmaceuticals in the Environment" Ann Rev Environ Res 35:57-75 (Nov. 1, 2010).

Layzer, R., "Section Five: Degenerative Diseases of the Nervous System" Cecil Textbook of Medicine 20(2):2050-2057 (Jan. 1, 1996).
Liu, F., et al., "Structure-Based Optimization of Pyridoxal 5'-Phosphate-Dependent Transaminase Enzyme (BioA) Inhibitors that Target Biotin Biosynthesis in Mycobacterium tuberculosis" J Med Chem 60(13):5507-5520 (Jul. 13, 2017).
Liu, Y. et al., "Discovery of 4-benzoylpiperidine and 3-(piperidin-4-yl)benzo[d]isoxazole derivatives as potential and selective GlyT1 inhibitors" RSC ADV 5(51):40964-40977 (Apr. 30, 2015).
Lleo, A., et al., "Molecular targets of non-steroidal anti-inflammatory drugs in neurodegenerative diseases" Cell Mol Life Sci 64(11):1403-1418 (Apr. 20, 2007).
Long, J.Z., et al., "Selective blockade of 2-arachidonoylglycerol hydrolysis produces cannabinoid behavioral effects" Nat Chem Biol 5(1):37-44 (Jan. 1, 2009).
Marino, S., et al., "JZL184, A Monoacylglycerol Lipase Inhibitor, Induces Bone Loss in a Multiple Myeloma Model of Immunocompetent Mice" Calcif Tissue Int 107(1):72-85 (Jul. 1, 2020).
Marquez, L., et al., "Ulcerative Colitis Induces Changes on the Expression of the Endocannabinoid System in the Human Colonic Tissue" PLOS ONE 4(9):e6893 (1-13) (Sep. 4, 2009).
Mcallister, L., et al., "Discovery of Trifluoromethyl Glycol Carbamates as Potent and Selective Covalent Monoacylglycerol Lipase (MAGL) Inhibitors for Treatment of Neuroinflammation" J Med Chem 61(7):3008-3026 (Apr. 12, 2018).
Merck Manual et al. Merck Manual—Online Professional "Acute Leukemia" Kenilworth, N.J.-USA:Merck and Company, Inc.,:1-6 (Jul. 10, 2013).
Muccioli, G., et al., "CAY10499, a Novel Monoglyceride Lipase Inhibitor Evidenced by an Expeditious MGL Assay" Chem Bio Chem 9(16):2704-2710 (Nov. 3, 2008).
Mulvihill, M., et al., "Therapeutic Potential of Monoacylglycerol Lipase Inhibitors" Life Sci 92(8-9):492-497 (Nov. 8, 2013).
Negishi, E., "Palladium- or Nickel-Catalyzed Cross Coupling. A New Selective Method for Carbon-Carbon Bond Formation" Acc Chem Res 15(11):340-348 (Nov. 1, 1982).
Nomura, D.K., et al., "Endocannabinoid Hydrolysis Generates Brain Prostaglandins That Promote Neuroinflammation" Science 334(6057):809-813 (Nov. 11, 2011).
Nomura, D.K., et al., "Monoacylglycerol Lipase Exerts Dual Control over Endocannabinoid and Fatty Acid Pathways to Support Prostate Cancer" Chem Biol 18(7):846-856 (Jul. 29, 2011).
Nomura, D.K., et al., "Monoacylglycerol Lipase Regulates a Fatty Acid Network that Promotes Cancer Pathogenesis" Cell 140(1):49-61 (Jan. 8, 2010).
Patel, J. et al., "Loratadine analogues as MAGL inhibitors" Bioorg Med Chem Lett 25(7):1436-1442 (Feb. 24, 2015).
Pearce, H., et al. Cancer Drug Design and Discovery "Chapter 18: Failure modes in anticancer drug discovery and development" Neidle, S., ed., 1st edition, New York, NY-USA:Academic Presss,:424-435 ( 2008).
Perisetti, A., et al., "Role of cannabis in inflammatory bowel diseases" Ann Gastroenterol 33(2):134-144 (Feb. 12, 2020).
Qin, H., et al., "The role of monoacylglycerol lipase (MAGL) in the cancer progress" Cell Biochem Biophys 70:33-36 (Mar. 16, 2014).
Rafinski, Z. et al., "Enantioselective Synthesis of Chromanones Bearing Quaternary Substituted Stereocenters Catalyzed by (1R)-Camphor-Derived N-Heterocyclic Carbenes" J Org Chem 80(15):7468-7476 (Aug. 7, 2015).
Scalvini, L., et al., "Monoglyceride lipase: Structure and inhibitors" Chem Phys Lipids 197:13-24 ( 2016).
Senter, T., et al., "Progress towards small molecule menin-mixed lineage leukemia (MLL) interaction inhibitors with in vivo utility" Bioorg Med Chem Lett 25(13):2720-2725 (Jul. 1, 2015).
Simone, J.V,, "Oncology: Introduction" Cecil Textbook of Medicine 1(20):1004-1010 (Jan. 1, 1996).
Surry, D., et al., "Biaryl Phosphane Ligands in Palladium-Catalyzed Amination" Angew Chem Int Ed Engl 47(34):6338-6361 (Aug. 11, 2008).
Thiel, K.,, "Structure-aided drug design's next generation" Nat Biotechnol 22(5):513-519 (May 1, 2004).
"U.S. Appl. No. 18/490,967, filed Oct. 20, 2023" , (Oct. 20, 2023).

(56) References Cited

OTHER PUBLICATIONS

Ukrorgsyntez, Ltd., CAS Registry Database, 1941372-36-6, (Stereosearch—C20 H27 N3 O3), p. 1Creation Date Jun. 29, 2016.
Viader, A., et al., "Metabolic Interplay between Astrocytes and Neurons Regulates Endocannabinoid Action" Cell Rep 12(5):798-808 (Aug. 4, 2015).
Walsh, D., et al., "Synthesis and antiallergy activity of 4-(diarylhydroxymethyl)-1-[3-(aryloxy)propyl]piperidines and structurally related compounds" J Med Chem 32(1):105-118 (Jan. 1, 1989).
Wang, J., et al., "Effect of monoacylglycerol lipase inhibition on intestinal permeability in chronic stress model" Biochem Biophys Res Commun 525(4):962-967 (May 14, 2020).
Williams, D., et al. Foye's Principles of Medicinal Chemistry, Chapter 2(5th edition):59-63 (2002).
Wright, K., et al., "Differential expression of cannabinoid receptors in the human colon: cannabinoids promote epithelial wound healing" Gastroenterology 129(2):437-453 (Aug. 1, 2005).
"Written Opinion of the International Searching Authority—PCT/EP2019/071520":pp. 1-6 (Sep. 17, 2019).
Wu, W., et al., "Synthesis and structure-activity relationships of piperidine-based melanin-concentrating hormone receptor 1 antagonists" Bioorg Med Chem Lett 16(14):3668-3673 (Jul. 15, 2006).
Yin, J., et al., "ARS2/MAGL signaling in glioblastoma stem cells promotes self-renewal and M2-like polarization of tumor-associated macrophages" Nat Commun 11(1):2978 (1-15) (Jun. 11, 2020).
Zhang, P., et al., "Silyl Radical Activation of Alkyl Halides in Metallaphotoredox Catalysis: A Unique Pathway for Cross-Electrophile Coupling" J Am Chem Soc 138(26):8084-8087 (Jul. 6, 2016).
Zhang, X., et al., "Direct Aldehyde C—H Arylation and Alkylation via the Combination of Nickel, Hydrogen Atom Transfer, and Photoredox Catalysis" J Am Chem Soc 139(33):11353-11356 (Aug. 23, 2017).
Zhong, P., et al., "Monoacylglycerol Lipase Inhibition Blocks Chronic Stress-Induced Depressive-Like Behaviors via Activation of mTOR Signaling" Neuropsychopharmacology 39(7):1763-1776 (Feb. 19, 2014).
Dyson, G., et al. Chemistry of Synthetic Medicinal Substances (Russian w/ English Translation), Moscow::12-19 (Jan. 1, 1964).

HETEROCYCLIC COMPOUNDS AS MONOACYLGLYCEROL LIPASE INHIBITORS

CROSS-REFERENCE TO RELATED APPLICATIONS

This application is a continuation of U.S. application Ser. No. 17/749,496, filed May 20, 2022, which is a continuation of U.S. application Ser. No. 16/844,262, filed Apr. 9, 2020, which is a continuation of International Application No. PCT/EP2019/071520, filed Aug. 12, 2019, which claims priority to EP Application No. 18188681.3, filed Aug. 13, 2018, the disclosure of each of which is incorporated herein by reference in its entirety.

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine and/or depression in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A., et al., *Progress in lipid research* 2016, 62, 107-28.). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K., et al., *Science* 2011, 334, 809.). MAGL is expressed throughout the brain and in most brain cell types, including neurons, astrocytes, oligodendrocytes and microglia cells (Chanda, P. K., et al., *Molecular pharmacology* 2010, 78, 996; Viader, A., et al., *Cell reports* 2015, 12, 798.). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclo-oxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll–/–) exhibit dramatically reduced 2-AG hydrolase activity and elevated 2-AG levels in the nervous system while other arachidonoyl-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ (PLA$_2$) enzymes have been viewed as the principal source of AA, but cPLA$_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll–/– mice. LPS treatment also induces a widespread elevation in pro-inflammatory cytokines including interleukin-1-a (IL-1-a), IL-1b, IL-6, and tumor necrosis factor-a (TNF-a) that is prevented in Mgll–/– mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and multiple sclerosis (Lleo A., *Cell Mol Life Sci.* 2007, 64, 1403.). Importantly, genetic and/or pharmacological disruption of MAGL activity also blocks LPS-induced activation of microglial cells in the brain (Nomura, D. K., et al., *Science* 2011, 334, 809.).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z., et al., *Nature chemical biology* 2009, 5, 37.). Systemic injection of such inhibitor recapitulates the Mgll–/– mice phenotype in the brain, including an increase in 2-AG levels, a reduction in AA levels and related eicosanoids production, as well as the prevention of cytokines production and microglia activation following LPS-induced neuroinflammation (Nomura, D. K., et al., *Science* 2011, 334, 809.), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska B. et al., *J. Pharmacol. Exp. Ther.* 2015, 353, 424.) and on mental disorders, such as depression in chronic stress models (Zhong P. et al., *Neuropsychopharmacology* 2014, 39, 1763.).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bernal-Chico, A., et al., Glia 2015, 63, 163.). Additionally, pharmacological inhibition of MAGL increases the number of myelinating OLs in the brain of mice, suggesting that MAGL inhibition may promote differentiation of OPCs in myelinating OLs in vivo (Alpar, A., et al., *Nature communications* 2014, 5, 4421.). Inhibition of MAGL was also shown to promote remyelination and functional recovery in a mouse model of progressive multiple sclerosis (Feliu A. et al., *Journal of Neuroscience* 2017, 37 (35), 8385.).

Finally, in recent years, metabolism is talked highly important in cancer research, especially the lipid metabolism. Researchers believe that the de novo fatty acid synthesis plays an important role in tumor development. Many studies illustrated that endocannabinoids have anti-tumorigenic actions, including anti-proliferation, apoptosis induction and anti-metastatic effects. MAGL as an important decomposing enzyme for both lipid metabolism and the endocannabinoids system, additionally as a part of a gene expression signature, contributes to different aspects of tumourigenesis (Qin, H., et al., *Cell Biochem. Biophys.* 2014, 70, 33; Nomura D K et al., *Cell* 2009, 140(1), 49-61; Nomura D K et al., *Chem. Biol.* 2011, 18(7), 846-856).

In conclusion, suppressing the action and/or the activation of MAGL is a promising new therapeutic strategy for the treatment or prevention of neuroinflammation, neurodegenerative diseases, pain, cancer and mental disorders. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides a compound of formula (I)

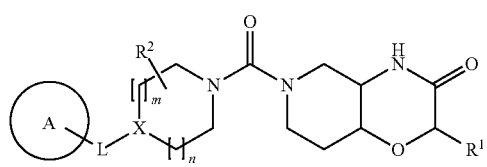

(I)

or a pharmaceutically acceptable salt thereof, wherein wherein A, L, X, m, n, $R^1$ and $R^2$ are as described herein.

In one aspect, the present invention provides a process of manufacturing the urea compounds of formula (I) described herein, comprising:

reacting a first amine of formula 1, wherein $R^1$ is as described herein, preferably wherein $R^1$ is hydrogen,

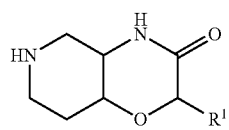

1 with a second amine 2, wherein A, L, m, n, X and $R^2$ are as described herein

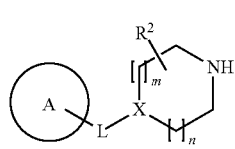

2 in the presence of a base and a urea forming reagent, to form said compound of formula (I).

In a further aspect, the present invention provides a compound of formula (I) as described herein, when manufactured according to the processes described herein.

In a further aspect, the present invention provides a compound of formula (I) as described herein, for use as therapeutically active substance.

In a further aspect, the present invention provides a pharmaceutical composition comprising a compound of formula (I) as described herein and a therapeutically inert carrier.

In a further aspect, the present invention provides the use of a compound of formula (I) as described herein or of a pharmaceutical composition described herein for inhibiting monoacylglycerol lipase (MAGL) in a mammal.

In a further aspect, the present invention provides the use of a compound of formula (I) as described herein or of a pharmaceutical composition described herein for the treatment or prophylaxis of neuroinflammation, neurodegenerative diseases, pain, cancer and/or mental disorders in a mammal.

In a further aspect, the present invention provides the use of a compound of formula (I) as described herein or of a pharmaceutical composition described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a further aspect, the present invention provides a compound of formula (I) as described herein or a pharmaceutical composition described herein for use in a method of inhibiting monoacylglycerol lipase in a mammal.

In a further aspect, the present invention provides a compound of formula (I) as described herein or a pharmaceutical composition described herein for use in the treatment or prophylaxis of neuroinflammation, neurodegenerative diseases, pain, cancer and/or mental disorders in a mammal.

In a further aspect, the present invention provides a compound of formula (I) as described herein or a pharmaceutical composition described herein, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a further aspect, the present invention provides the use of a compound of formula (I) as described herein for the preparation of a medicament for inhibiting monoacylglycerol lipase in a mammal.

In a further aspect, the present invention provides the use of a compound of formula (I) as described herein for the preparation of a medicament for the treatment or prophylaxis of neuroinflammation, neurodegenerative diseases, pain, cancer and/or mental disorders in a mammal.

In a further aspect, the present invention provides the use of a compound of formula (I) as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a further aspect, the present invention provides a method for inhibiting monoacylglycerol lipase in a mammal, which method comprises administering an effective amount of a compound of formula (I) as described herein or of a pharmaceutical composition described herein to the mammal.

In a further aspect, the present invention provides a method for the treatment or prophylaxis of neuroinflammation, neurodegenerative diseases, pain, cancer and/or mental disorders in a mammal, which method comprises administering an effective amount of a compound of formula (I) as described herein or of a pharmaceutical composition described herein to the mammal.

In a further aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal, which method comprises administering an effective amount of a compound of formula (I) as described herein or of a pharmaceutical composition described herein to the mammal.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 12 carbon atoms. In some preferred embodiments, the alkyl group contains 1 to 6 carbon atoms ("$C_{1-6}$-alkyl"), e.g., 1, 2, 3, 4, 5, or 6 carbon atoms. In other embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. Particularly preferred, yet non-limiting examples of alkyl are methyl and tert-butyl.

The term "alkoxy" refers to an alkyl group, as previously defined, attached to the parent molecular moiety via an oxygen atom. Unless otherwise specified, the alkoxy group contains 1 to 12 carbon atoms. In some preferred embodiments, the alkoxy group contains 1 to 6 carbon atoms ("$C_{1-6}$-alkoxy"). In other embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "cycloalkyl" as used herein refers to a saturated or partly unsaturated monocyclic or bicyclic hydrocarbon group of 3 to 10 ring carbon atoms. In some preferred embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. Preferably, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl, cyclohexyl and cycloheptyl.

The terms "heterocyclyl" and "heterocycloalkyl" are used herein interchangeably and refer to a saturated or partly unsaturated mono- or bicyclic, preferably monocyclic ring system of 3 to 10 ring atoms, preferably 3 to 8 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of monocyclic heterocyclyl groups include azetidin-3-yl, azetidin-2-yl, oxetan-3-yl, oxetan-2-yl, 1-piperidyl, 2-piperidyl, 3-piperidyl, 4-piperidyl, 2-oxopyrrolidin-1-yl, 2-oxopyrrolidin-3-yl, 5-oxopyrrolidin-2-yl, 5-oxopyrrolidin-3-yl, 2-oxo-1-piperidyl, 2-oxo-3-piperidyl, 2-oxo-4-piperidyl, 6-oxo-2-piperidyl, 6-oxo-3-piperidyl, morpholino, morpholin-2-yl and morpholin-3-yl.

The term "aryl" refers to a monocyclic, bicyclic, or tricyclic carbocyclic ring system having a total of 6 to 14 ring members, preferably, 6 to 12 ring members, and more preferably 6 to 10 ring members, and wherein at least one ring in the system is aromatic. Some non-limiting examples of aryl include phenyl and 9H-fluorenyl (e.g. 9H-fluoren-9-yl). A particularly preferred, yet non-limiting example of aryl is phenyl.

The term "heteroaryl" refers to a mono- or multivalent, monocyclic or bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O, S and N. Some preferred, yet non-limiting examples of heteroaryl include thiazolyl (e.g. thiazol-2-yl); oxazolyl (e.g. oxazol-2-yl); 5,6-dihydro-4H-cyclopenta[d]thiazol-2-yl; 1,2,4-oxadiazol-5-yl; pyridyl (e.g. 2-pyridyl); pyrazolyl (e.g. pyrazol-1-yl); imidazolyl (e.g. imidazole-1-yl); benzoxazolyl (e.g. benzoxazol-2-yl) and oxazolo[5,4-c]pyridin-2-yl.

The term "hydroxy" refers to an —OH group.

The term "cyano" refers to a —CN (nitrile) group.

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Particularly preferred, yet non-limiting examples of haloalkyl are trifluoromethyl ($CF_3$) and trifluoroethyl (e.g. 2,2,2-trifluoroethyl).

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. A particularly preferred, yet non-limiting example of haloalkoxy is trifluoromethoxy (—$OCF_3$).

The term "hydroxyalkyl" refers to an alkyl group, wherein at least one of the hydrogen atoms of the alkyl group has been replaced by a hydroxy group. Preferably, "hydroxyalkyl" refers to an alkyl group wherein 1, 2 or 3 hydrogen atoms, most preferably 1 hydrogen atom of the alkyl group have been replaced by a hydroxy group. Preferred, yet non-limiting examples of hydroxyalkyl are hydroxymethyl and hydroxyethyl (e.g. 2-hydroxyethyl). A particularly preferred, yet non-limiting example of hydroxyalkyl is hydroxymethyl.

The term "haloaryl" refers to an aryl group, wherein at least one of the hydrogen atoms of the aryl group has been replaced by a halogen atom. Preferably, "haloaryl" refers to an aryl group wherein 1, 2 or 3 hydrogen atoms, more preferably 1 or 2 hydrogen atoms, most preferably 1 hydrogen atom of the aryl group have been replaced by a halogen atom. A particularly preferred, yet non-limiting example of haloaryl is chlorophenyl, in particular 4-chlorophenyl.

The term "aryloxy" refers to an aryl group, as previously defined, attached to the parent molecular moiety via an oxygen atom. A preferred, yet non-limiting example of aryloxy is phenoxy.

The term "haloaryloxy" refers to a haloaryl group, as previously defined, attached to the parent molecular moiety via an oxygen atom. A preferred, yet non-limiting example of haloaryloxy is 4-fluorophenoxy.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochloride salts.

The term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates. Examples of pharmaceutically acceptable prodrug types are described in Higuchi and Stella, Pro-drugs as Novel Delivery Systems, Vol. 14 of the A.C.S. Symposium Series, and in Roche, ed., Bioreversible Carriers in Drug Design, American Pharmaceutical Association and Pergamon Press, 1987.

The term "protective group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, N.Y.

The term "urea forming reagent" refers to a chemical compound that is able to render a first amine to a species that will react with a second amine, thereby forming an urea derivative. Non-limiting examples of urea forming reagents include bis(trichloromethyl) carbonate, phosgene, trichloromethyl chloroformate, (4-nitrophenyl)carbonate and 1,1'-carbonyldiimidazole. The urea forming reagents described in G. Sartori et al., *Green Chemistry* 2000, 2, 140 are incorporated herein by reference.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates. In a preferred embodiment, the compound of formula (I) according to the invention is a cis-enantiomer of formula (Ia) or (Ib), respectively, as described herein.

According to the Cahn-Ingold-Prelog Convention, the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain including chemotherapy induced neuropathy, phantom pain and phsychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy. In one embodiment, "pain" is chemotherapy induced neuropathy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "cancer" refers to a disease characterized by the presence of a neoplasm or tumor resulting from abnormal uncontrolled growth of cells (such cells being "cancer cells"). As used herein, the term cancer explicitly includes, but is not limited to, hepatocellular carcinoma, colon carcinogenesis and ovarian cancer.

The term "mammal" as used herein includes both humans and non-humans and includes but is not limited to humans, non-human primates, canines, felines, murines, bovines, equines, and porcines. In a particularly preferred embodiment, the term "mammal" refers to humans.

Compounds of the Invention

In a first aspect, the present invention provides a compound of formula (I)

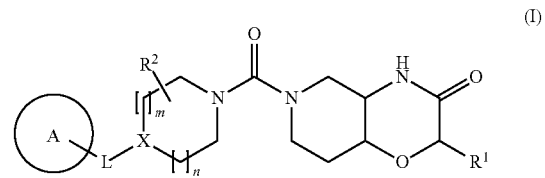

or a pharmaceutically acceptable salt thereof, wherein:

(i) X is C—$R^3$; m is 0 or 1; n is selected from 0, 1 and 2; and L is selected from —(CH$_2$)$_p$—, —O—, —OCH$_2$—, —CH$_2$O—, —CH$_2$OCH$_2$—, —CF$_2$CH$_2$—, and —CH$_2$CF$_2$—; or (ii) X is N; m is 1; n is 1 or 2; and L is —(CH$_2$)$_p$— or —CF$_2$CH$_2$—;

p is selected from 1, 2 and 3;

A is selected from:

(i) aryl substituted with $R^4$, $R^5$ and $R^6$;

(ii) heteroaryl substituted with $R^7$, $R^8$ and $R^9$; and (iii) heterocycloalkyl substituted with $R^{10}$, $R^{11}$ and $R^{12}$;

$R^1$ is hydrogen or $C_{1-6}$-alkyl;

$R^2$ is selected from hydrogen, $C_{1-6}$-alkyl and hydroxy-$C_{1-6}$-alkyl; $R^3$ is selected from hydrogen, halogen, hydroxy, $C_{1-6}$-alkoxy, $C_{1-6}$-alkyl and halo-$C_{1-6}$-alkyl;

each of $R^4$, $R^5$, $R^6$, $R^7$, $R^8$, $R^9$, $R^{10}$, $R^1$ and $R^{12}$ is independently selected from hydrogen, halogen, cyano, hydroxy, $C_{1-6}$-alkyl, halo-$C_{1-6}$-alkyl, hydroxy-$C_{1-6}$-alkyl, halo-$C_{1-5}$-alkyl-CH(OH)—, $C_{1-6}$-alkoxy, halo-$C_{1-6}$-alkoxy, SF$_5$, CH$_3$SO$_2$, $C_{3-10}$-cycloalkyl, $C_{3-10}$-cycloalkyl substituted with $R^{13}$, heterocycloalkyl, heterocycloalkyl substituted with $R^{14}$, heteroaryl, aryl and haloaryl; and each of $R^{13}$ and $R^{14}$ is independently $C_{1-6}$-alkyl, halo-$C_{1-6}$-alkyl or hydroxy.

In one embodiment, the present invention provides a compound of formula (I) as described herein, or a pharmaceutically acceptable salt thereof, wherein the compound of formula (I) is a compound of formula (Ia):

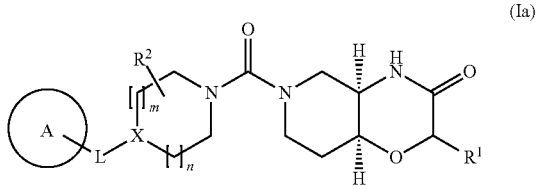

(Ia)

wherein A, L, X, m, n, $R^1$ and $R^2$ are as defined herein. Preferably, said compound of formula (Ia) has an enantiomeric excess (ee) of >80%, more preferably >90%, in particular >99%.

In one embodiment, the present invention provides a compound of formula (I) as described herein, or a pharmaceutically acceptable salt thereof, wherein the compound of formula (I) is a compound of formula (Ib):

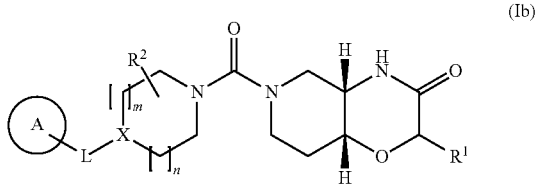

(Ib)

wherein A, L, X, m, n, $R^1$ and $R^2$ are as defined herein. Preferably, said compound of formula (Ib) has an enantiomeric excess (ee) of >80%, more preferably >90%, in particular >99%.

In one embodiment, the present invention provides a compound of formula (I) as described herein, or a pharmaceutically acceptable salt thereof, wherein the compound of formula (I) is a compound of formula (Ic):

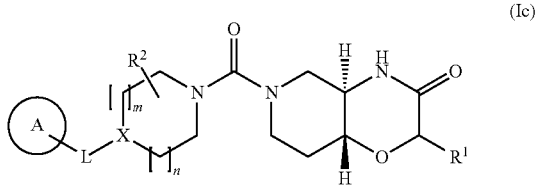

(Ic)

wherein A, L, X, m, n, $R^1$ and $R^2$ are as defined herein. Preferably, said compound of formula (Ic) has an enantiomeric excess (ee) of >80%, more preferably >90%, in particular >99%.

In one embodiment, the present invention provides a compound of formula (I) as described herein, or a pharmaceutically acceptable salt thereof, wherein the compound of formula (I) is a compound of formula (Id):

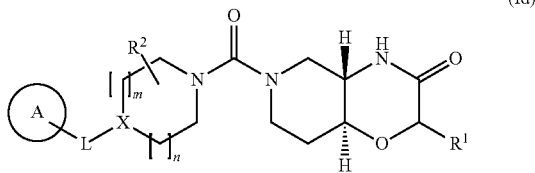

(Id)

wherein A, L, X, m, n, $R^1$ and $R^2$ are as defined herein. Preferably, said compound of formula (Id) has an enantiomeric excess (ee) of >80%, more preferably >90%, in particular >99%.

In one embodiment, there is provided a compound of formula (I) as described herein, wherein when X is C—$R^3$ and $R^3$ is hydroxy or halogen, L is not —O— or —CH$_2$O—.

In one embodiment, the present invention provides a compound of formula (I) as described herein, or a pharmaceutically acceptable salt thereof, wherein:
(i) X is C—$R^3$; m is 0 or 1; n is selected from 0, 1 and 2; and L is selected from —(CH$_2$)$_p$—, —O—, —OCH$_2$—, —CH$_2$O— and —CH$_2$OCH$_2$—; or
(ii) X is N; m and n are both 1; and L is —(CH$_2$)$_p$—.

In a preferred embodiment, the present invention provides a compound of formula (I) as described herein, or a pharmaceutically acceptable salt thereof, wherein:
X is C—R$_3$;
m and n are both 0; or
m and n are both 1; and
L is selected from —(CH$_2$)$_p$—, —O—, —OCH$_2$— and —CH$_2$O—.

In another preferred embodiment, the present invention provides a compound of formula (I) as described herein, or a pharmaceutically acceptable salt thereof, wherein:
X is C—$R^3$;
m and n are both 0; or
m and n are both 1;
L is selected from —(CH$_2$)$_p$—, —O—, —OCH$_2$— and —CH$_2$O—;
$R^3$ is selected from hydrogen, $C_{1-6}$-alkyl and halogen; and
p is 1 or 2.

In a particularly preferred embodiment, the present invention provides a compound of formula (I) as described herein, or a pharmaceutically acceptable salt thereof, wherein:
X is C—$R^3$;
m and n are both 0; or
m and n are both 1;
L is selected from —(CH$_2$)$_p$—, —O—, —OCH$_2$— and —CH$_2$O—;
$R^3$ is hydrogen; and
p is 1 or 2.

In one embodiment, the present invention provides a compound of formula (I) as described herein, or a pharmaceutically acceptable salt thereof, wherein p is 1 or 2.

In one embodiment, the present invention provides a compound of formula (I) as described herein, or a pharmaceutically acceptable salt thereof, wherein A is selected from:
(i) aryl substituted with $R^4$, $R^5$ and $R^6$; and
(ii) heteroaryl substituted with $R^7$, $R^8$ and $R^9$.

In a preferred embodiment, the present invention provides a compound of formula (I) as described herein, or a pharmaceutically acceptable salt thereof, wherein A is selected from:
(i) phenyl substituted with $R^4$, $R^5$ and $R^6$; and
(ii) oxazolyl substituted with $R^7$, $R^8$ and $R^9$.

In another preferred embodiment, the present invention provides a compound of formula (I) as described herein, or a pharmaceutically acceptable salt thereof, wherein A is aryl substituted with $R^4$, $R^5$ and $R^6$.

In a particularly preferred embodiment, the present invention provides a compound of formula (I) as described herein, or a pharmaceutically acceptable salt thereof, wherein A is phenyl substituted with $R^4$, $R^5$ and $R^6$.

In one embodiment, the present invention provides a compound of formula (I) as described herein, or a pharmaceutically acceptable salt thereof, wherein:
A is selected from:
(i) aryl substituted with $R^4$, $R^5$ and $R^6$; and
(ii) heteroaryl substituted with $R^7$, $R^8$ and $R^9$;
$R^4$ is selected from hydrogen, halogen, halo-$C_{1-6}$-alkoxy and halo-$C_{1-6}$-alkyl;
$R^5$ is selected from hydrogen, cyano, halogen, $C_{1-6}$-alkyl, $C_{1-6}$-alkoxy, heterocycloalkyl, $C_{3-10}$-cycloalkyl, heteroaryl and haloaryl;
$R^6$ is hydrogen or halogen; $R^7$ is selected from hydrogen, $C_{1-6}$-alkyl, aryl and halo-$C_{1-6}$-alkyl;
$R^8$ is hydrogen or $C_{1-6}$-alkyl; and
$R^9$ is hydrogen.

In a preferred embodiment, the present invention provides a compound of formula (I) as described herein, or a pharmaceutically acceptable salt thereof, wherein:
A is selected from:
(i) aryl substituted with $R^4$, $R^5$ and $R^6$; and
(ii) heteroaryl substituted with $R^7$, $R^8$ and $R^9$;
$R^4$ is selected from halogen, halo-$C_{1-6}$-alkoxy and halo-$C_{1-6}$-alkyl;
$R^5$ is selected from hydrogen, cyano, halogen, heterocycloalkyl, $C_{3-10}$-cycloalkyl and haloaryl;
$R^6$ is hydrogen;
$R^7$ is $C_{1-6}$-alkyl;
$R^8$ is hydrogen; and
$R^9$ is hydrogen.

In a particularly preferred embodiment, the present invention provides a compound of formula (I) as described herein, or a pharmaceutically acceptable salt thereof, wherein:
A is selected from:
(i) phenyl substituted with $R^4$, $R^5$ and $R^6$; and
(ii) oxazolyl substituted with $R^7$, $R^8$ and $R^9$;
$R^4$ is selected from chloro, $OCF_3$ and $CF_3$;
$R^5$ is selected from hydrogen, cyano, fluoro, chloro, pyrrolidinyl, cyclopentyl, cyclopropyl and chlorophenyl;
$R^6$ is hydrogen;
$R^7$ is tert-butyl;
$R^8$ is hydrogen; and
$R^9$ is hydrogen.

In a further particularly preferred embodiment, the present invention provides a compound of formula (I) as described herein, or a pharmaceutically acceptable salt thereof, wherein A is selected from phenyl, 4-tert-butylthiazol-2-yl, 4-tert-butyloxazol-2-yl, 2-chloro-4-fluoro-phenyl, 4-(trifluoromethyl)phenyl, 4-(trifluoromethoxy)phenyl, 4-chlorophenyl, 5,6-dihydro-4H-cyclopenta[d]thiazol-2-yl, 3-phenyl-1,2,4-oxadiazol-5-yl, 5-(trifluoromethyl)-2-pyridyl, 4-(trifluoromethyl)pyrazol-1-yl, 2-fluoro-4-(trifluoromethyl)phenyl, 2,4-difluorophenyl, 4-chloro-3-fluoro-phenyl, 4-cyanophenyl, 4,4-difluoro-1-piperidyl, 5-tert-butyloxazol-2-yl, 4-methoxy-2-fluoro-phenyl, 2-chloro-4 (trifluoromethyl)phenyl, 6-(trifluoromethyl)-3-pyridyl, 3-(trifluoromethyl)phenyl, 2-chloro-4-(trifluoromethoxy) phenyl, 4-chloro-2-fluoro-phenyl, 4-fluoro-2-(trifluoromethyl)phenyl, 2-pyrrolidin-1-yl-4-(trifluoromethyl)phenyl, 4-fluoro-2-cyano-phenyl, 2-cyclopentyl-4-(trifluoromethyl) phenyl, 2-chloro-4-cyanophenyl, 4-(trifluoromethyl)imidazol-1-yl, 4-fluoro-2-methyl-phenyl, 4-tert-butylpyrazol-1-yl, 1,3-benzoxazol-2-yl, 4-chloro-3-(4-chlorophenyl) phenyl, 2-(1H-pyrazol-4-yl)-4-(trifluoromethyl)phenyl, 2,4-dichlorophenyl, 3-methoxy-4-(trifluoromethyl)phenyl, 5-methyl-6-(trifluoromethyl)-3-pyridyl, 3-chlorophenyl, 2-chlorophenyl, 2-cyclopropyl-4-(trifluoromethyl)phenyl, 2-methyl-4-(trifluoromethyl)phenyl, 3-fluoro-5-(trifluoromethyl)phenyl, 2-fluoro-6-(trifluoromethyl)phenyl, 3-chloro-4-(trifluoromethyl)phenyl, 2,4-difluoro-5-(trifluoromethyl) phenyl, 2-fluoro-5-(trifluoromethyl)phenyl, 2-methoxy-4-(trifluoromethyl)phenyl, 4-chloro-2-(trifluoromethyl) phenyl, 4-chloro-3-(trifluoromethyl)phenyl, 4-chloro-3-cyclopropyl-phenyl, 4-chloro-3-morpholino-phenyl, 2-cyano-4-(trifluoromethyl)phenyl, oxazolo[5,4-c]pyridin-2-yl, 4-Methyl-3-(trifluoromethyl)phenyl, 3-cyclopropyl-4-(trifluoromethyl)phenyl, 2-fluoro-4-methyl-phenyl, 4-methoxy-2-(trifluoromethyl)phenyl, 4-methyl-2-(trifluoromethyl)phenyl, 3,4-dichlorophenyl, 2,5-dichlorophenyl, 5-methyl-6-(trifluoromethyl)-3-pyridyl, 4,5-bis(trifluoromethyl)-2-pyridyl, 2-fluoro-4-(trifluoromethyl)-phenyl, 2-fluoro-4-(pentafluoro-lambda6-sulfanyl)phenyl, 2,4-bis (trifluoromethyl)phenyl, 2-methyl-3-(trifluoromethyl)phenyl, 2-methyl-4-(trifluoromethoxy)phenyl, 3-chloro-4-(trifluoromethyl)phenyl, 3-cyclopropyl-4-chloro-phenyl, 2-chloro-3-(trifluoromethyl)phenyl, 2-chloro-3-cyclopropyl-phenyl, 3-(2-azaspiro[3.3]heptan-2-yl)-4-(trifluoromethyl)phenyl, 2-chloro-3-(2-azaspiro[3.3]heptan-2-yl)-phenyl, 2-chloro-3-(5-oxa-2-azaspiro[3.5]nonan-2-yl)phenyl, 2-fluoro-4-(trifluoromethyl)phenyl, 2-fluoro-4-methyl-phenyl, 2-fluoro-6-(trifluoromethyl)phenyl, and 2-(trifluoromethyl)-4-methyl-phenyl.

In one embodiment, the present invention provides a compound of formula (I) as described herein, or a pharmaceutically acceptable salt thereof, wherein $R^1$ is hydrogen or methyl.

In a preferred embodiment, the present invention provides a compound of formula (I) as described herein, or a pharmaceutically acceptable salt thereof, wherein $R^1$ is hydrogen.

In one embodiment, the present invention provides a compound of formula (I) as described herein, or a pharmaceutically acceptable salt thereof, wherein $R^2$ is hydrogen or $C_{1-6}$-alkyl.

In a preferred embodiment, the present invention provides a compound of formula (I) as described herein, or a pharmaceutically acceptable salt thereof, wherein $R^2$ is hydrogen or methyl.

In one embodiment, the present invention provides a compound of formula (I) as described herein, or a pharmaceutically acceptable salt thereof, wherein $R^3$ is selected from hydrogen, halogen, $C_{1-6}$-alkyl and halo-$C_{1-6}$-alkyl.

In a preferred embodiment, the present invention provides a compound of formula (I) as described herein, or a pharmaceutically acceptable salt thereof, wherein $R^3$ is selected from hydrogen, halogen and $C_{1-6}$-alkyl.

In a particularly preferred embodiment, the present invention provides a compound of formula (I) as described herein, or a pharmaceutically acceptable salt thereof, wherein $R^3$ is selected from hydrogen, fluoro and methyl.

In one embodiment, the present invention provides a compound of formula (I) as described herein, or a pharmaceutically acceptable salt thereof, wherein $R^3$ is selected from hydrogen, methyl, fluoro and trifluoromethyl.

In one embodiment, the present invention provides a compound of formula (I) as described herein, or a pharmaceutically acceptable salt thereof, wherein $R^4$ is selected from hydrogen, halogen, halo-$C_{1-6}$-alkoxy and halo-$C_{1-6}$-alkyl.

In a preferred embodiment, the present invention provides a compound of formula (I) as described herein, or a pharmaceutically acceptable salt thereof, wherein $R^4$ is selected from halogen, halo-$C_{1-6}$-alkoxy and halo-$C_{1-6}$-alkyl.

In a particularly preferred embodiment, the present invention provides a compound of formula (I) as described herein, or a pharmaceutically acceptable salt thereof, wherein $R^4$ is selected from chloro, $OCF_3$ and $CF_3$.

In one embodiment, the present invention provides a compound of formula (I) as described herein, or a pharmaceutically acceptable salt thereof, wherein $R^4$ is selected from hydrogen, chloro, fluoro, $OCF_3$ and $CF_3$.

In one embodiment, the present invention provides a compound of formula (I) as described herein, or a pharmaceutically acceptable salt thereof, wherein $R^5$ is selected from hydrogen, cyano, halogen, $C_{1-6}$-alkyl, $C_{1-6}$-alkoxy, heterocycloalkyl, $C_{3-10}$-cycloalkyl, heteroaryl and haloaryl.

In a preferred embodiment, the present invention provides a compound of formula (I) as described herein, or a pharmaceutically acceptable salt thereof, wherein $R^5$ is selected from hydrogen, cyano, halogen, heterocycloalkyl, $C_{3-10}$-cycloalkyl and haloaryl.

In a particularly preferred embodiment, the present invention provides a compound of formula (I) as described herein, or a pharmaceutically acceptable salt thereof, wherein $R^5$ is selected from hydrogen, cyano, fluoro, chloro, pyrrolidinyl, cyclopentyl, cyclopropyl and chlorophenyl.

In one embodiment, the present invention provides a compound of formula (I) as described herein, or a pharmaceutically acceptable salt thereof, wherein $R^5$ is selected from hydrogen, methyl, methoxy, cyano, fluoro, chloro, pyrolidinyl, morpholinyl, pyrazolyl, cyclopentyl, cyclopropyl and 4-chlorophenyl.

In one embodiment, the present invention provides a compound of formula (I) as described herein, or a pharmaceutically acceptable salt thereof, wherein $R^6$ is hydrogen or halogen.

In a preferred embodiment, the present invention provides a compound of formula (I) as described herein, or a pharmaceutically acceptable salt thereof, wherein $R^6$ is hydrogen or fluoro.

In a particularly preferred embodiment, the present invention provides a compound of formula (I) as described herein, or a pharmaceutically acceptable salt thereof, wherein $R^6$ is hydrogen.

In one embodiment, the present invention provides a compound of formula (I) as described herein, or a pharmaceutically acceptable salt thereof, wherein $R^7$ is selected from hydrogen, $C_{1-6}$-alkyl, aryl and halo-$C_{1-6}$-alkyl.

In a preferred embodiment, the present invention provides a compound of formula (I) as described herein, or a pharmaceutically acceptable salt thereof, wherein $R^7$ is $C_{1-6}$-alkyl.

In a particularly preferred embodiment, the present invention provides a compound of formula (I) as described herein, or a pharmaceutically acceptable salt thereof, wherein $R^7$ is tert-butyl.

In one embodiment, the present invention provides a compound of formula (I) as described herein, or a pharmaceutically acceptable salt thereof, wherein $R^7$ is selected from hydrogen, tert-butyl, phenyl and $CF_3$.

In one embodiment, the present invention provides a compound of formula (I) as described herein, or a pharmaceutically acceptable salt thereof, wherein $R^8$ is hydrogen or $C_{1-6}$-alkyl.

In a preferred embodiment, the present invention provides a compound of formula (I) as described herein, or a pharmaceutically acceptable salt thereof, wherein $R^8$ is hydrogen or methyl.

In a particularly preferred embodiment, the present invention provides a compound of formula (I) as described herein, or a pharmaceutically acceptable salt thereof, wherein $R^8$ is hydrogen.

In one embodiment, the present invention provides a compound of formula (I) as described herein, or a pharmaceutically acceptable salt thereof, wherein $R^9$ is hydrogen.

In one embodiment, the present invention provides a compound of formula (I) as described herein, or a pharmaceutically acceptable salt thereof, wherein $R^{10}$ is halogen.

In a preferred embodiment, the present invention provides a compound of formula (I) as described herein, or a pharmaceutically acceptable salt thereof, wherein $R^{10}$ is fluoro.

In one embodiment, the present invention provides a compound of formula (I) as described herein, or a pharmaceutically acceptable salt thereof, wherein $R^{11}$ is halogen.

In a preferred embodiment, the present invention provides a compound of formula (I) as described herein, or a pharmaceutically acceptable salt thereof, wherein $R^{11}$ is fluoro.

In a particularly preferred embodiment, the present invention provides a compound of formula (I) as described herein, or a pharmaceutically acceptable salt thereof, wherein $R^{10}$ and $R^{11}$ are both fluoro.

In one embodiment, the present invention provides a compound of formula (I) as described herein, or a pharmaceutically acceptable salt thereof, wherein $R^{12}$ is hydrogen.

In one embodiment, the present invention provides a compound of formula (I) as described herein, or a pharmaceutically acceptable salt thereof, wherein:
(i) X is C—$R^3$; m is 0 or 1; n is selected from 0, 1 and 2; and L is selected from —(CH$_2$)$_p$—, —O—, —OCH$_2$—, —CH$_2$O— and —CH$_2$OCH$_2$—; or
(ii) X is N; m and n are both 1; and L is —(CH$_2$)$_p$—;
p is 1 or 2;
A is selected from:
  (i) aryl substituted with $R^4$, $R^5$ and $R^6$;
  (ii) heteroaryl substituted with $R^7$, $R^8$ and $R^9$; and
  (iii) heterocycloalkyl substituted with $R^{10}$, $R^{11}$ and $R^{12}$;
$R^1$ is hydrogen or $C_{1-6}$-alkyl;
$R^2$ is selected from hydrogen or $C_{1-6}$-alkyl;
$R^3$ is selected from hydrogen, halogen, $C_{1-6}$-alkyl and halo-$C_{1-6}$-alkyl;
$R^4$ is selected from hydrogen, halogen, halo-$C_{1-6}$-alkoxy and halo-$C_{1-6}$-alkyl;
$R^5$ is selected from hydrogen, cyano, halogen, $C_{1-6}$-alkyl, $C_{1-6}$-alkoxy, heterocycloalkyl, $C_{3-10}$-cycloalkyl, heteroaryl and haloaryl;
$R^6$ is hydrogen or halogen;
$R^7$ is selected from hydrogen, $C_{1-6}$-alkyl, aryl and halo-$C_{1-6}$-alkyl;
$R^8$ is hydrogen or $C_{1-6}$-alkyl;
$R^9$ is hydrogen;
$R^{10}$ is halogen;
$R^{11}$ is halogen, and
$R^{12}$ is hydrogen.

In a preferred embodiment, the present invention provides a compound of formula (I) as described herein, or a pharmaceutically acceptable salt thereof, wherein:
X is C—$R^3$;
m and n are both 0; or
m and n are both 1;
L is selected from —(CH$_2$)$_p$—, —O—, —OCH$_2$— and —CH$_2$O—;
p is 1 or 2;
A is selected from:
  (i) aryl substituted with $R^4$, $R^5$ and $R^6$; and
  (ii) heteroaryl substituted with $R^7$, $R^8$ and $R^9$;

$R^1$ is hydrogen;
$R^2$ is selected from hydrogen or $C_{1-6}$-alkyl;
$R^3$ is selected from hydrogen, halogen and $C_{1-6}$-alkyl;
$R^4$ is selected from halogen, halo-$C_{1-6}$-alkoxy and halo-$C_{1-6}$-alkyl;
$R^5$ is selected from hydrogen, cyano, halogen, heterocycloalkyl, $C_{3-10}$-cycloalkyl and haloaryl;
$R^6$ is hydrogen;
$R^7$ is $C_{1-6}$-alkyl;
$R^8$ is hydrogen; and
$R^9$ is hydrogen.

In a particularly preferred embodiment, the present invention provides a compound of formula (I) as described herein, or a pharmaceutically acceptable salt thereof, wherein:
X is C—$R^3$;
m and n are both 0; or
m and n are both 1;
L is selected from —$(CH_2)_p$—, —O—, —$OCH_2$— and —$CH_2O$—;
p is 1 or 2;
A is selected from:
  (i) phenyl substituted with $R^4$, $R^5$ and $R^6$; and
  (ii) oxazolyl substituted with $R^7$, $R^8$ and $R^9$;
$R^1$ is hydrogen;
$R^2$ is selected from hydrogen or methyl;
$R^3$ is selected from hydrogen, fluoro and methyl;
$R^4$ is selected from chloro, $OCF_3$ and $CF_3$;
$R^5$ is selected from hydrogen, cyano, fluoro, chloro, pyrrolidinyl, cyclopentyl, cyclopropyl and chlorophenyl;
$R^6$ is hydrogen;
$R^7$ is tert-butyl;
$R^8$ is hydrogen; and
$R^9$ is hydrogen.

In one aspect, the present invention provides a compound of formula (I), or a pharmaceutically acceptable salt thereof, wherein:
(i) X is C—$R^3$; m is 0 or 1; n is selected from 0, 1 and 2; and L is selected from —$(CH_2)_p$—, —O—, —$OCH_2$—, —$CH_2OCH_2$—, —$CF_2CH_2$—, —$CH_2$=$CH_2$—, —$(CR^{16}R^{17})_q$—$CH_2O$—, and —$CH_2CF_2$—; or
(ii) X is N; m is 1; n is 1 or 2; and L is —$(CH_2)_p$— or —$CF_2CH_2$—;
p is selected from 1, 2 and 3;
q is 0 or 1;
A is selected from:
  (i) $C_6$-$C_{14}$-aryl substituted with $R^4$, $R^5$ and $R^6$;
  (ii) 5- to 14-membered heteroaryl substituted with $R^7$, $R^8$ and $R^9$; and
  (iii) 3- to 14-membered heterocycloalkyl substituted with $R^{10}$, $R^{11}$ and $R^{12}$;
$R^1$ is hydrogen or $C_{1-6}$-alkyl;
$R^2$ is selected from hydrogen, $C_{1-6}$-alkyl and hydroxy-$C_{1-6}$-alkyl;
$R^3$ is selected from hydrogen, halogen, hydroxy, $C_{1-6}$-alkoxy, $C_{1-6}$-alkyl and halo-$C_{1-6}$-alkyl;
each of $R^4$, $R^5$, $R^6$, $R^7$, $R^8$, $R^9$, $R^{10}$, $R^1$ and $R^{12}$ is independently selected from hydrogen, halogen, cyano, hydroxy, $C_{1-6}$-alkyl, halo-$C_{1-6}$-alkyl, hydroxy-$C_{1-6}$-alkyl, $C_{1-6}$-alkanoyl, halo-$C_{1-6}$-alkyl-CH(OH)—, $C_{1-6}$-alkoxy, halo-$C_{1-6}$-alkoxy, $SF_5$, $CH_3SO_2$, $C_{3-10}$-cycloalkyl, $C_{3-10}$-cycloalkyl substituted with $R^{13}$, 3- to 14-membered heterocycloalkyl, 3- to 14-membered heterocycloalkyl substituted with $R^{14}$ and $R^{15}$, 5- to 14-membered heteroaryl, $C_6$-$C_{14}$-aryl, $C_6$-$C_{14}$-aryloxy, halo-$C_6$-$C_{14}$-aryl, and halo-$C_6$-$C_{14}$-aryloxy;

each of $R^{13}$, $R^{14}$, and $R^{15}$ is independently selected from $C_{1-6}$-alkyl, $C_{1-6}$-alkoxy, halo-$C_{1-6}$-alkyl, halo-$C_{1-6}$-alkoxy, halogen, and hydroxy; and
$R^{16}$ and $R^{17}$, taken together with the carbon atom to which they are attached, form a $C_{3-10}$-cycloalkyl.

In one embodiment, the present invention provides a compound of formula (I) as described herein, or a pharmaceutically acceptable salt thereof, wherein:
(i) X is C—$R^3$; m is 0 or 1; n is selected from 0, 1 and 2; and L is selected from —$(CH_2)_p$—, —O—, —$OCH_2$—, —$CF_2CH_2$—, —$CH_2$=$CH_2$—, —$(CR^{16}R^{17})_q$—$CH_2O$—, and —$CH_2OCH_2$—; or
(ii) X is N; m and n are both 1; and L is —$(CH_2)_p$—.

In one embodiment, the present invention provides a compound of formula (I) as described herein, or a pharmaceutically acceptable salt thereof, wherein p is 2.

In one embodiment, the present invention provides a compound of formula (I) as described herein, or a pharmaceutically acceptable salt thereof, wherein q is 0 or 1.

In a preferred embodiment, the present invention provides a compound of formula (I) as described herein, or a pharmaceutically acceptable salt thereof, wherein q is 0.

In one embodiment, the present invention provides a compound of formula (I) as described herein, or a pharmaceutically acceptable salt thereof, wherein A is selected from:
  (i) $C_6$-$C_{14}$-aryl substituted with $R^4$, $R^5$ and $R^6$; and
  (ii) 5- to 14-membered heteroaryl substituted with $R^7$, $R^8$ and $R^9$.

In a preferred embodiment, the present invention provides a compound of formula (I) as described herein, or a pharmaceutically acceptable salt thereof, wherein A is selected from:
  (i) phenyl substituted with $R^4$, $R^5$ and $R^6$;
  (ii) oxazolyl substituted with $R^7$, $R^8$ and $R^9$; and
  (iii) pyridyl substituted with $R^7$, $R^8$ and $R^9$.

In one embodiment, the present invention provides a compound of formula (I) as described herein, or a pharmaceutically acceptable salt thereof, wherein $R^4$ is selected from hydrogen, halogen, hydroxy, cyano, $C_{1-6}$-alkyl, $C_{1-6}$-alkanoyl, $SF_5$, $C_{1-6}$-alkoxy, halo-$C_{1-6}$-alkoxy, halo-$C_{1-6}$-alkyl, $C_{3-10}$-cycloalkyl, 3- to 14-membered heterocyclyl, 3- to 14-membered heterocycloalkyl substituted with $R^{14}$ and $R^{15}$, 5- to 14-membered heteroaryl, $C_6$-$C_{14}$-aryloxy, and halo-$C_6$-$C_{14}$-aryl.

In a preferred embodiment, the present invention provides a compound of formula (I) as described herein, or a pharmaceutically acceptable salt thereof, wherein $R^4$ is selected from halogen, $SF_5$, $C_{1-6}$-alkyl, $C_{1-6}$-alkoxy, halo-$C_{1-6}$-alkoxy, halo-$C_{1-6}$-alkyl, $C_{3-10}$-cycloalkyl, and 3- to 14-membered heterocycloalkyl.

In a particularly preferred embodiment, the present invention provides a compound of formula (I) as described herein, or a pharmaceutically acceptable salt thereof, wherein $R^4$ is selected from chloro, $SF_5$, methyl, methoxy, $OCF_3$, $CF_3$, cyclopropyl, and 2-azaspiro[3.3]heptan-2-yl.

In one embodiment, the present invention provides a compound of formula (I) as described herein, or a pharmaceutically acceptable salt thereof, wherein $R^5$ is selected from hydrogen, cyano, halogen, $C_{1-6}$-alkyl, halo-$C_{1-6}$-alkyl, $C_{1-6}$-alkoxy, 3- to 14-membered heterocycloalkyl, $C_{3-10}$-cycloalkyl, 5- to 14-membered heteroaryl. and halo-$C_6$-$C_{14}$-aryl.

In a preferred embodiment, the present invention provides a compound of formula (I) as described herein, or a pharmaceutically acceptable salt thereof, wherein $R^5$ is selected from hydrogen, cyano, halogen, $C_{1-6}$-alkyl, halo-$C_{1-6}$-alkyl, 3- to 14-membered heterocycloalkyl, $C_{3-10}$-cycloalkyl and halo-$C_6$-$C_{14}$-aryl.

In a particularly preferred embodiment, the present invention provides a compound of formula (I) as described herein, or a pharmaceutically acceptable salt thereof, wherein $R^5$ is selected from hydrogen, cyano, fluoro, chloro, methyl, $CF_3$, pyrrolidinyl, cyclopentyl, cyclopropyl and chlorophenyl.

In one embodiment, the present invention provides a compound of formula (I) as described herein, or a pharmaceutically acceptable salt thereof, wherein $R^7$ is selected from hydrogen, $C_{1-6}$-alkyl, $C_6$-$C_{14}$-aryl, halo-$C_6$-$C_{14}$-aryl, halo-$C_6$-$C_{14}$-aryloxy, and halo-$C_{1-6}$-alkyl.

In a preferred embodiment, the present invention provides a compound of formula (I) as described herein, or a pharmaceutically acceptable salt thereof, wherein $R^7$ is $C_{1-6}$-alkyl or halo-$C_{1-6}$-alkyl.

In a particularly preferred embodiment, the present invention provides a compound of formula (I) as described herein, or a pharmaceutically acceptable salt thereof, wherein $R^7$ is tert-butyl or $CF_3$.

In one embodiment, the present invention provides a compound of formula (I) as described herein, or a pharmaceutically acceptable salt thereof, wherein $R^8$ is selected from hydrogen, halogen, $C_{1-6}$-alkyl, and halo-$C_{1-6}$-alkyl.

In a preferred embodiment, the present invention provides a compound of formula (I) as described herein, or a pharmaceutically acceptable salt thereof, wherein $R^8$ is hydrogen or halo-$C_{1-6}$-alkyl.

In a particularly preferred embodiment, the present invention provides a compound of formula (I) as described herein, or a pharmaceutically acceptable salt thereof, wherein $R^8$ is hydrogen or $CF_3$.

In one embodiment, the present invention provides a compound of formula (I) as described herein, or a pharmaceutically acceptable salt thereof, wherein $R^{14}$ is selected from $C_{1-6}$-alkyl, $C_{1-6}$-alkoxy, and halogen.

In one embodiment, the present invention provides a compound of formula (I) as described herein, or a pharmaceutically acceptable salt thereof, wherein $R^{15}$ is hydrogen or halogen.

In one embodiment, the present invention provides a compound of formula (I) as described herein, or a pharmaceutically acceptable salt thereof, wherein:
(i) X is C—$R^3$; m is 0 or 1; n is selected from 0, 1 and 2; and L is selected from —$(CH_2)_p$—, —O—, —$OCH_2$—, —$(CR^{16}R^{17})_q$—$CH_2O$—, —$CH_2OCH_2$—, —$CF_2CH_2$—, and —CH=$CH_2$—; or
(ii) X is N; m and n are both 1; and L is —$(CH_2)_p$—;
p is 1 or 2;
q is 0 or 1;
A is selected from:
(i) $C_6$-$C_{14}$-aryl substituted with $R^4$, $R^5$ and $R^6$;
(ii) 5- to 14-membered heteroaryl substituted with $R^7$, $R^8$ and $R^9$; and
(iii) 3- to 14-membered heterocycloalkyl substituted with $R^{10}$, $R^{11}$ and $R^{12}$;
$R^1$ is hydrogen or $C_{1-6}$-alkyl;
$R^2$ is hydrogen or $C_{1-6}$-alkyl;
$R^3$ is selected from hydrogen, halogen, $C_{1-6}$-alkyl and halo-$C_{1-6}$-alkyl;
$R^4$ is selected from hydrogen, halogen, cyano, $SF_5$, $C_{1-6}$-alkyl, $C_{1-6}$-alkanoyl, $C_{1-6}$-alkoxy, halo-$C_{1-6}$-alkoxy, halo-$C_{1-6}$-alkyl, $C_{3-10}$-cycloalkyl, 3- to 14-membered heterocycloalkyl, 3- to 14-membered heterocycloalkyl substituted with $R^{14}$ and $R^{15}$, 5- to 14-membered heteroaryl, halo-$C_6$-$C_{14}$-aryl, and $C_6$-$C_{14}$-aryloxy;
$R^5$ is selected from hydrogen, cyano, halogen, $C_{1-6}$-alkyl, halo-$C_{1-6}$-alkyl, $C_{1-6}$-alkoxy, 3- to 14-membered heterocycloalkyl, $C_{3-10}$-cycloalkyl, 5- to 14-membered heteroaryl and halo-$C_6$-$C_{14}$-aryl;
$R^6$ is hydrogen or halogen;
$R^7$ is selected from hydrogen, $C_{1-6}$-alkyl, $C_6$-$C_{14}$-aryl, halo-$C_6$-$C_{14}$-aryl, halo-$C_6$-$C_{14}$-aryloxy, and halo-$C_{1-6}$-alkyl;
$R^8$ is selected from hydrogen, halogen, $C_{1-6}$-alkyl, and halo-$C_{1-6}$-alkyl;
$R^9$ is hydrogen;
$R^{10}$ is halogen;
$R^{11}$ is halogen;
$R^{12}$ is hydrogen;
$R^{14}$ is selected from halogen, $C_{1-6}$-alkyl, and $C_{1-6}$-alkoxy;
$R^{15}$ is hydrogen or halogen; and
$R^{16}$ and $R^{17}$, taken together with the carbon atom to which they are attached, form a $C_{3-10}$-cycloalkyl.

In a preferred embodiment, the present invention provides a compound of formula (I) as described herein, or a pharmaceutically acceptable salt thereof, wherein:
X is C—$R^3$;
m and n are both 0; or
m and n are both 1;
L is selected from —$(CH_2)_p$—, —O—, —$OCH_2$— and —$CH_2O$—;
p is 1 or 2;
A is selected from:
(i) $C_6$-$C_{14}$-aryl substituted with $R^4$, $R^5$ and $R^6$; and
(ii) 5- to 14-membered heteroaryl substituted with $R^7$, $R^8$ and $R^9$;
$R^1$ is hydrogen;
$R^2$ is hydrogen or $C_{1-6}$-alkyl;
$R^3$ is selected from hydrogen, halogen and $C_{1-6}$-alkyl;
$R^4$ is selected from halogen, $SF_5$, $C_{1-6}$-alkyl, $C_{1-6}$-alkoxy, halo-$C_{1-6}$-alkoxy, halo-$C_{1-6}$-alkyl, $C_{3-10}$-cycloalkyl, and 3- to 14-membered heterocycloalkyl;
$R^5$ is selected from hydrogen, cyano, halogen, $C_{1-6}$-alkyl, halo-$C_{1-6}$-alkyl, 3- to 14-membered heterocycloalkyl, $C_{3-10}$-cycloalkyl and halo-$C_6$-$C_{14}$-aryl;
$R^6$ is hydrogen;
$R^7$ is $C_{1-6}$-alkyl or halo-$C_{1-6}$-alkyl;
$R^8$ is hydrogen or halo-$C_{1-6}$-alkyl; and
$R^9$ is hydrogen.

In a particularly preferred embodiment, the present invention provides a compound of formula (I) as described herein, or a pharmaceutically acceptable salt thereof, wherein:
X is C—$R^3$;
m and n are both 0; or
m and n are both 1;
L is selected from —$(CH_2)_p$—, —O—, —$OCH_2$— and —$CH_2O$—;
p is 1 or 2;
A is selected from:
(i) phenyl substituted with $R^4$, $R^5$ and $R^6$;
(ii) oxazolyl substituted with $R^7$, $R^8$ and $R^9$; and
(iii) pyridyl substituted with $R^7$, $R^8$ and $R^9$;
$R^1$ is hydrogen;
$R^2$ is hydrogen or methyl;
$R^3$ is selected from hydrogen, fluoro and methyl;
$R^4$ is selected from chloro, $SF_5$, methyl, methoxy, $OCF_3$, $CF_3$, cyclopropyl, and 2-azaspiro[3.3]heptan-2-yl;
$R^5$ is selected from hydrogen, cyano, fluoro, chloro, methyl, $CF_3$, pyrrolidinyl, cyclopentyl, cyclopropyl and chlorophenyl;

$R^6$ is hydrogen;
$R^7$ is selected from tert-butyl, methyl, and $CF_3$;
$R^8$ is hydrogen or $CF_3$; and
$R^9$ is hydrogen.

In a preferred embodiment, the present invention provides a compound of formula (I) as described herein, or a pharmaceutically acceptable salt thereof, wherein:
X is C—$R^3$; and
$R^3$ is selected from hydrogen, halogen and $C_{1-6}$-alkyl.

In a particularly preferred embodiment, the present invention provides a compound of formula (I) as described herein, or a pharmaceutically acceptable salt thereof, wherein:
X is C—$R^3$; and
$R^3$ is selected from hydrogen, fluoro and methyl.

In one embodiment, the present invention provides a compound of formula (I) as described herein, or a pharmaceutically acceptable salt thereof, wherein:
(i) X is C—$R^3$; m is 0 or 1; n is selected from 0, 1 and 2; and L is selected from —$(CH_2)_p$—, —O—, —$OCH_2$—, —$(CR^{16}R^{17})_q$—$CH_2O$—, —$CH_2OCH_2$—, —$CF_2CH_2$—, and —$CH_2$=$CH_2$—;
or
(ii) X is N; m and n are both 1; and L is —$(CH_2)_p$—;
p is 1 or 2;
q is 0 or 1;
$R^3$ is selected from hydrogen, halogen and $C_{1-6}$-alkyl; and
$R^{16}$ and $R^{17}$, taken together with the carbon atom to which they are attached, form a $C_{3-10}$-cycloalkyl.

In a preferred embodiment, the present invention provides a compound of formula (I) as described herein, or a pharmaceutically acceptable salt thereof, wherein:
X is C—$R^3$;
m and n are both 0; or
m and n are both 1;
L is selected from —$(CH_2)_p$—, —O—, —$OCH_2$— and —$CH_2O$—;
p is 1 or 2; and
$R^3$ is selected from hydrogen, halogen and $C_{1-6}$-alkyl.

In a particularly preferred embodiment, the present invention provides a compound of formula (I) as described herein, or a pharmaceutically acceptable salt thereof, wherein:
X is C—$R^3$;
m and n are both 0; or
m and n are both 1;
L is selected from —$(CH_2)_p$—, —O—, —$OCH_2$— and —$CH_2O$—;
p is 1 or 2; and
$R^3$ is selected from hydrogen, fluoro and methyl.

In one embodiment, the present invention provides a compound of formula (I) as described herein, or a pharmaceutically acceptable salt thereof, wherein:
A is selected from:
(i) $C_6$-$C_{14}$-aryl substituted with $R^4$, $R^5$ and $R^6$;
(ii) 5- to 14-membered heteroaryl substituted with $R^7$, $R^8$ and $R^9$; and
(iii) 3- to 14-membered heterocycloalkyl substituted with $R^{10}$, $R^{11}$ and $R^{12}$;
$R^4$ is selected from hydrogen, halogen, cyano, $SF_5$, $C_{1-6}$-alkyl, $C_{1-6}$-alkanoyl, $C_{1-6}$-alkoxy, halo-$C_{1-6}$-alkoxy, halo-$C_{1-6}$-alkyl, $C_{3-10}$-cycloalkyl, 3- to 14-membered heterocycloalkyl, 3- to 14-membered heterocycloalkyl substituted with $R^{14}$ and $R^{15}$, 5- to 14-membered heteroaryl, halo-$C_6$-$C_{14}$-aryl, and $C_6$-$C_{14}$-aryloxy;
$R^5$ is selected from hydrogen, cyano, halogen, $C_{1-6}$-alkyl, halo-$C_{1-6}$-alkyl, $C_{1-6}$-alkoxy, 3- to 14-membered heterocycloalkyl, $C_{3-10}$-cycloalkyl, 5- to 14-membered heteroaryl and halo-$C_6$-$C_{14}$-aryl;
$R^6$ is hydrogen or halogen;
$R^7$ is selected from hydrogen, $C_{1-6}$-alkyl, $C_6$-$C_{14}$-aryl, halo-$C_6$-$C_{14}$-aryl, halo-$C_6$-$C_{14}$-aryloxy, and halo-$C_{1-6}$-alkyl;
$R^8$ is selected from hydrogen, halogen, $C_{1-6}$-alkyl, and halo-$C_{1-6}$-alkyl;
$R^9$ is hydrogen;
$R^{10}$ is halogen;
$R^{11}$ is halogen;
$R^{12}$ is hydrogen;
$R^{14}$ is selected from halogen, $C_{1-6}$-alkyl, and $C_{1-6}$-alkoxy; and
$R^{15}$ is hydrogen or halogen.

In a preferred embodiment, the present invention provides a compound of formula (I) as described herein, or a pharmaceutically acceptable salt thereof, wherein:
A is selected from:
(i) $C_6$-$C_{14}$-aryl substituted with $R^4$, $R^5$ and $R^6$; and
(ii) 5- to 14-membered heteroaryl substituted with $R^7$, $R^8$ and $R^9$;
$R^4$ is selected from halogen, $SF_5$, $C_{1-6}$-alkyl, $C_{1-6}$-alkoxy, halo-$C_{1-6}$-alkoxy, halo-$C_{1-6}$-alkyl, $C_{3-10}$-cycloalkyl, and 3- to 14-membered heterocycloalkyl;
$R^5$ is selected from hydrogen, cyano, halogen, $C_{1-6}$-alkyl, halo-$C_{1-6}$-alkyl, 3- to 14-membered heterocycloalkyl, $C_{3-10}$-cycloalkyl and halo-$C_6$-$C_{14}$-aryl;
$R^6$ is hydrogen;
$R^7$ is $C_{1-6}$-alkyl or halo-$C_{1-6}$-alkyl;
$R^8$ is hydrogen or halo-$C_{1-6}$-alkyl; and
$R^9$ is hydrogen.

In a particularly preferred embodiment, the present invention provides a compound of formula (I) as described herein, or a pharmaceutically acceptable salt thereof, wherein:
A is selected from:
(i) phenyl substituted with $R^4$, $R^5$ and $R^6$;
(ii) oxazolyl substituted with $R^7$, $R^8$ and $R^9$; and
(iii) pyridyl substituted with $R^7$, $R^8$ and $R^9$;
$R^4$ is selected from chloro, $SF_5$, methyl, methoxy, $OCF_3$, $CF_3$, cyclopropyl, and 2-azaspiro[3.3]heptan-2-yl;
$R^5$ is selected from hydrogen, cyano, fluoro, chloro, methyl, $CF_3$, pyrrolidinyl, cyclopentyl, cyclopropyl and chlorophenyl;
$R^6$ is hydrogen;
$R^7$ is tert-butyl, methyl, and $CF_3$;
$R^8$ is hydrogen or $CF_3$; and
$R^9$ is hydrogen.

In a preferred embodiment, the present invention provides a compound of formula (I) as described herein, or a pharmaceutically acceptable salt thereof, wherein:
X is C—H;
m and n are both 0;
L is —$CH_2O$—;
A is $C_6$-$C_{14}$-aryl substituted with $R^4$, $R^5$ and $R^6$;
$R^1$, $R^2$, and $R^6$ are all hydrogen;
$R^4$ is halo-$C_{1-6}$-alkyl; and
$R^5$ is halogen or $C_{1-6}$-alkyl.

In a particularly preferred embodiment, the present invention provides a compound of formula (I) as described herein, or a pharmaceutically acceptable salt thereof, wherein:
X is C—H;
m and n are both 0;
L is —$CH_2O$—;
A is $C_6$-$C_{14}$-aryl substituted with $R^4$, $R^5$ and $R^6$;
$R^1$, $R^2$, and $R^6$ are all hydrogen;
$R^4$ is halo-$C_{1-6}$-alkyl; and
$R^5$ is halogen.

In a preferred embodiment, the present invention provides a compound of formula (I) as described herein, or a pharmaceutically acceptable salt thereof, wherein:
X is C—H;
m and n are both 0;
L is —CH$_2$O—;
A is phenyl substituted with R$^4$, R$^5$ and R$^6$;
R$^1$, R$^2$, and R$^6$ are all hydrogen;
R$^4$ is CF$_3$; and
R$^5$ is fluoro or methyl.

In a particularly preferred embodiment, the present invention provides a compound of formula (I) as described herein, or a pharmaceutically acceptable salt thereof, wherein:
X is C—H;
m and n are both 0;
L is —CH$_2$O—;
A is phenyl substituted with R$^4$, R$^5$ and R$^6$;
R$^1$, R$^2$, and R$^6$ are all hydrogen;
R$^4$ is CF$_3$; and
R$^5$ is fluoro.

In one embodiment, the present invention provides a compound of formula (I) as described herein, or a pharmaceutically acceptable salt thereof, selected from the compounds disclosed in Table 1.

In a preferred embodiment, the present invention provides a compound of formula (I) as described herein, or a pharmaceutically acceptable salt thereof, selected from:
(+)-(4aR,8aS)-6-(4-((4-(tert-Butyl)oxazol-2-yl)methyl)piperidine-1-carbonyl)hexahydro-2H-pyrido[4,3-b][1,4]oxazin-3(4H)-one;
(+)-(4aR,8aS)-6-[4-[[4-(Trifluoromethyl)phenyl]methyl]piperidine-1-carbonyl]-4,4a,5,7,8,8a-hexahydropyrido[4,3-b][1,4]oxazin-3-one;
(+)-(4aR,8aS)-6-(4-((2-Chloro-4-fluorophenoxy)methyl)piperidine-1-carbonyl)hexahydro-2H-pyrido[4,3-b][1,4]oxazin-3(4H)-one;
rac-(4aR,8aS)-6-(3-((2-Fluoro-4-(trifluoromethyl)benzyl)oxy)azetidine-1-carbonyl)hexahydro-2H-pyrido[4,3-b][1,4]oxazin-3(4H)-one;
(+)- or (−)-(4aR,8aS)-6-(3-((2-Chloro-4-fluorobenzyl)oxy)azetidine-1-carbonyl)hexahydro-2H-pyrido[4,3-b][1,4]oxazin-3(4H)-one;
(+)- or (−)-(4aR,8aS)-6-(3-((2-Fluoro-4-(trifluoromethyl)benzyl)oxy)azetidine-1-carbonyl)hexahydro-2H-pyrido[4,3-b][1,4]oxazin-3(4H)-one;
(+)- or (−)-(4aR,8aS)-6-(4-(4-(Trifluoromethoxy)benzyl)piperidine-1-carbonyl)hexahydro-2H-pyrido[4,3-b][1,4]oxazin-3(4H)-one;
(+)- or (−)-(4aR,8aS)-6-(4-(4-Chloro-3-fluorobenzyl)piperidine-1-carbonyl)hexahydro-2H-pyrido[4,3-b][1,4]oxazin-3(4H)-one;
(+)- or (−)-(4aR,8aS)-6-(4-(2-Chloro-4-(trifluoromethyl)phenoxy)piperidine-1-carbonyl)hexahydro-2H-pyrido[4,3-b][1,4]oxazin-3(4H)-one;
(+)- or (−)-(4aR,8aS)-6-(4-(3-(Trifluoromethyl)phenoxy)piperidine-1-carbonyl)hexahydro-2H-pyrido[4,3-b][1,4]oxazin-3(4H)-one;
(+)- or (−)-(4aR,8aS)-6-[4-[[2-Chloro-4-(trifluoromethoxy)phenoxy]methyl]piperidine-1-carbonyl]-4,4a,5,7,8,8a-hexahydropyrido[4,3-b][1,4]oxazin-3-one;
(+)- or (−)-(4aR,8aS)-6-(3-((2-Fluoro-4-(trifluoromethyl)phenoxy)methyl)azetidine-1-carbonyl)hexahydro-2H-pyrido[4,3-b][1,4]oxazin-3(4H)-one;
(+)- or (−)-(4aR,8aS)-6-(4-((4-Chloro-2-fluorophenoxy)methyl)piperidine-1-carbonyl)hexahydro-2H-pyrido[4,3-b][1,4]oxazin-3(4H)-one;
(+)- or (−)-(4aR,8aS)-6-(4-((4-Fluoro-2-(trifluoromethyl)phenoxy)methyl)piperidine-1-carbonyl)hexahydro-2H-pyrido[4,3-b][1,4]oxazin-3(4H)-one;
(+)- or (−)-(4aR,8aS)-6-(4-((2-Fluoro-4-(trifluoromethyl)phenoxy)methyl)piperidine-1-carbonyl)hexahydro-2H-pyrido[4,3-b][1,4]oxazin-3(4H)-one;
(+)- or (−)-(4aR,8aS)-6-(4-(2-(Pyrrolidin-1-yl)-4-(trifluoromethyl)benzyl)piperidine-1-carbonyl)hexahydro-2H-pyrido[4,3-b][1,4]oxazin-3(4H)-one;
(+)- or (−)-(4aR,8aS)-6-(4-((2-Chloro-4-(trifluoromethyl)phenoxy)methyl)piperidine-1-carbonyl)hexahydro-2H-pyrido[4,3-b][1,4]oxazin-3(4H)-one;
(+)- or (−)-(4aR,8aS)-6-[4-[[2-Cyclopentyl-4-(trifluoromethyl)phenyl]methyl]piperidine-1-carbonyl]-4,4a,5,7,8,8a-hexahydropyrido[4,3-b][1,4]oxazin-3-one;
(+)- or (−)-3-Chloro-4-((1-((4aR,8aS)-3-oxooctahydro-2H-pyrido[4,3-b][1,4]oxazine-6-carbonyl)piperidin-4-yl)methoxy)benzonitrile;
(+)- or (−)-(4aR,8aS)-6-(3-((2-Chloro-4-(trifluoromethyl)phenoxy)methyl)azetidine-1-carbonyl)hexahydro-2H-pyrido[4,3-b][1,4]oxazin-3(4H)-one;
(+)- or (−)-(4aR,8aS)-6-(4-((2-Chloro-4-fluorophenoxy)methyl)-4-fluoropiperidine-1-carbonyl)hexahydro-2H-pyrido[4,3-b][1,4]oxazin-3(4H)-one;
(+)- or (−)-(4aR,8aS)-6-(4-((4',6-Dichloro-[1,1'-biphenyl]-3-yl)oxy)piperidine-1-carbonyl)hexahydro-2H-pyrido[4,3-b][1,4]oxazin-3(4H)-one;
(+)- or (−)-(4aR,8aS)-6-(cis-4-((2-Chloro-4-fluorophenoxy)methyl)-3-methylpiperidine-1-carbonyl)hexahydro-2H-pyrido[4,3-b][1,4]oxazin-3(4H)-one;
(+)- or (−)-(4aR,8aS)-6-(3-((2-Chloro-4-(trifluoromethyl)benzyl)oxy)azetidine-1-carbonyl)hexahydro-2H-pyrido[4,3-b][1,4]oxazin-3(4H)-one;
(+)- or (−)-(4aR,8aS)-6-(3-((2-Fluoro-4-(trifluoromethoxy)benzyl)oxy)azetidine-1-carbonyl)hexahydro-2H-pyrido[4,3-b][1,4]oxazin-3(4H)-one;
(+)- or (−)-(4aR,8aS)-6-(4-((2-Chloro-4-fluorophenoxy)methyl)-4-methylpiperidine-1-carbonyl)hexahydro-2H-pyrido[4,3-b][1,4]oxazin-3(4H)-one;
(4aR,8aS)-6-[3-[(2,4-Dichlorophenyl)methoxy]azetidine-1-carbonyl]-4,4a,5,7,8,8a-hexahydropyrido[4,3-b][1,4]oxazin-3-one;
(4aR,8aS)-6-[4-[[2-Fluoro-4-(trifluoromethyl)phenyl]methyl]piperidine-1-carbonyl]-4,4a,5,7,8,8a-hexahydropyrido[4,3-b][1,4]oxazin-3-one;
(4aR,8aS)-6-[4-[[2-Cyclopropyl-4-(trifluoromethyl)phenyl]methyl]piperidine-1-carbonyl]-4,4a,5,7,8,8a-hexahydropyrido[4,3-b][1,4]oxazin-3-one;
(4aR,8aS)-6-[3-[[3-Chloro-4-(trifluoromethyl)phenyl]methoxy]azetidine-1-carbonyl]-4,4a,5,7,8,8a-hexahydropyrido[4,3-b][1,4]oxazin-3-one;
(4aR,8aS)-6-[3-[[2-Fluoro-5-(trifluoromethyl)phenyl]methoxy]azetidine-1-carbonyl]-4,4a,5,7,8,8a-hexahydropyrido[4,3-b][1,4]oxazin-3-one;
(4aR,8aS)-6-[3-[2-[2-Fluoro-6-(trifluoromethyl)phenyl]ethyl]azetidine-1-carbonyl]-4,4a,5,7,8,8a-hexahydropyrido[4,3-b][1,4]oxazin-3-one;
(4aR,8aS)-6-(3-(2-fluoro-4-(trifluoromethyl)phenethyl)azetidine-1-carbonyl)hexahydro-2H-pyrido[4,3-b][1,4]oxazin-3(4H)-one;
6-(3-((2,4-bis(trifluoromethyl)benzyl)oxy)azetidine-1-carbonyl)hexahydro-2H-pyrido[4,3-b][1,4]oxazin-3(4H)-one;
(4aR,8aS)-6-[4-[3-chloro-4-(trifluoromethyl)phenoxy]piperidine-1-carbonyl]-4,4a,5,7,8,8a-hexahydropyrido[4,3-b][1,4]oxazin-3-one;

(4aR,8aS)-6-(3-methyl-4-(((5-methyl-6-(trifluoromethyl)pyridin-3-yl)oxy)methyl)piperidine-1-carbonyl)hexahydro-2H-pyrido[4,3-b][1,4]oxazin-3(4H)-one;

(4aR,8aS)-6-(3-((3,4-dichlorobenzyl)oxy)azetidine-1-carbonyl)hexahydro-2H-pyrido[4,3-b][1,4]oxazin-3(4H)-one;

(4aR,8aS)-6-(3-((2,5-dichlorobenzyl)oxy)azetidine-1-carbonyl)hexahydro-2H-pyrido[4,3-b][1,4]oxazin-3(4H)-one;

rac-(4aR,8aS)-6-(2-methyl-3-((4-methyl-3-(trifluoromethyl)benzyl)oxy)azetidine-1-carbonyl)hexahydro-2H-pyrido[4,3-b][1,4]oxazin-3(4H)-one;

(4aR,8aS)-6-(3-(((4,5-bis(trifluoromethyl)pyridin-2-yl)oxy)methyl)azetidine-1-carbonyl)hexahydro-2H-pyrido[4,3-b][1,4]oxazin-3(4H)-one;

rac-(4aR,8aS)-6-(3-((2-fluoro-4-(trifluoromethyl)benzyl)oxy)-2-methylazetidine-1-carbonyl)hexahydro-2H-pyrido[4,3-b][1,4]oxazin-3(4H)-one;

(4aR,8aS)-6-(3-((2-fluoro-4-(pentafluoro-16-sulfaneyl)benzyl)oxy)azetidine-1-carbonyl)hexahydro-2H-pyrido[4,3-b][1,4]oxazin-3(4H)-one;

(4aR,8aS)-6-(3-((4-methyl-2-(trifluoromethoxy)benzyl)oxy)azetidine-1-carbonyl)hexahydro-2H-pyrido[4,3-b][1,4]oxazin-3(4H)-one;

(4aR,8aS)-6-[4-[3-cyclopropyl-4-(trifluoromethyl)phenoxy]piperidine-1-carbonyl]-4,4a,5,7,8,8a-hexahydropyrido[4,3-b][1,4]oxazin-3-one;

(4aR,8aS)-6-[3-[2-(2-fluoro-4-methyl-phenyl)ethyl]azetidine-1-carbonyl]-4,4a,5,7,8,8a-hexahydropyrido[4,3-b][1,4]oxazin-3-one;

(4aR,8aS)-6-[3-[2-[4-methoxy-2-(trifluoromethyl)phenyl]ethyl]azetidine-1-carbonyl]-4,4a,5,7,8,8a-hexahydropyrido[4,3-b][1,4]oxazin-3-one;

(4aR,8aS)-6-[3-[3-(2-azaspiro[3.3]heptan-2-yl)-4-(trifluoromethyl)phenoxy]azetidine-1-carbonyl]-4,4a,5,7,8,8a-hexahydropyrido[4,3-b][1,4]oxazin-3-one;

(4aR,8aS)-6-[3-[2-[4-methyl-2-(trifluoromethyl)phenyl]ethyl]azetidine-1-carbonyl]-4,4a,5,7,8,8a-hexahydropyrido[4,3-b][1,4]oxazin-3-one;

(4aR,8aS)-6-(3-((4-methyl-3-(trifluoromethyl)benzyl)oxy)azetidine-1-carbonyl)hexahydro-2H-pyrido[4,3-b][1,4]oxazin-3(4H)-one;

(4aR,8aS)-6-(3-((2-methyl-3-(trifluoromethyl)benzyl)oxy)azetidine-1-carbonyl)hexahydro-2H-pyrido[4,3-b][1,4]oxazin-3(4H)-one;

rac-(4aR,8aS)-6-[2-methyl-3-[[2-methyl-4-(trifluoromethoxy)phenyl]methoxy]azetidine-1-carbonyl]-4,4a,5,7,8,8a-hexahydropyrido[4,3-b][1,4]oxazin-3-one;

rac-(4aR,8aS)-6-[2-methyl-3-[[2-methyl-3-(trifluoromethyl)phenyl]methoxy]azetidine-1-carbonyl]-4,4a,5,7,8,8a-hexahydropyrido[4,3-b][1,4]oxazin-3-one;

(4aR,8aS)-6-[3-(4-chloro-3-cyclopropylphenoxy)azetidine-1-carbonyl]-4,4 #a!,5,7,8,8a-hexahydropyrido[4,3-b][1,4]oxazin-3-one;

(4aR,8aS)-6-[4-[2-chloro-3-(trifluoromethyl)phenoxy]piperidine-1-carbonyl]-4,4a,5,7,8,8a-hexahydropyrido[4,3-b][1,4]oxazin-3-one;

(4aR,8aS)-6-[3-(2-chloro-3-cyclopropyl-phenoxy)azetidine-1-carbonyl]-4,4a,5,7,8,8a-hexahydropyrido[4,3-b][1,4]oxazin-3-one;

(4aR,8aS)-6-[3-[3-(2-azaspiro[3.3]heptan-2-yl)-2-chlorophenoxy]azetidine-1-carbonyl]-4,4a,5,7,8,8a-hexahydropyrido[4,3-b][1,4]oxazin-3-one;

(4aR,8aS)-6-[3-[2-chloro-3-(5-oxa-2-azaspiro[3.5]nonan-2-yl)phenoxy]azetidine-1-carbonyl]-4,4a,5,7,8,8a-hexahydropyrido[4,3-b][1,4]oxazin-3-one;

(4aR,8aS)-6-[3-[(E)-2-(2-fluoro-4-methyl-phenyl)vinyl]azetidine-1-carbonyl]-4,4a,5,7,8,8a-hexahydropyrido[4,3-b][1,4]oxazin-3-one;

(4aR,8aS)-6-(3-((E)-2-fluoro-6-(trifluoromethyl)styryl)azetidine-1-carbonyl)hexahydro-2H-pyrido[4,3-b][1,4]oxazin-3(4H)-one; and (4aR,8aS)-6-(3-((4-methyl-3-(trifluoromethyl)benzyl)oxy)azetidine-1-carbonyl)hexahydro-2H-pyrido[4,3-b][1,4]oxazin-3(4H)-one.

In one embodiment, the present invention provides pharmaceutically acceptable salts or esters of the compounds of formula (I) as described herein. In a particular embodiment, the present invention provides pharmaceutically acceptable salts of the compounds according to formula (I) as described herein, especially hydrochloride salts. In a further particular embodiment, the present invention provides pharmaceutically acceptable esters of the compounds according to formula (I) as described herein. In yet a further particular embodiment, the present invention provides compounds according to formula (I) as described herein.

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$ $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (I) contain one or more functional groups which are not stable or are reactive under the reaction conditions of one or more reaction steps, appropriate protective groups (as described e.g., in "Protective Groups in Organic Chemistry" by T. W. Greene and P. G. M. Wutts, 5th Ed., 2014, John Wiley & Sons, N.Y.) can be introduced before the critical step applying methods well known in the art. Such protective groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I). A person skilled in the art will acknowledge that in the synthesis of compounds of formula (I)—insofar not desired otherwise—an "orthogonal protection group strategy" will be applied, allowing the cleavage of several protective groups one at a time each without affecting other protective groups in the molecule. The principle of orthogonal protection is well known in the art and has also been described in literature (e.g. Barany and R. B. Merrifield, *J. Am. Chem. Soc.* 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations*, 2nd Edition, Richard C. Larock. John Wiley & Sons, New York, NY. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

The following abbreviations are used in the present text: AcOH=acetic acid, ACN=acetonitrile, Bn=benzyl, Boc=tert-butyloxycarbonyl, CAS RN=chemical abstracts registration number, Cbz=benzyloxycarbonyl, $Cs_2CO_3$=cesium carbonate, CO=carbon monoxide, CuCi=copper(I) chloride, CuCN=copper(I) cyanide, CuI=copper(I) iodide, DAST=(diethylamino)sulfur trifluoride, DBU=1,8-diazabicyclo[5,4,0]undec-7-ene, DCM=dichloromethane, DEAD=diethyl azodicarboxylate, DIAD=diisopropyl azodicarboxylate, DMAP=4-dimethylaminopyridine, DME=dimethoxyethane, DMEDA=N,N'-dimethylethylenediamine, DMF=N,N-dimethylformamide, DIPEA=N,N-diisopropylethylamine, dppf=1,1 bis(diphenyl phosphino)ferrocene, EDC·HCl=N-(3-dimethylaminopropyl)-N'-ethylcarbodiimide hydrochloride, EI=electron impact, ESI=electrospray ionization, EtOAc=ethyl acetate, EtOH=ethanol, h=hour(s), FA=formic acid, $H_2O$=water, $H_2SO_4$=sulfuric acid, HATU=1-[bis(dimethylamino)methylene]-1H-1,2,3-triazolo[4,5-b]pyridinium-3-oxide hexafluorophosphate, HBTU=O-benzotriazole-N,N,N',N'-tetramethyl-uronium-hexafluoro-phosphate, HCl=hydrogen chloride, HOBt=1-hydroxy-1H-benzotriazole; HPLC=high performance liquid chromatography, iPrMgCl=isopropylmagnesium chloride, $I_2$=iodine, IPA=2-propanol, ISP=ion spray positive (mode), ISN=ion spray negative (mode), $K_2CO_3$=potassium carbonate, $KHCO_3$=potassium bicarbonate, KI=potassium iodide, KOH=potassium hydroxide, $K_3PO_4$=potassium phosphate tribasic, $LiAlH_4$ or LAH=lithium aluminium hydride, LiHMDS=lithium bis(trimethylsilyl)amide, LiOH=lithium hydroxide, $MgSO_4$=magnesium sulfate, min=minute(s), mL=milliliter, MPLC=medium pressure liquid chromatography, MS=mass spectrum, nBuLi=n-butyllithium, $NaBH_3CN$=sodium cyanoborohydride, NaH=sodium hydride, $NaHCO_3$=sodium hydrogen carbonate, $NaNO_2$=sodium nitrite, $NaBH(OAc)_3$=sodium triacetoxyborohydride, NaOH=sodium hydroxide, $Na_2CO_3$=sodium carbonate, $Na_2SO_4$=sodium sulfate, $Na_2S_2O_3$=sodium thiosulfate, NBS=N-bromosuccinimide, nBuLi=n-butyllithium, $NEt_3$=triethylamine (TEA), $NH_4Cl$=ammonium chloride, NMP=N-methyl-2-pyrrolidone, OAc=Acetoxy, $T_3P$=propylphosphonic anhydride, PE=petroleum ether, PG=protective group, Pd—C=palladium on activated carbon, $PdCl_2$(dppf)-$CH_2Cl_2$=1,1'-bis(diphenylphosphino)ferrocene-palladium(II)dichloride dichloromethane complex, $Pd_2(dba)_3$=tris(dibenzylideneacetone)dipalladium(0), $Pd(OAc)_2$=palladium(II) acetate, $Pd(OH)_2$=palladium hydroxide, $Pd(PPh_3)_4$=tetrakis(triphenylphosphine)palladium(0), PTSA=p-toluenesulfonic acid, R=any group, RT=room temperature, SFC=Supercritical Fluid Chromatography, S—PHOS=2-dicyclohexylphosphino-2',6'-dimethoxybiphenyl, TBAI=tetra butyl ammonium iodide, TEA=triethylamine, TFA=trifluoroacetic acid, THF=tetrahydrofuran, TMEDA=N,N,N',N'-tetramethylethylenediamine, $ZnCl_2$=zinc chloride, Hal=halogen.

Compounds of formula I wherein A, L, X, m, n, $R^1$ and $R^2$ are as described herein can be synthesized in analogy to literature procedures and/or as depicted for example in Scheme 1.

Scheme 1

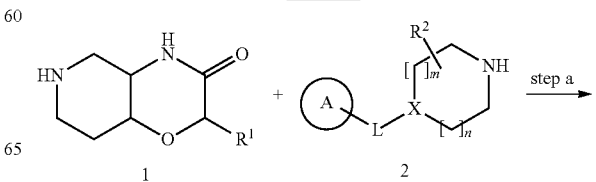

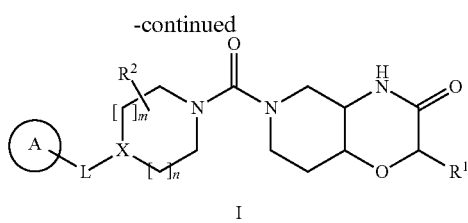

Accordingly, 4a,5,6,7,8,8a-hexahydro-4H-pyrido[4,3-b][1,4]oxazin-3-ones 1 are reacted with intermediates 2 in the presence of a urea forming reagent, such as bis(trichloromethyl) carbonate using a suitable base and solvent such as, e.g. sodium bicarbonate in DCM, to give compounds of formula I (step a). Further urea forming reagents include but are not limited to phosgene, trichloromethyl chloroformate, (4-nitrophenyl)carbonate or 1,1'-carbonyldiimidazole. Reactions of this type and the use of these reagents are widely described in literature (e.g. G. Sartori et al., *Green Chemistry* 2000, 2, 140). A person skilled in the art will acknowledge that the order of the addition of the reagents can be important in this type of reactions due to the reactivity and stability of the intermediary formed carbamoyl chlorides, as well as for avoiding formation of undesired symmetrical urea by-products.

Intermediates 1 may be synthesized as depicted for example in Scheme 2 and/or in analogy to methods described in literature.

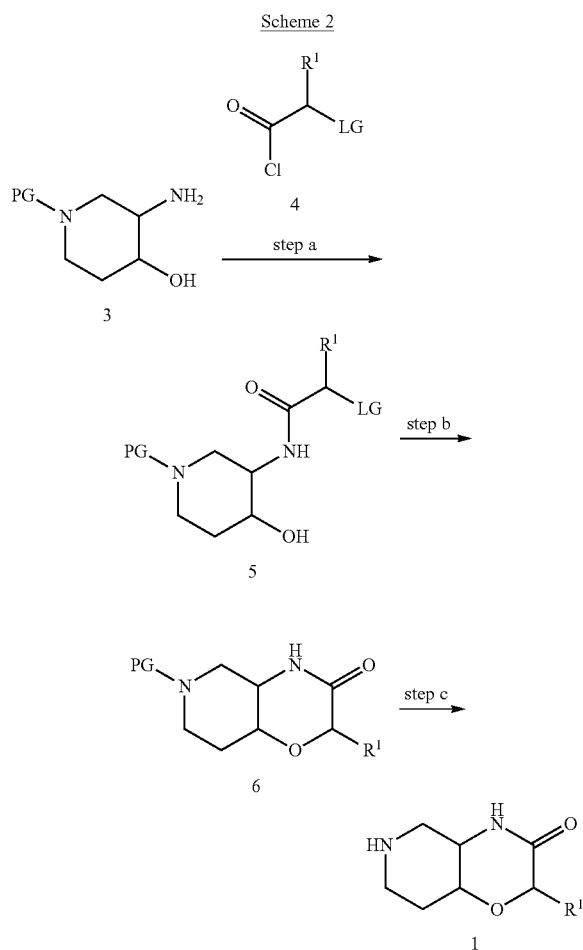

Thus, 3-aminopiperidin-4-ol derivatives 3 in which "PG" signifies a suitable protective group such as a Cbz or Boc protective group can be acylated for example with acyl chlorides 4 in which $R^1$ is as defined herein and "LG" signifies a suitable leaving group (e.g., Cl or Br), using a suitable base such as sodium or potassium carbonate, sodium hydroxide or sodium acetate in an appropriate solvent such as THF, water, acetone or mixtures thereof, to provide intermediates 5 (step a). Intermediates 4 are either commercially available or can be prepared according to literature methods in achiral ($R^1$=H), racemic ($R^1$ not H) or enantiomerically pure form ($R^1$ not H).

Intermediates 5 can be cyclized to intermediates 6 using methods well known in the art, for example by treatment of 5 with sodium hydride in THF or potassium tert-butoxide in IPA and water (step b). Reactions of that type are described in literature (e.g. Z. Rafinski et al., *J. Org. Chem.* 2015, 80, 7468; S. Dugar et al., *Synthesis* 2015, 47(5), 712; WO2005/066187).

Removal of the protective group in intermediates 6, applying methods known in the art (e.g., a Boc group using TFA in DCM at temperatures between 0° C. and room temperature, a Cbz group using hydrogen in the presence of a suitable catalyst such as Pd or Pd(OH)$_2$ on charcoal in a suitable solvent such as MeOH, EtOH, EtOAc or mixtures thereof and as described for example in "Protective Groups in Organic Chemistry" by T. W. Greene and P. G. M. Wuts, 4th Ed., 2006, Wiley N.Y.), furnishes intermediates 1 (step c).

Intermediates 1 can be obtained as mixtures of diastereomers and enantiomers, respectively, or as single stereoisomers depending on whether racemic mixtures or enantiomerically pure forms of cis- or trans-3-aminopiperidin-4-ol derivatives 3 or intermediates 4 are employed in their syntheses. Intermediates 3 are commercially available and their synthesis has also been described in literature (e.g. WO2005/066187; WO2011/059118; WO2016/185279). Optically pure cis-configured intermediates 1B and 1C can be obtained for example according to Scheme 3 by chiral separation of commercially available rac-(4aR,8aS)-4a,5,6,7,8,8a-hexahydro-4H-pyrido[4,3-b][1,4]oxazin-3-one (1A) (optionally in form of a salt such as, e.g. a hydrochloride salt) using methods known in the art, e.g. by diastereomeric salt crystallization or by chiral chromatography (step a).

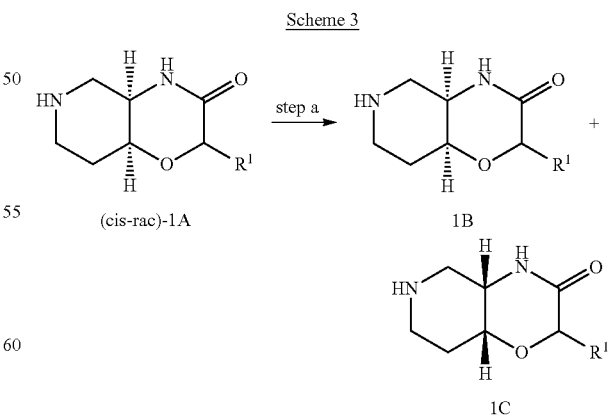

In some embodiments, intermediates 2 are intermediates of type B. Intermediates of type B in which A, m, n and $R^2$ are as described herein can be prepared by methods well known by a person skilled in the art and as exemplified by the general synthetic procedures outlined in Scheme 4.

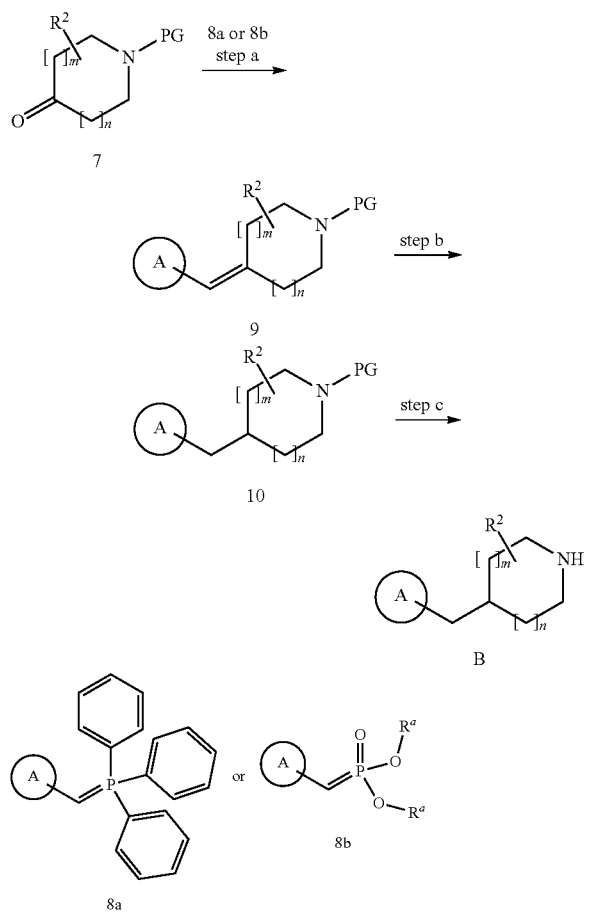

Ketones 7, either commercially available or prepared by methods known in the art, can be subjected for example to a Wittig reaction with alkylidene triphenylphosphoranes of type 8a in a suitable solvent such as, e.g. THF, Methyl-THF or DMSO to give intermediates 9 (step a). Phosphoranes 8a can be formed by treating the corresponding phosphonium salts with a suitable base such as BuLi, NaH, or KOtBu in a suitable solvent such as THF, dioxane or Methyl-THF and may be isolated or used in situ. Phosphonium salts in turn are readily available from an aryl/heteroaryl/heterocyclic-substituted alkylhalide (with halide being Cl, Br and iodo) and triphenylphosphine in a suitable solvent such as toluene. Heating may be applied to accelerate the reaction or drive the reaction to completion (e.g. H. J. Cristau, F. Plénat in PATAIS Chemistry of Functional Groups, Editor(s): Frank R. Hartley, 7 Aug. 2006, Series Editor(s): Prof Saul Patai).

Alternatively, intermediates 9 can be obtained using a Horner-Wadsworth-Emmons (HWE) reaction using ketones 7 and phosphonates 8b, wherein Ra is alkyl, for example methyl or ethyl. Phosphonates 8b are in situ α-metalated using a suitable base and solvent such as NaH, nBuLi or KOtBu in THF (step a). Phosphonates 8b are readily prepared using for example the Arbuzov reaction by alkylation of an aryl/heteroaryl/heterocyclic halide (with halide being Cl, Br and iodo) with commercially available trialkyl phosphite (e.g. *Chem. Rev.* 1984, 84, 577).

Olefination reactions of both types are broadly described in literature (e.g. *Current Org. Chem.* 2015, 19(9), page 744; *Chem. Rev.* 1989, 89(4), 863; *Org. React.* 1977, 25, 73; *Liebigs Ann. Recueil* 1997, 1283; *Acc. Chem. Res.* 1983, 16, 411).

Reduction of the double bond in intermediates 9 using, e.g. hydrogen in the presence of a suitable catalyst such as palladium on charcoal in an appropriate solvent or solvent mixture such as EtOAc, MeOH or AcOH yields compounds 10 (step b).

Removal of the protective group from intermediates 10 applying methods known in the art (e.g., a Boc group using TFA in DCM or 4M HCl in dioxane at temperatures between 0° C. and room temperature, a Cbz group using hydrogen in the presence of a suitable catalyst such as Pd or Pd(OH)$_2$ on charcoal in a suitable solvent such as MeOH, EtOH, EtOAc or mixtures thereof and as described for example in "Protective Groups in Organic Chemistry" by T. W. Greene and P. G. M. Wuts, 4th Ed., 2006, Wiley N.Y.), furnishes intermediates B (step c).

In some embodiments, intermediates 2 are intermediates of type C. Intermediates of type C in which A, R$^2$ and p are as described herein, r=0, 1 or 2 and (m+n)=2 or 3 can be prepared by methods well known in the art and as exemplified by the general synthetic procedures outlined in Scheme 5.

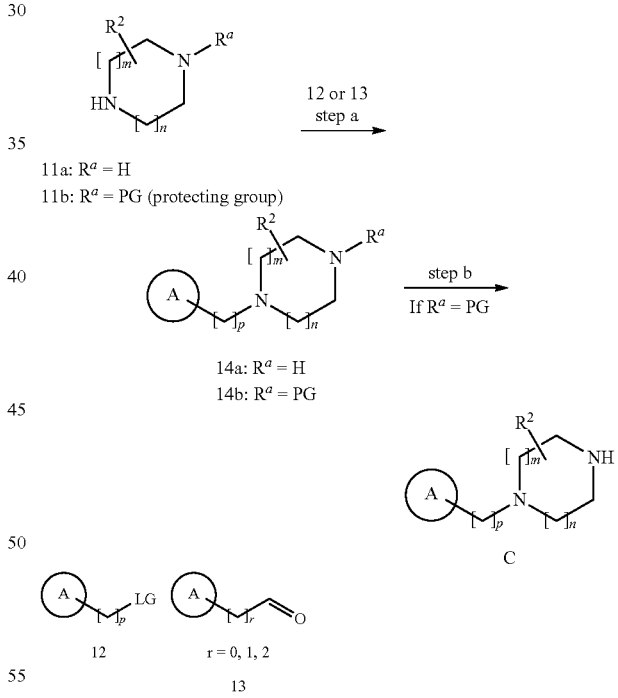

Alkylation of optionally mono-protected piperazine or 1,4-diazepane derivatives 11a,b (commercially available or synthesized in analogy to literature methods) with aryl/heteroaryl/heterocyclyl-substituted alkyl derivatives 12, either commercially available or synthesized according to literature procedures and in which LG signifies a suitable leaving group such as chlorine, bromine, iodine, OSO$_2$alkyl (e.g. mesylate (methanesulfonate), OSO$_2$fluoroalkyl (e.g. triflate (trifluoromethanesulfonate) or OSO$_2$aryl (e.g. tosylate (p-toluenesulfonate using a suitable base in an appropriate solvent (e.g. sodium hydride in DMF) at temperatures between 0° C. and the boiling temperature of the solvent, gives intermediates 14a,b (step a).

Alternatively, compounds 11a,b can be subjected to a reductive amination reaction with aldehydes of type 13 using a suitable reducing agent and solvent such as NaBH$_3$CN in MeOH, AcOH or mixtures thereof to give intermediates 14a,b (step a).

Removal of the protective group from intermediates 14b applying methods known in the art (e.g., a Boc group using TFA in DCM or 4M HCl in dioxane at temperatures between 0° C. and room temperature, a Cbz group using hydrogen in the presence of a suitable catalyst such as Pd or Pd(OH)$_2$ on charcoal in a suitable solvent such as MeOH, EtOH, EtOAc or mixtures thereof and as described for example in "Protective Groups in Organic Chemistry" by T. W.

Greene and P. G. M. Wuts, 4th Ed., 2006, Wiley N.Y.), furnishes intermediates C (step c). In some embodiments, compounds of formula I are compounds of type Ie. Compounds Ie in which A, p, R$^1$ and R$^2$ are defined as herein and (m+n)=2 or 3 can be prepared in analogy to literature procedures or the methods described under Scheme 6 below.

Compounds 1 can be coupled with piperazine or 1,4-diazepane derivatives 11a applying for example the conditions outlined under Scheme 1, step a, to give intermediates 15 (step a). Intermediates 15 can be converted to compounds IC in analogy to the procedure described under Scheme 5, step a (step b).

Alternatively, compounds 1 can be coupled with mono-protected piperazine or 1,4-diazepane derivatives 11b in which PG signifies a suitable protective group such as a Cbz or Boc protective group applying for example the conditions outlined under Scheme 1, step a, to give intermediates 16 (step c).

Removal of the protective group by published methods or as described under Scheme 5, step c, furnishes intermediates 15 (step d).

In some embodiments, intermediates 2 are intermediates of type D. Intermediates of type D in which A, m, n and R$^2$ are as described herein and R$^3$ is selected from hydrogen, halogen, C$_{1-6}$-alkoxy, C$_{1-6}$-alkyl and halo-C$_{1-6}$-alkyl, can be prepared by methods well known in the art and as exemplified by the general synthetic procedures outlined in Scheme 7.

Scheme 6

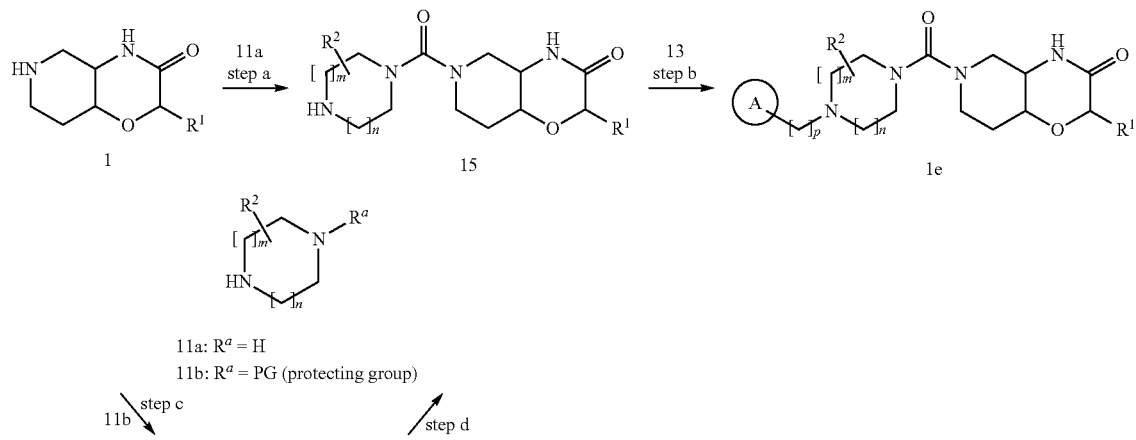

11a: R$^a$ = H
11b: R$^a$ = PG (protecting group)

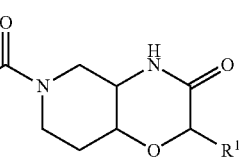

16

Scheme 7

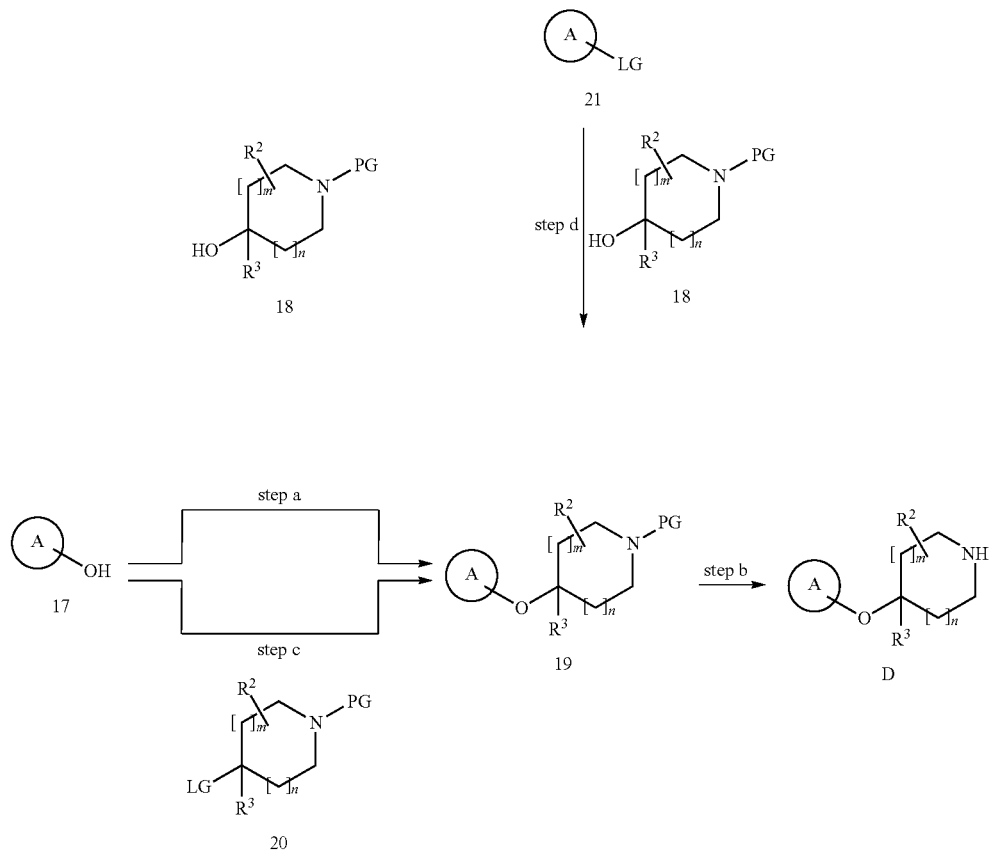

Alcohols of type 17 can be subjected to a Mitsunobu reaction with intermediates 18 in which PG is a suitable protective group such as a Cbz, Boc or Bn, using an appropriate phosphine such as triphenylphosphine and a dialkyl azodicarboxylate such as DEAD or DIAD in a suitable solvent such as THF to give intermediates 19 (step a). Mitsunobu reactions of that type are broadly described in literature (e.g. *Org. Chem. Front.* 2015, 2, 739; *Chem. Rev.* 2009, 109 (6), 2551).

Removal of the protective group from intermediates 19 applying literature methods and as described for example under Scheme 3, step c, furnishes intermediates D (step b).

Alternatively, intermediates 19 may be prepared from alcohols 17 that can be alkylated with compounds 20 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate using a suitable base in an appropriate solvent (e.g. sodium hydride in DMF) at temperatures between 0° C. and the boiling temperature of the solvent (step c).

Furthermore, intermediates 19 may be synthesized via alkylation of alcohols of type 18 with compounds 21 under the conditions described under step c (step d).

In another embodiment, intermediates 2 are intermediates of type E. Intermediates of type E in which A, m, n, $R^2$ and $R^3$ are as described herein, can be prepared by methods well known in the art and as exemplified by the general synthetic procedures outlined in Scheme 8. In case $R^3$ is a hydroxy group a suitable protective group strategy known to those skilled in the art may be applied.

Scheme 8

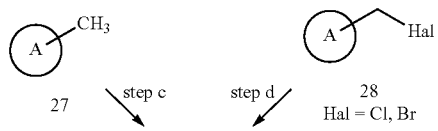

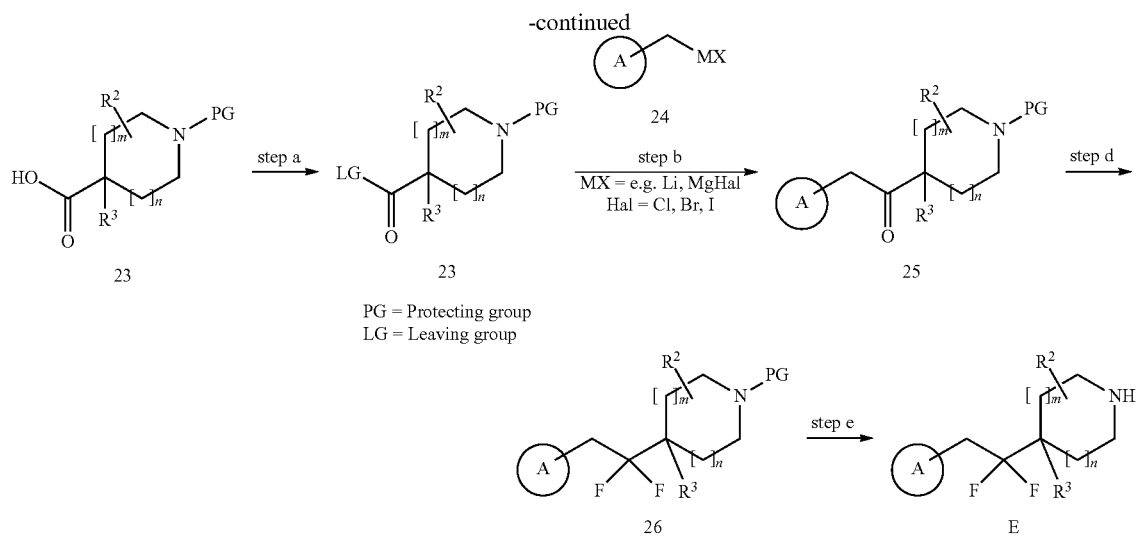

PG = Protecting group
LG = Leaving group

The carboxylic acid functionality in derivatives 22 in which PG signifies a suitable protecting group such as, e.g. a Boc, Cbz or Bn protecting group, either commercially available or prepared by methods known in the art, can be converted into an acid chloride (LG=Cl) or Weinreb amide (LG=NMeOMe) by applying methods broadly described in literature to give intermediates 23 (step a).

Intermediates 23 can be reacted with compounds of type 24, either commercially available or synthesized by methods known in the art and as described below to yield intermediates 25 (step b).

If compounds 24 are commercially not available they can be prepared in analogy to literature methods. For example, deprotonation of a reactive methyl group in optionally substituted heterocycles 27 using an appropriate base such nBuLi or LiHMDS in a suitable solvent, e.g. THF, hexane or mixtures thereof, at temperatures ranging from −78° C. to room temperature, gives intermediates 24 in which MX=Li (step d).

Compounds 24 in which MX=MgHal with Hal being Cl, Br or I (Grignard reagents) may be prepared by reaction of the corresponding substituted benzyl halides 28 with magnesium in a suitable solvent such as THF, optionally in the presence of catalytic amounts of iodine at temperatures ranging from 0° C. to the boiling point of the solvent (step d).

Compounds 25 can be further converted into compounds 26 by a deoxyfluorination reaction using a suitable fluorinating agent such as DAST, Deoxo-Fluor (bis(2-methoxyethyl)aminosulfur trifluoride) or aminodifluorosulfinium tetrafluoroborates (XtalFluor-E®, XtalFluor-M® in the presence of, e.g. triethylamine trihydrofluoride and TEA or DBU) in a suitable solvent such as DCM or ACN (step d).

Removal of the protective group from intermediates 26 applying literature methods and as described for example under Scheme 3, step c, furnishes intermediates E (step e).

In a further embodiment, intermediates 2 are intermediates of type F. Intermediates F in which A, m, n, R² and R³ are as described herein, can be prepared by methods well known in the art and as exemplified by the general synthetic procedures outlined in Scheme 9. In case R³ is a hydroxy group a suitable protective group strategy known to those skilled in the art may be applied.

Scheme 9

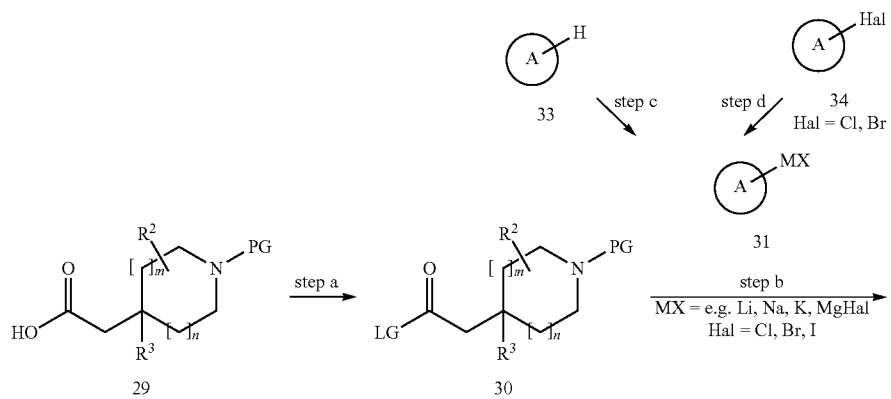

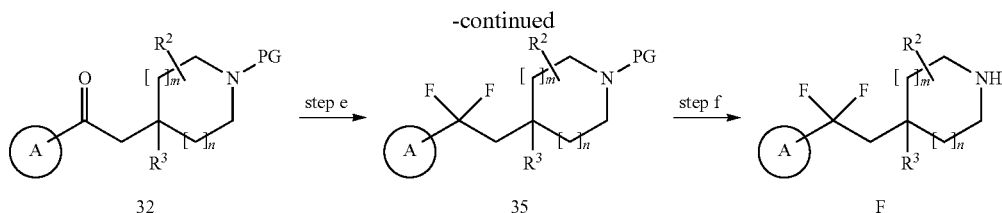

The carboxylic acid functionality in intermediates 29, either commercially available or prepared by methods known in the art, in which PG signifies a suitable protecting group such as, e.g. a Boc, Cbz or Bn protecting group, can be converted for example into an acid chloride (LG=Cl) or Weinreb amide (LG=NMeOMe) by applying methods broadly described in literature to give intermediates 30 (step a).

Intermediates 30 can be reacted with compounds of type 31, either commercially available or synthesized by methods known in the art and as described below to yield intermediates 32 (step b).

In case compounds 31 are commercially not available they can be prepared in analogy to literature methods. For example, deprotonation of optionally substituted aryl or heteroaryl rings 33 using an appropriate base such n-BuLi, sec-BuLi, tert-BuLi, LiHMDS, NaH, KH in a suitable solvent, such as THF, n-hexane or mixtures thereof, at temperatures ranging from −78° C. to room temperature, gives intermediates 31 in which, depending on the base used, MX =Li, Na or K (step c).

Compounds 31 in which MX=MgHal with Hal being Cl, Br or I (Grignard reagents) may be prepared by reaction of the corresponding optionally substituted aryl or heteroaryl halides 34 via direct insertion of magnesium (e.g. magnesium turnings optionally in the presence of catalytic amounts of iodine, powder in the presence of LiCl or Rieke magnesium, organic halides) or by halogen-magnesium exchange by treating 34 in which Hal is preferably bromine or iodine, with an alkylmagnesium halide such as iPrMgCl (optionally in the presence of LiCl) in suitable solvents such as diethyl ether or THF at temperatures ranging from 0° C. to the boiling point of the solvent (step d).

Compounds 32 can be further converted into compounds 35 by a deoxyfluorination reaction using a suitable fluorinating agent such as DAST, Deoxo-Fluor (bis(2-methoxyethyl)aminosulfur trifluoride) or aminodifluorosulfinium tetrafluoroborates (XtalFluor-E®, XtalFluor-M®) in the presence of, e.g. triethylamine trihydrofluoride and TEA or DBU) in a suitable solvent such as DCM or ACN (step e).

Removal of the protective group from intermediates 35 applying literature methods and as described for example under Scheme 3, step c, furnishes intermediates F (step f).

In some embodiments, intermediates 2 are intermediates of type G. Intermediates of type G in which A, m, n, R² are as described herein and R³ is hydrogen, $C_{1-6}$-alkoxy, $C_{1-6}$-alkyl and halo-$C_{1-6}$-alkyl, can be prepared by methods well known in the art and as exemplified by the general synthetic procedures outlined in Scheme 10.

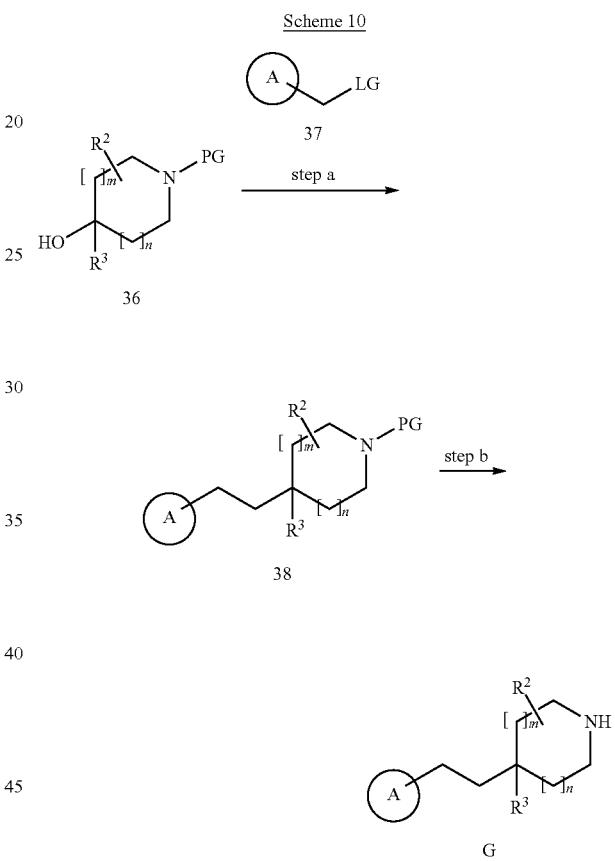

Scheme 10

Intermediates 38 may be prepared from alcohols 36 in which PG is a suitable protective group such as a Cbz, Boc or Bn, that can be alkylated with compounds 37 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base, such as sodium hydride, potassium tert-butoxide, in an appropriate solvent (e.g. in DMF or THF) at temperatures between 0° C. and the boiling temperature of the solvent (step a).

Removal of the protective group from intermediates 38 applying literature methods and as described for example under Scheme 4, step c, furnishes intermediates G (step b).

In some embodiments, intermediates 2 are intermediates of type H. Intermediates of type H in which A, m, n, R² and R³ are as described herein, can be prepared by methods well known in the art and as exemplified by the general synthetic procedures outlined in Scheme 11.

Scheme 11

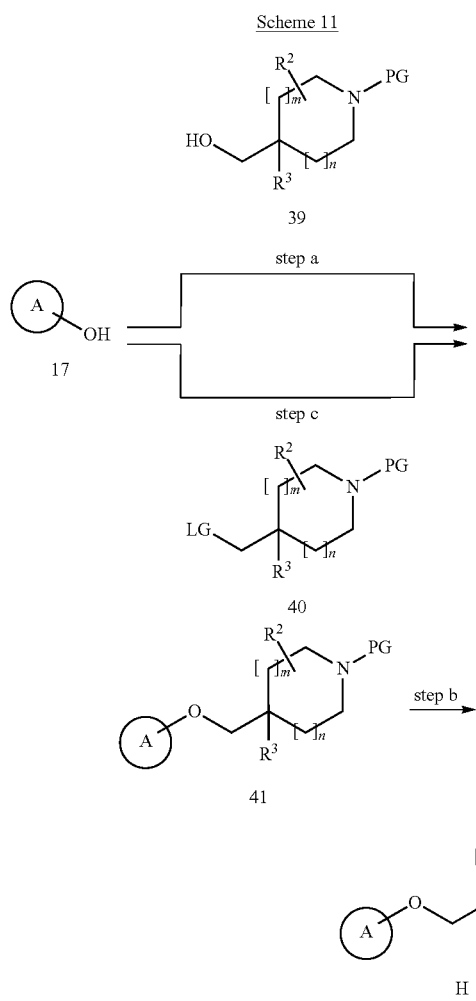

Alcohols of type 17 can be subjected to a Mitsunobu reaction with intermediates 39 in which PG is a suitable protective group such as a Cbz, Boc or Bn, using an appropriate phosphine such as triphenylphosphine and a dialkyl azodicarboxylate such as DEAD or DIAD in a suitable solvent such as THF to give intermediates 41 (step a). Mitsunobu reactions of that type are broadly described in literature (e.g. *Org. Chem. Front.* 2015, 2, 739; *Chem. Rev.* 2009, 109 (6), 2551).

Removal of the protective group from intermediates 41 applying literature methods and as described for example under Scheme 4, step c, furnishes intermediates H (step b).

Alternatively, intermediates 41 may be prepared from alcohols 17 that can be alkylated with compounds 40 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base such as $Cs_2CO_3$, NaH, in an appropriate solvent, such as DMF at temperatures between 0° C. and the boiling temperature of the solvent (step c).

Reacting intermediates H with intermediates 1, for example using the conditions described under scheme 1, step a, affords compounds of type If, wherein A, $R^1$, $R^2$, $R^3$, m and n are as defined herein.

Alternatively, compounds of type If may be prepared according to Scheme 12.

Scheme 12

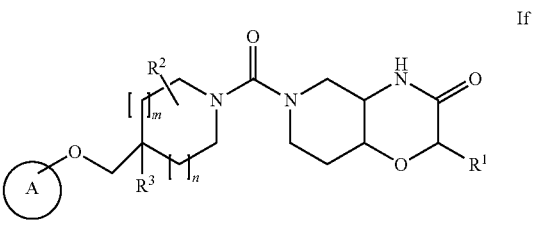

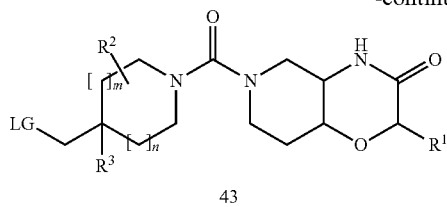

43

Alcohols of type 17 can be subjected to a Mitsunobu reaction with intermediates 42, using an appropriate phosphine such as triphenylphosphine and a dialkyl azodicarboxylate such as DEAD or DIAD in a suitable solvent such as THF to give compounds ID (step a). Mitsunobu reactions of that type are broadly described in literature (e.g. *Org. Chem. Front.* 2015, 2, 739; *Chem. Rev.* 2009, 109 (6), 2551).

Alternatively, compounds ID may be directly prepared from alcohols 17 that can be alkylated with compounds 43 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base such as $Cs_2CO_3$, NaH, in an appropriate solvent, such as DMF at temperatures between 0° C. and the boiling temperature of the solvent (step b).

In some embodiments, intermediates 2 are intermediates of type J. Intermediates of type J in which A, m, n, $R^2$ and $R^3$ are as described herein, can be prepared by methods well known in the art and as exemplified by the general synthetic procedures outlined in Scheme 13.

Scheme 13

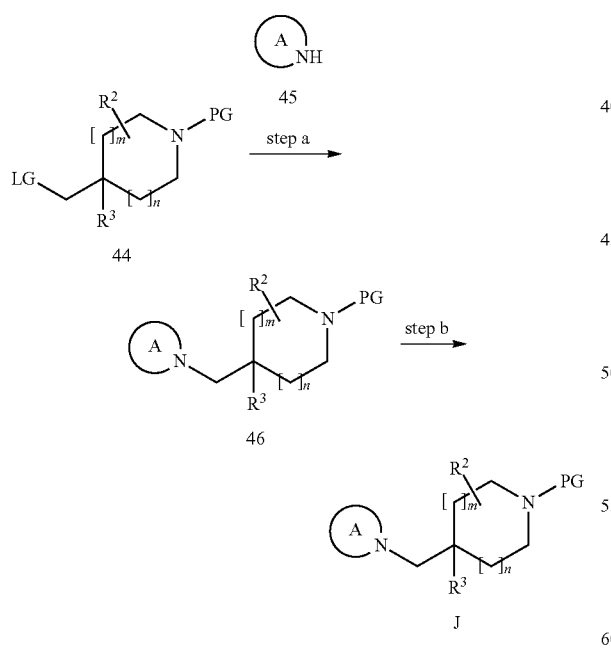

Intermediates 46 may be prepared from heterocycloalkyls or heteroaryls 45 that can be alkylated with compounds 44 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base such as $Cs_2CO_3$, $K_2CO_3$, NaH, in an appropriate solvent, such as DMF at temperatures between 0° C. and the boiling temperature of the solvent (step a).

Removal of the protective group from intermediates 46 applying literature methods and as described for example under Scheme 4, step c, furnishes intermediates J (step b).

Reacting intermediates J with intermediates 1 affords compounds of type Ig, wherein A, $R^1$, $R^2$, $R^3$, m and n are as defined herein.

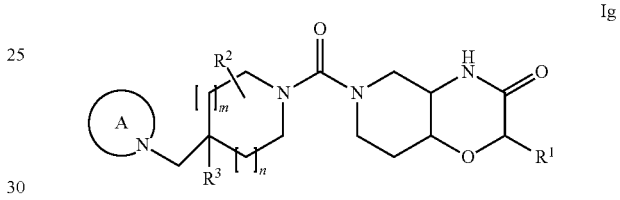

Alternatively, compounds of type Ig may be directly prepared from from heterocycloalkyls or heteroaryls 45 that can be alkylated with compounds 47 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base such as $Cs_2CO_3$, $K_2CO_3$, NaH, in an appropriate solvent, such as DMF at temperatures between 0° C. and the boiling temperature of the solvent (Scheme 14).

Scheme 14

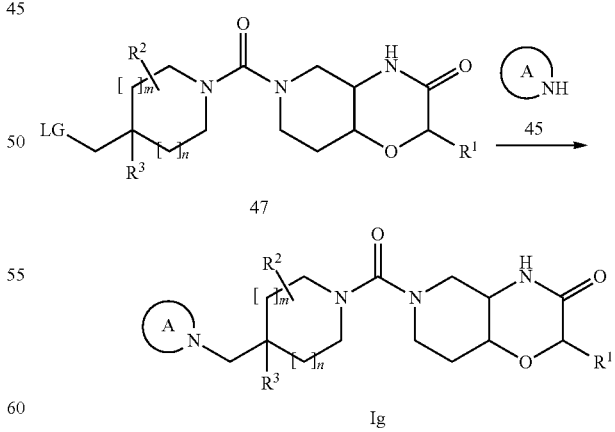

In some embodiments, intermediates 2 are intermediates of type K. Intermediates of type K in which A, m, n, $R^2$ and $R^3$ are as described herein, can be prepared by methods well known in the art and as exemplified by the general synthetic procedures outlined in Scheme 15.

Scheme 15

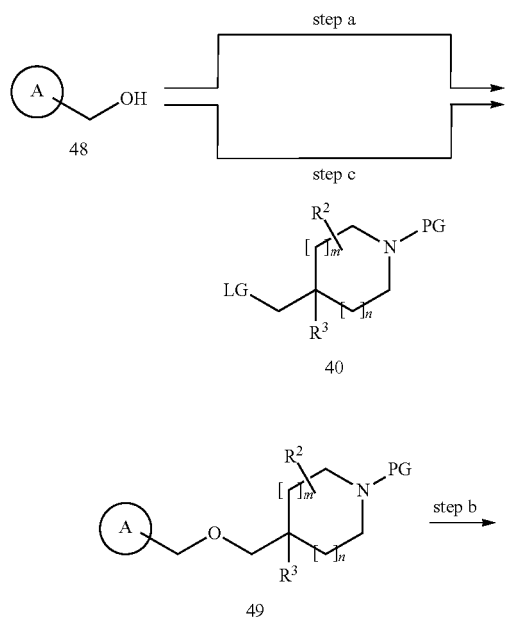

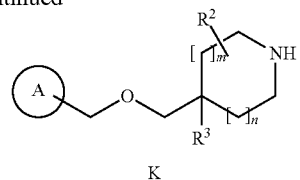

Alcohols of type 48 can be subjected to a Mitsunobu reaction with intermediates 39 in which PG is a suitable protective group such as a Cbz, Boc or Bn, using an appropriate phosphine such as triphenylphosphine and a dialkyl azodicarboxylate such as DEAD or DIAD in a suitable solvent such as THF to give intermediates 49 (step a). Mitsunobu reactions of that type are broadly described in literature (e.g. *Org. Chem. Front.* 2015, 2, 739; *Chem. Rev.* 2009, 109 (6), 2551).

Removal of the protective group from intermediates 49 applying literature methods and as described for example under Scheme 4, step c, furnishes intermediates K (step b).

Alternatively, intermediates 49 may be prepared from alcohols 48 that can be alkylated with compounds 40 in which LG is a suitable leaving group such as chlorine, bromine, iodine, $OSO_2$alkyl (e.g. methanesulfonate), $OSO_2$fluoroalkyl (e.g. trifluoromethanesulfonate) or $OSO_2$aryl (e.g. p-toluenesulfonate) using a suitable base such as $Cs_2CO_3$, NaH, in an appropriate solvent, such as DMF at temperatures between 0° C. and the boiling temperature of the solvent (step c).

In some embodiments, intermediates 2 are intermediates of type L. Intermediates of type L in which A, m, n, $R^2$ and $R^3$ are as described herein can be prepared by methods well known by a person skilled in the art and as exemplified by the general synthetic procedures outlined in Scheme 16.

Scheme 16

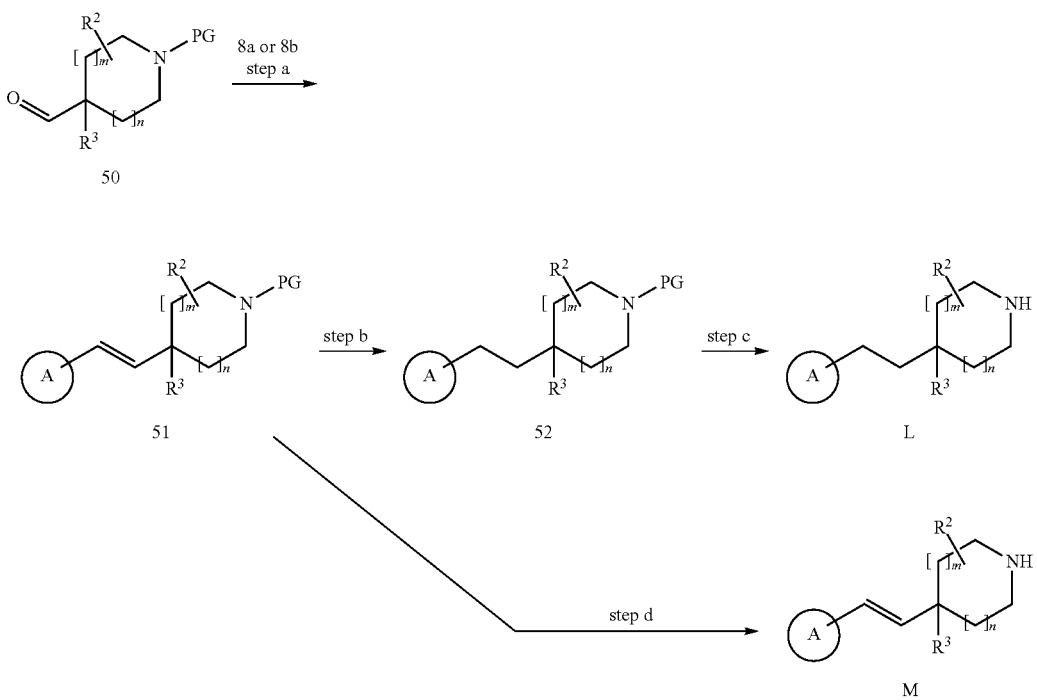

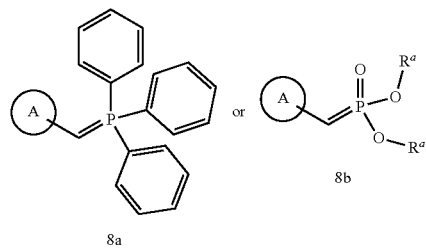

Intermediates 51 can be prepared for example from aldehydes 50, either commercially available or prepared by methods known in the art, using a Wittig reaction or Horner-Wadsworth-Emmons (HWE) reaction using alkylidene triphenylphosphoranes of type 8a and phosphonates 8b, respectively, as described under step a in Scheme 4 (step a).

Reduction of the double bond in intermediates 51 applying the conditions described under step b in Scheme 4 yields compounds 52 (step b).

Removal of the protective group from intermediates 52 applying methods known in the art and as outlined under step c in Scheme 4 furnishes intermediates L (step c).

Removal of the protective group from intermediates 51 applying methods known in the art and as outlined under step c in Scheme 4 furnishes intermediates M (step d).

In one aspect, the present invention provides a process of manufacturing the urea compounds of formula (I) described herein, comprising:
reacting a first amine of formula 1, wherein $R^1$ is as described herein, preferably wherein $R^1$ is hydrogen,

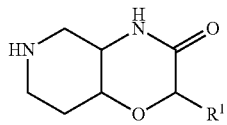

with a second amine 2, wherein A, L, m, n, X and $R^2$ are as described herein

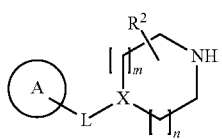

in the presence of a base and a urea forming reagent, to form said compound of formula (I).

In one embodiment, there is provided a process according to the invention, wherein said base is sodium bicarbonate.

In one embodiment, there is provided a process according to the invention, wherein said urea forming reagent is selected from bis(trichloromethyl) carbonate, phosgene, trichloromethyl chloroformate, (4-nitrophenyl)carbonate and 1,1'-carbonyldiimidazole, preferably wherein said urea forming reagent is bis(trichloromethyl) carbonate.

In one aspect, the present invention provides a compound of formula (I) as described herein, when manufactured according to any one of the processes described herein.

MAGL Inhibitory Activity

Compounds of the present invention are MAGL inhibitors. Thus, in one aspect, the present invention provides the use of compounds of formula (I) as described herein for inhibiting MAGL in a mammal.

In a further aspect, the present invention provides compounds of formula (I) as described herein for use in a method of inhibiting MAGL in a mammal.

In a further aspect, the present invention provides the use of compounds of formula (I) as described herein for the preparation of a medicament for inhibiting MAGL in a mammal.

In a further aspect, the present invention provides a method for inhibiting MAGL in a mammal, which method comprises administering an effective amount of a compound of formula (I) as described herein to the mammal.

Compounds were profiled for MAGL inhibitory activity by measuring the enzymatic activity of MAGL by following the hydrolysis of 4-nitrophenylacetate resulting in 4-nitrophenol, which absorbs at 405-412 nm (G. G. Muccioli, G. Labar, D. M. Lambert, Chem. Bio. Chem. 2008, 9, 2704-2710). This assay is hereinafter abbreviated "4-NPA assay".

The 4-NPA assay was carried out in 384 well assay plates (black with clear bottom, non-binding surface treated, Corning Ref. 3655) in a total volume of 40 µL. Compound dilutions were made in 100% DMSO (VWR Chemicals 23500.297) in a polypropylene plate in 3-fold dilution steps to give a final concentration range in the assay from 25 µM to 1.7 nM. 1 µL compound dilutions (100% DMSO) were added to 19 µL MAGL (recombinant wild-type) in assay buffer (50 mM TRIS (GIBCO, 15567-027), 1 mM EDTA (Fluka, 03690-100 ml)). The plate was shaked for 1 min at 2000 rpm (Variomag Teleshake) and then incubated for 15 min at RT. To start the reaction, 20 µL 4-Nitrophenlyacetate (Sigma N-8130) in assay buffer with 6% EtOH was added. The final concentrations in the assay were 1 nM MAGL and 300 µM 4-Nitrophenylacetate. After shaking (1 min, 2000 rpm) and 5 min incubation at RT, the absorbance at 405 nm was measured for a first time (Molecular Devices, SpectraMax Paradigm). A second measurement was then done after incubation for 80 min at RT. From the two measurements, the slope was calculated by subtracting the first from the second measurement.

Alternatively, compounds were profiled for MAGL inhibitory activity by determining the enzymatic activity by following the hydrolysis of the natural substrate 2-arachidonoylglycerol resulting in arachidonic acid, which can be followed by mass spectrometry. This assay is hereinafter abbreviated "2-AG assay".

The 2-AG assay was carried out in 384 well assay plates (PP, Greiner Cat #784201) in a total volume of 20 µL. Compound dilutions were made in 100% DMSO (VWR Chemicals 23500.297) in a polypropylene plate in 3-fold dilution steps to give a final concentration range in the assay from 12.5 µM to 0.8 µM. 0.25 µL compound dilutions (100%

DMSO) were added to 9 μL MAGL in assay buffer (50 mM TRIS (GIBCO, 15567-027), 1 mM EDTA (Fluka, 03690-100 ml), 0.01% (v/v) Tween. After shaking, the plate was incubated for 15 min at RT. To start the reaction, 10 μL 2-arachidonoylglycerol in assay buffer was added. The final concentrations in the assay was 50 μM MAGL and 8 μM 2-arachidonoylglyerol. After shaking and 30 min incubation at RT, the reaction was quenched by the addition of 40 μL of acetonitrile containing 4 μM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an acetonitrile/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].

TABLE 1

| Ex. | IC$_{50}$ MAGL [μM][a] |
|---|---|
| 1 | 0.040 |
| 2 | 0.046 |
| 3 | 0.066 |
| 4 | 0.092 |
| 5 | 1.3 |
| 6 | 5.7 |
| 7 | 0.011 |
| 8 | 0.013 |
| 9 | 0.035 |
| 10 | 0.039 |
| 11 | 0.042 |
| 12 | 0.077 |
| 13 | 0.087 |
| 14 | 0.191 |
| 15 | 0.190 |
| 16 | 0.208 |
| 17 | 0.268 |
| 18 | 0.892 |
| 19 | 1.5 |
| 20 | 1.8 |
| 21 | 0.909 |
| 22 | 2.1 |
| 23 | 0.856 |
| 24 | 0.004 |
| 25 | 0.452 |
| 26 | 0.684 |
| 27 | 0.007 |
| 28 | 0.018 |
| 29 | 0.005 |
| 30 | 0.273 |
| 31 | 0.049 |
| 32 | 0.020 |
| 33 | 0.004 |
| 34 | 0.438 |
| 35 | 0.019 |
| 36 | 0.119 |
| 37 | 1.3 |
| 38 | 0.160 |
| 39 | 0.116 |
| 40 | 0.012 |
| 42 | 1.2 |
| 43 | 0.529 |
| 44 | 0.038 |
| 45 | 0.850 |
| 46 | 0.005 |
| 47 | 0.005 |
| 48 | 0.288 |
| 49 | 0.363 |
| 50 | 0.008 |
| 51 | 0.010 |
| 52 | 0.058 |
| 53 | 0.006 |
| 54 | 0.001 |
| 55 | 0.079 |
| 56 | 0.042 |
| 57 | 0.049 |
| 58 | 0.003 |
| 59 | 0.012 |
| 60 | 0.680 |
| 61 | 0.011 |
| 62 | 0.009 |
| 64 | 0.040 |
| 66 | 0.351 |
| 67 | 0.120 |
| 72 | 0.108 |
| 73 | 0.008 |
| 74 | 0.003 |
| 75 | 0.002 |
| 76 | 0.008 |
| 77 | 0.016 |
| 79 | 0.001 |
| 81 | 0.006 |
| 87 | 0.006[b] |
| 88 | 0.005[b] |
| 89 | 0.034[b] |
| 90 | 0.168[b] |
| 91 | 0.099[b] |
| 92 | 0.014[b] |
| 93 | 0.124 |
| 94 | 0.150 |
| 95 | 0.008 |
| 96 | 0.293 |
| 97 | 0.146 |
| 98 | 0.010 |
| 99 | 0.012 |
| 100 | 0.082 |
| 101 | 0.011 |
| 102 | 0.022 |
| 103 | 0.005 |
| 104 | 0.451 |
| 105 | 0.285 |
| 108 | 0.001 |
| 109 | 0.223 |
| 110 | 2.179 |
| 111 | 0.020 |
| 112 | 0.012 |
| 113 | 0.005 |
| 114 | 0.005 |
| 115 | 0.003 |
| 116 | 0.004 |
| 117 | 0.010 |
| 118 | 0.132[b] |
| 119 | 0.014[b] |
| 120 | 0.007[b] |
| 121 | 0.151[b] |
| 122 | 0.008[b] |
| 123 | 0.082[b] |
| 124 | 1.035[b] |
| 139 | 0.002[b] |
| 140 | 0.059[b] |
| 141 | 0.040[b] |
| 142 | 0.075[b] |
| 201 | 0.239[b] |
| 202 | 0.054[b] |
| 203 | 0.871[b] |
| 204 | 0.100[b] |
| 205 | 0.086[b] |
| 206 | 0.023[b] |
| 207 | 0.050[b] |
| 208 | 0.003[b] |
| 209 | 0.074[b] |
| 210 | 0.080[b] |
| 211 | 0.017[b] |
| 212 | 0.003[b] |
| 213 | 0.098[b] |
| 214 | 0.036[b] |
| 215 | 0.005[b] |
| 216 | 0.006[b] |
| 217 | 0.010[b] |
| 218 | 0.003[b] |
| 219 | 0.002[b] |
| 220 | 0.003[b] |

TABLE 1-continued

| Ex. | IC$_{50}$ MAGL [μM][a] |
|---|---|
| 221 | 0.0007[b] |
| 222 | 0.143[b] |
| 223 | 0.075[b] |
| 224 | 0.003[b] |
| 225 | 0.007[b] |
| 226 | 0.045[b] |
| 227 | 0.067[b] |
| 228 | 0.126[b] |
| 229 | 0.0009[b] |
| 230 | 0.073[b] |
| 231 | 0.005[b] |
| 232 | 0.061[b] |
| 233 | 0.022[b] |
| 234 | 0.002[b] |
| 235 | 0.033[b] |
| 236 | 0.175[b] |
| 237 | 0.254[b] |
| 238 | 0.002[b] |
| 239 | 0.0004[b] |
| 240 | 0.016[b] |
| 241 | 0.015[b] |
| 242 | 0.012[b] |
| 243 | 0.010[b] |
| 244 | 0.030[b] |
| 245 | 1.7[b] |
| 246 | 1.0[b] |
| 247 | 1.1[b] |
| 248 | 0.607[b] |
| 249 | 0.005[b] |
| 250 | 0.008[b] |
| 251 | 0.005[b] |
| 252 | 0.005[b] |
| 253 | 0.010[b] |
| 254 | 0.064[b] |
| 255 | 0.010[b] |
| 256 | 0.011[b] |
| 257 | 0.014[b] |
| 258 | 0.048[b] |
| 259 | 0.015[b] |
| 260 | 0.018[b] |
| 261 | 0.048[b] |
| 262 | 0.181[b] |
| 263 | 1.1[b] |
| 264 | 0.084[b] |
| 265 | 0.006[b] |
| 266 | 0.018[b] |
| 267 | 0.042[b] |
| 268 | 0.028[b] |
| 269 | 0.024[b] |
| 270 | 0.061[b] |
| 271 | 0.020[b] |
| 272 | 0.094[b] |
| 273 | 0.089[b] |
| 274 | 0.126[b] |
| 275 | 0.032[b] |
| 276 | 0.019[b] |
| 277 | 0.455[b] |
| 278 | 0.211[b] |
| 279 | 0.001[b] |
| 280 | 0.041[b] |
| 281 | 0.035[b] |
| 282 | 0.136[b] |
| 283 | 0.179[b] |
| 284 | 0.072[b] |
| 285 | 2.6[b] |
| 286 | 0.128[b] |
| 287 | 0.006[b] |
| 288 | 0.053[b] |
| 289 | 0.003[b] |
| 290 | 0.044[b] |
| 291 | 0.028[b] |
| 292 | 0.005[b] |
| 293 | 0.030[b] |
| 294 | 3.0[b] |

[a]if not indicated otherwise (see [b]), the activity was measured in 4-NPA assay;
[b]measured in 2-AG assay.

In one aspect, the present invention provides compounds of formula (I) and their pharmaceutically acceptable salts or esters as described herein, wherein said compounds of formula (I) and their pharmaceutically acceptable salts or esters have IC$_{50}$'s for MAGL inhibition below 25 μM, preferably below 10 μM, more preferably below 5 μM as measured in the MAGL assay described herein.

In one embodiment, compounds of formula (I) and their pharmaceutically acceptable salts or esters as described herein have IC$_{50}$ (MAGL inhibition) values between 0.000001 μM and 25 μM, particular compounds have IC$_{50}$ values between 0.000005 μM and 10 μM, further particular compounds have IC$_{50}$ values between 0.00005 μM and 5 μM, as measured in the MAGL assay described herein.

In one embodiment, the present invention provides compounds of formula (I) and their pharmaceutically acceptable salts or esters as described herein, wherein said compounds of formula (I) and their pharmaceutically acceptable salts or esters have an IC$_{50}$ for MAGL below 25 μM, preferably below 10 μM, more preferably below 5 μM as measured in an assay comprising the steps of:

a) providing a solution of a compound formula (I), or a pharmaceutically acceptable salt or ester thereof, in DMSO;
b) providing a solution of MAGL (recombinant wild-type) in assay buffer (50 mM tris(hydroxymethyl)aminomethane; 1 mM ethylenediaminetetraacetic acid);
c) adding 1 μL of compound solution from step a) to 19 μL of MAGL solution from step b);
d) shaking the mixture for 1 min at 2000 rpm;
e) incubating for 15 min at RT;
f) adding 20 μL of a solution of 4-nitrophenlyacetate in assay buffer (50 mM tris(hydroxymethyl)aminomethane; 1 mM ethylenediaminetetraacetic acid, 6% EtOH);
g) shaking the mixture for 1 min at 2000 rpm;
h) incubating for 5 min at RT;
i) measuring the absorbance of the mixture at 405 nm a first time;
j) incubating a further 80 min at RT;
k) measuring the absorbance of the mixture at 405 nm a second time;
l) subtracting the absorbance measured under i) from the absorbance measured under k) and calculating the slope of absorbance;

wherein:
i) the concentration of the compound of formula (I), or the pharmaceutically acceptable salt or ester thereof in the assay after step f) is in the range of 25 μM to 1.7 nM;
ii) the concentration of MAGL in the assay after step f) is 1 nM;
iii) the concentration of 4-nitrophenylacetate in the assay after step f) is 300 μM; and
iv) steps a) to l) are repeated for at least 3 times, each time with a different concentration of the compound of formula (I), or the pharmaceutically acceptable salt or ester thereof.

Using the Compounds of the Invention

In one aspect, the present invention provides compounds of formula (I) as described herein for use as therapeutically active substance.

In a further aspect, the present invention provides the use of compounds of formula (I) as described herein for the treatment or prophylaxis of neuroinflammation, neurodegenerative diseases, pain, cancer and/or mental disorders in a mammal.

In one embodiment, the present invention provides the use of compounds of formula (I) as described herein for the treatment or prophylaxis of neuroinflammation and/or neurodegenerative diseases in a mammal.

In one embodiment, the present invention provides the use of compounds of formula (I) as described herein for the treatment or prophylaxis of neurodegenerative diseases in a mammal.

In one embodiment, the present invention provides the use of compounds of formula (I) as described herein for the treatment or prophylaxis of cancer in a mammal.

In one aspect, the present invention provides the use of compounds of formula (I) as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides the use of compounds of formula (I) as described herein for the treatment or prophylaxis of multiple sclerosis, Alzheimer's disease and/or Parkinson's disease in a mammal.

In a particularly preferred embodiment, the present invention provides the use of compounds of formula (I) as described herein for the treatment or prophylaxis of multiple sclerosis in a mammal.

In one aspect, the present invention provides compounds of formula (I) as described herein for use in the treatment or prophylaxis of neuroinflammation, neurodegenerative diseases, pain, cancer and/or mental disorders in a mammal.

In one embodiment, the present invention provides compounds of formula (I) as described herein for use in the treatment or prophylaxis of neuroinflammation and/or neurodegenerative diseases in a mammal.

In one embodiment, the present invention provides compounds of formula (I) as described herein for use in the treatment or prophylaxis of cancer in a mammal.

In one embodiment, the present invention provides compounds of formula (I) as described herein for use in the treatment or prophylaxis of neurodegenerative diseases in a mammal.

In one aspect, the present invention provides compounds of formula (I) as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides compounds of formula (I) as described herein for use in the treatment or prophylaxis of multiple sclerosis, Alzheimer's disease and/or Parkinson's disease in a mammal.

In a particularly preferred embodiment, the present invention provides compounds of formula (I) as described herein for use in the treatment or prophylaxis of multiple sclerosis in a mammal.

In one aspect, the present invention provides the use of compounds of formula (I) as described herein for the preparation of a medicament for the treatment or prophylaxis of neuroinflammation, neurodegenerative diseases, pain, cancer and/or mental disorders in a mammal.

In one embodiment, the present invention provides the use of compounds of formula (I) as described herein for the preparation of a medicament for the treatment or prophylaxis of neuroinflammation and/or neurodegenerative diseases in a mammal.

In one embodiment, the present invention provides the use of compounds of formula (I) as described herein for the preparation of a medicament for the treatment or prophylaxis of neurodegenerative diseases in a mammal.

In one embodiment, the present invention provides the use of compounds of formula (I) as described herein for the preparation of a medicament for the treatment or prophylaxis of cancer in a mammal.

In a further aspect, the present invention provides the use of compounds of formula (I) as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, hepatocellular carcinoma, colon carcinogenesis, ovarian cancer, neuropathic pain, chemotherapy induced neuropathy, acute pain, chronic pain and/or spasticity associated with pain in a mammal.

In a preferred embodiment, the present invention provides the use of compounds of formula (I) as described herein for the preparation of a medicament for the treatment or prophylaxis of multiple sclerosis, Alzheimer's disease and/or Parkinson's disease in a mammal.

In a particularly preferred embodiment, the present invention provides the use of compounds of formula (I) as described herein for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer and/or mental disorders in a mammal, which method comprises administering an effective amount of a compound of formula (I) as described herein to the mammal.

In one embodiment, the present invention provides a method for the treatment or prophylaxis of neuroinflammation and/or neurodegenerative diseases in a mammal, which method comprises administering an effective amount of a compound of formula (I) as described herein to the mammal.

In one embodiment, the present invention provides a method for the treatment or prophylaxis of neurodegenerative diseases in a mammal, which method comprises administering an effective amount of a compound of formula (I) as described herein to the mammal.

In one aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression and/or pain in a mammal, which method comprises administering an effective amount of a compound of formula (I) as described herein to the mammal.

In a preferred embodiment, the present invention provides a method for the treatment or prophylaxis of multiple sclerosis, Alzheimer's disease and/or Parkinson's disease in a mammal, which method comprises administering an effective amount of a compound of formula (I) as described herein to the mammal.

In a particularly preferred embodiment, the present invention provides a method for the treatment or prophylaxis of multiple sclerosis in a mammal, which method comprises administering an effective amount of a compound of formula (I) as described herein to the mammal.

Pharmaceutical Compositions and Administration

In one aspect, the present invention provides a pharmaceutical composition comprising a compound of formula (I) as described herein and a therapeutically inert carrier.

The compounds of formula (I) and their pharmaceutically acceptable salts and esters can be used as medicaments (e.g. in the form of pharmaceutical preparations). The pharmaceutical preparations can be administered internally, such as orally (e.g. in the form of tablets, coated tablets, dragees, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts and esters can be processed with pharmaceutically inert, inorganic or organic adjuvants for the production of tablets, coated tablets, dragees and hard gelatin capsules. Lactose, corn starch or derivatives thereof, talc, stearic acid or its salts etc. can be used, for example, as such adjuvants for tablets, dragees and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of type 2 diabetes related microvascular complications (such as, but not limited to diabetic retinopathy, diabetic neuropathy and diabetic nephropathy), coronary artery disease, obesity and underlying inflammatory diseases, chronic inflammatory and autoimmune/inflammatory diseases.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Method A1

Example 11 rac-(4aR,8aS)-6-[4-[[4-(Trifluoromethyl)phenyl]methyl]piperidine-1-carbonyl]-4,4a,5,7,8,8a-hexahydropyrido[4,3-b][1,4]oxazin-3-one

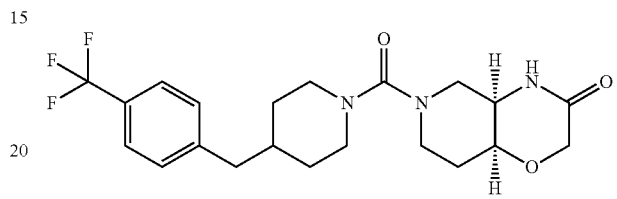

To a solution of 4-nitrophenyl 4-(4-(trifluoromethyl)benzyl)piperidine-1-carboxylate (100 mg, 245 µmol, BB2) in DMF (1.5 mL), rac-(4aR,8aS)-hexahydro-2H-pyrido[4,3-b][1,4]oxazin-3(4H)-one dihydrochloride (45.9 mg, 294 µmol, ChemBridge Corporation, BB1) and TEA (49.6 mg, 68.3 µL, 490 µmol) were added. The resultant reaction mixture was heated at 80° C. for 18 h. The reaction mixture was diluted with EtOAc and washed three times with $H_2O$ and $NaHCO_3$. The combined organic layers were washed with brine, dried over $Na_2SO_4$, filtered and concentrated in vacuo. The crude material was purified by flash chromatography (silica gel, eluting with a gradient of MeOH/EtOAc 0-10%) to afford the title compound as an off-white oil (0.045 g; 43.2%). MS (ESI): m/z=426.4 $[M+H]^+$.

Method A2

Example 3 rac-(4aR,8aS)-6-[4-[(4-tert-Butylthiazol-2-yl)methyl]piperidine-1-carbonyl]-4,4a,5,7,8,8a-hexahydropyrido[4,3-b][1,4]oxazin-3-one

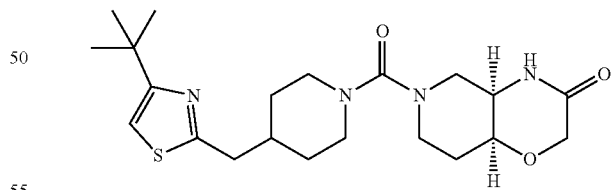

To an ice-cold suspension of bis(trichloromethyl) carbonate (45.3 mg, 153 µmol, CAS RN 32315-10-9) and $NaHCO_3$ (73.3 mg, 873 µmol) in DCM (2 mL) was added in one portion 4-tert-butyl-2-(4-piperidylmethyl)thiazole hydrochloride (60 mg, 218 µmol, Enamine Ltd) and the mixture was stirred at RT overnight. The suspension was filtered and the filtrate was evaporated. The residue was diluted in DCM (1 mL) and added dropwise to an ice-cold solution of rac-(4aR,8aS)-hexahydro-2H-pyrido[4,3-b][1,4]oxazin-3(4H)-one dihydrochloride (50 mg, 218 µmol, ChemBridge Corporation, BB1) and DIPEA (152 µL, 870 µmol) in DCM (1 mL). The suspension was stirred at RT for 19 h to become a solution. The reaction mixture was poured on H₂O and DCM and the layers were separated. The aqueous layer was extracted three times with DCM. The organic layers were washed twice with water, dried over MgSO₄, filtered, treated with silica gel and evaporated. The compound was purified by silica gel chromatography on a 4 g column using an MPLC system eluting with a gradient of DCM:MeOH (100:0 to 90:10) to provide the desired compound as a colorless foam (0.039 g; 42.5%). MS (ESI): m/z=421.2 [M+H]⁺.

Method A3

Example 34

(+)- or (−)-4-[[1-[(4aR,8aS)-3-Oxo-4,4a,5,7,8,8a-hexahydropyrido[4,3-b][1,4]oxazine-6-carbonyl]-4-piperidyl]methyl]benzonitrile

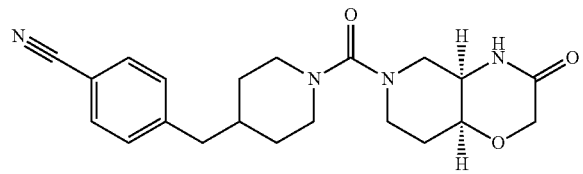 [SMILES: N#Cc1ccc(CC2CCN(C(=O)N3CC[C@@H]4OCC(=O)N[C@@H]4C3)CC2)cc1]

To an ice-cold solution of bis(trichloromethyl) carbonate (39.9 mg, 134 µmol, CAS RN 32315-10-9) in DCM were added NaHCO₃ (64.5 mg, 768 µmol) and (+)-cis-hexahydro-2H-pyrido[4,3-b][1,4]oxazin-3(4H)-one (30 mg, 192 µmol, BB1a) and the mixture was stirred at RT overnight. To the suspension was added 4-(piperidin-4-ylmethyl)benzonitrile (38.5 mg, 192 µmol, CAS RN 333987-57-8) and DIPEA (99.3 mg, 134 µL, 768 µmol). The suspension was stirred at RT for 4.5 h. The reaction mixture was poured on H₂O and DCM and the layers were separated. The aqueous layer was extracted three times with DCM. The organic layers were washed twice with H₂O, dried over MgSO₄, filtered, treated with silica gel and evaporated. The compound was purified by silica gel chromatography on a 4 g column using an MPLC system eluting with a gradient of DCM:MeOH (100:0 to 90:10) to furnish the desired compound as a colorless gum (0.023 g; 31.3%). MS (ESI): m/z=383.2 [M+H]⁺.

Method A4

Example 79

(4aR,8aS)-6-(4-((2-chloro-4-fluorophenoxy)methyl)-4-methylpiperidine-1-carbonyl)hexahydro-2H-pyrido[4,3-b][1,4]oxazin-3(4H)-one

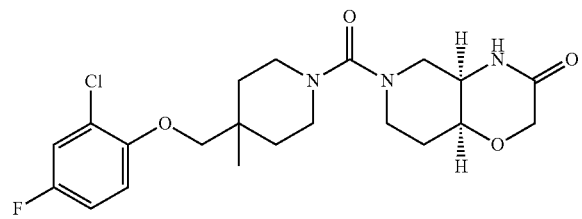 [SMILES: CC1(COc2ccc(F)cc2Cl)CCN(C(=O)N2CC[C@@H]3OCC(=O)N[C@@H]3C2)CC1]

To a solution of 4-nitrophenyl (4aR,8aS)-3-oxohexahydro-2H-pyrido[4,3-b][1,4]oxazine-6(5H)-carboxylate (25 mg, 77.8 µmol, BB7a) in NMP (1 mL) was added DIPEA (25.1 mg, 34 µL, 195 µmol) and 4-((2-chloro-4-fluorophenoxy)methyl)-4-methylpiperidine; hydrochloride salt (19.5 mg, 66.1 µmol, BB12). The reaction vial was stirred at 140° C. for 45 min. The crude material was purified by reversed-phase HPLC to yield 23.2 mg of the desired product. MS (ESI): m/z=440.2 [M+H]⁺.

Method A5

Example 64

(4aR,8aS)-6-(4-((2-Chloro-4-fluorophenoxy)methyl)-4-fluoropiperidine-1-carbonyl)hexahydro-2H-pyrido[4,3-b][1,4]oxazin-3(4H)-one

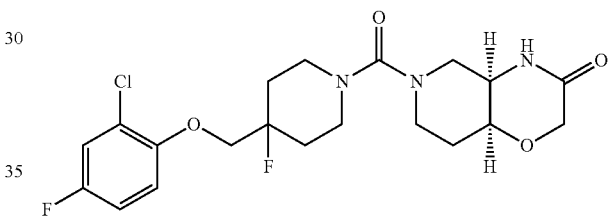

A microwave vial was heat gun-dried and charged with bis(trichloromethyl) carbonate (26.6 mg, 89.6 µmol) and sodium bicarbonate (32.3 mg, 384 µmol). The flask was placed under argon and DCM (1 mL) was added to give a suspension. The suspension was cooled by an ice-bath and 4-((2-chloro-4-fluorophenoxy)methyl)-4-fluoropiperidine; hydrochloride salt (36.1 mg, 121 µmol, BB15) was added. The mixture was stirred at 0° C. for 15 min and at RT overnight. The reaction mixture was cooled down in an-ice bath and DCM (500 µL) and DIPEA (49.7 mg, 67.1 µL, 384 µmol) followed by (4aR,8aS)-6-(4-((2-chloro-4-fluorophenoxy)methyl)-4-fluoropiperidine-1-carbonyl)hexahydro-2H-pyrido[4,3-b][1,4]oxazin-3(4H)-one (21.1 mg, 47.5 µmol, BB1a) were added. The resulting off-white suspension was stirred at room temperature for 7 h. The reaction mixture was poured on water, DCM was added and the layers were separated. The aqueous layer was extracted twice with DCM. The combined organic layers were washed with brine, dried over MgSO₄, filtered and evaporated to afford a yellow oil (58 mg). The crude product was purified by reverse-phase HPLC and lyophilized to provide the title compound as a white solid (21.1 mg, 37.1% yield). MS (ESI): m/z=444.2 [M+H]⁺.

Method A6

Example 39

(4aR,8aS)-6-[4-[(2-Fluoro-4-methoxyphenoxy)methyl]piperidine-1-carbonyl]-4,4a,5,7,8,8a-hexahydropyrido[4,3-b][1,4]oxazin-3-one

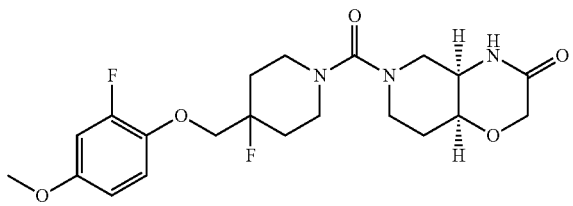 [SMILES: COc1ccc(OCC2(F)CCN(C(=O)N3CC[C@@H]4OCC(=O)N[C@@H]4C3)CC2)c(F)c1]

To a solution of 2-fluoro-4-methoxyphenol (16.5 mg, 13 μL, 116 μmol), (4aR,8aS)-6-[4-(hydroxymethyl)piperidine-1-carbonyl]-4,4a,5,7,8,8a-hexahydropyrido[4,3-b][1,4]oxazin-3-one (34.5 mg, 116 μmol, BB16) and triphenylphosphine (33.5 mg, 128 μmol) in DCM (580 μL) was added DIAD (25.8 mg, 24.8 μL, 128 μmol) dropwise and the reaction was stirred at room temperature for 22 h. The reaction mixture was diluted with DCM and washed with 1M aq. NaOH. The phases were separated and the aq. phase was extracted with DCM twice. The combined organic layers were dried over sodium sulfate, filtered and concentrated to dryness to give a red oil (99 mg). The crude product was purified by reverse-phase HPLC and lyophilized to afford the desired compound (20 mg, 40.9% yield) as a white solid. MS (ESI): m/z=422.3[M+H]$^+$.

Method A7

Example 42 and 43

(4aS,8aR)-6-(4-(((6-(Trifluoromethyl)pyridin-3-yl)oxy)methyl)piperidine-1-carbonyl)hexahydro-2H-pyrido[4,3-b][1,4]oxazin-3(4H)-one (Example 42)

and (4aR,8aS)-6-(4-(((6-(trifluoromethyl)pyridin-3-yl)oxy)methyl)piperidine-1-carbonyl)hexahydro-2H-pyrido[4,3-b][1,4]oxazin-3(4H)-one (Example 43)

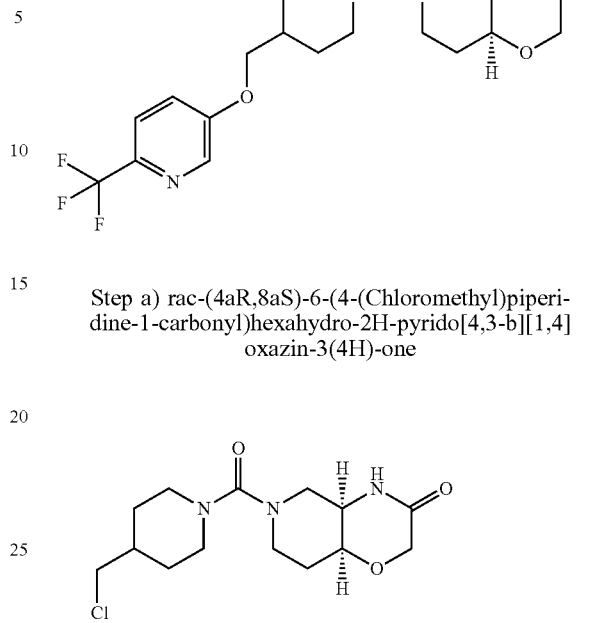

Step a) rac-(4aR,8aS)-6-(4-(Chloromethyl)piperidine-1-carbonyl)hexahydro-2H-pyrido[4,3-b][1,4]oxazin-3(4H)-one To a solution of rac-(4aR,8aS)-6-(4-(hydroxymethyl)piperidine-1-carbonyl)hexahydro-2H-pyrido[4,3-b][1,4]oxazin-3(4H)-one (80 mg, 269 μmol, BB16) in dry DMF (2 mL) was added DIPEA (52.2 mg, 70.5 μL, 404 μmol), DMAP (1.64 mg, 13.5 μmol) and methanesulfonyl chloride (46.2 mg, 404 μmol) and the reaction mixture was stirred at room temperature for 2 h. Addition of 4,4-difluoropiperidine; hydrochloride salt (84.8 mg, 538 μmol), DIPEA (139 mg, 188 μL, 1.08 mmol) and the reaction mixture was stirred at room temperature for 2 h. The reaction was then stirred at 70° C. for 14 h. The crude reaction was submitted for reversed-phase HPLC purification to yield the title compound as a side product (35 mg). MS (ESI): m/z=315.1 [M+H]$^+$.

Step b) (4aS,8aR)-6-(4-(((6-(trifluoromethyl)pyridin-3-yl)oxy)methyl)piperidine-1-carbonyl)hexahydro-2H-pyrido[4,3-b][1,4]oxazin-3(4H)-one (Example 42) and (4aR,8aS)-6-(4-(((6-(trifluoromethyl)pyridin-3-yl)oxy)methyl)piperidine-1-carbonyl)hexahydro-2H-pyrido[4,3-b][1,4]oxazin-3(4H)-one (Example 43)

Example 42

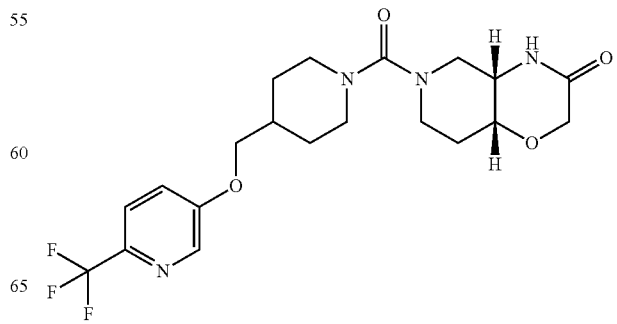

Example 43

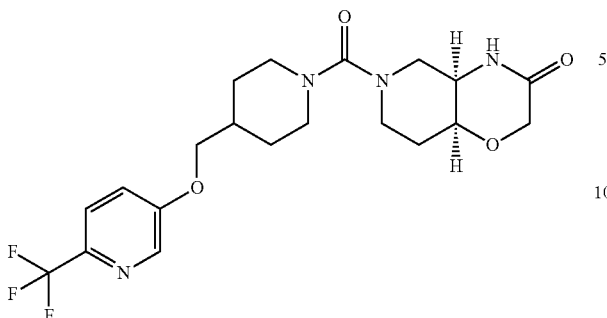

To a solution of rac-(4aR,8aS)-6-(4-(chloromethyl)piperidine-1-carbonyl)hexahydro-2H-pyrido[4,3-b][1,4]oxazin-3(4H)-one (70 mg, 222 µmol) in dry DMF (1 mL) was added 6-(trifluoromethyl)pyridin-3-ol (54.2 mg, 332 µmol) and Cs₂CO₃ (108 mg, 332 µmol). The reaction mixture was stirred at 95° C. for 18 h. Insolubles were removed by filtration over Celite, the filtrate was concentrated down to dryness and the crude residue was purified and the enantiomers separated by chiral SFC to yield Example 42 (33.8 mg) and Example 43 (32.5 mg). MS (ESI): m/z=443.2 [M+H]⁺ for both examples.

Method A8

Example 26

(4aS,8aR)-6-(4-((4-(Trifluoromethyl)-1H-pyrazol-1-yl)methyl)piperidine-1-carbonyl)hexahydro-2H-pyrido[4,3-b][1,4]oxazin-3(4H)-one

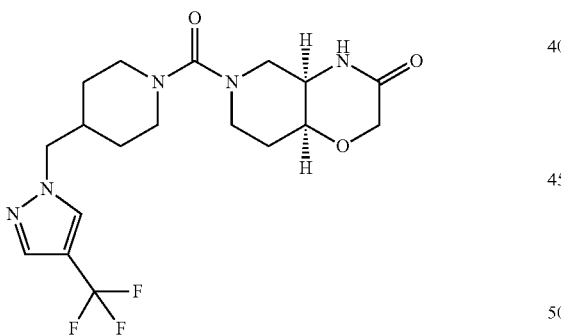

To a solution of rac-(4aR,8aS)-6-(4-(hydroxymethyl)piperidine-1-carbonyl)hexahydro-2H-pyrido[4,3-b][1,4]oxazin-3(4H)-one (75 mg, 252 µmol, BB16) in dry DMF (2 mL) was added DIPEA (39.1 mg, 52.9 µL, 303 µmol), DMAP (3.08 mg, 25.2 µmol) and methanesulfonyl chloride (30.3 mg, 265 µmol) and the reaction mixture was stirred at room temperature for 2 h. 4-(Trifluoromethyl)-1H-pyrazole (68.6 mg, 504 µmol) and K₂CO₃ (87.1 mg, 631 µmol) were added and the reaction mixture was stirred at 90° C. for 18 h. Insolubles were removed by filtration over celite, the filtrate was concentrated to dryness in vacuo and the crude residue was directly purified by flash chromatography with an eluent mixture of DCM and MeOH (0% to 10%), to yield 90 mg of the desired product as a racemate. This was submitted for SFC chiral separation to yield Example 26 (25 mg) as a colorless oil and the enantiomer (31 mg) as a colorless oil. MS (ESI): m/z=416.2 [M+H]⁺.

Method A9

Example 37

(4aR,8aS)-6-(4-((4,4-Difluoropiperidin-1-yl)methyl)piperidine-1-carbonyl)hexahydro-2H-pyrido[4,3-b][1,4]oxazin-3(4H)-one

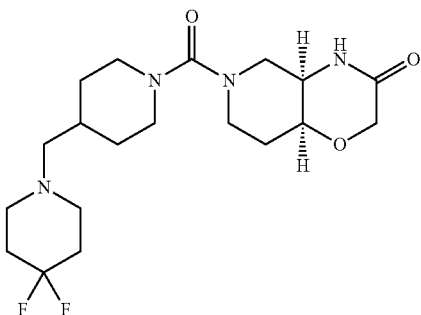 [SMILES: O=C1CO[C@H]2CCN(C(=O)N3CCC(CN4CCC(F)(F)CC4)CC3)C[C@H]2N1]

To a solution of (4aR,8aS)-hexahydro-2H-pyrido[4,3-b][1,4]oxazin-3(4H)-one (40 mg, 256 µmol, BB1a) in dry DMF (2 mL) cooled down to 0° C. was added DIPEA (39.7 mg, 53.7 µL, 307 µmol) and 4-nitrophenyl carbonochloridate (61.9 mg, 307 µmol). The reaction mixture was stirred at 0° C. for 20 min. LCMS control showed formation of the intermediate carbamate. DIPEA (116 mg, 157 µL, 896 µmol) and 4,4-difluoro-1-(piperidin-4-ylmethyl)piperidine; dihydrochloride salt (89.5 mg, 307 µmol, BB17) were added and the reaction mixture was then stirred at room temperature for 30 min, then stirred at 100° C. for 14 h. Volatiles were removed in vacuo and the crude residue was directly submitted for SFC purification to yield the desired compound (9.5 mg) as a light orange oil. MS (ESI): m/z=401.3 [M+H]⁺.

Method A10

Example 125

(+)-(4aR,8aS)-6-[4-[2-(2-Chlorophenyl)ethynyl]piperidine-1-carbonyl]-4,4a,5,7,8,8a-hexahydropyrido[4,3-b][1,4]oxazin-3-one

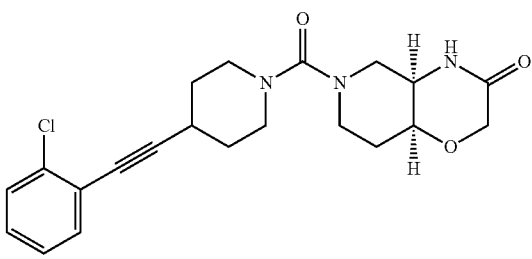 [SMILES: O=C1CO[C@H]2CCN(C(=O)N3CCC(C#Cc4ccccc4Cl)CC3)C[C@H]2N1]

In a sealed tube, 4-[2-(2-chlorophenyl)ethynyl]piperidine (BB18, 0.02 g, 0.078 mmol) and 4-nitrophenyl (4aR,8aS)-3-oxohexahydro-2H-pyrido[4,3-b][1,4]oxazine-6(5H)-carboxylate (BB7a, 0.025 g, 0.078 mmol) were mixed in ACN (0.6 mL). Then, Huenig's base (0.041 mL, 0.234 mmol) was added, followed by DMAP (0.005 g, 0.039 mmol) and the reaction mixture was heated to 90° C. overnight. The mixture was evaporated to dryness and the crude residue purified by reverse phase HPLC to give the title compound (0.013 g, 41%) as a colorless solid. MS (ESI): m/z=402.2 [M+H]⁺.

Method B1

Example 1

(+)-(4aR,8aS)-6-(4-((4-(tert-Butyl)thiazol-2-yl)methyl)piperidine-1-carbonyl)hexahydro-2H-pyrido[4,3-b][1,4]oxazin-3(4H)-one

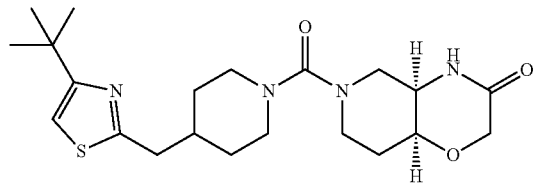 [SMILES: CC(C)(C)c1csc(CC2CCN(C(=O)N3CC[C@@H]4OCC(=O)N[C@@H]4C3)CC2)n1]

The enantiomers of example 3 were separated by preparative chiral HPLC (Chiralcel OD column) using an isocratic mixture of EtOH (containing 0.05% of NH₄OAc):n-heptane (20:80). The fractions were evaporated to provide the desired compound as a colorless solid (0.012 g; 34.3%). MS (ESI): m/z=421.2 [M+H]⁺.

Method B2

Example 12

(+)- or (−)-(4aR,8aS)-6-(4-(4-(Trifluoromethyl)phenoxy)piperidine-1-carbonyl)hexahydro-2H-pyrido[4,3-b][1,4]oxazin-3(4H)-one

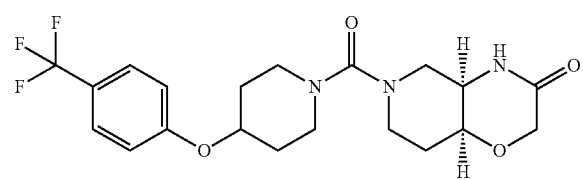 [SMILES: O=C1CO[C@H]2CCN(C(=O)N3CCC(Oc4ccc(C(F)(F)F)cc4)CC3)C[C@H]2N1]

The enantiomers of example 13 were separated using preparative chiral HPLC (Chiralpak AD column) using an isocratic mixture of EtOH (containing 0.05% of NH₄OAc):n-heptane (40:60). The fractions were evaporated to yield the desired compound as a light brown oil (0.013 g; 28.4%). MS (ESI): m/z=428.2 [M+H]⁺.

Method B3

Examples 103, 104 and 105

(4aR,8aS)-6-[2-Methyl-3-[[4-(trifluoromethyl)phenyl]methoxy]azetidine-1-carbonyl]-4,4a,5,7,8,8a-hexahydropyrido[4,3-b][1,4]oxazin-3-one (Isomer A+B, Isomer C, Isomer D)

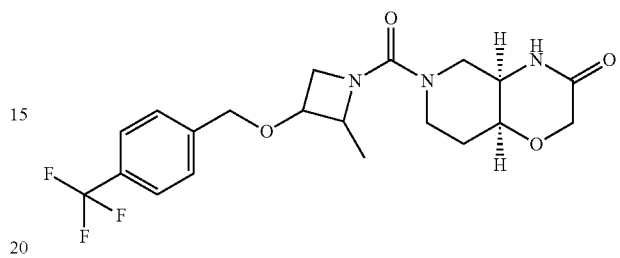

The stereoisomers of example 117 were separated by preparative chiral HPLC (Reprosil Chiral NR column) using an isocratic mixture of EtOH (containing 0.05% of NH₄OAc):n-heptane (40:60) to provide examples 103 and 104 as single isomers and example 105 as mixture of two stereoisomers. The fractions were evaporated to provide the desired compounds as colorless solids.

Method C

Example 21 rac-(4aR,8aS)-6-(4-(4-(Trifluoromethyl)benzyl)piperazine-1-carbonyl)hexahydro-2H-pyrido[4,3-b][1,4]oxazin-3(4H)-one

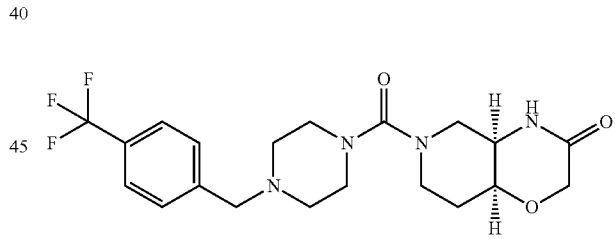

A mixture of rac-cis-6-(piperazine-1-carbonyl)hexahydro-2H-pyrido[4,3-b][1,4]oxazin-3(4H)-one (35 mg, 130 μmol, BB3), 4-(trifluoromethyl)benzaldehyde (22.7 mg, 17.4 μL, 130 μmol) and sodium triacetoxyborohydride (27.6 mg, 130 μmol) in DCM (1 mL) was stirred at RT for 15 h. The reaction mixture was concentrated and the residue was purified by preparative HPLC to give the desired compound as a white solid (8 mg, 14.40%). MS (ESI): m/z=427.4 [M+H]⁺.

If not indicated otherwise the following examples were synthesized from rac-(4aR,8aS)-hexahydro-2H-pyrido[4,3-b][1,4]oxazin-3(4H)-one dihydrochloride (ChemBridge Corporation) and the suitable building blocks in analogy to the reaction methods described herein.

| Ex. | Systematic Name/Structure | Building block(s) | MS, m/z | Method |
|---|---|---|---|---|
| 2 | (+)-(4aR,8aS)-6-(4-((4-(tert-Butyl)oxazol-2-yl)methyl)piperidine-1-carbonyl)hexahydro-2H-pyrido[4,3-b][1,4]oxazin-3(4H)-one | Example 4 | 405.3 [M + H]+ | B1 |
| 4 | rac-(4aR,8aS)-6-(4-((4-(tert-Butyl)oxazol-2-yl)methyl)piperidine-1-carbonyl)hexahydro-2H-pyrido[4,3-b][1,4]oxazin-3(4H)-one | Supplier of building block: BCH Research (UK) and BB1 | 405.4 [M + H]+ | A2 |
| 5 | (−)-(4aS,8aR)-6-(4-((4-(tert-Butyl)thiazol-2-yl)methyl)piperidine-1-carbonyl)hexahydro-2H-pyrido[4,3-b][1,4]oxazin-3(4H)-one | Example 3 | 421.2 [M + H]+ | B1 |
| 6 | (−)-(4aS,8aR)-6-(4-((4-(tert-Butyl)oxazol-2-yl)methyl)piperidine-1-carbonyl)hexahydro-2H-pyrido[4,3-b][1,4]oxazin-3(4H)-one | Example 4 | 405.3 [M + H]+ | B1 |
| 7 | rac-(4aR,8aS)-6-(4-((2-Chloro-4-fluorophenoxy)methyl)piperidine-1-carbonyl)hexahydro-2H-pyrido[4,3-b][1,4]oxazin-3(4H)-one | Supplier of building block: UkrOrgSyntez Ltd. and BB1 | 426.2 [M + H]+ | A2 |

-continued

| Ex. | Systematic Name/Structure | Building block(s) | MS, m/z | Method |
|---|---|---|---|---|
| 8 | (+)-(4aR,8aS)-6-[4-[[4-(Trifluoromethyl)phenyl]methyl]piperidine-1-carbonyl]-4,4a,5,7,8,8a-hexahydropyrido[4,3-b][1,4]oxazin-3-one | Example 11 | 426.4 [M + H]+ | B1 |
| 9 | rac-(4aR,8aS)-6-(4-((4-Chlorophenoxy)methyl)piperidine-1-carbonyl)hexahydro-2H-pyrido[4,3-b][1,4]oxazin-3(4H)-one | 4-[(4-Chlorophenoxy)methylpiperidine (CAS RN 63608-33-3) and BB1 | 408.3 [M + H]+ | A2 |
| 10 | rac-(4aR,8aS)-6-(4-(4-Chlorobenzyl)piperidine-1-carbonyl)hexahydro-2H-pyrido[4,3-b][1,4]oxazin-3(4H)-one | 4-(4-Chloro-benzyl)-piperidine hydrochloride (CAS RN 36938-76-8) and BB1 | 392.2 [M + H]+ | A2 |
| 13 | rac-(4aR,8aS)-6-(4-(4-(Trifluoromethyl)phenoxy)piperidine-1-carbonyl)hexahydro-2H-pyrido[4,3-b][1,4]oxazin-3(4H)-one | 4-(4-Trifluoromethylphenoxy) piperidine hydrochloride (CAS RN 28033-37-6) and BB1 | 428.2 [M + H]+ | A2 |
| 14 | (+)-(4aS,8aS)-6-(4-(4-(Trifluoromethyl)benzyl)piperidine-1-carbonyl)hexahydro-2H-pyrido[4,3-b][1,4]oxazin-3(4H)-one | Example 17 | 426.3 [M + H]+ | B1 |

-continued

| Ex. | Systematic Name/Structure | Building block(s) | MS, m/z | Method |
|---|---|---|---|---|
| 15 | rac-(4aR,8aS)-6-[4-(Phenoxymethyl)piperidine-1-carbonyl]-4,4a,5,7,8,8a-hexahydropyrido[4,3-b][1,4]oxazin-3-one | BB4 and BB1 | 374.4 [M + H]+ | A1 |
| 16 | rac-(4aR,8aS)-6-(4-((5,6-Dihydro-4H-cyclopenta[d]thiazol-2-yl)methyl)piperidine-1-carbonyl)hexahydro-2H-pyrido[4,3-b][1,4]oxazin-3(4H)-one | FCH Group and BB1 | 405.2 [M + H]+ | A2 |
| 17 | rac-(4aS,8aS)-6-(4-(4-(Trifluoromethyl)benzyl)piperidine-1-carbonyl)hexahydro-2H-pyrido[4,3-b][1,4]oxazin-3(4H)-one | 4-(4-Trifluoromethyl benzyl) piperidine HCl (CAS RN 192990-03-7) and BB6 | 426.3 [M + H]+ | A2 |
| 18 | rac-(4aR,8aS)-6-(4-((3-Phenyl-1,2,4-oxadiazol-5-yl)methyl)piperidine-1-carbonyl)hexahydro-2H-pyrido[4,3-b][1,4]oxazin-3(4H)-one | 3-Phenyl-5-(piperidin-4-ylmethyl)-1,2,4-oxadiazole (CAS RN 1239730-22-3) and BB1 | 426.3 [M + H]+ | A2 |
| 19 | (−)-(4aR,8aR)-6-(4-(4-(Trifluoromethyl)benzyl)piperidine-1-carbonyl)hexahydro-2H-pyrido[4,3-b][1,4]oxazin-3(4H)-one | Example 17 | 426.4 [M + H]+ | B1 |

| Ex. | Systematic Name/Structure | Building block(s) | MS, m/z | Method |
|---|---|---|---|---|
| 20 | (−)-(4aS,8aR)-6-[4-[[4-(Trifluoromethyl)phenyl]methyl]piperidine-1-carbonyl]-4,4a,5,7,8,8a-hexahydropyrido[4,3-b][1,4]oxazin-3-one | Example 11 | 426.4 [M + H]+ | B1 |
| 22 | rac-(4aR,8aS)-6-(4-(4-Chlorobenzyl)piperidine-1-carbonyl)hexahydro-2H-pyrido[4,3-b][1,4]oxazin-3(4H)-one | 1-(4-Chlorobenzyl)-piperazine (CAS RN 23145-88-2) and BB1 | 393.2 [M + H]+ | A2 |
| 23 | (−)-(4aS,8aR)-6-(4-((2-Chloro-4-fluorophenoxy)methyl)piperidine-1-carbonyl)hexahydro-2H-pyrido[4,3-b][1,4]oxazin-3(4H)-one | Example 7 | 426.2 [M + H]+ | B1 |
| 24 | (+)-(4aR,8aS)-6-(4-((2-Chloro-4-fluorophenoxy)methyl)piperidine-1-carbonyl)hexahydro-2H-pyrido[4,3-b][1,4]oxazin-3(4H)-one | Example 7 | 426.2 [M + H]+ | B1 |
| 25 | rac-(4aR,8aS)-6-[4-[[5-(Trifluoromethyl)-2-pyridyl]methyl]piperidine-1-carbonyl]-4,4a,5,7,8,8a-hexahydropyrido[4,3-b][1,4]oxazin-3-one | BB5 and BB1 | 427.2 [M + H]+ | A2 |

-continued

| Ex. | Systematic Name/Structure | Building block(s) | MS, m/z | Method |
|---|---|---|---|---|
| 27 | rac-(4aR,8aS)-6-(3-((2-Fluoro-4-(trifluoromethyl)benzyl)oxy)azetidine-1-carbonyl)hexahydro-2H-pyrido[4,3-b][1,4]oxazin-3(4H)-one | Supplier of building block: HDH Pharma, Inc. and BB1 | 432.2 [M + H]+ | A2 |
| 28 | (+)- or (−)-(4aR,8aS)-6-(3-((2-Chloro-4-fluorobenzyl)oxy)azetidine-1-carbonyl)hexahydro-2H-pyrido[4,3-b][1,4]oxazin-3(4H)-one | Supplier of building block: ZereneX Molecular Limited and BB1a | 398.1 [M + H]+ | A2 |
| 29 | (+)- or (−)-(4aR,8aS)-6-(3-((2-Fluoro-4-(trifluoromethyl)benzyl)oxy)azetidine-1-carbonyl)hexahydro-2H-pyrido[4,3-b][1,4]oxazin-3(4H)-one | Example 27 | 432.2 [M + H]+ | B1 |
| 30 | (+)- or (−)-(4aS,8aR)-6-(3-((2-Fluoro-4-(trifluoromethyl)benzyl)oxy)azetidine-1-carbonyl)hexahydro-2H-pyrido[4,3-b][1,4]oxazin-3(4H)-one | Example 27 | 432.2 [M + H]+ | B1 |

| Ex. | Systematic Name/Structure | Building block(s) | MS, m/z | Method |
|---|---|---|---|---|
| 31 | (+)- or (−)-(4aR,8aS)-6-(4-(4-(Trifluoromethoxy)benzyl)piperidine-1-carbonyl)hexahydro-2H-pyrido[4,3-b][1,4]oxazin-3(4H)-one | 4-[4-(Trifluoromethoxy)benzyl]piperidine (CAS RN 681482-50-8) and BB1a | 442.2 [M + H]+ | A2 |
| 32 | (+)- or (−)-(4aR,8aS)-6-(4-((2,4-Difluorophenoxy)methyl)piperidine-1-carbonyl)hexahydro-2H-pyrido[4,3-b][1,4]oxazin-3(4H)-one | 4-((2,4-Difluorophenoxy)methyl)piperidine HCl CAS RN 614731-39-4 and BB1a | 410.2 [M + H]+ | A5 |
| 33 | (+)- or (−)-(4aR,8aS)-6-(4-(4-Chloro-3-fluorobenzyl)piperidine-1-carbonyl)hexahydro-2H-pyrido[4,3-b][1,4]oxazin-3(4H)-one | Building block prepared as described in WO2013/179024 and BB1a | 410.2 [M + H]+ | A2 |
| 35 | (+)- or (−)-(4aR,8aS)-6-(4-(4-Chlorobenzyl)piperidine-1-carbonyl)hexahydro-2H-pyrido[4,3-b][1,4]oxazin-3(4H)-one | 4-(4-Chloro-benzyl)-piperidine hydrochloride (CAS RN 36938-76-8) and BB1a | 392.2 [M + H]+ | A2 |
| 36 | (+)- or (−)-(4aR,8aS)-6-[3-[[4-(Trifluoromethyl)phenyl]methyl]azetidine-1-carbonyl]-4,4a,5,7,8,8a-hexahydropyrido[4,3-b][1,4]oxazin-3-one | 3-[[4-(Trifluoromethyl)phenyl]methyl]azetidine (CAS RN 937614-88-5) and BB1a | 398.3 [M + H]+ | A1 |

-continued

| Ex. | Systematic Name/Structure | Building block(s) | MS, m/z | Method |
|---|---|---|---|---|
| 38 | (+)- or (−)-(4aR,8aS)-6-(4-((5-(tert-Butyl)oxazol-2-yl)methyl)piperidine-1-carbonyl)hexahydro-2H-pyrido[4,3-b][1,4]oxazin-3(4H)-one | BB8 and BB1a | 405.3 [M + H]$^+$ | A2 |
| 40 | (+)- or (−)-(4aR,8aS)-6-(4-(2-Chloro-4-(trifluoromethyl)phenoxy)piperidine-1-carbonyl)hexahydro-2H-pyrido[4,3-b][1,4]oxazin-3(4H)-one | BB9 and BB1a | 462.1 [M + H]$^+$ | A2 |
| 41 | (4aR,8aS)-6-[3-[[[2,2,2-Trifluoro-1-[4-(trifluoromethyl)phenyl]ethyl]amino]methyl]azetidine-1-carbonyl]hexahydro-2H-pyrido[4,3-b][1,4]oxazin-3(4H)-one | BB19 and BB1a | 495.18 [M + H]$^+$ | A3 |
| 44 | (+)- or (−)-(4aR,8aS)-6-(4-(3-(Trifluoromethyl)phenoxy)piperidine-1-carbonyl)hexahydro-2H-pyrido[4,3-b][1,4]oxazin-3(4H)-one | 4-(3-Trifluoromethyl)phenoxy)piperidine (CAS RN 337912-66-0) and BB1a | 428.2 [M + H]$^+$ | A3 |
| 45 | (4aS,8aR)-6-[4-[[2-Chloro-4-(trifluoromethoxy)phenoxy]methyl]piperidine-1-carbonyl]-4,4a,5,7,8,8a-hexahydropyrido[4,3-b][1,4]oxazin-3-one | 2-Chloro-4-(trifluoromethoxy)phenol (CAS: 35852-58-5) and BB1b | 492.2 [M + H]$^+$ | A6 |

-continued

| Ex. | Systematic Name/Structure | Building block(s) | MS, m/z | Method |
|---|---|---|---|---|
| 46 | (4aR,8aS)-6-[4-[[2-Chloro-4-(trifluoromethoxy)phenoxy]methyl]piperidine-1-carbonyl]-4,4a,5,7,8,8a-hexahydropyrido[4,3-b][1,4]oxazin-3-one | 2-Chloro-4-(trifluoromethoxy)phenol (CAS RN: 35852-58-5) and BB1a | 492.2 [M + H]$^+$ | A6 |
| 47 | (4aR,8aS)-6-(3-((2-Fluoro-4-(trifluoromethyl)phenoxy)methyl)azetidine-1-carbonyl)hexahydro-2H-pyrido[4,3-b][1,4]oxazin-3(4H)-one | BB20 and BB1a | 432.2 [M + H]$^+$ | A5 |
| 48 | (4aS,8aR)-6-[4-[(2-Chloro-4-fluorophenoxy)methyl]-4-methylpiperidine-1-carbonyl]-4,4a,5,7,8,8a-hexahydropyrido[4,3-b][1,4]oxazin-3-one | BB12 and BB7b | 440.2 [M + H]$^+$ | A4 (1:1 ACN: iPrOH) |
| 49 | (4aS,8aR)-6-(4-((2,4-Difluorophenoxy)methyl)piperidine-1-carbonyl)hexahydro-2H-pyrido[4,3-b][1,4]oxazin-3(4H)-one | 4-[(2,4-Difluorophenoxy)methyl]piperidine hydrochloride (CAS RN: 614731-39-4) and BB7b | 410.2 [M + H]$^+$ | A4 |

-continued

| Ex. | Systematic Name/Structure | Building block(s) | MS, m/z | Method |
|---|---|---|---|---|
| 50 | (4aR,8aS)-6-(4-((4-Chloro-2-fluorophenoxy)methyl)piperidine-1-carbonyl)hexahydro-2H-pyrido[4,3-b][1,4]oxazin-3(4H)-one | 4-Chloro-2-fluorophenyl 4-piperidinylmethyl ether; hydrochloride salt (CAS: 946680-87-1) and BB7A | 426.2 [M + H]$^+$ | A4 (microwave heating) |
| 51 | (4aR,8aS)-6-(4-((4-Fluoro-2-(trifluoromethyl)phenoxy)methyl)piperidine-1-carbonyl)hexahydro-2H-pyrido[4,3-b][1,4]oxazin-3(4H)-one | BB21 and BB7a | 460.2 [M + H]$^+$ | A4 |
| 52 | (4aR,8aS)-6-(4-((2-Fluoro-4-(trifluoromethyl)phenoxy)methyl)piperidine-1-carbonyl)hexahydro-2H-pyrido[4,3-b][1,4]oxazin-3(4H)-one | BB22 and BB7a | 460.2 [M + H]$^+$ | A4 |
| 53 | (+)- or (−)-(4aR,8aS)-6-(4-(2-(Pyrrolidin-1-yl)-4-(trifluoromethyl)benzyl)piperidine-1-carbonyl)hexahydro-2H-pyrido[4,3-b][1,4]oxazin-3(4H)-one | BB91 and BB1a | 495.3 [M + H]$^+$ | A3 |

| Ex. | Systematic Name/Structure | Building block(s) | MS, m/z | Method |
|---|---|---|---|---|
| 54 | (4aR,8aS)-6-(4-((2-Chloro-4-(trifluoromethyl)phenoxy)methyl)piperidine-1-carbonyl)hexahydro-2H-pyrido[4,3-b][1,4]oxazin-3(4H)-one | BB23 and BB1a | 476.3 [M + H]⁺ | A5 |
| 55 | 5-Fluoro-2-((1-((4aR,8aS)-3-oxooctahydro-2H-pyrido[4,3-b][1,4]oxazine-6-carbonyl)piperidin-4-yl)methoxy)benzonitrile | BB24 and BB1a | 417.2 [M + H]⁺ | A5 |
| 56 | (4aR,8aS)-6-(4-(2-Pyrrolidin-1-yl)-4-(trifluoromethyl)benzyl)piperazine-1-carbonyl)hexahydro-2H-pyrido[4,3-b][1,4]oxazin-3(4H)-one | 1-[[2-(Pyrrolidin-1-yl)-4-(trifluoromethyl)phenyl]methyl]piperazine (synthesized according to WO2015/179559) and BB1a | 496.26 [M + H]⁺ | A3 |
| 57 | (4aR,8aS)-6-(3-((2-Chloro-4-fluorophenoxy)methyl)azetidine-1-carbonyl)hexahydro-2H-pyrido[4,3-b][1,4]oxazin-3(4H)-one | BB25 and BB1a | 398.2 [M + H]⁺ | A5 |

-continued

| Ex. | Systematic Name/Structure | Building block(s) | MS, m/z | Method |
|---|---|---|---|---|
| 58 | (+)- or (−)-(4aR,8aS)-6-[4-[[2-Cyclopentyl-4-(trifluoromethyl)phenyl]methyl]piperidine-1-carbonyl]-4,4a,5,7,8,8a-hexahydropyrido[4,3-b][1,4]oxazin-3-one | BB10 and BB1a | 494.3 [M + H]⁺ | A3 |
| 59 | (4aR,8aS)-3-Chloro-4-((1-(3-oxooctahydro-2H-pyrido[4,3-b][1,4]oxazine-6-carbonyl)piperidin-4-yl)methoxy)benzonitrile | BB26 and BB1a | 433.2 [M + H]⁺ | A5 |
| 60 | (4aR,8aS)-6-(4-((4-(Trifluoromethyl)-1H-imidazol-1-yl)methyl)piperidine-1-carbonyl)hexahydro-2H-pyrido[4,3-b][1,4]oxazin-3(4H)-one | BB27 and BB1a | 416.3 [M + H]⁺ | A9 |
| 61 | (4aR,8aS)-6-(4-((4-Fluoro-2-methylphenoxy)methyl)piperidine-1-carbonyl)hexahydro-2H-pyrido[4,3-b][1,4]oxazin-3(4H)-one | BB28 and BB1a | 406.3 [M + H]⁺ | A5 |

| Ex. | Systematic Name/Structure | Building block(s) | MS, m/z | Method |
|---|---|---|---|---|
| 62 | (4aR,8aS)-6-(3-((2-Chloro-4-(trifluoromethyl)phenoxy)methyl)azetidine-1-carbonyl)hexahydro-2H-pyrido[4,3-b][1,4]oxazin-3(4H)-one | BB29 and BB1a | 448.2 [M + H]+ | A5 |
| 63 | N-Benzyl-N-(2-hydroxyethyl)-1-((4aR,8aS)-3-oxooctahydro-2H-pyrido[4,3-b][1,4]oxazine-6-carbonyl)piperidine-4-carboxamide | BB30 and BB1a | 445.24 [M + H]+ | A3 |
| 65 | N-Benzyl-1-((4aR,8aS)-3-oxooctahydro-2H-pyrido[4,3-b][1,4]oxazine-6-carbonyl)piperidine-4-carboxamide | BB31 and BB1a | 401.22 [M + H]+ | A3 |
| 66 | (4aR,8aS)-6-(4-((4-(tert-Butyl)-1H-pyrazol-1-yl)methyl)piperidine-1-carbonyl)hexahydro-2H-pyrido[4,3-b][1,4]oxazin-3(4H)-one | BB32 and BB1a | 404.3 [M + H]+ | A9 (purified by RP-HPLC) |

-continued

| Ex. | Systematic Name/Structure | Building block(s) | MS, m/z | Method |
|-----|--------------------------|-------------------|---------|--------|
| 67 | (2R,4aR,8aS)-2-Methyl-6-[4-[[4-(trifluoromethyl)phenyl]methyl]piperidine-1-carbonyl]-4,4a,5,7,8,8a-hexahydropyrido[4,3-b][1,4]oxazin-3-one | 4-(4-Trifluoromethyl benzyl)piperidine HCl (CAS RN 192990-03-7) and BB33 | 440.3 [M + H]$^+$ | A3 |
| 68 | (4aR,8aS)-6-(3-(((2,2,2-Trifluoro-1-(3-(trifluoromethyl)phenyl)ethyl)amino)methyl)azetidine-1-carbonyl)hexahydro-2H-pyrido[4,3-b][1,4]oxazin-3(4H)-one | BB34 and BB1a | 495.18 [M + H]$^+$ | A3 |
| 69 | (4aR,8aS)-6-(3-(((1-(2,4-Dichlorophenyl)-2,2,2-trifluoroethyl)amino)methyl)azetidine-1-carbonyl)hexahydro-2H-pyrido[4,3-b][1,4]oxazin-3(4H)-one | BB35 and BB1a | 495.11 [M + H]$^+$ | A3 followed by RP-HPLC |
| 70 | (4aR,8aS)-6-(3-(((1-(2-Chlorophenyl)-2,2,2-trifluoroethyl)amino)methyl)azetidine-1-carbonyl)hexahydro-2H-pyrido[4,3-b][1,4]oxazin-3(4H)-one | BB35 and BB1a | 461.16 [M + H]$^+$ | A3 followed by RP-HPLC |

| Ex. | Systematic Name/Structure | Building block(s) | MS, m/z | Method |
| --- | --- | --- | --- | --- |
| 71 | (4aR,8aS)-6-(3-(((2,2,2-Trifluoro-1-phenylethyl)amino)methyl)azetidine-1-carbonyl)hexahydro-2H-pyrido[4,3-b][1,4]oxazin-3(4H)-one | BB35 and BB1a | 427.2 [M + H]+ | A3 followed by RP-HPLC |
| 72 | (+)- or (−)-(4aR,8aS)-6-(4-(Benzo[d]oxazol-2-ylmethyl)piperidine-1-carbonyl)hexahydro-2H-pyrido[4,3-b][1,4]oxazin-3(4H)-one | BB11 and BB7a | 399.2 [M + H]+ | A1 |
| 73 | (+)- or (−)-(4aR,8aS)-6-(4-((4′,6-Dichloro-[1,1′-biphenyl]-3-yl)oxy)piperidine-1-carbonyl)hexahydro-2H-pyrido[4,3-b][1,4]oxazin-3(4H)-one | BB13 and BB7a | 504.1 [M + H]+ | A1 |
| 74 | (4aR,8aS)-6-cis-4-((2-Chloro-4-fluorophenyl)methyl)-3-methylpiperidine-1-carbonyl)hexahydro-2H-pyrido[4,3-b][1,4]oxazin-3(4H)-one | BB36 and BB1a | 440.1 [M + H]+ | A3 |

| Ex. | Systematic Name/Structure | Building block(s) | MS, m/z | Method |
|---|---|---|---|---|
| 75 | (4aR,8aS)-6-(3-((2-Chloro-4-(trifluoromethyl)benzyl)oxy)azetidine-1-carbonyl)hexahydro-2H-pyrido[4,3-b][1,4]oxazin-3(4H)-one | BB7a and BB37 | 448.2 [M + H]+ | A4 (solvent ACN instead of NMP) |
| 76 | (4aR,8aS)-6-(3-((4-(Trifluoromethyl)benzyl)oxy)azetidine-1-carbonyl)hexahydro-2H-pyrido[4,3-b][1,4]oxazin-3(4H)-one | BB7a and BB38 | 414.2 [M + H]+ | A4 (solvent ACN instead of NMP) |
| 77 | (4aR,8aS)-6-(3-((2-Fluoro-4-(trifluoromethoxy)benzyl)oxy)azetidine-1-carbonyl)hexahydro-2H-pyrido[4,3-b][1,4]oxazin-3(4H)-one | BB7a and BB39 | 448.2 [M + H]+ | A4 (solvent ACN instead of NMP) |
| 78 | 2-chloro-4-fluoro-N-(1-((4aR,8aS)-3-oxooctahydro-2H-pyrido[4,3-b][1,4]oxazine-6-carbonyl)azetidine-3-yl)benzamide | BB7a and BB40 | 411.2 [M + H]+ | A4 (solvent ACN not NMP) |

| Ex. | Systematic Name/Structure | Building block(s) | MS, m/z | Method |
|---|---|---|---|---|
| 80 | (4aS,8aS)-6-(3-((Methyl(2,2,2-trifluoro-1-(4-(trifluoromethyl)phenyl)ethyl)amino)methyl)azetidine-1-carbonyl)hexahydro-2H-pyrido[4,3-b][1,4]oxazin-3(4H)-one | BB41 and BB1a | 509.2 [M + H]+ | A3 |
| 81 | (+)- or (−)-(4aR,8aS)-6-(4-(2-(1H-Pyrazol-4-yl)-4-(trifluoromethyl)benzyl)piperidine-1-carbonyl)hexahydro-2H-pyrido[4,3-b][1,4]oxazin-3(4H)-one | BB14 and BB7a | 492.2 [M + H]+ | A1 |
| 82 | N-[1-[(4aR,8aS)-3-oxo-4,4a,5,7,8,8a-hexahydropyrido[4,3-b][1,4]oxazine-6-carbonyl]piperidin-4-yl]-N-methyl-1-[3-(trifluoromethyl)phenyl]cyclopropane-1-carboxamide | BB42 and BB1a | 509.2 [M + H]+ | A3 |
| 83 | N-[1-[(4aR,8aS)-3-oxo-4,4a,5,7,8,8a-hexahydropyrido[4,3-b][1,4]oxazine-6-carbonyl]piperidin-4-yl]-2-[2-chloro-3-(trifluoromethyl)phenyl]-N-methylacetamide | BB43 and BB1a | 517.18 [M + H]+ | A3 |

-continued

| Ex. | Systematic Name/Structure | Building block(s) | MS, m/z | Method |
|---|---|---|---|---|
| 84 | N-[1-[(4aR,8aS)-3-oxo-4,4a,5,7,8,8a-hexahydropyrido[4,3-b][1,4]oxazine-6-carbonyl]piperidin-4-yl]-2-[2-chloro-5-(trifluoromethyl)phenyl]-N-methylacetamide | BB44 and BB1a | 517.18 [M + H]⁺ | A3 |
| 85 | N-[1-[(4aS,8aS)-3-oxo-4,4a,5,7,8,8a-hexahydropyrido[4,3-b][1,4]oxazine-6-carbonyl]piperidin-4-yl]-N-methyl-4-(trifluoromethyl)benzamide | N-methyl-N-(piperidin-4-yl)-4-(trifluoromethyl)benzamide hydrochloride (CAS RN 1580795-67-0) and BB1a | 469.20 [M + H]⁺ | A3 |
| 86 | N-[1-[(4aR,8aS)-3-oxo-4,4a,5,7,8,8a-hexahydropyrido[4,3-b][1,4]oxazine-6-carbonyl]piperidin-4-yl]-N-methyl-2-[3-(trifluoromethyl)phenyl]acetamide | BB94 and BB1a | 483.22 [M + H]⁺ | A3 |
| 87 | (4aR,8aS)-6-[3-[(2,4-Dichlorophenyl)methoxy]azetidine-1-carbonyl]-4,4a,5,7,8,8a-hexahydropyrido[4,3-b][1,4]oxazin-3-one | BB88 and BB1a | 414.3 [M + H]⁺ | A5 |

-continued

| Ex. | Systematic Name/Structure | Building block(s) | MS, m/z | Method |
|---|---|---|---|---|
| 88 | (4aR,8aS)-6-[3-[[3-Methoxy-4-(trifluoromethyl)phenyl]methoxy]azetidine-1-carbonyl]-4,4a,5,7,8,8a-hexahydropyrido[4,3-b][1,4]oxazin-3-one | BB45 and BB1a | 444.3 [M + H]⁺ | A4 (ACN as solvent) |
| 89 | (4aR,8aS)-6-[4-[[5-Methyl-6-(trifluoromethyl)pyridin-3-yl]oxymethyl]piperidine-1-carbonyl]-4,4a,5,7,8,8a-hexahydropyrido[4,3-b][1,4]oxazin-3-one | BB46 and BB1a | 457.2 [M + H]⁺ | A3 |
| 90 | (4aR,8aS)-6-[3-[(3-Chlorophenoxy)methyl]pyrrolidine-1-carbonyl]-4,4a,5,7,8,8a-hexahydropyrido[4,3-b][1,4]oxazin-3-one | 3-[(3-Chlorophenoxy)methyl]pyrrolidine (CAS RN 914299-54-0) and BB1a | 394.15 [M + H]⁺ | A4 (ACN as solvent) |
| 91 | (4aR,8aS)-6-[3-[(2-Chlorophenoxy)methyl]pyrrolidine-1-carbonyl]-4,4a,5,7,8,8a-hexahydropyrido[4,3-b][1,4]oxazin-3-one | BB47 and BB1a | 394.15 [M + H]⁺ | A4 (ACN as solvent) |

| Ex. | Systematic Name/Structure | Building block(s) | MS, m/z | Method |
|---|---|---|---|---|
| 92 | (4aR,8aS)-6-[4-[[2-Fluoro-4-(trifluoromethyl)phenyl]methyl]piperidine-1-carbonyl]-4,4a,5,7,8,8a-hexahydropyrido[4,3-b][1,4]oxazin-3-one | BB48 and BB1a | 444.2 [M + H]⁺ | A4 (ACN as solvent) |
| 93 | (4aR,8aS)-6-[3-[(2-Chlorophenyl)methoxy]pyrrolidine-1-carbonyl]-4,4a,5,7,8,8a-hexahydropyrido[4,3-b][1,4]oxazin-3-one | BB49 and BB1a | 394.15 [M + H]⁺ | A4 (ACN as solvent) |
| 94 | (4aR,8aS)-6-[3-[(3-Chlorophenyl)methoxy]pyrrolidine-1-carbonyl]-4,4a,5,7,8,8a-hexahydropyrido[4,3-b][1,4]oxazin-3-one | BB50 and BB1a | 394.15 [M + H]⁺ | A4 (ACN as solvent) |
| 95 | (4aR,8aS)-6-[4-[[2-Cyclopropyl-4-(trifluoromethyl)phenyl]methyl]piperidine-1-carbonyl]-4,4a,5,7,8,8a-hexahydropyrido[4,3-b][1,4]oxazin-3-one | BB51 and BB1a | 466.23 [M + H]⁺ | A4 (ACN as solvent) |
| 96 | (4aR,8aS)-6-[3-[(4-Chlorophenoxy)methyl]pyrrolidine-1-carbonyl]-4,4a,5,7,8,8a-hexahydropyrido[4,3-b][1,4]oxazin-3-one | BB52 and BB1a | 394.15 [M + H]⁺ | A4 (ACN as solvent) |

| Ex. | Systematic Name/Structure | Building block(s) | MS, m/z | Method |
|---|---|---|---|---|
| 97 | (4aR,8aS)-6-[3-[(4-Chlorophenyl)methoxy]pyrrolidine-1-carbonyl]-4,4a,5,7,8,8a-hexahydropyrido[4,3-b][1,4]oxazin-3-one | BB53 and BB1a | 394.15 [M + H]$^+$ | A4 (ACN as solvent) |
| 98 | (4aR,8aS)-6-[4-[[2-Methyl-4-(trifluoromethyl)phenyl]methyl]piperidine-1-carbonyl]-4,4a,5,7,8,8a-hexahydropyrido[4,3-b][1,4]oxazin-3-one | BB54 and BB1a | 440.4 [M + H]$^+$ | A3 |
| 99 | (4aR,8aS)-6-[4-[[2-Chloro-4-(trifluoromethyl)phenyl]methyl]piperidine-1-carbonyl]-4,4a,5,7,8,8a-hexahydropyrido[4,3-b][1,4]oxazin-3-one | BB55 and BB1a | 460.16 [M + H]$^+$ | A3 |
| 100 | (4aR,8aS)-6-[3-[[4-(Trifluoromethyl)phenyl]methyl]pyrrolidine-1-carbonyl]-4,4a,5,7,8,8a-hexahydropyrido[4,3-b][1,4]oxazin-3-one | 3-(4-Trifluoromethylbenzyl)pyrrolidine hydrochloride salt (CAS RN: 957988-84-4) and BB1a | 412.19 [M + H]$^+$ | A3 |

-continued

| Ex. | Systematic Name/Structure | Building block(s) | MS, m/z | Method |
|---|---|---|---|---|
| 101 | (4aR,8aS)-6-[3-[[3-Fluoro-5-(Trifluoromethyl)phenyl]methoxy]azetidine-1-carbonyl]-4,4a,5,7,8,8a-hexahydropyrido[4,3-b][1,4]oxazin-3-one | BB56 and BB1a | 432.2 [M + H]$^+$ | A4 (ACN as solvent) |
| 102 | (4aR,8aS)-6-[3-[[2-Fluoro-6-(trifluoromethyl)phenyl]methoxymethyl]azetidine-1-carbonyl]-4,4a,5,7,8a,8a-hexahydropyrido[4,3-b][1,4]oxazin-3-one | BB1a and BB57 | 446.3 [M + H]$^+$ | A4 (ACN as solvent) |
| 103 | (4aR,8aS)-6-[2-Methyl-3-[[4-(trifluoromethyl)phenyl]methoxy]azetidine-1-carbonyl]-4,4a,5,7,8,8a-hexahydropyrido[4,3-b][1,4]oxazin-3-one (Isomer D) | Example 117 | 428.19 [M + H]$^+$ | B3 |
| 104 | (4aR,8aS)-6-[2-Methyl-3-[[4-(trifluoromethyl)phenyl]methoxy]azetidine-1-carbonyl]-4,4a,5,7,8,8a-hexahydropyrido[4,3-b][1,4]oxazin-3-one (Isomer C) | Example 117 | 428.19 [M + H]$^+$ | B3 |

| Ex. | Systematic Name/Structure | Building block(s) | MS, m/z | Method |
|---|---|---|---|---|
| 105 | (4aR,8aS)-6-[2-Methyl-3-[[4-(trifluoromethyl)phenyl]methoxy]azetidine-1-carbonyl]-4,4a,5,7,8,8a-hexahydropyrido[4,3-b][1,4]oxazin-3-one (Isomers A or D) | Example 117 | 428.19 [M + H]⁺ | B3 |
| 106 | (4aR,8aS)-6-[3-[[[2,2,2-Trifluoro-1-(4-fluorophenyl)ethyl]amino]methyl]azetidine-1-carbonyl]-4,4a,5,7,8,8a-hexahydro[4,3-b][1,4]oxazin-3-one | BB58 and BB1a | 455.19 [M + H]⁺ | A3 |
| 107 | (4aR,8aS)-6-[4-[2,2,2-Trifluoro-1-[[3-(trifluoromethyl)phenyl]methylamino]ethyl] piperidine-1-carbonyl]-4,4a,5,7,8,8a-hexahydropyrido[4,3-b][1,4]oxazin-3-one | BB59 and BB1a | 523.22 [M + H]⁺ | A3 |
| 108 | (4aR,8aS)-6-[3-[[3-Chloro-4-(trifluoromethyl)phenyl]methoxy]azetidine-1-carbonyl]-4,4a,5,7,8,8a-hexahydropyrido[4,3-b][1,4]oxazin-3-one | BB60 and BB1a | 448.2 [M + H]⁺ | A4 (1:1 iPrOH: ACN as solvent) |

-continued

| Ex. | Systematic Name/Structure | Building block(s) | MS, m/z | Method |
|---|---|---|---|---|
| 109 | (4aR,8aS)-6-[3-[(2-Chloro-4-fluorophenoxy)methyl]-3-fluoroazetidine-1-carbonyl]-4,4a,5,7,8,8a-hexahydropyrido[4,3-b][1,4]oxazin-3-one | BB61 and BB1a | 416.2 [M + H]⁺ | A4 (1:1 iPrOH: ACN as solvent) |
| 110 | (4aR,8aS)-6-[3-[[2-Fluoro-4-(trifluoromethyl)phenyl]methoxy]-3-(trifluoromethyl)azetidine-1-carbonyl]-4,4a,5,7,8,8a-hexahydropyrido[4,3-b][1,4]oxazin-3-one | BB62 and BB1a | 500.2 [M + H]⁺ | A4 (ACN as solvent) |
| 111 | (4aR,8aS)-6-[3-[[2-Fluoro-4-(trifluoromethyl)phenyl]methoxy]-3-methylazetidine-1-carbonyl]-4,4a,5,7,8,8a-hexahydropyrido[4,3-b][1,4]oxazin-3-one | BB63 and BB1a | 446.2 [M + H]⁺ | A4 (ACN as solvent) |

| Ex. | Systematic Name/Structure | Building block(s) | MS, m/z | Method |
|---|---|---|---|---|
| 112 | (4aR,8aS)-6-[3-[[2,4-Difluoro-5-(trifluoromethyl)phenyl]methoxy]azetidine-1-carbonyl]-4,4a,5,7,8,8a-hexahydropyrido[4,3-b][1,4]oxazin-3-one | BB64 and BB1a | 450.2 [M + H]$^+$ | A4 (ACN as solvent) |
| 113 | (4aR,8aS)-6-[3-[[2-Fluoro-5-(trifluoromethyl)phenyl]methoxy]azetidine-1-carbonyl]-4,4a,5,7,8,8a-hexahydropyrido[4,3-b][1,4]oxazin-3-one | BB65 and BB1a | 432.2 [M + H]$^+$ | A4 (ACN as solvent) |
| 114 | (4aR,8aS)-6-[3-[[3-Fluoro-4-(trifluoromethyl)phenyl]methoxy]azetidine-1-carbonyl]-4,4a,5,7,8,8a-hexahydropyrido[4,3-b][1,4]oxazin-3-one | BB66 and BB1a | 432.2 [M + H]$^+$ | A4 (ACN as solvent) |

| Ex. | Systematic Name/Structure | Building block(s) | MS, m/z | Method |
|---|---|---|---|---|
| 115 | (4aR,8aS)-6-[3-[[2-Methoxy-4-(trifluoromethyl)phenyl]methoxy]azetidine-1-carbonyl]-4,4a,5,7,8,8a-hexahydropyrido[4,3-b][1,4]oxazin-3-one | BB67 and BB1a | 444.3 [M + H]$^+$ | A4 (ACN as solvent) |
| 116 | (4aR,8aS)-6-[3-[[4-Chloro-2-(trifluoromethyl)phenyl]methoxy]azetidine-1-carbonyl]-4,4a,5,7,8,8a-hexahydropyrido[4,3-b][1,4]oxazin-3-one | BB68 and BB1a | 448.2 [M + H]$^+$ | A4 (1:1 iPrOH:ACN as solvent) |
| 117 | (4aR,8aS)-6-[2-Methyl-3-[[4-(trifluoromethyl)phenyl]methoxy]azetidine-1-carbonyl]-4,4a,5,7,8,8a-hexahydropyrido[4,3-b][1,4]oxazin-3-one | BB69 and BB1a | 428.18 [M + H]$^+$ | A3 |
| 118 | (4aR,8aS)-6-[3-[4-(Trifluoromethyl)phenoxy]azetidine-1-carbonyl]-4,4a,5,7,8,8a-hexahydropyrido[4,3-b][1,4]oxazin-3-one | BB70 and BB1a | 400.2 [M + H]$^+$ | A4 (ACN as solvent) |

-continued

| Ex. | Systematic Name/Structure | Building block(s) | MS, m/z | Method |
|---|---|---|---|---|
| 119 | (4aR,8aS)-6-[4-[4-Chloro-3-(trifluoromethyl)phenoxy]piperidine-1-carbonyl]-4,4a,5,7,8,8a-hexahydropyrido[4,3-b][1,4]oxazin-3-one | BB71 and BB1a | 462.2 [M + H]⁺ | A4 (ACN as solvent) |
| 120 | (4aR,8aS)-6-[4-(4-Chloro-3-cyclopropylphenoxy)piperidine-1-carbonyl]-4,4a,5,7,8,8a-hexahydropyrido[4,3-b][1,4]oxazin-3-one | BB72 and BB1a | 434.1 [M + H]⁺ | A4 (ACN as solvent) |
| 121 | (4aR,8aS)-6-[4-(4-Chloro-3-morpholin-4-ylphenoxy)piperidine-1-carbonyl]-4,4a,5,7,8,8a-hexahydropyrido[4,3-b][1,4]oxazin-3-one | BB73 and BB1a | 479.2 [M + H]⁺ | A4 (ACN as solvent) |
| 122 | (4aR,8aS)-6-[4-[2-Methyl-4-(trifluoromethyl)phenoxy]piperidine-1-carbonyl]-4,4a,5,7,8,8a-hexahydropyrido[4,3-b][1,4]oxazin-3-one | BB74 and BB1a | 442.1 [M + H]⁺ Hans | A4 (ACN as solvent) |

-continued

| Ex. | Systematic Name/Structure | Building block(s) | MS, m/z | Method |
|---|---|---|---|---|
| 123 | 2-[1-[(4aR,8aS)-3-Oxo-4,4a,5,7,8,8a-hexahydropyrido[4,3-b][1,4]oxazine-6-carbonyl]piperidin-4-yl]oxy-5-(trifluoromethyl)benzonitrile | BB75 and BB1a | 453.0 [M + H]+ Hans | A4 (ACN as solvent) |
| 124 | (4aR,8aS)-6-[4-(Oxazolo[5,4-c]pyridin-2-ylmethyl)piperidine-1-carbonyl]-4,4a,5,7,8,8a-hexahydropyrido[4,3-b][1,4]oxazin-3-one | BB76 and BB1a | 400.2 [M + H]+ | A4 (ACN as solvent) |
| 126 | (+)-(4aR,8aS)-6-[4-[2-(4-Chloropyridin-3-yl)ethynyl]piperidine-1-carbonyl]-4,4a,5,7,8,8a-hexahydropyrido[4,3-b][1,4]oxazin-3-one | BB77 | 403.3 [M + H]+ | A10 |
| 127 | (+)-(4aR,8aS)-6-[4-[2-(3-Chloropyridin-2-yl)ethynyl]piperidine-1-carbonyl]-4,4a,5,7,8,8a-hexahydropyrido[4,3-b][1,4]oxazin-3-one | BB78 | 403.2 [M + H]+ | A10 |

-continued

| Ex. | Systematic Name/Structure | Building block(s) | MS, m/z | Method |
|---|---|---|---|---|
| 128 | (+)-(4aR,8aS)-6-[4-[2-(2-Chloro-4-fluorophenyl)ethynyl]piperidine-1-carbonyl]-4,4a,5,7,8,8a-hexahydropyrido[4,3-b][1,4]oxazin-3-one | BB79 | 420.3 [M + H]$^+$ | A10 |
| 129 | (+)-(4aR,8aS)-6-[4-[2-(3-Chlorophenyl)ethynyl]piperidine-1-carbonyl]-4,4a,5,7,8,8a-hexahydropyrido[4,3-b][1,4]oxazin-3-one | BB80 | 402.3 [M + H]$^+$ | A10 |
| 130 | (+)-(4aR,8aS)-6-[4-[2-(4-Chlorophenyl)ethynyl]piperidine-1-carbonyl]-4,4a,5,7,8,8a-hexahydropyrido[4,3-b][1,4]oxazin-3-one | BB81 | 402.3 [M + H]$^+$ | A10 |
| 131 | (+)-(4aR,8aS)-6-[4-[2-(2,4-Dichlorophenyl)ethynyl]piperidine-1-carbonyl]-4,4a,5,7,8,8a-hexahydropyrido[4,3-b][1,4]oxazin-3-one | BB82 | 436.3 [M + H]$^+$ | A10 |

-continued

| Ex. | Systematic Name/Structure | Building block(s) | MS, m/z | Method |
|---|---|---|---|---|
| 132 | (+)-(4aR,8aS)-6-[4-[2-(2-Chlorophenyl)ethynyl]-4-hydroxypiperidine-1-carbonyl]-4,4a,5,7,8,8a-hexahydropyrido[4,3-b][1,4]oxazin-3-one | BB83 | 418.4 [M + H]⁺ | A10 |
| 133 | (+)-(4aR,8aS)-6-[3-[2-(2-Chlorophenyl)ethynyl]azetidine-1-carbonyl]-4,4a,5,7,8,8a-hexahydropyrido[4,3-b][1,4]oxazin-3-one | BB84 | 374.2 [M + H]⁺ | A10 |
| 134 | (+)-(4aR,8aS)-6-(3-((2,4-Dichlorophenyl)ethynyl)azetidine-1-carbonyl)hexahydro-2H-pyrido[4,3-b][1,4]oxazin-3(4H)-one | BB85 | 408.3 [M + H]⁺ | A10 |
| 135 | (+)-(4aR,8aS)-6-[3-[2-(2-Chloro-4-fluorophenyl)ethynyl]azetidine-1-carbonyl]-4,4a,5,7,8,8a-hexahydropyrido[4,3-b][1,4]oxazin-3-one | BB86 | 392.2 [M + H]⁺ | A10 |

-continued

| Ex. | Systematic Name/Structure | Building block(s) | MS, m/z | Method |
|---|---|---|---|---|
| 136 | rac-(4aR,8aS)-6-[4-[N-methyl-4-(trifluoromethyl)anilino]piperidine-1-carbonyl]-4,4a,5,7,8,8a-hexahydropyrido[4,3-b][1,4]oxazin-3-one | BB92 | 413.2 [M + H]+ | A1 (ACN as solvent DIPEA as base) |
| 137 | rac-(4aR,8aS)-6-[3-[N-methyl-4-(trifluoromethyl)anilino]azetidine-1-carbonyl]-4,4a,5,7,8,8a-hexahydropyrido[4,3-b][1,4]oxazin-3-one | BB93 | 441.2 [M + H]+ | A1 (ACN as solvent DIPEA as base) |
| 139 | (4aR,8aS)-6-[3-[2-[2-Fluoro-6-(trifluoromethyl)phenyl]ethyl]azetidine-1-carbonyl]-4,4a,5,7,8,8a-hexahydropyrido[4,3-b][1,4]oxazin-3-one | BB95 | 430.4 [M + H]+ | A1 (ACN as solvent DIPEA as base) |
| 140 | (4aR,8aS)-6-[4-[(2-Chloro-4-fluorophenoxy)methyl]azepane-1-carbonyl]-4,4a,5,7,8,8a-hexahydropyrido[4,3-b][1,4]oxazin-3-one [Epimer A] | BB96 | 440.18 [M + H]+ | A3 followed by chiral SFC |

-continued

| Ex. | Systematic Name/Structure | Building block(s) | MS, m/z | Method |
|---|---|---|---|---|
| 141 | (4aR,8aS)-6-[4-[(2-Chloro-4-fluorophenoxy)methyl]azepane-1-carbonyl]-4,4a,5,7,8,8a-hexahydropyrido[4,3-b][1,4]oxazin-3-one [Epimer B] | BB96 | 440.18 [M + H]⁺ | A3 followed by chiral SFC |
| 142 | (4aR,8aS)-6-[4-[[4-(Trifluoromethyl)phenyl]methyl]azepane-1-carbonyl]-4,4a,5,7,8,8a-hexahydropyrido[4,3-b][1,4]oxazin-3-one | BB97 | 440.2 [M + H]⁺ | A3 |
| 143 | (4aR,8aS)-6-[3-[2-Chloro-4-(trifluoromethyl)phenyl]sulfanylazetidine-1-carbonyl]-4,4a,5,7,8,8a-hexahydropyrido[4,3-b][1,4]oxazin-3-one | BB98 and BB1a | 450.1 [M + H]⁺ | A3 |
| 144 | (4aR,8aS)-6-[3-[2-Chloro-4-(trifluoromethyl)phenyl]sulfonylazetidine-1-carbonyl]-4,4a,5,7,8,8a-hexahydropyrido[4,3-b][1,4]oxazin-3-one | BB99 and BB1a | 482.2 [M + H]⁺ | A3 |

| Ex. | Systematic Name/Structure | Building block(s) | MS, m/z | Method |
|---|---|---|---|---|
| 145 | (4aR,8aS)-6-[3-[2-Chloro-4-(trifluoromethyl)phenyl]sulfinylazetidine-1-carbonyl]-4,4a,5,7,8,8a-hexahydropyrido[4,3-b][1,4]oxazin-3-one (mixture of sulfoxide isomers) | BB100 and BB1a | 466.2 [M + H]$^+$ | A3 |
| 146 | (4aR,8aS)-6-[3-[2-Chloro-4-(trifluoromethyl)phenyl]sulfinylazetidine-1-carbonyl]-4,4a,5,7,8,8a-hexahydropyrido[4,3-b][1,4]oxazin-3-one (sulfoxide isomer A) | Example 145 | 466.2 [M + H]$^+$ | SFC, Chiralpak AD, 40% MeOH |
| 147 | (4aR,8aS)-6-[3-[2-Chloro-4-(trifluoromethyl)phenyl]sulfinylazetidine-1-carbonyl]-4,4a,5,7,8,8a-hexahydropyrido[4,3-b][1,4]oxazin-3-one (sulfoxide isomer B) | Example 145 | 466.2 [M + H]$^+$ | SFC, Chiralpak AD, 40% MeOH |
| 148 | (4aR,8aS)-6-[3-[[2-Chloro-4-(trifluoromethyl)phenyl]sulfanylmethyl]azetidine-1-carbonyl]-4,4a,5,7,8,8a-hexahydropyrido[4,3-b][1,4]oxazin-3-one | BB101 and BB1a | 464.1 [M + H]$^+$ | A3 |

| Ex. | Systematic Name/Structure | Building block(s) | MS, m/z | Method |
|---|---|---|---|---|
| 152 | (4aR,8aS)-6-[3-[[2-Chloro-4-(trifluoromethyl)phenyl]sulfonylmethyl]azetidine-1-carbonyl]-4,4a,5,7,8,8a-hexahydropyrido[4,3-b][1,4]oxazin-3-one | BB104 and BB1a | 496.1 [M + H]⁺ | A3 |
| 153 | (4aR,8aS)-6-[3-[[2-Chloro-4-(trifluoromethyl)phenyl]sulfinylmethyl]azetidine-1-carbonyl]-4,4a,5,7,8,8a-hexahydropyrido[4,3-b][1,4]oxazin-3-one (mixture of sulfoxide isomers) | BB105 and BB1a | 480.1 [M + H]⁺ | A3 |
| 154 | (4aR,8aS)-6-[3-[[2-Chloro-4-(trifluoromethyl)phenyl]sulfinylmethyl]azetidine-1-carbonyl]-4,4a,5,7,8,8a-hexahydropyrido[4,3-b][1,4]oxazin-3-one (sulfoxide isomer A) | Example 153 | 480.1 [M + H]⁺ | A3, then HPLC Reprosil Chiral NR, 60% heptane, 40% EtOH + NH₄Ac |
| 155 | (4aR,8aS)-6-[3-[[2-Chloro-4-(trifluoromethyl)phenyl]sulfinylmethyl]azetidine-1-carbonyl]-4,4a,5,7,8,8a-hexahydropyrido[4,3-b][1,4]oxazin-3-one (sulfoxide isomer B) | Example 153 | 480.1 [M + H]⁺ | A3, then HPLC Reprosil Chiral NR, 60% heptane, 40% EtOH + NH₄Ac |

-continued

| Ex. | Systematic Name/Structure | Building block(s) | MS, m/z | Method |
|---|---|---|---|---|
| 156 | (4aR,8aS)-6-[3-[[2-Fluoro-4-(trifluoromethyl)phenyl]methylsulfanyl]azetidine-1-carbonyl]-4,4a,5,7,8,8a-hexahydropyrido[4,3-b][1,4]oxazin-3-one | BB106 and BB1a | 448.1 [M + H]+ | A3 |
| 157 | (+)-(4aR,8aS)-6-(3-((2,6-Dichlorophenyl)ethynyl)azetidine-1-carbonyl)hexahydro-2H-pyrido[4,3-b][1,4]oxazin-3(4H)-one | BB107 | 408.2 [M + H]+ | A10 |
| 158 | (4aR,8aS)-6-[3-[2-[2-Fluoro-4-(trifluoromethyl)phenyl]ethynyl]azetidine-1-carbonyl]-4,4a,5,7,8,8a-hexahydropyrido[4,3-b][1,4]oxazin-3-one | BB108 | 426.3 [M + H]+ | A10 |
| 159 | (4aR,8aS)-6-(3-((2,6-Difluorophenyl)ethynyl)azetidine-1-carbonyl)hexahydro-2H-pyrido[4,3-b][1,4]oxazin-3(4H)-one | BB109 | 376.3 [M + H]+ | A10 |

-continued

| Ex. | Systematic Name/Structure | Building block(s) | MS, m/z | Method |
|---|---|---|---|---|
| 160 | (4aR,8aS)-6-(3-((3-Chloro-4-(trifluoromethyl)phenyl)ethynyl)azetidine-1-carbonyl)hexahydro-2H-pyrido[4,3-b][1,4]oxazin-3(4H)-one | BB110 | 442.3 [M + H]+ | A10 |
| 161 | (4aR,8aS)-6-(3-((2-Chloro-6-fluorophenyl)ethynyl)azetidine-1-carbonyl)hexahydro-2H-pyrido[4,3-b][1,4]oxazin-3(4H)-one | BB111 | 392.3 [M + H]+ | A10 |
| 162 | (4aR,8aS)-6-(3-((2-Chloro-4-cyclopropylphenyl)ethynyl)azetidine-1-carbonyl)hexahydro-2H-pyrido[4,3-b][1,4]oxazin-3(4H)-one | BB112 | 414.4 [M + H]+ | A10 |
| 163 | (4aR,8aS)-6-(3-((2-Methoxyphenyl)ethynyl)azetidine-1-carbonyl)hexahydro-2H-pyrido[4,3-b][1,4]oxazin-3(4H)-one | BB113 | 370.4 [M + H]+ | A10 |

| Ex. | Systematic Name/Structure | Building block(s) | MS, m/z | Method |
|---|---|---|---|---|
| 164 | (4aR,8aS)-6-[3-[2-[4-Chloro-2-(trifluoromethyl)phenyl]ethynyl]azetidine-1-carbonyl]-4,4a,5,7,8,8a-hexahydropyrido[4,3-b][1,4]oxazin-3-one | BB114 | 442.3 [M + H]+ | A10 |
| 165 | (4aR,8aS)-6-[3-[2-(3-Chlorophenyl)ethynyl]azetidine-1-carbonyl]-4,4a,5,7,8,8a-hexahydropyrido[4,3-b][1,4]oxazin-3-one | BB115 | 374.3 [M + H]+ | A10 |
| 166 | (4aR,8aS)-6-[3-[2-[4-(Trifluoromethoxy)phenyl]ethynyl]azetidine-1-carbonyl]-4,4a,5,7,8,8a-hexahydropyrido[4,3-b][1,4]oxazin-3-one | BB116 | 424.3 [M + H]+ | A10 |
| 167 | (4aR,8aS)-6-[3-[2-[4-(Trifluoromethyl)phenyl]ethynyl]azetidine-1-carbonyl]-4,4a,5,7,8,8a-hexahydropyrido[4,3-b][1,4]oxazin-3-one | BB117 | 408.4 [M + H]+ | A10 |

-continued

| Ex. | Systematic Name/Structure | Building block(s) | MS, m/z | Method |
|---|---|---|---|---|
| 168 | (4aR,8aS)-6-[3-[2-(3-Fluoro-2-methylphenyl)ethynyl]azetidine-1-carbonyl]-4,4a,5,7,8,8a-hexahydropyrido[4,3-b][1,4]oxazin-3-one | BB118 | 372.2 [M + H]+ | A10 |
| 169 | (4aR,8aS)-6-[3-[2-(2,6-Dimethylphenyl)ethynyl]azetidine-1-carbonyl]-4,4a,5,7,8,8a-hexahydropyrido[4,3-b][1,4]oxazin-3-one | BB119 | 368.4 [M + H]+ | A10 |
| 170 | (4aR,8aS)-6-[3-[2-[2-(Trifluoromethoxy)phenyl]ethynyl]azetidine-1-carbonyl]-4,4a,5,7,8,8a-hexahydropyrido[4,3-b][1,4]oxazin-3-one | BB120 | 424.3 [M + H]+ | A10 |
| 171 | (4aR,8aS)-6-[3-[2-(2-Bromophenyl)ethynyl]azetidine-1-carbonyl]-4,4a,5,7,8,8a-hexahydropyrido[4,3-b][1,4]oxazin-3-one | BB121 | 420.3 [M + H]+ | A10 |

-continued

| Ex. | Systematic Name/Structure | Building block(s) | MS, m/z | Method |
|---|---|---|---|---|
| 172 | (4aR,8aS)-6-(3-((2-Chloro-3-fluorophenyl)ethynyl)azetidine-1-carbonyl)hexahydro-2H-pyrido[4,3-b][1,4]oxazin-3(4H)-one | BB122 | 392.3 [M + H]+ | A10 |
| 173 | (4aR,8aS)-6-(3-o-Tolylethynyl)azetidine-1-carbonyl)hexahydro-2H-pyrido[4,3-b][1,4]oxazin-3(4H)-one | BB123 | 354.3 [M + H]+ | A10 |
| 174 | (4aR,8aS)-6-[3-[2-(4-Chloro-2-fluorophenyl)ethynyl]azetidine-1-carbonyl]-4,4a,5,7,8,8a-hexahydropyrido[4,3-b][1,4]oxazin-3-one | BB124 | 392.3 [M + H]+ | A10 |
| 175 | (4aR,8aS)-6-[3-[2-[2-(Difluoromethoxy)phenyl]ethynyl]azetidine-1-carbonyl]-4,4a,5,7,8,8a-hexahydropyrido[4,3-b][1,4]oxazin-3-one | BB125 | 406.3 [M + H]+ | A10 |

-continued

| Ex. | Systematic Name/Structure | Building block(s) | MS, m/z | Method |
|---|---|---|---|---|
| 176 | 2-[2-[1-[(4aR,8aS)-3-oxo-4,4a,5,7,8,8a-Hexahydropyrido[4,3-b][1,4]oxazine-6-carbonyl]azetidin-3-yl]ethynyl]-3-chlorobenzonitrile | BB126 | 399.3 [M + H]⁺ | A10 |
| 177 | (4aR,8aS)-6-[3-[2-[4-(Difluoromethoxy)phenyl]ethynyl]azetidine-1-carbonyl]-4,4a,5,7,8,8a-hexahydropyrido[4,3-b][1,4]oxazin-3-one | BB127 | 406.3 [M + H]⁺ | A10 |
| 178 | 1-[4-[2-[1-[(4aR,8aS)-3-Oxo-4,4a,5,7,8,8a-hexahydro[4,3-b][1,4]oxazine-6-carbonyl]azetidin-3-yl]ethynyl]phenyl]cyclopropane-1-carbonitrile | BB128 | 405.4 [M + H]⁺ | A10 |
| 179 | (4aR,8aS)-6-[3-[2-(4-Cyclopropylphenyl)ethynyl]azetidine-1-carbonyl]-4,4a,5,7,8,8a-hexahydropyrido[4,3-b][1,4]oxazin-3-one | BB129 | 380.4 [M + H]⁺ | A10 |

-continued

| Ex. | Systematic Name/Structure | Building block(s) | MS, m/z | Method |
|---|---|---|---|---|
| 180 | (4aR,8aS)-6-[3-[2-[4-(1-Hydroxycyclopropyl)phenyl]ethynyl]azetidine-1-carbonyl]-4,4a,5,7,8,8a-hexahydropyrido[4,3-b][1,4]oxazin-3-one | BB130 | 396.4 [M + H]+ | A10 |
| 181 | (4aR,8aS)-6-[3-[2-(3-Methoxyphenyl)ethynyl]azetidine-1-carbonyl]-4,4a,5,7,8,8a-hexahydropyrido[4,3-b][1,4]oxazin-3-one | BB131 | 370.3 [M + H]+ | A10 |
| 182 | (4aR,8aS)-6-[3-[2-[2-(Difluoromethyl)phenyl]ethynyl]azetidine-1-carbonyl]-4,4a,5,7,8,8a-hexahydropyrido[4,3-b][1,4]oxazin-3-one | BB132 | 390.3 [M + H]+ | A10 |
| 183 | (4aR,8aS)-6-[3-[2-(3-Methoxy-2-methylphenyl)ethynyl]azetidine-1-carbonyl]-4,4a,5,7,8,8a-hexahydropyrido[4,3-b][1,4]oxazin-3-one | BB133 | 384.3 [M + H]+ | A10 |

-continued

| Ex. | Systematic Name/Structure | Building block(s) | MS, m/z | Method |
|---|---|---|---|---|
| 184 | (4aR,8aS)-6-[3-[2-(2-Chloro-6-methylphenyl)ethynyl]azetidine-1-carbonyl]-4,4a,5,7,8,8a-hexahydropyrido[4,3-b][1,4]oxazin-3-one | BB134 | 388.3 [M + H]$^+$ | A10 |
| 185 | (4aR,8aS)-6-[3-[2-(2-Chloro-5-fluorophenyl)ethynyl]azetidine-1-carbonyl]-4,4a,5,7,8,8a-hexahydropyrido[4,3-b][1,4]oxazin-3-one | BB135 | 392.2 [M + H]$^+$ | A10 |
| 186 | (4aR,8aS)-6-[3-[2-(4-Methylsulfonylphenyl)ethynyl]azetidine-1-carbonyl]-4,4a,5,7,8,8a-hexahydropyrido[4,3-b][1,4]oxazin-3-one | BB136 | 418.3 [M + H]$^+$ | A10 |
| 187 | (4aR,8aS)-6-[3-[2-(5-Chlorothiophen-2-yl)ethynyl]azetidine-1-carbonyl]-4,4a,5,7,8,8a-hexahydropyrido[4,3-b][1,4]oxazin-3-one | BB137 | 380.2 [M + H]$^+$ | A10 |

| Ex. | Systematic Name/Structure | Building block(s) | MS, m/z | Method |
|---|---|---|---|---|
| 188 | (4aR,8aS)-6-[3-[2-(5-Chlorothiophen-3-yl)ethynyl]azetidine-1-carbonyl]-4,4a,5,7,8,8a-hexahydropyrido[4,3-b][1,4]oxazin-3-one | BB138 | 380.2 [M + H]⁺ | A10 |
| 189 | (4aR,8aS)-6-[3-[2-[2-Chloro-6-fluoro-4-(trifluoromethyl)phenyl]ethynyl]azetidine-1-carbonyl]-4,4a,5,7,8,8a-hexahydropyrido[4,3-b][1,4]oxazin-3-one | BB139 | 460.3 [M + H]⁺ | A10 |
| 190 | (4aR,8aS)-6-[3-[2-(2-Chlorophenyl)ethynyl]-3-hydroxyazetidine-1-carbonyl]-4,4a,5,7,8,8a-hexahydropyrido[4,3-b][1,4]oxazin-3-one | BB140 | 390.3 [M + H]⁺ | A10 |
| 191 | (4aR,8aS)-6-[3-[2-[2-(Methoxymethyl)phenyl]ethynyl]azetidine-1-carbonyl]-4,4a,5,7,8,8a-hexahydropyrido[4,3-b][1,4]oxazin-3-one | BB141 | 384.3 [M + H]⁺ | A10 |

-continued

| Ex. | Systematic Name/Structure | Building block(s) | MS, m/z | Method |
|---|---|---|---|---|
| 192 | (4aR,8aS)-6-(4-((2-(Trifluoromethyl)phenyl)ethynyl)piperidine-1-carbonyl)hexahydro-2H-pyrido[4,3-b][1,4]oxazin-3(4H)-one | BB143 | 436.4 [M + H]+ | A10 |
| 193 | (4aR,8aS)-6-(4-((2-Methoxyphenyl)ethynyl)piperidine-1-carbonyl)hexahydro-2H-pyrido[4,3-b][1,4]oxazin-3(4H)-one | BB144 | 398.4 [M + H]+ | A10 |
| 194 | (4aR,8aS)-6-(4-(o-Tolyethynyl)piperidine-1-carbonyl)hexahydro-2H-pyrido[4,3-b][1,4]oxazin-3(4H)-one | BB145 | 382.4 [M + H]+ | A10 |
| 195 | (4aR,8aS)-6-(4-((2,6-Dimethylphenyl)ethynyl)piperidine-1-carbonyl)hexahydro-2H-pyrido[4,3-b][1,4]oxazin-3(4H)-one | BB146 | 396.4 [M + H]+ | A10 |

-continued

| Ex. | Systematic Name/Structure | Building block(s) | MS, m/z | Method |
| --- | --- | --- | --- | --- |
| 196 | (4aR,8aS)-6-(4-((2,4-Dichlorophenyl)ethynyl)-4-methylpiperidine-1-carbonyl)hexahydro-2H-pyrido[4,3-b][1,4]oxazin-3(4H)-one | BB147 | 450.3 [M + H]$^+$ | A10 |
| 197 | (4aR,8aS)-6-(4-((2-Chloro-4-fluorophenyl)ethynyl)-4-methylpiperidine-1-carbonyl)hexahydro-2H-pyrido[4,3-b][1,4]oxazin-3(4H)-one | BB148 | 434.4 [M + H]$^+$ | A10 |
| 198 | (4aR,8aS)-6-[3-[2-(1-Hydroxycyclopentyl)ethynyl]azetidine-1-carbonyl]-4,4a,5,7,8,8a-hexahydropyrido[4,3-b][1,4]oxazin-3-one | BB149 | 330.3 [M − H$_2$O + H]$^+$ | A10 |
| 199 | (4aR,8aS)-6-[3-[2-(Cyclopenten-1-yl)ethynyl]azetidine-1-carbonyl]-4,4a,5,7,8,8a-hexahydropyrido[4,3-b][1,4]oxazin-3-one | BB149 (Elimination product isolated during synthesis of example 198) | 330.3 [M + H]$^+$ | A10 |

-continued

| Ex. | Systematic Name/Structure | Building block(s) | MS, m/z | Method |
|---|---|---|---|---|
| 200 | (4aR,8aS)-6-(3-((2-Chloro-4-(trifluoromethyl)phenyl)ethynyl)azetidine-1-carbonyl)hexahydro-2H-pyrido[4,3-b][1,4]oxazin-3(4H)-one | BB142 | 442.3 [M + H]+ | A10 |
| 201 | (4aR,8aS)-6-[4-[3-Pyrazol-1-yl-5-(trifluoromethyl)phenoxy]piperidine-1-carbonyl]-4,4a,5,7,8,8a-hexahydropyrido[4,3-b][1,4]oxazin-3-one | BB7a and BB98 | 494.2 [M + H]+ | A4 |
| 202 | (4aR,8aS)-6-[4-[[2-(2,2,2-Trifluoroethoxy)-4-(trifluoromethyl)phenyl]methyl]piperidine-1-carbonyl]-4,4a,5,7,8,8a-hexahydropyrido[4,3-b][1,4]oxazin-3-one | BB7a and BB99 | 524.2 [M + H]+ | A4 |
| 203 | (4aR,8aS)-6-[4-[3-(1,2,4-Triazol-1-yl)-5-(trifluoromethyl)phenoxy]piperidine-1-carbonyl]-4,4a,5,7,8,8a-hexahydropyrido[4,3-b][1,4]oxazin-3-one | BB7a and BB100 | 495.2 [M + H]+ | A4 |

-continued

| Ex. | Systematic Name/Structure | Building block(s) | MS, m/z | Method |
|---|---|---|---|---|
| 204 | (4aR,8aS)-6-[3-[4-Chloro-3-(trifluoromethyl)phenoxy]azetidine-1-carbonyl]-4,4a,5,7,8,8a-hexahydropyrido[4,3-b][1,4]oxazin-3-one | BB7a and BB101 | 434.1 [M + H]⁺ | A4 |
| 205 | (4aR,8aS)-6-[4-(4-Chloro-3-pyrazol-1-yl-phenoxy)piperidine-1-carbonyl]-4,4a,5,7,8,8a-hexahydropyrido[4,3-b][1,4]oxazin-3-one | BB7a and BB102 | 460.2 [M + H]⁺ | A4 |
| 206 | (4aR,8aS)-6-(4-(3-Morpholino-4-(trifluoromethyl)phenoxy)piperidine-1-carbonyl)hexahydro-2H-pyrido[4,3-b][1,4]oxazin-3(4H)-one | BB7a and BB103 | 513.3 [M + H]⁺ | A4 |
| 207 | (4aR,8aS)-6-[4-[4-Chloro-3-(1,2,4-triazol-1-yl)phenoxy]piperidine-1-carbonyl]-4,4a,5,7,8,8a-hexahydropyrido[4,3-b][1,4]oxazin-3-one | BB7a and BB104 | 461.2 [M + H]⁺ | A4 |

| Ex. | Systematic Name/Structure | Building block(s) | MS, m/z | Method |
|---|---|---|---|---|
| 208 | (4aR,8aS)-6-[4-[3-Cyclopropyl-4-(trifluoromethyl)phenoxy]piperidine-1-carbonyl]-4,4a,5,7,8,8a-hexahydropyrido[4,3-b][1,4]oxazin-3-one | BB7a and BB105 | 468.2 [M + H]⁺ | A4 |
| 209 | (4aR,8aS)-6-[4-[3-Pyrazol-1-yl-4-(trifluoromethyl)phenoxy]piperidine-1-carbonyl]-4,4a,5,7,8,8a-hexahydropyrido[4,3-b][1,4]oxazin-3-one | BB7a and BB106 | 494.3 [M + H]⁺ | A4 |
| 210 | (4aR,8aS)-6-[4-(4-Chlorophenoxy)piperidine-1-carbonyl]-4,4a,5,7,8,8a-hexahydropyrido[4,3-b][1,4]oxazin-3-one | BB7a and 4-(4-Chlorophenoxy)piperidine hydrochloride (CAS RN 63843-53-8) | 394.1 [M + H]⁺ | A4 |
| 211 | (4aR,8aS)-6-[4-[[2,6-Difluoro-4-(trifluoromethyl)phenyl]methyl]piperidine-1-carbonyl]-4,4a,5,7,8,8a-hexahydropyrido[4,3-b][1,4]oxazin-3-one | BB7a and BB107 | 462.2 [M + H]⁺ | A4 |

-continued

| Ex. | Systematic Name/Structure | Building block(s) | MS, m/z | Method |
|---|---|---|---|---|
| 212 | (4aR,8aS)-6-[4-[4-Chloro-3-(4-chlorophenyl)-2-fluoro-phenoxy]piperidine-1-carbonyl]-4,4a,5,7,8,8a-hexahydropyrido[4,3-b][1,4]oxazin-3-one | BB7a and BB108 | 522.2 [M + H]⁺ | A4 |
| 213 | (4aR,8aS)-6-[3-[2-Chloro-4-(trifluoromethyl)phenoxy]azetidine-1-carbonyl]-4,4a,5,7,8,8a-hexahydropyrido[4,3-b][1,4]oxazin-3-one | BB7a and BB109 | 434.1 [M + H]⁺ | A4 |
| 214 | (4aR,8aS)-6-[3-[[2-Fluoro-6-(trifluoromethyl)phenyl]methoxy]azetidine-1-carbonyl]-4,4a,5,7,8,8a-hexahydropyrido[4,3-b][1,4]oxazin-3-one | BB7a and BB110 | 432.1 [M + H]⁺ | A4 |
| 215 | (4aR,8aS)-6-[3-[2-(2-Fluoro-4-methyl-phenyl)ethyl]azetidine-1-carbonyl]-4,4a,5,7,8,8a-hexahydropyrido[4,3-b][1,4]oxazin-3-one | BB7a and BB111 | 376.0 [M + H]⁺ | A4 |

| Ex. | Systematic Name/Structure | Building block(s) | MS, m/z | Method |
|---|---|---|---|---|
| 216 | (4aR,8aS)-6-[3-[2-[4-Methoxy-2-(trifluoromethyl)phenyl]ethyl]azetidine-1-carbonyl]-4,4a,5,7,8,8a-hexahydropyrido[4,3-b][1,4]oxazin-3-one | BB7a and BB112 | 442.3 [M + H]+ | A4 |
| 217 | (4aR,8aS)-6-[3-[[4-Methyl-2-(trifluoromethyl)phenyl]methoxy]azetidine-1-carbonyl]-4,4a,5,7,8,8a-hexahydropyrido[4,3-b][1,4]oxazin-3-one | BB7a and BB113 | 428.3 [M + H]+ | A4 |
| 218 | (4aR,8aS)-6-[3-[2-[2-Methoxy-6-(trifluoromethyl)phenyl]ethyl]azetidine-1-carbonyl]-4,4a,5,7,8,8a-hexahydropyrido[4,3-b][1,4]oxazin-3-one | BB7a and BB114 | 442.1 [M + H]+ | A4 |
| 219 | (4aR,8aS)-6-[3-[2-[4-methyl-2-(trifluoromethyl)phenyl]ethyl]azetidine-1-carbonyl]-4,4a,5,7,8,8a-hexahydropyrido[4,3-b][1,4]oxazin-3-one | BB7a and BB115 | 426.1 [M + H]+ | A4 |

| Ex. | Systematic Name/Structure | Building block(s) | MS, m/z | Method |
|---|---|---|---|---|
| 220 | (4aR,8aS)-6-[3-[2-[2-Acetyl-4-(trifluoromethyl)phenyl]ethyl]azetidine-1-carbonyl]-4,4a,5,7,8,8a-hexahydropyrido[4,3-b][1,4]oxazin-3-one | BB7a and BB116 | 454.3 [M + H]⁺ | A4 |
| 221 | (4aR,8aS)-6-[3-[2-[2-Bromo-4-(trifluoromethyl)phenyl]ethyl]azetidine-1-carbonyl]-4,4a,5,7,8,8a-hexahydropyrido[4,3-b][1,4]oxazin-3-one | BB7a and BB117 | 491.0 [M + H]⁺ | A4 |
| 224 | (4aR,8aS)-6-[3-[(3,4-Dichlorophenyl)methoxy]azetidine-1-carbonyl]-4,4a,5,7,8,8a-hexahydropyrido[4,3-b][1,4]oxazin-3-one | BB170 and BB1a | 414.1 [M + H]⁺ | A3 |
| 225 | (4aR,8aS)-6-[3-[(2,5-Dichlorophenyl)methoxy]azetidine-1-carbonyl]-4,4a,5,7,8,8a-hexahydropyrido[4,3-b][1,4]oxazin-3-one | BB171 and BB1a | 414.1 [M + H]⁺ | A3 |

| Ex. | Systematic Name/Structure | Building block(s) | MS, m/z | Method |
|---|---|---|---|---|
| 226 | (4aR,8aS)-6-[3-[[3-(Trifluoromethoxy)phenyl]methoxy]azetidine-1-carbonyl]-4,4a,5,7,8,8a-hexahydropyrido[4,3-b][1,4]oxazin-3-one | BB173 and BB1a | 429.4 [M + H]⁺ | A3 |
| 227 | (4aR,8aS)-6-[2-Methyl-3-[[4-methyl-3-(trifluoromethyl)phenyl]methoxy]azetidine-1-carbonyl]-4,4a,5,7,8,8a-hexahydropyrido[4,3-b][1,4]oxazin-3-one (fraction A, mixture of 2 isomers) | BB173 and BB1a | 442.2 [M + H]⁺ | A3 Chiral HPLC (Reprosil Chiral NR, 60% n-heptane, 40% EtOH + NH₄Ac |
| 228 | (4aR,8aS)-6-[2-Methyl-3-[[4-methyl-3-(trifluoromethyl)phenyl]methoxy]azetidine-1-carbonyl]-4,4a,5,7,8,8a-hexahydropyrido[4,3-b][1,4]oxazin-3-one (fraction B, one isomer) | BB173 and BB1a | 442.2 [M + H]⁺ | A3 Chiral HPLC (Reprosil Chiral NR, 60% n-heptane, 40% EtOH + NH₄Ac |
| 229 | (4aR,8aS)-6-[2-Methyl-3-[[4-methyl-3-(trifluoromethyl)phenyl]methoxy]azetidine-1-carbonyl]-4,4a,5,7,8,8a-hexahydropyrido[4,3-b][1,4]oxazin-3-one (fraction C, one isomer) | BB173 and BB1a | 442.2 [M + H]⁺ | A3 Chiral HPLC (Reprosil Chiral NR, 60% n-heptane, 40% EtOH + NH₄Ac |

| Ex. | Systematic Name/Structure | Building block(s) | MS, m/z | Method |
|---|---|---|---|---|
| 230 | (4aR,8aS)-6-[3-[[5-(Trifluoromethyl)-2-pyridyl]oxymethyl]azetidine-1-carbonyl]-4,4a,5,7,8,8a-hexahydropyrido[4,3-b][1,4]oxazin-3-one | BB174 and BB1a | 415.2 [M + H]$^+$ | A3 |
| 231 | (4aR,8aS)-6-[rel-(3R,4R)-3-Methyl-4-[[5-methyl-6-(trifluoromethyl)-3-pyridyl]oxymethyl]piperidine-1-carbonyl]-4,4a,5,7,8,8a-hexahydropyrido[4,3-b][1,4]oxazin-3-one (piperidine subst. cis, isomer A) | BB175 and BB1a | 471.2 [M + H]$^+$ | A3 SFC: OD-H column, 20% EtOH |
| 232 | (4aR,8aS)-6-[rel-(3S,4S)-3-Methyl-4-[[5-methyl-6-(trifluoromethyl)-3-pyridyl]oxymethyl]piperidine-1-carbonyl]-4,4a,5,7,8,8a-hexahydropyrido[4,3-b][1,4]oxazin-3-one (piperidine subst. cis, isomer B) | BB175 and BB1a | 471.2 [M + H]$^+$ | A3 SFC: OD-H column, 20% EtOH |

| Ex. | Systematic Name/Structure | Building block(s) | MS, m/z | Method |
|---|---|---|---|---|
| 233 | (4aR,8aS)-6-[3-[[2-Fluoro-4-(trifluoromethyl)phenyl]methoxy]-2-methyl-azetidine-1-carbonyl]-4,4a,5,7,8,8a-hexahydropyrido[4,3-b][1,4]oxazin-3-one (mixture of 4 stereoisomers) | BB176 and BB1a | 464.2 [M + H]+ | A3 |
| 234 | (4aR,8aS)-6-[3-[[4,5-bis(Trifluoromethyl)-2-pyridyl]oxymethyl]azetidine-1-carbonyl]-4,4a,5,7,8,8a-hexahydropyrido[4,3-b][1,4]oxazin-3-one | BB177 and BB1a | 483.2 [M + H]+ | A3 |
| 235 | (4aR,8aS)-6-[3-[[2-Fluoro-4-(trifluoromethyl)phenyl]methoxymethyl]azetidine-1-carbonyl]-4,4a,5,7,8,8a-hexahydropyrido[4,3-b][1,4]oxazin-3-one | BB178 and BB1a | 464.1 [M + H]+ | A3 HPLC: YMC-Triart C18, 25-45-60-100% ACN in water |
| 236 | (4aR,8aS)-6-[3-[[2-Fluoro-4-(trifluoromethyl)phenyl]methoxy]-2-methyl-azetidine-1-carbonyl]-4,4a,5,7,8,8a-hexahydropyrido[4,3-b][1,4]oxazin-3-one (fraction A, mixture of 2 stereoisomers) | Example 233 | 464.4 [M + H]+ | Reprosil Chiral NR, 70% Heptan, 30% EtOH + NH4Ac |

-continued

| Ex. | Systematic Name/Structure | Building block(s) | MS, m/z | Method |
|---|---|---|---|---|
| 237 | (4aR,8aS)-6-[3-[[2-Fluoro-4-(trifluoromethyl)phenyl]methoxy]-2-methyl-azetidine-1-carbonyl]-4,4a,5,7,8,8a-hexahydropyrido[4,3-b][1,4]oxazin-3-one (fraction B, one stereoisomer) | Example 233 | 464.3 [M + H]+ | Reprosil Chiral NR, 70% Heptan, 30% EtOH + NH4Ac |
| 238 | (4aR,8aS)-6-[3-[[2-Fluoro-4-(trifluoromethyl)phenyl]methoxy]-2-methyl-azetidine-1-carbonyl]-4,4a,5,7,8,8a-hexahydropyrido[4,3-b][1,4]oxazin-3-one (fraction C, one stereoisomer) | Example 233 | 464.4 [M + H]+ | Reprosil Chiral NR, 70% n-heptane, 30% EtOH + NH4Ac |
| 239 | (4aR,8aS)-6-[3-[(4-Chloro-2-phenoxy-phenyl)methoxy]azetidine-1-carbonyl]-4,4a,5,7,8,8a-hexahydropyrido[4,3-b][1,4]oxazin-3-one | BB179 and BB1a | 472.2 [M + H]+ | A3 |

| Ex. | Systematic Name/Structure | Building block(s) | MS, m/z | Method |
| --- | --- | --- | --- | --- |
| 240 | (4aR,8aS)-6-[3-[[2-Fluoro-4-(pentafluoro-lambda6-sulfanyl)phenyl]methoxy]azetidine-1-carbonyl]-4,4a,5,7,8,8a-hexahydropyrido[4,3-b][1,4]oxazin-3-one | BB180 and BB1a | 490.1 [M + H]$^+$ | A3 |
| 241 | (4aR,8aS)-6-[3-[[1-(2,4-Dichlorophenyl)cyclopropyl]methoxy]azetidine-1-carbonyl]-4,4a,5,7,8,8a-hexahydropyrido[4,3-b][1,4]oxazin-3-one | BB181 and BB1a | 454.3 [M + H]$^+$ | A3 |
| 242 | (4aR,8aS)-6-[3-[[6-(4-Fluorophenoxy)-4-(trifluoromethyl)-2-pyridyl]methoxy]azetidine-1-carbonyl]-4,4a,5,7,8,8a-hexahydropyrido[4,3-b][1,4]oxazin-3-one | BB182 and BB1a | 525.3 [M + H]$^+$ | A3 |

| Ex. | Systematic Name/Structure | Building block(s) | MS, m/z | Method |
|---|---|---|---|---|
| 243 | (4aR,8aS)-6-[3-[[6-(4-Fluorophenoxy)-5-(trifluoromethyl)-2-pyridyl]methoxy]azetidine-1-carbonyl]-4,4a,5,7,8,8a-hexahydropyrido[4,3-b][1,4]oxazin-3-one | BB183 and BB1a | 525.3 [M + H]+ | A3 |
| 244 | (4aR,8aS)-6-[3-[[4-(4-Fluorophenyl)thiazol-2-yl]methoxy]azetidine-1-carbonyl]-4,4a,5,7,8,8a-hexahydropyrido[4,3-b][1,4]oxazin-3-one | BB184 and BB1a | 447.2 [M + H]+ | A3 |
| 245 | (4aR,8aS)-6-[3-[[2-Fluoro-4-(trifluoromethyl)phenyl]methoxy]-3-(trifluoromethyl)pyrrolidine-1-carbonyl]-4,4a,5,7,8,8a-hexahydropyrido[4,3-b][1,4]oxazin-3-one | BB185 and BB1a | 514.2 [M + H]+ | A3 |

| Ex. | Systematic Name/Structure | Building block(s) | MS, m/z | Method |
|---|---|---|---|---|
| 246 | (4aR,8aS)-6-[rac-(2R,3S)-3-[2-Bromo-5-(trifluoromethyl)phenoxy]-2-methyl-pyrrolidine-1-carbonyl]-4,4a,5,7,8,8a-hexahydropyrido[4,3-b][1,4]oxazin-3-one (mixture of two stereoisomers) | BB186 and BB1a | 508.1 [M + H]⁺ | A3 |
| 247 | (4aR,8aS)-6-[rel-(2R,3S)-3-[2-Bromo-5-(trifluoromethyl)phenoxy]-2-methyl-pyrrolidine-1-carbonyl]-4,4a,5,7,8,8a-hexahydropyrido[4,3-b][1,4]oxazin-3-one (fraction A, one stereoisomer) | Example 246 | 508.0 [M + H]⁺ | HPLC: Reprosil Chiral NR, 60% n-heptane, 40% EtOH + NH₄Ac |
| 248 | (4aR,8aS)-6-[rel-(2S,3S)-3-[2-Bromo-5-(trifluoromethyl)phenoxy]-2-methyl-pyrrolidine-1-carbonyl]-4,4a,5,7,8,8a-hexahydropyrido[4,3-b][1,4]oxazin-3-one (fraction B, one stereoisomer) | Example 246 | 508.0 [M + H]⁺ | HPLC: Reprosil Chiral NR, 60% n-heptane, 40% EtOH + NH₄Ac |
| 249 | (+)-(4aR,8aS)-6-[3-[[2,4-bis(Trifluoromethyl)phenyl]methoxy]azetidine-1-carbonyl]-4,4a,5,7,8,8a-hexahydropyrido[4,3-b][1,4]oxazin-3-one | BB7a and BB187 | 482.1 [M + H]⁺ | A10 |

| Ex. | Systematic Name/Structure | Building block(s) | MS, m/z | Method |
|---|---|---|---|---|
| 250 | (+)-(4aR,8aS)-6-(3-((2-Methyl-3-(trifluoromethyl)benzyl)oxy)azetidine-1-carbonyl)hexahydro-2H-pyrido[4,3-b][1,4]oxazin-3(4H)-one | BB7a and BB188 | 428.3 [M + H]$^+$ | A10 |
| 251 | (+)-(4aR,8aS)-6-(3-((4-Methyl-2-(trifluoromethoxy)benzyl)oxy)azetidine-1-carbonyl)hexahydro-2H-pyrido[4,3-b][1,4]oxazin-3(4H)-one | BB7a and BB189 | 444.2 [M + H]$^+$ | A10 |
| 252 | (4aR,8aS)-6-[2-Methyl-3-[[2-methyl-4-(trifluoromethoxy)phenyl]methoxy]azetidine-1-carbonyl]-4,4a,5,7,8,8a-hexahydropyrido[4,3-b][1,4]oxazin-3-one | BB7a and BB190 | 458.2 [M + H]$^+$ | A10 |
| 253 | (4aR,8aS)-6-[2-Methyl-3-[[2-methyl-3-(trifluoromethyl)phenyl]methoxy]azetidine-1-carbonyl]-4,4a,5,7,8,8a-hexahydropyrido[4,3-b][1,4]oxazin-3-one | BB7a and BB191 | 442.3 [M + H]$^+$ | A10 |
| 254 | (+)-(4aR,8aS)-6-[4-[2-Fluoro-4-(trifluoromethyl)phenoxy]piperidine-1-carbonyl]-4,4a,5,7,8,8a-hexahydropyrido[4,3-b][1,4]oxazin-3-one | BB7a and BB192 | 446.3 [M + H]$^+$ | A10 |

| Ex. | Systematic Name/Structure | Building block(s) | MS, m/z | Method |
|---|---|---|---|---|
| 255 | (+)-(4aR,8aS)-6-[4-[3-Chloro-4-(trifluoromethyl)phenoxy]piperidine-1-carbonyl]-4,4a,5,7,8,8a-hexahydropyrido[4,3-b][1,4]oxazin-3-one | BB7a and BB193 | 462.3 [M + H]$^+$ | A10 |
| 256 | (+)-(4aR,8aS)-6-[3-(4-Chloro-3-cyclopropylphenoxy)azetidine-1-carbonyl]-4,4a,5,7,8,8a-hexahydropyrido[4,3-b][1,4]oxazin-3-one | BB194 | 406.4 [M + H]$^+$ | A10 |
| 257 | (+)-(4aR,8aS)-6-[4-[2-Chloro-3-(trifluoromethyl)phenoxy]piperidine-1-carbonyl]-4,4a,5,7,8,8a-hexahydropyrido[4,3-b][1,4]oxazin-3-one | BB7a and BB195 | 462.3 [M + H]$^+$ | A10 |
| 258 | (+)-(4aR,8aS)-6-[3-(3-Bromo-2-chloro-phenoxy)azetidine-1-carbonyl]-4,4a,5,7,8,8a-hexahydropyrido[4,3-b][1,4]oxazin-3-one | BB7a and BB196 | 446.0 [M + H]$^+$ | A10 |
| 259 | (+)-(4aR,8aS)-6-[3-(2-Chloro-3-cyclopropyl-phenoxy)azetidine-1-carbonyl]-4,4a,5,7,8,8a-hexahydropyrido[4,3-b][1,4]oxazin-3-one | BB7a and BB197 | 406.4 [M + H]$^+$ | A10 |

-continued

| Ex. | Systematic Name/Structure | Building block(s) | MS, m/z | Method |
|---|---|---|---|---|
| 260 | (+)-(4aR,8aS)-6-[3-[3-Cyclopropyl-4-(trifluoromethyl)phenoxy]azetidine-1-carbonyl]-4,4a,5,7,8,8a-hexahydropyrido[4,3-b][1,4]oxazin-3-one | BB7a and BB199 | 440.1 [M + H]⁺ | A10 |
| 261 | (+)-(4aR,8aS)-6-[3-[3-Chloro-4-(trifluoromethyl)phenoxy]azetidine-1-carbonyl]-4,4a,5,7,8,8a-hexahydropyrido[4,3-b][1,4]oxazin-3-one | BB7a and BB200 | 434.1 [M + H]⁺ | A10 |
| 262 | (+)-5-[[1-[(4aR,8aS)-3-Oxo-4,4a,5,7,8,8a-hexahydropyrido[4,3-b][1,4]oxazine-6-carbonyl]-4-piperidyl]oxy]-2-(trifluoromethyl)benzonitrile | BB7a and BB202 | 453.4 [M + H]⁺ | A10 |
| 264 | (+)-(4aR,8aS)-6-[3-(3-Bromo-4-chlorophenoxy)azetidine-1-carbonyl]-4,4a,5,7,8,8a-hexahydropyrido[4,3-b][1,4]oxazin-3-one | BB7a and BB205 | 444.2 [M + H]⁺ | A10 |

| Ex. | Systematic Name/Structure | Building block(s) | MS, m/z | Method |
|---|---|---|---|---|
| 279 | (4aR,8aS)-6-[3-[2-[2-Fluoro-4-(trifluoromethyl)phenyl]ethyl]azetidine-1-carbonyl]-4,4a,5,7,8,8a-hexahydropyrido[4,3-b][1,4]oxazin-3-one | BB7a and BB206 | 430.2 [M + H]$^+$ | A4 ACN as solvent followed by prep-HPLC |
| 280 | (4aR,8aS)-6-[3-[[4-Fluoro-2-(trifluoromethyl)phenyl]methoxy]azetidine-1-carbonyl]-4,4a,5,7,8,8a-hexahydropyrido[4,3-b][1,4]oxazin-3-one | BB7a and BB207 | 432.2 [M + H]$^+$ | A4 ACN as solvent followed by prep-HPLC |
| 281 | (4aR,8aS)-6-[3-[2,2-Difluoro-2-[4-(trifluoromethyl)phenyl]ethyl]azetidine-1-carbonyl]-4,4a,5,7,8,8a-hexahydropyrido[4,3-b][1,4]oxazin-3-one | BB7a and BB208 | 448.3 [M + H]$^+$ | A4 ACN as solvent followed by prep-HPLC |
| 282 | (4aR,8aS)-6-[3-[[3-(Trifluoromethoxy)phenyl]methyl]azetidine-1-carbonyl]-4,4a,5,7,8,8a-hexahydropyrido[4,3-b][1,4]oxazin-3-one | BB7a and 3-(3-(Trifluoromethoxy)benzyl)azetidine hydrochloride (CAS RN 1354963-49-7) | 414.3 [M + H]$^+$ | A4 ACN as solvent followed by prep-HPLC |

| Ex. | Systematic Name/Structure | Building block(s) | MS, m/z | Method |
|---|---|---|---|---|
| 283 | (4aR,8aS)-6-[3-[2-Fluoro-5-(trifluoromethyl)phenoxy]pyrrolidine-1-carbonyl]-4,4a,5,7,8,8a-hexahydropyrido[4,3-b][1,4]oxazin-3-one | BB7a and BB209 | 432.2 [M + H]+ | A4 ACN as solvent followed by MPLC (n-heptane: EtOAc/EtOH 3/1 (70:30 to 10:90) |
| 284 | (4aR,8aS)-6-[3-[2-Chloro-5-(trifluoromethyl)phenoxy]pyrrolidine-1-carbonyl]-4,4a,5,7,8,8a-hexahydropyrido[4,3-b][1,4]oxazin-3-one | BB7a and BB210 | 448.2 [M + H]+ | A4 ACN as solvent followed by MPLC (n-heptane: EtOAc/EtOH 3/1 (70:30 to 10:90) |
| 285 | (4aR,8aS)-6-[(3R or 3S)-3-[2-Fluoro-5-(trifluoromethyl)phenoxy]pyrrolidine-1-carbonyl]-4,4a,5,7,8,8a-hexahydropyrido[4,3-b][1,4]oxazin-3-one | Example 283 | 432.2 [M + H]+ | B3 |
| 286 | (4aR,8aS)-6-[(3S or 3R)-3-[2-Fluoro-5-(trifluoromethyl)phenoxy]pyrrolidine-1-carbonyl]-4,4a,5,7,8,8a-hexahydropyrido[4,3-b][1,4]oxazin-3-one | Example 283 | 432.2 [M + H]+ | B3 |

| Ex. | Systematic Name/Structure | Building block(s) | MS, m/z | Method |
|---|---|---|---|---|
| 287 | | BB1a and BB211 | 374.2 [M + H]⁺ | A3 |
| 288 | (4aR,8aS)-6-(3-((3-Fluoro-4-(trifluoromethoxy)benzyl)oxy)azetidine-1-carbonyl)hexahydro-2H-pyrido[4,3-b][1,4-oxazin-3(4H)-one | BB7a and BB212 | 448.3 [M + H]⁺ | A4 |
| 289 | (4aR,8aS)-6-(3-((E)-2-Fluoro-6-(trifluoromethyl)styryl)azetidine-1-carbonyl)hexahydro-2H-pyrido[4,3-b][1,4]oxazin-3(4H)-one | BB1a and BB213 | 428.2 [M + H]⁺ | A3 |
| 290 | (4aR,8aS)-6-(3-((2,3-Dimethylbenzyl)oxy)azetidine-1-carbonyl)hexahydro-2H-pyrido[4,3-b][1,4]oxazin-3(4H)-one | BB7a and BB214 | 374.2 [M + H]⁺ | A4 (ACN as solvent) |

-continued

| Ex. | Systematic Name/Structure | Building block(s) | MS, m/z | Method |
|---|---|---|---|---|
| 291 | (4aR,8aS)-6-(3-((2,4-Dimethylbenzyl)oxy)azetidine-1-carbonyl)hexahydro-2H-pyrido[4,3-b][1,4]oxazin-3(4H)-one | BB7a and BB215 | 374.2 [M + H]$^+$ | A4 (ACN as solvent) |
| 292 | (4aR,8aS)-6-(3-((2-Methyl-4-(trifluoromethyl)benzyl)oxy)azetidine-1-carbonyl)hexahydro-2H-pyrido[4,3-b][1,4]oxazin-3(4H)-one | BB7a and BB 216 | 428.2 [M + H]$^+$ | A4 (ACN as solvent) |
| 293 | (4aR,8aS)-6-(3-(4-Hydroxy-2-(Trifluoromethyl)phenethyl)azetidine-1-carbonyl)hexahydro-2H-pyrido[4,3-b][1,4]oxazin-3(4H)-one | Example 216 | 427.2 [M + H]$^+$ | G |

193

-continued

| Ex. | Systematic Name/Structure | Building block(s) | MS, m/z | Method |
|---|---|---|---|---|
| 294 | (4aR,8aS)-6-[3-[[4-Methyl-3-(trifluoromethyl)phenyl]methoxy]azetidine-1-carbonyl]-4,4a,5,7,8,8a-hexahydropyrido[4,3-b][1,4]oxazin-3-one | BB217 | 428.2 [M + H]+ | A3 |
| 295 | (4aR,8aS)-6-(3-((2-Fluoro-6-(trifluoromethyl)benzyl)thio)azetidine-1-carbonyl)hexahydro-2H-pyrido[4,3-b][1,4]oxazin-3(4H)-one | BB1a and BB218 | 448.1 [M + H]+ | A3 |

Example 222

(4aR,8aS)-6-[3-[[6-Fluoro-4-(trifluoromethyl)-2-pyridyl]oxymethyl]azetidine-1-carbonyl]-4,4a,5,7,8,8a-hexahydropyrido[4,3-b][1,4]oxazin-3-one

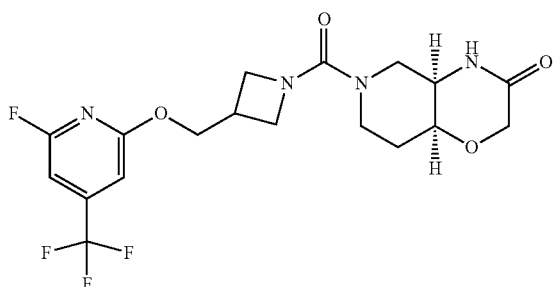

Step a) tert-Butyl 3-[[6-chloro-4-(trifluoromethyl)-2-pyridyl]oxymethyl]azetidine-1-carboxylate To a solution of tert-butyl 3-(hydroxymethyl)azetidine-1-carboxylate (CAS Nr. 142253-56-3) (2.60 g, 13.9 mmol) and 2,6-dichloro-4-(trifluoromethyl)pyridine (CAS Nr. 39890-98-7) (3.00 g, 13.9 mmol) in THF (60 mL) was added NaH (60%, 1.11 g, 27.8 mmol) and the mixture was stirred 3 h at 25° C. The solution was poured into sat. aq. NH4Cl (50 mL) and extracted with EtOAc (2×50 mL). The combined organic layers were concentrated under vacuum to give crude tert-butyl 3-[[6-chloro-4-(trifluoromethyl)-2-pyridyl]oxymethyl]azetidine-1-carboxylate (3.00 g, 59%) as colorless oil, which was used directly in the next step. LC-MS (ESI): m/z=367.1 [M+H]+.

Step b) 2-(Azetidin-3-ylmethoxy)-6-chloro-4-(trifluoromethyl)pyridine

A solution of trifluoroacetic acid (6.3 mL, 81.8 mmol, 10 eq) and tert-butyl 3-[[6-chloro-4-(trifluoromethyl)-2-pyridyl]oxymethyl]azetidine-1-carboxylate (3.00 g, 8.18 mmol) in DCM (30 mL) was stirred at 25° C. for 4 h. The solution was concentrated under vacuum to give a residue, which was purified by Prep-HPLC (HCl condition) to give 2-(azetidin-3-ylmethoxy)-6-chloro-4-(trifluoromethyl)pyridine (1.00 g, 46%) as white solid. LC-MS (ESI): m/z=267.0 [M+H]+.

Step c) (4aR,8aS)-6-[3-[[6-Chloro-4-(trifluoromethyl)-2-pyridyl]oxymethyl]azetidine-1-carbonyl]-4,4a,5,7,8,8a-hexahydropyrido[4,3-b][,4]oxazin-3-one A solution of 2-(azetidin-3-ylmethoxy)-6-chloro-4-(trifluoromethyl)pyridine (150 mg, 0.560 mmol), N,N-diisopropylethylamine (0.29 mL, 1.69 mmol) and 4-nitrophenyl (4aR,8aS)-3-oxohexahydro-2H-pyrido[4,3-b][1,4]oxazine-6(5H)-carboxylate (BB7a) (199 mg, 0.620 mmol) in ACN (5 mL) was stirred at 25° C. for 16 h. The solution was concentrated under vacuum to give a residue, which was purified by prep-HPLC (TFA conditions) to give (4aR,8aS)-6-[3-[[6-chloro-4-(trifluoromethyl)-2-pyridyl]oxymethyl]

azetidine-1-carbonyl]-4,4a,5,7,8,8a-hexahydropyrido[4,3-b]
[1,4]oxazin-3-one (100 mg, 40%) as colorless oil. LC-MS
(ESI): m/z=449.2 [M+H]⁺.

Step d) (4aR,8aS)-6-[3-[[6-Fluoro-4-(trifluorom-
ethyl)-2-pyridyl]oxymethyl]azetidine-1-carbonyl]-4,
4a,5,7,8,8a-hexahydropyrido[4,3-b][1,4]oxazin-3-
one A solution of (4aR,8aS)-6-[3-[[6-chloro-4-(trifluorom-
ethyl)-2-pyridyl]oxymethyl]azetidine-1-carbonyl]-4,4a,5,7,
8,8a-hexahydropyrido[4,3-b][1,4]oxazin-3-one (75 mg,
0.17 mmol) and cesium fluoride (101 mg, 0.670 mmol) in
DMSO (3 mL) was stirred at 80° C. for 16 h. The solution
was filtered and purified by prep-HPLC (TFA conditions) to
give (4aR,8aS)-6-[3-[[6-fluoro-4-(trifluoromethyl)-2-
pyridyl]oxymethyl]azetidine-1-carbonyl]-4,4a,5,7,8,8a-
hexahydropyrido[4,3-b][1,4]oxazin-3-one (22 mg, 28%) as
white solid. LC-MS (ESI): m/z=433.0 [M+H]⁺.

Example 223

(4aR,8aS)-6-[3-[[6-Fluoro-5-(trifluoromethyl)-2-
pyridyl]oxymethyl]azetidine-1-carbonyl]-4,4a,5,7,8,
8a-hexahydropyrido[4,3-b][1,4]oxazin-3-one

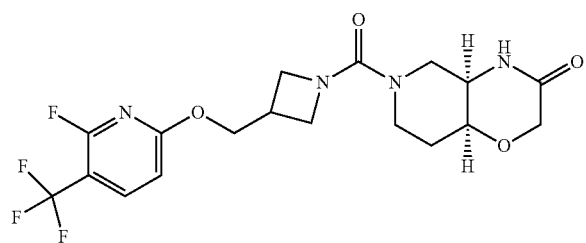 [SMILES: O=C1CO[C@H]2CCN(C(=O)N3CC(COc4ccc(C(F)(F)F)c(F)n4)C3)C[C@H]2N1]

Step a) tert-Butyl 3-[[6-chloro-5-(trifluoromethyl)-
2-pyridyl]oxymethyl]azetidine-1-carboxylate To a solution of tert-butyl 3-(hydroxymethyl)azetidine-1-
carboxylate (CAS Nr. 142253-56-3) (1.56 g, 8.33 mmol) in
THF (50 mL) was added NaH (60%, 741 mg, 18.5 mmol)
followed by 2,6-dichloro-3-(trifluoromethyl)pyridine (CAS
Nr. 55304-75-1) (2.00 g, 9.26 mmol). The resulting mixture
was stirred at 25° C. for 3 h. The solution was poured into
sat.aq. NH₄Cl (50 mL) and extracted with EtOAc (2×30
mL). The combined organic layers were concentrated under
vacuum to give a residue, which was purified by flash
column chromatography (petroleum ether:EtOAc=5:1) to
give tert-butyl 3-[[6-chloro-5-(trifluoromethyl)-2-pyridyl]
oxymethyl]azetidine-1-carboxylate (1.10 g, 32%) as color-
less oil. LC-MS (ESI): m/z=311.0 [M−56+H]⁺.

Step b) 6-(Azetidin-3-ylmethoxy)-2-chloro-3-(trif-
luoromethyl)pyridine

A solution of trifluoroacetic acid (0.37 mL, 4.8 mmol) and
tert-butyl 3-[[6-chloro-5-(trifluoromethyl)-2-pyridyl]oxym-
ethyl]azetidine-1-carboxylate (1.1 g, 3.0 mmol) in DCM (30
mL) was stirred at 25° C. for 4 h. The solution was
concentrated under vacuum to give a residue, which was
purified by Prep-HPLC (HCl condition) to give 6-(azetidin-
3-ylmethoxy)-2-chloro-3-(trifluoromethyl)pyridine (600
mg, 75%) as white solid. LC-MS (ESI): m/z=267.0 [M+H]⁺.

Step c) (4aR,8aS)-6-[3-[[6-Chloro-5-(trifluorom-
ethyl)-2-pyridyl]oxymethyl]azetidine-1-carbonyl]-4,
4a,5,7,8,8a-hexahydropyrido[4,3-b][1,4]oxazin-3-
one To a solution of 6-(azetidin-3-ylmethoxy)-2-chloro-3-(tri-
fluoromethyl)pyridine (100 mg, 0.380 mmol) and 4-nitrop-
henyl (4aR,8aS)-3-oxohexahydro-2H-pyrido[4,3-b][1,4]
oxazine-6(5H)-carboxylate (BB7a) (120 mg, 0.380 mmol)
in ACN (5 mL) was added N,N-diisopropylethylamine (0.13
mL, 0.75 mmol) with stirring at 25° C. The solution was
stirred at 25° C. for 16 h. The solution was concentrated
under vacuum to give a residue, which was purified by
Prep-HPLC (TFA conditions) to give (4aR,8aS)-6-[3-[[6-
chloro-5-(trifluoromethyl)-2-pyridyl]oxymethyl]azetidine-
1-carbonyl]-4,4a,5,7,8,8a-hexahydropyrido[4,3-b][1,4]
oxazin-3-one (76 mg, 45%) as white solid. LC-MS (ESI):
m/z=449.1 [M+H]⁺.

Step d) (4aR,8aS)-6-[3-[[6-Fluoro-5-(trifluorom-
ethyl)-2-pyridyl]oxymethyl]azetidine-1-carbonyl]-4,
4a,5,7,8,8a-hexahydropyrido[4,3-b][1,4]oxazin-3-
one A solution of (4aR,8aS)-6-[3-[[6-chloro-5-(trifluorom-
ethyl)-2-pyridyl]oxymethyl]azetidine-1-carbonyl]-4,4a,5,7,
8,8a-hexahydropyrido[4,3-b][1,4]oxazin-3-one (70 mg,
0.16 mmol) and cesium fluoride (95 mg, 0.62 mmol) in
DMSO (3 mL) was stirred at 60° C. for 24 h. The solution
was filtered and then purified by Prep-HPLC (TFA condi-
tions) to give (4aR,8aS)-6-[3-[[6-fluoro-5-(trifluoromethyl)-
2-pyridyl]oxymethyl]azetidine-1-carbonyl]-4,4a,5,7,8,8a-
hexahydropyrido[4,3-b][1,4]oxazin-3-one (38 mg, 49%) as
white solid. LC-MS (ESI): m/z=433.3 [M+H]⁺.

Synthesis of Building Blocks

BB1a & BB1b (+)-cis-4a,5,6,7,8,8a-Hexahydro-4H-pyrido[4,3-b][1,
4]oxazin-3-one and (−)-cis-4a,5,6,7,8,8a-Hexahydro-4H-pyrido[4,3-b][1,
4]oxazin-3-one The enantiomers of rac-(4aR,8aS)-hexahydro-2H-pyrido
[4,3-b][1,4]oxazin-3(4H)-one dihydrochloride (BB1, 500
mg, 2.18 mmol, ChemBridge Corporation) were separated
by preparative chiral HPLC (ReprosilChiral NR column)
using an isocratic mixture of EtOH (containing 0.05% of
NH₄OAc):n-heptane (30:70).
First eluting enantiomer: (+)-cis-4a,5,6,7,8,8a-Hexa-
hydro-4H-pyrido[4,3-b][1,4]oxazin-3-one (BB1a). Yellow
solid (0.150 g; 44.0%). MS (ESI): m/z=157.1 [M+H]⁺.
Second eluting enantiomer: (−)-cis-4a,5,6,7,8,8a-Hexa-
hydro-4H-pyrido[4,3-b][1,4]oxazin-3-one. (BB1b). Yellow
solid (0.152 g; 44.6%). MS (ESI): m/z=157.1 [M+H]⁺.

BB2

(4-Nitrophenyl) 4-[[4-(trifluoromethyl)phenyl]
methyl]piperidine-1-carboxylate

To a solution of 4-(4-(trifluoromethyl)benzyl)piperidine
(100 mg, 411 μmol, CAS RN 192990-03-7) in DCM (1 mL), TEA (83.2 mg, 115 µL, 822 µmol) was added. On cooling to 0° C., 4-nitrophenyl carbonochloridate (91.1 mg, 452 µmol, CAS RN 7693-46-1) was added, the reaction mixture was allowed to warm to RT and stirred for 18 hours. The reaction mixture was diluted with DCM and subsequently washed with H$_2$O and sat. aqueous NaHCO$_3$ solution. The combined organic layers were washed with brine, dried over Na$_2$SO$_4$, filtered and concentrated in vacuo. The crude material was purified by flash chromatography (silica 10 g, eluting with EtOAc/Heptane 0-50%), to afford title compound as a light yellow solid. (0.165 g; 98.3%). MS (ESI): m/z=409.3 [M+H]$^+$.

BB3 rac-(4aR,8aS)-6-(Piperazine-1-carbonyl)-4,4a,5,7,8,
8a-hexahydropyrido[4,3-b][1,4]oxazin-3-one To a mixture of rac-tert-butyl 4-((4aR,8aS)-3-oxooctahydro-2H-pyrido[4,3-b][1,4]oxazine-6-carbonyl)piperazine-1-carboxylate (100 mg, 271 µmol) in DCM (3 mL) was added TFA (155 mg, 105 µL, 1.36 mmol) and the mixture was stirred at RT for 15 h under an argon atmosphere. The reaction mixture was washed with a saturated aqueous NaHCO$_3$ solution. The H$_2$O layer was concentrated in vacuo to give a white solid which was triturated with DCM for 30 min. before it was filtered. The filtrate was concentrated to give a light yellow gum (70 mg, 96.1%). MS (ESI): m/z=269.3 [M+H]$^+$.

Step a) rac-tert-Butyl 4-((4aR,8aS)-3-oxooctahydro-
2H-pyrido[4,3-b][1,4]oxazine-6-carbonyl)piperazine-1-carboxylate To a mixture of triphosgene (1.29 g, 4.36 mmol) and Na$_2$CO$_3$ (1.98 g, 18.7 mmol) in THF (3 mL) at 0° C. were added dropwise a solution of tert-butyl piperazine-1-carboxylate (1.16 g, 6.23 mmol, CAS RN 57260-71-6) in THF (90 mL). The reaction mixture was stirred for 10 min. at 0° C., then allowed to warm up to RT and stirring was continued at RT for 5 h. The suspension was filtered off and the filtrate was concentrated in vacuo. The residue was dissolved in THF (40 mL) and added dropwise to a stirred suspension of rac-(4aR,8aS)-hexahydro-2H-pyrido[4,3-b][1,4]oxazin-3(4H)-one hydrochloride (1200 mg, 6.23 mmol, Chembridge Corporation) and DIPEA (4.83 g, 6.53 mL, 37.4 mmol) in THF (40 mL) at 0° C. After 30 min. at 0° C., the reaction mixture was allowed to warm up to RT, and stirred at RT for 15 h. The mixture was filtered and the filtrate concentrated in vacuo. The residue was diluted with DCM and washed with water, aq. NaHCO$_3$ solution and brine. The organic layer was dried over Na$_2$SO$_4$, filtered and concentrated to give a white solid (1.13 g, 58.6%). MS (ESI): m/z=313.3 [M+H]$^+$.

BB4

(4-Nitrophenyl)
4-(phenoxymethyl)piperidine-1-carboxylate

The compound was prepared in analogy to BB2 using 4-(phenoxymethyl)piperidine (CAS N63614-86-8) to afford title compound as a white solid which was used in the next step without further purification.

BB5

2-(4-Piperidylmethyl)-5-(trifluoromethyl)pyridine;
hydrochloride salt tert-Butyl 4-[[5-(trifluoromethyl)-2-pyridyl]methyl]piperidine-1-carboxylate (320 mg, 0.930 mmol) was dissolved in 4 M HCl in EtOAc (10.0 mL, 40 mmol) and the solution stirred at 20° C. for 2 h. The mixture was concentrated to yield the desired compound as light yellow solid (0.259, 94.8%). MS (ESI): m/z=245.0 [M–HCl+H]$^+$.

Step a) tert-Butyl 4-[[5-(trifluoromethyl)-2-pyridyl]
methyl]piperidine-1-carboxylate 2-Bromo-5-(trifluoromethyl)pyridine (500.0 mg, 2.21 mmol, CAS RN 1000773-62-5) was degassed before 9-BBN solution 0.5 M in THF (4.87 mL, 2.43 mmol, CAS RN 280-64-8) was added. The resulting solution was refluxed for 1 h. After cooling to RT, the solution was added to a solution of tert-butyl 4-methylenepiperidine-1-carboxylate (480.1 mg, 2.43 mmol, CAS RN 159635-49-1), [1,1'-bis(diphenylphosphino)ferrocene]palladium (II) chloride (161.89 mg, 0.220 mmol, CAS RN 72287-26-4) and K$_2$CO$_3$ (611.56 mg, 4.42 mmol) in DMF (5 mL) and water (0.5 mL). The resulting mixture was heated at 80° C. for 4 h. The mixture was cooled to RT and poured into water, the pH was adjusted to 11 with 10% aqueous NaOH and the mixture was extracted with EtOAc. The combined organic extracts were washed with brine, dried over Na$_2$SO$_4$, filtered, and evaporated to give a crude oil, which was purified by column chromatography (silica adsorbent; gradient of PE:EtOAc 10:1 then 5:1) to yield the desired compound as a light yellow oil (320 mg, 0.930 mmol, 42%). MS (ESI): m/z=289.0 [M-C$_4$H8+H]$^+$.

BB6 rac-(4aS,8aS)-Hexahydro-2H-pyrido[4,3-b][1,4]
oxazin-3(4H)-one rac-Benzyl (4aS,8aS)-3-oxohexahydro-2H-pyrido[4,3-b][1,4]oxazine-6(5H)-carboxylate (125 mg, 431 µmol) was dissolved in MeOH (5 mL). The reaction solution was degassed in vacuo and backfilled with argon. Pd—C (20 mg, 188 µmol) was added under an argon atmosphere. Argon was evacuated from the reaction mixture and backfilled with hydrogen. The reaction mixture was stirred at RT for 15 h under a hydrogen atmosphere. The reaction mixture was filtered through a syringe filter and concentrated in vacuo to afford the desired product as a white solid (62 mg, 92.2%). MS (ESI): m/z=157.098 [M+H]$^+$.

Step a) rac-Benzyl (3S,4S)-3-(2-chloroacetamido)-
4-hydroxypiperidine-1-carboxylate To a stirred suspension of rac-benzyl (3S,4S)-3-amino-4-hydroxypiperidine-1-carboxylate (317 mg, 1.27 mmol, synthesized according to patent US 2011/59118 A1) and sodium acetate (208 mg, 2.53 mmol, CAS RN 127-09-3) in a mixture of acetone (4 mL)/H$_2$O (0.5 mL) was added dropwise a solution of chloroacetyl chloride (150 mg, 107 µL, 1.33 mmol, CAS RN 79-04-9) in acetone (3 mL) between 0-5° C. After the addition the reaction mixture was stirred at RT for 1 h and subsequently evaporated to dryness giving a yellow gum. The crude product was purified by silica gel chromatography to afford the desired product as a yellow solid (385 mg, 93%). MS (ESI): m/z=325.2 [M−H]⁻.

Step b) rac-Benzyl (4aS,8aS)-3-oxohexahydro-2H-pyrido[4,3-b][1,4]oxazine-6(5H)-carboxylate To a stirred solution of rac-Benzyl (3S,4S)-3-(2-chloroacetamido)-4-hydroxypiperidine-1-carboxylate (385 mg, 1.18 mmol) in dry THF (4 mL) was added NaH (67.9 mg, 1.7 mmol) at 0° C. The mixture was allowed to reach RT and then stirred for 90 min under an argon atmosphere. $H_2O$ (5 mL) was added and stirring was continued for 10 min at RT. THF was removed in vacuo from the reaction mixture. The residue was treated with DCM and the organic phase was washed with $H_2O$ and brine, dried over $Na_2SO_4$, filtered and then concentrated in vacuo. The residue was purified by flash chromatography (12 g reversed phase column, gradient 0-100% ACN (0.1% FA) in water (0.1% FA) to afford the desired product as a white solid (133 mg, 38.9%). MS (ESI): m/z=291.3 $[M+H]^+$.

BB7a and BB7b

4-Nitrophenyl (4aR,8aS)-3-oxohexahydro-2H-pyrido[4,3-b][1,4]oxazine-6(5H)-carboxylate (BB7a)

and 4-nitrophenyl (4aS,8aR)-3-oxohexahydro-2H-pyrido[4,3-b][1,4]oxazine-6(5H)-carboxylate (BB7b)

To a suspension of rac-(4aR,8aS)-hexahydro-2H-pyrido[4,3-b][1,4]oxazin-3(4H)-one; dihydrochloride salt (4.5 g, 19.6 mmol, BB1) in dry DCM (125 mL) at 0° C. was added DIPEA (6.35 g, 8.58 mL, 49.1 mmol) followed by 4-nitrophenyl carbonochloridate (4.35 g, 21.6 mmol). The reaction mixture was stirred at 0° C. for 10 min and at RT for 2 h. The crude reaction was diluted with DCM and transferred into a separating funnel for extraction with sat. aq. $Na_2CO_3$ solution. The organic phase was collected and the aqueous phase was back-extracted with DCM. The combined organic phases were dried over $Na_2SO_4$ and evaporated down to dryness to yield 6.62 g of a crude racemic product (BB7) as a yellow solid. The crude material was directly submitted for a chiral SFC separation to yield enantiomer BB7b (2.72 g, second eluting enantiomer) as a yellow solid and enantiomer BB7a (3.25 g, first eluting enantiomer) as a light beige solid but contaminated with BB7b. A further SFC chiral separation was carried out to yield 2.71 g of BB7a. MS (ESI): m/z=322.2 $[M+H]^+$ for both enantiomers.

BB8

5-tert-Butyl-2-(4-piperidylmethyl)oxazole; hydrochloride salt

A solution of tert-butyl 4-[(5-tert-butyloxazol-2-yl)methyl]piperidine-1-carboxylate (167 mg, 518 µmol) in HCl 2M in diethyl ether (2.59 mL, 5.18 mmol) was stirred at RT for 5 h before another 1.29 mL (2.59 mmol) of HCl 2M in diethyl ether was added. The white suspension was stirred at RT overnight. The mixture was cooled down in an ice-bath, then filtered and washed with diethyl ether to get the desired compound as a colorless solid (0.126 g, 94.0%). MS (ESI): m/z=223.2 $[M+H]^+$.

Step a) (5-tert-Butyloxazol-2-yl)methyl-triphenyl-phosphonium bromide

To a solution of 2-(bromomethyl)-5-(tert-butyl)oxazole (600 mg, 2.75 mmol, CAS RN 1334492-54-4) in diethyl ether (5 mL) was added triphenylphosphine (722 mg, 2.75 mmol, CAS RN 603-35-0) and the mixture was stirred at RT for 64 h. The suspension was cooled down in an ice-bath and then filtered. The filter cake was washed a small volume of cold diethyl ether to give the desired compound as a light yellow solid (0.864 g, 65.4%). MS (ESI): m/z=400.2 $[M-Br+H]^+$.

Step b) tert-Butyl 4-[(5-tert-butyloxazol-2-yl)methylene]piperidine-1-carboxylate To an ice-cold suspension of (5-tert-butyloxazol-2-yl)methyl-triphenyl-phosphonium bromide (355 mg, 739 µmol) in THF (7 mL) was added potassium tert-butylate 1M solution in THF (738 µL, 738 µmol) and the reaction stirred at this temperature for 15 min. Then, tert-butyl 4-oxopiperidine-1-carboxylate (162 mg, 813 µmol, CAS RN 79099-07-3) was added to the turbid, orange solution and stirring was continued at 0° C. for another 15 min., then at RT for 42 h. The reaction mixture was poured on half-saturated aqueous $NH_4Cl$ solution and EtOAc and the layers were separated. The aqueous layer was extracted twice with EtOAc. The combined organic layers were dried over $MgSO_4$, filtered, treated with silica gel and evaporated. The compound was purified by silica gel chromatography on a 12 g column using an MPLC system eluting with a gradient of n-heptane:EtOAc (100:0 to 50:50) to provide the desired compound as a colorless solid (0.180 mg; 76.0%). MS (ESI): m/z=321.3 $[M+H]^+$.

Step c) tert-Butyl 4-[(5-tert-butyloxazol-2-yl)methyl]piperidine-1-carboxylate

To a solution of tert-butyl 4-[(5-tert-butyloxazol-2-yl)methylene]piperidine-1-carboxylate (180 mg, 562 µmol) in MeOH (1 mL) and EtOAc (1 mL) was added Pd/C 10% (17.9 mg, 16.9 µmol) and the suspension was stirred under a hydrogen atmosphere at 1.3 bar for 2 h. The suspension was filtered over a microfilter and the filtrate was evaporated to get the desired compound as a colorless oil (0.167 g; 92.2%). MS (ESI): m/z=323.3 $[M+H]^+$.

BB12

4-[(2-Chloro-4-fluoro-phenoxy)methyl]-4-methyl-piperidine; hydrochloride salt

To a solution of tert-butyl 4-[(2-chloro-4-fluoro-phenoxy)methyl]-4-methyl-piperidine-1-carboxylate (186 mg, 0.520 mmol) in EtOAc (1.5 mL) was added HCl in EtOAc (4 M, 1.5 mL) at 0° C. The solution was stirred at 15° C. for 3 h. The solution was concentrated under vacuum, then dried by lyophilization to give desired product as a white solid (64.0 mg, 0.220 mmol, 40.3% yield). MS (ESI): m/z=258 $[M+H]^+$.

Step a) tert-Butyl 4-methyl-4-(methylsulfonyloxymethyl)piperidine-1-carboxylate

To a solution of tert-butyl 4-(hydroxymethyl)-4-methyl-piperidine-1-carboxylate (500 mg, 2.14 mmol, CAS RN: 614730-97-1) in DCM (5 mL) was added $NEt_3$ (0.45 mL, 3.22 mmol) and methanesulfonyl chloride (0.23 mL, 3.0 mmol) at 0° C. The mixture was stirred at 0° C. for 2 h. The mixture was washed twice with water (3 mL each) at 0° C., and dried over $Na_2SO_4$. The organic layer was concentrated in vacuum to yield the desired compound as colorless oil (766 mg, 2.46 mmol, 98.5%) which was used in the next step without further purification. MS (ESI): m/z=256 [M−56+H]$^+$.

Step b) tert-Butyl 4-[(2-chloro-4-fluoro-phenoxy) methyl]-4-methyl-piperidine-1-carboxylate To a solution of tert-butyl 4-methyl-4-(methylsulfonyloxymethyl)piperidine-1-carboxylate (450 mg, 1.46 mmol) in DMF (5 mL) was added $Cs_2CO_3$ (620 mg, 1.9 mmol) and 2-chloro-4-fluorophenol (0.14 mL, 1.46 mmol) at 15° C. The mixture was heated to 90° C. and stirred for 16 h. The reaction solution was diluted by EtOAc (10 mL), washed twice with brine (10 mL each), and dried over $Na_2SO_4$. The organic layer was concentrated under vacuum to give the crude product (0.7 g) as light yellow oil. The crude product was purified by prep-HPLC and dried by lyophilization to give the desired compound as colorless solid (186 mg, 0.520 mmol, 35.5% yield). MS (ESI): m/z=302 [M−56+H]$^+$.

BB15

4-[(2-Chloro-4-fluoro-phenoxy)methyl]-4-fluoro-piperidine; hydrochloride salt

To a solution of tert-butyl 4-[(2-chloro-4-fluoro-phenoxy) methyl]-4-fluoro-piperidine-1-carboxylate (220 mg, 0.610 mmol) in EtOAc (2 mL) was added HCl/EtOAc (0.4 mL, 3.6 mmol) at 0° C. The solution was stirred at 15° C. for 2.5 h. The solution was concentrated in vacuo, then dried by lyophilization to give desired product as a white solid (136.7 mg, 75.4%).

Step a) tert-Butyl 4-fluoro-4-(methylsulfonyloxymethyl)piperidine-1-carboxylate

To a solution of tert-butyl 4-fluoro-4-(hydroxymethyl) piperidine-1-carboxylate (500 mg, 2.14 mmol) in DCM (5 mL) was added $NEt_3$ (0.45 mL, 3.22 mmol) and methanesulfonyl chloride (0.23 mL, 3 mmol) at 0° C. The mixture was stirred at 0° C. for 2 h. The mixture was washed twice with $H_2O$ (3 mL each) at 0° C., and dried over $Na_2SO_4$. The organic layer was concentrated to provide the compound as a colorless oil (766 mg, 98.5%) which was used in next step without further purification. MS (ESI): m/z=256 [M−56+H]$^+$.

Step b) tert-Butyl 4-[(2-chloro-4-fluoro-phenoxy) methyl]-4-fluoro-piperidine-1-carboxylate To a solution of tert-butyl 4-fluoro-4-(methylsulfonyloxymethyl)piperidine-1-carboxylate (383 mg, 1.23 mmol) in DMF (4 mL) was added $Cs_2CO_3$ (601 mg, 1.85 mmol), 2-chloro-4-fluorophenol (0.13 mL, 1.35 mmol) and 2-chloro-4-fluorophenol (0.13 mL, 1.35 mmol) at 15° C. The mixture was heated to 85° C. and stirred for 16 h. The mixture was extracted three times with EtOAc (5 mL each) at 15° C., the combined organic layers washed three times with brine (5 mL each), dried over $Na_2SO_4$, filtered and evaporated. The crude product was purified by preparative HPLC and dried by lyophilization to give the desired compound as light yellow oil (275 mg, 0.760 mmol, 61.5%). MS (ESI): m/z=306 [M−56+H]$^+$.

BB16 rac-(4aR,8aS)-6-(4-(Hydroxymethyl)piperidine-1-carbonyl)hexahydro-2H-pyrido[4,3-b][1,4]oxazin-3(4H)-one To a suspension of rac-(4aR,8aS)-hexahydro-2H-pyrido [4,3-b][1,4]oxazin-3(4H)-one; dihydrochloride salt (450 mg, 1.96 mmol, BB1) in dry DMF (9 mL) cooled down to 0° C. under an inert atmosphere was added DIPEA (787 mg, 1.06 mL, 6.09 mmol) and 4-nitrophenyl carbonochloridate (475 mg, 2.36 mmol). The reaction mixture was stirred at 0° C. for 30 min. Piperidin-4-ylmethanol (271 mg, 2.36 mmol, CAS RN 6457-49-4) and DIPEA (381 mg, 515 µL, 2.95 mmol) were added, and the reaction mixture was stirred at 100° C. for 14 h. Volatiles were removed in vacuo and the crude residue was purified by flash chromatography with a 24 g $SiO_2$ column using an eluent mixture of DCM and MeOH (5% to 25%). The crude product was submitted for SFC purification to yield the desired compound as a light yellow oil (338 mg). MS (ESI): m/z=298.3 [M+H]$^+$.

BB17

4,4-Difluoro-1-(piperidin-4-ylmethyl)piperidine; dihydrochloride salt

To a solution of tert-butyl 4-((4,4-difluoropiperidin-1-yl) methyl)piperidine-1-carboxylate (453 mg, 1.07 mmol) in dioxane (2.5 mL) was added HCl (4.0M solution in dioxane) (2.67 mL, 10.7 mmol) and the reaction mixture was stirred at room temperature for 14 h. Volatiles were removed in vacuo to yield the desired compound as a white solid (286 mg) which was used in the next step without further purification. MS (ESI): m/z=219.3 [M+H]$^+$.

Step a) tert-Butyl 4-((4,4-difluoropiperidin-1-yl) methyl)piperidine-1-carboxylate To a solution of a tert-butyl 4-(bromomethyl)piperidine-1-carboxylate (0.5 g, 1.8 mmol, CAS RN: 158407-04-6) in dry DMF (4 mL) was added 4,4-difluoropiperidine; dihydrochloride salt (425 mg, 2.7 mmol) and $Cs_2CO_3$ (1.17 g, 3.59 mmol). The reaction mixture was then stirred at 80° C. under microwave radiation for 60 min. Insolubles were removed by filtration, the filtrate was then concentrated in vacuo, and the obtained crude residue was suspended in DCM and filtered through a pad of Celite to give a crude yellow oil, which was purified by flash chromatography on a $SiO_2$ column, using an eluent mixture of n-heptane and EtOAc (10% to 60%) to yield the desired product as a colorless oil (453 mg). The compound was carried forwards to the next step without further purification. MS (ESI): m/z=319.3 [M+H]$^+$.

BB19

N-(azetidin-3-ylmethyl)-2,2,2-trifluoro-1-(4-(trifluoromethyl)phenyl)ethan-1-amine; bis(trifluoroacetate) salt To a solution of tert-butyl 3-(((2,2,2-trifluoro-1-(4-(trifluoromethyl)phenyl)ethyl)amino)methyl)azetidine-1-carboxylate (1 g, 2.42 mmol) in DCM (10 mL) was added TFA (5.53 g, 3.74 mL, 48.5 mmol). The resulting reaction mixture was stirred at RT for 1 h. The reaction mixture was concentrated in vacuo to yield the desired compound as colorless oil (1.29 g). MS (ESI): m/z=313.5 [M+H]$^+$.

Step a) tert-Butyl 3-(((2,2,2-trifluoro-1-(4-(trifluoromethyl)phenyl)ethyl)amino)methyl)azetidine-1-carboxylate To a dry flask with septum was added under nitrogen tert-butyl 3-(aminomethyl)azetidine-1-carboxylate (0.852 g, 4.57 mmol), triethylamine (1.39 g, 1.91 mL, 13.7 mmol), 2,2,2-trifluoro-1-(4-(trifluoromethyl)phenyl)ethan-1-one (1.11 g, 780 µL, 4.57 mmol), and dry DCM (28 mL). Titanium tetrachloride 1 M in DCM (2.29 mL, 2.29 mmol) was added via a syringe to the ice-cooled flask (exothermic). The reaction was stirred overnight at RT, then carefully quenched with a solution of NaCNBH$_3$ (862 mg, 13.7 mmol) in MeOH (8.79 g, 11.1 mL, 274 mmol) and stirred overnight. The reaction was basified with sat. NaHCO$_3$ solution. The obtained insoluble material was filtered off over celite. Extraction of the filtrate with DCM, the organic layers were combined, washed with brine, dried over Na$_2$SO$_4$ and concentrated. The crude material was purified by flash chromatography (silica gel, 50 g, 0% to 50% EtOAc in n-heptane to yield tert-butyl 3-(((2,2,2-trifluoro-1-(4-(trifluoromethyl)phenyl)ethyl)amino)methyl)azetidine-1-carboxylate which was used in the next step without further purification.

BB26

3-Chloro-4-(4-piperidylmethoxy)benzonitrile; hydrochloride salt

To a solution of tert-butyl 4-[(2-chloro-4-cyano-phenoxy)methyl]piperidine-1-carboxylate (300 mg, 0.860 mmol) in EtOAc (3 mL) was added HCl in EtOAc (4M, 2.0 mL) at 0° C. The solution was stirred at 15° C. for 3 h. The solution was concentrated in vacuo, then dried by lyophilization to give desired product as a white solid (238 mg, 0.830 mmol, 96% yield). MS (ESI): m/z=251 [M+H]$^+$.

Step a) tert-Butyl 4-(((methylsulfonyl)oxy)methyl)piperidine-1-carboxylate

To a solution of N-Boc-4-piperidinemethanol (10.0 g, 46.5 mmol, 1 eq) in DCM (200 mL) was added NEt$_3$ (7.04 g, 69.7 mmol), then methanesulfonyl chloride (3.95 mL, 51.1 mmol) was added at 0° C. and the mixture was stirred at 0° C. for 1 h. The mixture was poured into ice-water, the aqueous phase was extracted twice with DCM (50 mL each). The combined organic layers were washed with brine (50 mL), and concentrated under vacuum. The residue was directly used without any purification. MS (ESI): m/z=238.1 [M+H]$^+$.

Step b) tert-Butyl 4-[(2-chloro-4-cyano-phenoxy)methyl]piperidine-1-carboxylate

To a solution of tert-butyl 4-(methylsulfonyloxymethyl)piperidine-1-carboxylate (700 mg, 2.39 mmol) in DMF (7 mL) was added Cs$_2$CO$_3$ (855 mg, 2.62 mmol) and 3-chloro-4-hydroxybenzonitrile (0.25 mL, 2.39 mmol) at 15° C. The mixture was heated to 85° C. and stirred for 16 h. The reaction mixture was diluted with EtOAc (8 mL) at 15° C., washed three times with brine (8 mL each), the combined organic layers were dried over Na$_2$SO$_4$ and evaporated. The colorless residue (0.75 g) was purified by prep-HPLC and dried by lyophilization to give the desired product as a white solid (531 mg, 1.51 mmol, 53.4%). MS (ESI): m/z=295 [M−56+H]$^+$.

BB27

4-((4-(Trifluoromethyl)-1H-imidazol-1-yl)methyl)piperidine; hydrochloride salt

To a solution of tert-butyl 4-((4-(trifluoromethyl)-1H-imidazol-1-yl)methyl)piperidine-1-carboxylate (430 mg, 1.29 mmol) in dioxane (3 mL) was added HCl (4 M solution in dioxane; 3.22 mL, 12.9 mmol) and the reaction mixture was stirred at RT for 14 h. Volatiles were removed in vacuo to give the crude product (362 mg) which was used in the next step without further purification. MS (ESI): m/z=234.2 [M+H]$^+$.

Step a) tert-Butyl 4-((4-(trifluoromethyl)-1H-imidazol-1-yl)methyl)piperidine-1-carboxylate To a solution of a tert-butyl 4-(bromomethyl)piperidine-1-carboxylate (0.5 g, 1.8 mmol, CAS RN: 158407-04-6) in dry DMF (4 mL) was added 4-(trifluoromethyl)-1H-imidazole (293 mg, 2.16 mmol) and Cs$_2$CO$_3$ (1.17 g, 3.59 mmol). The reaction mixture was then stirred at 80° C. for 14 h. Insolubles were removed by filtration, and the filtrate was concentrated in vacuo. The crude residue was suspended in DCM and filtered through a pad of Celite to give a yellow oil, which was purified by flash chromatography with a SiO$_2$ column, using an eluent mixture of n-heptane and EtOAc (10% to 90%). This yielded the first fraction (301 mg) of the desired product as a colorless oil, and a second fraction (261 mg) of a mixture of the desired product with impurities. The second fraction was submitted for SFC purification, and the purified product was combined with the first fraction to yield 430 mg of the desired product as a colorless oil. MS (ESI): m/z=334.2 [M+H]$^+$.

BB29

3-((2-Chloro-4-(trifluoromethyl)phenoxy)methyl)azetidine

Trifluoroacetic acid (2 g, 1.35 mL, 17.5 mmol) was added to a solution of tert-butyl 3-((2-chloro-4-(trifluoromethyl)phenoxy)methyl)azetidine-1-carboxylate (320 mg, 875 µmol) in DCM (4.37 mL) and the solution was stirred at RT for 2 h. The solvent was removed under reduced pressure and the resulting pale oil (470 mg) was diluted with EtOAc and washed with aq. Na$_2$CO$_3$ solution. The aqueous phase was extracted three times with EtOAc, and the combined organic layers were washed with brine, dried over Na$_2$SO$_4$ and concentrated under reduced pressure to afford the compound as a yellow oil (259 mg, 877 µmol). MS (ESI): m/z=266.1 [M+H]$^+$.

Step a) tert-Butyl 3-((2-chloro-4-(trifluoromethyl)phenoxy)methyl)azetidine-1-carboxylate To a solution of 2-chloro-4-(trifluoromethyl)phenol (525 mg, 357 µL, 2.67 mmol), tert-butyl 3-(hydroxymethyl)azetidine-1-carboxylate (500 mg, 2.67 mmol, CAS RN: 142253-56-3) and triphenylphosphine (770 mg, 2.94 mmol) in DCM (13.4 mL) was added DIAD (594 mg, 571 µL, 2.94 mmol) dropwise and the reaction was stirred at RT for 17 h.

The reaction mixture was quenched by addition of sat. aq. NaHCO$_3$ solution (20 mL). The phases were separated and the aq. phase was extracted with DCM twice. The combined organic layers were dried over Na$_2$SO$_4$ and concentrated to dryness. The residue was dissolved in EtOH (7 mL) and a homogeneous solution of zinc chloride (218 mg, 1.6 mmol) in EtOH (2 mL, 0.5 M) was added. The mixture was stirred for 30 min during which a white solid precipitated. The white solid was filtered off and washed with EtOH. The filtrate was concentrated to give a yellow oil with a white precipitate. The crude was immobilized on Isolute and purified by column chromatography (40 g, 0 to 30% EtOAc in heptanes) to afford the title compound as a white solid (764.6 mg, 1.99 mmol, 74.4%). MS (ESI): m/z=310.1[M−56+H]$^+$.

BB30

N-benzyl-N-(2-hydroxyethyl)piperidine-4-carboxamide hydrochloride

To a solution of tert-butyl 4-(benzyl(2-hydroxyethyl)carbamoyl)piperidine-1-carboxylate (0.080 g, 221 μmol) in DCM (1 mL) was added HCl 2 M in diethyl ether (1.1 mL, 2.21 mmol). The resultant reaction mixture was stirred at RT for 1 h and then concentrated under vacuum at 22° C. to yield the desired compound as a colorless oil (63 mg) (BB30). MS (ESI): m/z=263.18 [M+H]$^+$.

Step a) tert-Butyl 4-(benzyl(2-hydroxyethyl)carbamoyl)piperidine-1-carboxylate

In a 10 mL glasstube, to 1-(tert-butoxycarbonyl)piperidine-4-carboxylic acid (0.1 g, 436 μmol) in DMF (2 mL) was added 2-(benzylamino)ethan-1-ol (72.5 mg, 480 μmol), DIPEA (169 mg, 229 μL, 1.31 mmol) and HATU (182 mg, 480 μmol), stirred at RT for 1 h and extracted with H$_2$O/DCM. The crude material was purified by flash chromatography (silica gel, 20 g, 50% to 100% EtOAc in n-heptane) to yield the compound as a light yellow oil (156 mg).

BB31

N-benzylpiperidine-4-carboxamide hydrochloride tert-Butyl 4-(benzylcarbamoyl)piperidine-1-carboxylate (0.138 g, 433 μmol) was dissolved in DCM (1 mL) and HCl 2M in diethyl ether (2.17 mL, 4.33 mmol) was added. The reaction mixture was stirred for 2 h. The residue was concentrated in vacuo to yield the compound (108 mg) as a colorless oil. MS (ESI): m/z=219.15 [M+H]$^+$.

Step a) tert-Butyl 4-(benzylcarbamoyl)piperidine-1-carboxylate

In a 10 mL glasstube, to 1-(tert-butoxycarbonyl)piperidine-4-carboxylic acid (0.1 g, 436 μmol) in DMF (2 mL) was added phenylmethanamine (51.4 mg, 52.4 μL, 480 μmol), DIPEA (169 mg, 229 μL, 1.31 mmol) and HATU (182 mg, 480 μmol), stirred at RT for 2 h and extracted with H$_2$O/DCM. The crude material was purified by flash chromatography (silica gel, 20 g, 50% to 100% EtOAc in n-heptane) to yield the compound as a colorless oil (0.138 g).

BB32

4-((4-(tert-Butyl)-1H-pyrazol-1-yl)methyl)piperidine; hydrochloride salt

To a solution of tert-butyl 4-((4-(tert-butyl)-1H-pyrazol-1-yl)methyl)piperidine-1-carboxylate (100 mg, 311 μmol) in dioxane (1 mL) was added HCl (4.0M solution in dioxane; 1.17 mL, 4.67 mmol) and the reaction mixture was stirred at RT for 14 h. Volatiles were removed in vacuo to give 84 mg of a crude product which was used in the next step without further purification. MS (ESI): m/z=222.3 [M+H]$^+$.

Step a) tert-Butyl 4-((4-(tert-butyl)-1H-pyrazol-1-yl)methyl)piperidine-1-carboxylate To a solution of a tert-butyl 4-(bromomethyl)piperidine-1-carboxylate (0.5 g, 1.8 mmol, CAS RN 158407-04-6) in dry DMF (4 mL) was added 4-(tert-butyl)-1H-pyrazole (268 mg, 2.16 mmol) and NaH (86.3 mg, 2.16 mmol). The reaction mixture was stirred at 80° C. for 14 h. The reaction was quenched by addition of few drops of sat. aq. NH$_4$Cl solution, and transferred into a separating funnel for partitioning between DCM and sat. aq. NaHCO$_3$ solution. The organic phase was collected and the aqueous phase was back-extracted with DCM. The combined organic phases were dried over Na$_2$SO$_4$ and evaporated down to dryness. The crude material was purified by flash chromatography with a SiO$_2$ column, eluting with a mixture of n-heptane and EtOAc (5% to 60%) to yield the desired compound as a colorless oil (102 mg). MS (ESI): m/z=322.3 [M+H]$^+$.

BB33

(2R,4aR,8aS)-2-methyl-4a,5,6,7,8,8a-hexahydro-4H-pyrido[4,3-b][1,4]oxazin-3-one

To a solution of 6-benzyl-2-methyl-5,6,7,8-tetrahydro-2H-pyrido[4,3-b][1,4]oxazin-3(4H)-one (Isomer A, 1.10 g, 4.26 mmol) in EtOAc (16 mL) and MeOH (16 mL) was added under argon Pd—C (227 mg, 213 μmol) and the suspension was stirred under a hydrogen atmosphere (balloon) at 1 bar for 24 h. The suspension was filtered over a microglass filter and washed with 20 mL EtOAc under inert gas. The filtrate was evaporated to give BB33 as a colorless solid (715 mg). MS (ESI): m/z=170.8 [M+H]$^+$. Note: Only the single enantiomer formed during the reduction.

Step a) 2-Methyl-4H-pyrido[4,3-b][1,4]oxazin-3-one

To a solution of 3-aminopyridin-4-ol (2.5 g, 22.7 mmol) in DMF (100 mL) was added dropwise 2-chloropropanoyl chloride (3.03 g, 2.31 mL, 23.8 mmol) and the mixture was stirred at RT for 30 min. After addition of K$_2$CO$_3$ (7.84 g, 56.8 mmol), the suspension was heated to 100° C. (oil bath) for 20 h. The DMF was removed in vacuo, then 100 mL EtOAc were added and stirred at RT for 10 min, and it was washed with 50 mL H$_2$O, extracted 3 times with EtOAc. The organic phases were combined, dried with MgSO$_4$ and concentrated under vacuo to yield 3.72 g of 2-methyl-4H-pyrido[4,3-b][1,4]oxazin-3-one which was used in the next step without further purification.

Step b) 6-Benzyl-2-methyl-3-oxo-3,4-dihydro-2H-pyrido[4,3-b][1,4]oxazin-6-ium bromide A suspension of 2-methyl-2H-pyrido[4,3-b][1,4]oxazin-3(4H)-one (3.72 g, 22.7 mmol) in DCM (32 mL) and MeOH (8 mL) was treated with (bromomethyl)benzene (4.65 g, 3.23 mL, 27.2 mmol) and the mixture was stirred at RT for 60 h. A suspension formed, which was cooled down to 0° C., 20 mL n-hexane were added and then the precipitate was filtered. The residue was washed with 15 mL of cold DCM/n-hexan to yield the compound as an off-white solid (5.2 g). MS (ESI): m/z=255 [M+H]$^+$.

Step c) 6-Benzyl-2-methyl-5,6,7,8-tetrahydro-2H-pyrido[4,3-b][1,4]oxazin-3(4H)-one To a suspension of 6-benzyl-2-methyl-3-oxo-3,4-dihydro-2H-pyrido[4,3-b][1,4]oxazin-6-ium bromide (5.2 g, 15.5 mmol) in EtOH (38 mL) was added in portions NaBH$_4$ (763 mg, 20.2 mmol) (exothermic, 22° C. to 30° C., yellow suspension). After the exothermic reaction faded out the mixture was stirred at room temperature for 3 h, then at 60° C. for 1 h and at 22° C. for 1 h. The reaction mixture was evaporated, partitioned between H$_2$O and EtOAc and the layers were separated. The aqueous layer was extracted once with EtOAc. The organic layers were washed twice with H$_2$O, dried over MgSO$_4$, filtered, treated with silica gel and evaporated. The compound was purified by silica gel chromatography on a 120 g column using an MPLC system eluting with a gradient of n-heptane:EtOAc (50 to 100 in 30 min.) to provide the compound as a light yellow solid (2.48 g) which could be used in the following step without further purification.

Step d) 6-Benzyl-2-methyl-5,6,7,8-tetrahydro-2H-pyrido[4,3-b][1,4]oxazin-3(4H)-one The enantiomers were separated by preparative chiral HPLC (Chiralcel OD column) using an isocratic mixture of EtOH (containing 0.05% of NH$_4$OAc):n-heptane (10:90). The fractions were evaporated to provide the desired compounds as light yellow solids (Isomer A 1.17 g, Isomer B 1.10 g).

BB34

N-(azetidin-3-ylmethyl)-2,2,2-trifluoro-1-(3-(trifluoromethyl)phenyl)ethan-1-amine In a 100 mL two-necked flask, benzyl 3-(((2,2,2-trifluoro-1-(3-(trifluoromethyl)phenyl)ethyl)amino)methyl)azetidine-1-carboxylate (0.913 g, 2.05 mmol) was dissolved in a mixture of THF (5 mL) and MeOH (5 mL). Pd/C 10% (109 mg, 102 µmol) was added under argon. The flask was purged and backfilled with H$_2$ gas (3 times). The reaction mixture was then stirred at 25° C. for 4 h. The suspension was filtered over decalite, concentrated and the resulting title compound (611 mg, colorless oil) used directly for the next step. MS (ESI): m/z=313.4 [M+H]$^+$.

Step a) Benzyl 3-(((2,2,2-trifluoro-1-(3-(trifluoromethyl)phenyl)ethyl)amino)methyl)azetidine-1-carboxylate To a dry flask with septum was added benzyl 3-(aminomethyl)azetidine-1-carboxylate (0.5 g, 2.27 mmol), NEt$_3$ (689 mg, 949 µL, 6.81 mmol), 2,2,2-trifluoro-1-(3-(trifluoromethyl)phenyl)ethan-1-one (554 mg, 391 µL, 2.27 mmol), and dry DCM (15 mL). Titanium tetrachloride 1M in DCM (1.13 mL, 1.13 mmol) was added via a syringe and the flask was cooled in an ice bath (exothermic). The reaction was stirred at RT overnight, carefully quenched with a solution of NaCNBH$_3$ (428 mg, 6.81 mmol) in MeOH (4.36 g, 5.51 mL, 136 mmol) and acetic acid (0.1 mL) and stirred at RT overnight. The reaction was basified with sat. aq. NaHCO$_3$ solution and the insoluble material obtained was filtered away over celite. The filtrate was extracted with DCM. The organic layers were combined, washed with brine, dried over Na$_2$SO$_4$ and concentrated in vacuo. The crude material was purified by flash chromatography (silica gel, 50 g, 0% to 50% EtOAc in n-heptane) to yield the desired compound as a colorless oil (913 mg). MS (ESI): m/z=447.2 [M+H]$^+$.

BB35

N-(azetidin-3-ylmethyl)-1-(2,4-dichlorophenyl)-2,2,2-trifluoroethan-1-amine

In a 100 mL two-necked flask, benzyl 3-(((1-(2,4-dichlorophenyl)-2,2,2-trifluoroethyl)amino)methyl)azetidine-1-carboxylate (0.660 g, 1.48 mmol) was dissolved in EtOAc (20 mL) to give a colorless solution. Pd/C 10% (78.5 mg, 73.8 µmol) was added under argon. The flask was purged and backfilled with H$_2$ gas (3 times). The reaction mixture was stirred at 25° C. for 4 h. LC-MS showed a mixture of the title product N-(azetidin-3-ylmethyl)-1-(2,4-dichlorophenyl)-2,2,2-trifluoroethan-1-amine together with the dehalogenated side-products N-(azetidin-3-ylmethyl)-1-(2-chlorophenyl)-2,2,2-trifluoroethan-1-amine and N-(azetidin-3-ylmethyl)-1-phenyl-2,2,2-trifluoroethan-1-amine. The reaction mixture was filtered over decalite, concentrated in vacuo and used directly for the next step.

Step a) Benzyl 3-[[[1-(2,4-dichlorophenyl)-2,2,2-trifluoro-ethylidene]amino]methyl]azetidine-1-carboxylate To a dry flask with septum was added under nitrogen benzyl 3-(aminomethyl)azetidine-1-carboxylate (0.500 g, 2.27 mmol, CAS RN 1016731-24-0), NEt$_3$ (689 mg, 949 µL, 6.81 mmol), 1-(2,4-dichlorophenyl)-2,2,2-trifluoroethan-1-one (556 mg, 2.27 mmol, and dry DCM (16.4 mL). Titanium tetrachloride (1 M solution in DCM; 1.13 mL, 1.13 mmol) was added via a syringe to the ice-cooled flask (exothermic). The reaction was stirred at RT overnight, carefully quenched with a solution of NaCNBH$_3$ (428 mg, 6.81 mmol) in MeOH (4.36 g, 5.51 mL, 136 mmol) and stirred for 6 h. LCMS indicated the reaction stopped at the imine.

The reaction was basified with sat. NaHCO$_3$. The obtained insoluble material was filtered over celite and the filtrate was extracted with DCM. The organic layers were combined, washed with brine, dried over Na$_2$SO$_4$ and concentrated. The crude material was purified by flash chromatography (silica gel, 50 g, 0% to 50% EtOAc in n-heptane) to give the desired compound as a colorless oil (1 g).

Step b) Benzyl 3-(((1-(2,4-dichlorophenyl)-2,2,2-trifluoroethyl)amino)methyl)azetidine-1-carboxylate In a 25 mL two-necked flask, benzyl 3-[[[1-(2,4-dichlorophenyl)-2,2,2-trifluoro-ethylidene]amino]methyl]azetidine-1-carboxylate (1 g, 2.25 mmol) was dissolved in THF (10 mL) and MeOH (1 mL) to give a colorless solution. Acetic acid (135 mg, 129 µL, 2.25 mmol) and NaCNBH$_3$ (423 mg, 6.74 mmol) were added. The reaction mixture was stirred at 25° C. for 6 h. The reaction was basified with sat. NaHCO$_3$. The obtained insoluble material was filtered over celite and the filtrate was extracted with DCM. The organic layers were combined, washed with brine, dried over Na$_2$SO$_4$ and concentrated. The crude material was purified by flash chromatography (silica gel, 50 g, 0% to 50% EtOAc in heptane) to afford the title compound as a colorless oil (660 mg) which used in the next step without further purification.

BB36 cis-4-((2-Chloro-4-fluorophenoxy)methyl)-3-methylpiperidine; hydrochloride salt tert-Butyl cis-4-((2-chloro-4-fluorophenoxy)methyl)-3-methylpiperidine-1-carboxylate (115 mg, 321 μmol) was dissolved in DCM (2 mL) and 2M HCl in ether (161 μL, 321 μmol) was added. The reaction was stirred at RT for 6 h, then the solvent was removed in vacuo. The crude product (94 mg, colorless foam) was used in the next step without purification. MS (ESI): m/z=258.2 [M+H]$^+$.

Step a) tert-Butyl cis-4-((2-chloro-4-fluorophenoxy)methyl)-3-methylpiperidine-1-carboxylate Mitsunobu reaction: In a 50 mL four-necked sulphonation flask under argon, tert-butyl cis-4-(hydroxymethyl)-3-methylpiperidine-1-carboxylate (840 mg, 3.66 mmol) was dissolved in THF (15 mL), 2-chloro-4-fluorophenol (590 mg, 439 μL, 4.03 mmol) and triphenylphosphine (1.06 g, 4.03 mmol) were added. The clear solution was stirred 5 min at RT, then cooled to 0-2° C. and DEAD (702 mg, 638 μL, 4.03 mmol) was added over 10 min. The reaction mixture was stirred at 2-4° C. for 1 h, then stirred over night at RT. 50 mL diethylether were added, the mixture was washed with 2×25 mL water, 3×20 mL 1 N NaOH, 1×20 mL brine, the organic phase was dried with Mg$_2$SO$_4$, after removing the solvent in vacuo 2.7 g yellow oil were obtained. To remove the triphenylphosphinoxide, the residue was stirred in n-Heptane/diethylether for 30 min, the solids was filtered away, the filtrate was concentrated in vacuo, to obtain 1.8 g crude product that was purified by flash chromatography (silica gel, 50 g, 0% to 30% EtOAc in heptane, 40 min): tert-butyl cis-4-((2-chloro-4-fluorophenoxy)methyl)-3-methylpiperidine-1-carboxylate, 1.21 g white solid.

BB39

3-((2-Fluoro-4-(trifluoromethoxy)benzyl)oxy)azetidine; trifluoroacetate salt To a solution of tert-butyl 3-((2-fluoro-4-(trifluoromethoxy)benzyl)oxy)azetidine-1-carboxylate (415 mg, 1.14 mmol) in DCM (5 mL) was added TFA (1.3 g, 875 μL, 11.4 mmol) and the reaction mixture was stirred at RT for 3 h. Volatiles were removed in vacuo to yield 455 mg of a light yellow oil that was used in the next step without further purification. MS (ESI): m/z=266.1 [M+H]$^+$.

Step a) tert-Butyl 3-((2-fluoro-4-(trifluoromethoxy)benzyl)oxy)azetidine-1-carboxylate To a solution of tert-butyl 3-hydroxyazetidine-1-carboxylate (200 mg, 1.15 mmol) in dry THF (5 mL) was added potassium tert-butoxide (1.65 M solution in THF, 735 μL, 1.21 mmol) and the reaction mixture was stirred at RT for 15 min followed by addition of 1-(bromomethyl)-2-fluoro-4-(trifluoromethoxy)benzene (315 mg, 1.15 mmol). The reaction mixture was then stirred at room temperature for 14 h. The crude reaction was diluted with EtOAc and extracted with aq. 1 M NaHCO$_3$ solution, the organic phase was collected and the aqueous phase was back-extracted with EtOAc. The combined organic phases were dried over NaSO$_4$ and evaporated down to dryness to yield 418 mg of the crude product which was used in the next step without further purification. MS (ESI): m/z=310.1 [M−56+H]$^+$.

BB40

N-(azetidin-3-yl)-2-chloro-4-fluoro-benzamide; trifluoroacetate salt

To a solution of tert-butyl 3-[(2-chloro-4-fluoro-benzoyl)amino]azetidine-1-carboxylate (346 mg, 1.05 mmol) in DCM (3.5 mL) was added TFA (0.7 mL) at 0° C. The solution was stirred at 0° C. for 2 h. The reaction was concentrated in vacuum to give the crude product (600 mg) as light yellow oil. The crude product was purified by prep-HPLC (0.1% TFA in H$_2$O and MeCN) and dried by lyophilization to give desired compound as colorless solid (223 mg, 0.650 mmol, 59.2% yield). MS (ESI): m/z=229 [M+H]$^+$.

Step a) tert-Butyl 3-[(2-chloro-4-fluoro-benzoyl)amino]azetidine-1-carboxylate To a solution of 2-chloro-4-fluorobenzoic acid (500 mg, 2.86 mmol), 1-Boc-3-(amino)azetidine (493 mg, 2.86 mmol) and DMAP (35.0 mg, 0.290 mmol) in THF (10 mL) was added 1-(3-dimethylaminopropyl)-3-ethylcarbodiimide hydrochloride (714 mg, 3.72 mmol) at 0° C. The mixture was heated to 30° C. and stirred for 16 h. The reaction was diluted with EtOAc (5 mL), washed three times with brine (10 mL each) and dried over Na$_2$SO$_4$. The organic layer was concentrated in vacuum to give the crude product (0.72 g) as yellow oil. The crude product was purified by prep-HPLC and dried by lyophilization to give desired compound as a colorless solid (546 mg, 1.66 mmol, 57.9% yield). MS (ESI): m/z=273 [M−56+H]$^+$.

BB41

N-(azetidin-3-ylmethyl)-2,2,2-trifluoro-N-methyl-1-[4-(trifluoromethyl)phenyl]ethanamine; trifluoroacetate salt To a solution of tert-butyl 3-((methyl(2,2,2-trifluoro-1-(4-(trifluoromethyl)phenyl)ethyl)amino)methyl)azetidine-1-carboxylate (0.256 g, 600 μmol) in DCM (5 mL) was added TFA (1.37 g, 925 μL, 12 mmol). The resulting reaction mixture was stirred at RT for 1 h. The reaction mixture was concentrated in vacuo to provide the desired compound as a colorless oil (268 mg). MS (ESI): m/z=327.4 [M+H]$^+$.

Step a) tert-Butyl 3-((methyl(2,2,2-trifluoro-1-(4-(trifluoromethyl)phenyl)ethyl)amino)methyl)azetidine-1-carboxylate To a dry flask with septum and 3 Å molecular sieves was added under nitrogen tert-butyl 3-((methylamino)methyl)azetidine-1-carboxylate (0.300 g, 293 μL, 1.5 mmol), TEA (455 mg, 626 μL, 4.49 mmol), 2,2,2-trifluoro-1-(4-(trifluoromethyl)phenyl)ethan-1-one (363 mg, 255 μL, 1.5 mmol), and dry DCM (9.86 mL). Titanium tetrachloride 1 M in DCM (749 μL, 749 μmol) was added via a syringe to the ice-cooled flask (exothermic). The reaction was stirred at RT overnight, carefully quenched with a solution of NaCNBH$_3$ (282 mg, 4.49 mmol) in MeOH (3.64 mL, 89.9 mmol) and stirred at RT for 2 h. The reaction was basified with sat. NaHCO$_3$ solution. The obtained insoluble material was filtered over celite and the filtrate was extracted with DCM. The organic layers were combined, washed with brine, dried over Na$_2$SO$_4$ and concentrated. The crude material was purified by flash chromatography (silica gel, 50 g, 0% to 50% EtOAc in n-heptane) and was used directly for the next step.

BB42

N-methyl-N-(piperidin-4-yl)-1-(3-(trifluoromethyl) phenyl)cyclopropane-1-carboxamide hydrochloride To a solution of tert-butyl 4-(N-methyl-1-(3-(trifluoromethyl)phenyl)cyclopropane-1-carboxamido)piperidine-1-carboxylate (0.301 g, 706 µmol) in DCM (2 mL) was added HCl 2M in diethyl ether (3.53 mL, 7.06 mmol). The resulting reaction mixture was stirred at RT overnight and then concentrated under vacuum at 22° C. to give 256 mg of BB42 as off white solid, MS (ESI): m/z=327.2 [M+H]$^+$ Step a) tert-butyl 4-(N-methyl-1-(3-(trifluoromethyl)phenyl)cyclopropane-1-carboxamido)piperidine-1-carboxylate In a 20 mL glasstube, to 1-(3-(trifluoromethyl)phenyl)cyclopropane-1-carboxylic acid (177 mg, 770 µmol) in DMF (5 mL) was added HATU (293 mg, 770 µmol) and DIPEA (271 mg, 367 µL, 2.1 mmol). The reaction mixture was stirred for 15 min and then tert-butyl 4-(methylamino) piperidine-1-carboxylate (0.15 g, 700 µmol) was added. The reaction mixture was stirred at RT for 2 hours. The reaction mixture was extracted with Water/DCM. The crude material was purified by flash chromatography (silica gel, 20 g, 0% to 100% EtOAc in heptane) to yield the desired compound as a light yellow oil (301 mg). MS (ESI): m/z=371.2 [M−56+H]$^+$

BB43

2-(2-chloro-3-(trifluoromethyl)phenyl)-N-methyl-N-(piperidin-4-yl)acetamide; hydrochloride salt To a solution of tert-butyl 4-(2-(2-chloro-3-(trifluoromethyl)phenyl)-N-methylacetamido)piperidine-1-carboxylate (0.301 g, 692 µmol) in DCM (2 mL) was added HCl (3.46 mL, 6.92 mmol). The resulting reaction mixture was stirred at RT for 2 days and then concentrated under vacuum at 22° C. to yield 252 mg of BB43 as off white solid. MS (ESI): m/z=335.1 [M+H]$^+$.

Step a) tert-butyl 4-(2-(2-chloro-3-(trifluoromethyl) phenyl)-N-methylacetamido)piperidine-1-carboxylate In a 20 mL glass tube, to 2-(2-chloro-3-(trifluoromethyl) phenyl)acetic acid (184 mg, 770 µmol) in DMF (5 mL) was added HATU (293 mg, 770 µmol), DIPEA (271 mg, 367 µL, 2.1 mmol). The reaction mixture was stirred for 15 min and then tert-butyl 4-(methylamino)piperidine-1-carboxylate (0.150 g, 700 µmol) was added. The reaction mixture was stirred at RT for 2 hours, and then extracted with Water/DCM. The crude material was purified by flash chromatography (silica gel, 20 g, 0% to 100% EtOAc in heptane) to yield tert-butyl 4-(2-(2-chloro-3-(trifluoromethyl)phenyl)-N-methylacetamido)piperidine-1-carboxylate as light yellow oil, 301 mg, MS (ESI): m/z=379.1 [M−56+H]$^+$

BB44

2-(2-Chloro-5-(trifluoromethyl)phenyl)-N-methyl-N-(piperidin-4-yl)acetamide; hydrochloride salt Synthesized from 2-(2-chloro-5-(trifluoromethyl)phenyl) acetic and tert-butyl 4-(methylamino)piperidine-1-carboxylate. See synthesis of BB43 for details. MS (ESI): m/z=335.1 [M+H]$^+$.

BB46

3-Methyl-5-(piperidin-4-ylmethoxy)-2-(trifluoromethyl)pyridine; dihydrochloride salt In a 25 mL tube tert-butyl 4-(((5-methyl-6-(trifluoromethyl)pyridin-3-yl)oxy)methyl)piperidine-1-carboxylate (87 mg, 232 µmol) was dissolved in DCM (2 mL) and then HCl in ether 2M (697 µL, 1.39 mmol) was added, the reaction mixture was stirred 12 h at RT. The mixture was concentrated in vacuum, yielding 80 mg of BB46 as a white solid. MS (ESI): m/z=275.2 [M+H]$^+$.

Step a) tert-Butyl 4-(((5-methyl-6-(trifluoromethyl) pyridin-3-yl)oxy)methyl)piperidine-1-carboxylate In a 5 mL tube, tert-butyl 4-(hydroxymethyl)piperidine-1-carboxylate (80.7 mg, 375 µmol) was dissolved in DMF (1.5 mL), then NaH in Oil 60% (18 mg, 450 µmol) was added at room temperature, the mixture was stirred for 20 min, then 5-bromo-3-methyl-2-(trifluoromethyl)pyridine (90 mg, 60 µL, 375 µmol) was added, and it was stirred for 2 hr at RT, yielding a brown solution. 10 mL sat. NH$_4$Cl were added, it was extracted with water/ethyl acetate, dried over MgSO$_4$, the solvent was removed at 40° C./150 mbar. The crude product was purified by flash chromatography (silica gel, 20 g, 0 to 40% EtOAc in n-heptane, in 35 min) to yield 87 mg of tert-butyl 4-(((5-methyl-6-(trifluoromethyl)pyridin-3-yl)oxy)methyl)piperidine-1-carboxylate. MS (ESI): m/z=319.2 [M−56+H]$^+$

BB58

N-(azetidin-3-ylmethyl)-2,2,2-trifluoro-1-(4-fluorophenyl)ethan-1-amine

In a 100 mL two-necked flask, benzyl 3-(((1-(2-chloro-4-fluorophenyl)-2,2,2-trifluoroethyl)amino)methyl)azetidine-1-carboxylate (707 mg, 1.64 mmol) was combined with THF (5 mL) and MeOH (5 mL) to give a colorless solution. Pd/C 10% (87.3 mg, 82.1 µmol) was added under argon. The flask was purged and backfilled with H$_2$ (3 times). The reaction mixture was stirred at 25° C. for 1 h. The reaction mixture was filtered over decalite, concentrated and used directly for the next step. Colorless oil (472 mg). MS (ESI): m/z=263.2 [M+H]$^+$ (the ortho-chlorine was lost during the hydrogenation).

Step a:) Benzyl 3-(((1-(2-chloro-4-fluorophenyl)-2, 2,2-trifluoroethyl)amino)methyl)azetidine-1-carboxylate To a dry flask under a stream of nitrogen was added benzyl 3-(aminomethyl)azetidine-1-carboxylate (0.5 g, 2.27 mmol), triethylamine (689 mg, 949 µL, 6.81 mmol), 1-(2-chloro-4-fluoro-phenyl)-2,2,2-trifluoro-ethanone (519 mg, 2.27 mmol), and dry DCM (15 mL). Titanium tetrachloride 1M in DCM (1.13 mL, 1.13 mmol) was added via a syringe to the ice-cooled flask (exothermic). The reaction was stirred overnight at RT, carefully quenched with a methanolic solution of sodium cyanoborohydride (428 mg, 6.81 mmol) in methanol (4.36 g, 5.51 mL, 136 mmol)+Acetic Acid (0.1 mL) and stirred overnight at RT. The reaction was basified with sat. NaHCO$_3$. The insoluble material obtained was filtered away over celite, the filtrate was extracted with DCM, the organic layers were combined, washed with brine, dried over Na$_2$SO$_4$ and concentrated. Purification: The crude material was purified by flash chromatography (silica gel, 50 g, 0% to 50% EtOAc in heptane) to yield 707 mg of Benzyl 3-(((1-(2-chloro-4-fluorophenyl)-2,2,2-trifluoroethyl)amino)methyl)azetidine-1-carboxylate as a colorless oil. MS (ESI): m/z=431.2 [M+H]$^+$.

BB59

2,2,2-Trifluoro-1-(piperidin-4-yl)-N-(3-(trifluoromethyl)benzyl)ethan-1-amine; hydrochloride salt To a solution of tert-butyl 4-(2,2,2-trifluoro-1-((3-(trifluoromethyl)benzyl)amino)ethyl)piperidine-1-carboxylate (0.140 g, 318 µmol) in DCM (2 mL) was added HCl 2M in diethyl ether (1.59 mL, 3.18 mmol). The resulting reaction mixture was stirred at RT overnight and then concentrated under vacuum at 22° C. to yield 119 mg of the title compound as off-white solid. MS (ESI): m/z=340.8 [M+H]$^+$.

Step a) tert-Butyl 4-(2,2,2-trifluoro-1-((3-(trifluoromethyl)benzyl)amino)ethyl)piperidine-1-carboxylate A solution of tert-butyl 4-(1-amino-2,2,2-trifluoroethyl)piperidine-1-carboxylate (0.150 g, 531 µmol) and 3-(trifluoromethyl)benzaldehyde (92.5 mg, 71.1 µL, 531 µmol) in 1,2-DCE (1 mL) was stirred for 1 hour at RT. Sodium triacetoxyborohydride (225 mg, 1.06 mmol) was then added at 0° C., and the reaction mixture was stirred at RT overnight. The reaction mixture was poured onto sat. NaHCO$_3$ and extracted with DCM. The organic layers were combined, washed with brine, dried over Na$_2$SO$_4$ and concentrated in vacuo. The crude material was purified by flash chromatography (silica gel, 20 g, 0% to 100% EtOAc in heptane) to yield 145 mg of the desired compound as a colorless oil. MS (ESI): m/z=383.1 [M−56+H]$^+$

BB69

2-methyl-3-((4-(trifluoromethyl)benzyl)oxy)azetidine; trifluoroacetate salt

To a solution of tert-butyl 2-methyl-3-((4-(trifluoromethyl)benzyl)oxy)azetidine-1-carboxylate (0.36 g, 1.04 mmol) in DCM (4 mL) was added trifluoroacetic acid (1.19 g, 10.4 mmol). The resulting reaction mixture was stirred at RT for 1 hour. The reaction mixture was concentrated on high vacuum to yield BB69 as a light yellow oil, 399 mg, mixture of all four stereoisomers. MS (ESI): m/z=246.1 [M+H]$^+$.

Step a) tert-Butyl 2-methyl-3-((4-(trifluoromethyl)benzyl)oxy)azetidine-1-carboxylate In a 25 mL two-necked flask, tert-butyl-3-hydroxy-2-methylazetidine-1-carboxylate (215 mg, 1.15 mmol) was dissolved in DMF (5 mL) to give a colorless solution. At 0° C., sodium hydride (60% dispersion in mineral oil) (41.8 mg, 1.05 mmol) was added. The reaction mixture was stirred at 0° C. for 15 min. Then 1-(bromomethyl)-4-(trifluoromethyl)benzene (0.250 g, 1.05 mmol) was added at 0° C. The reaction mixture was stirred at RT overnight. The reaction mixture was poured onto 20 mL sat. NH$_4$Cl and extracted with EtOAc (2×50 mL). The organic layers were combined, washed with brine, dried over Na$_2$SO$_4$ and concentrated in vacuo. The crude material was purified by flash chromatography (silica gel, 20 g, 0% to 70% EtOAc in heptane) to yield 360 mg of tert-butyl 2-methyl-3-((4-(trifluoromethyl)benzyl)oxy)azetidine-1-carboxylate as a colorless oil. MS (ESI): m/z=290.1 [M−56+H]$^+$

BB87

3-Fluoro-5-(trifluoromethyl)benzyl 4-methylbenzenesulfonate

To a solution of (3-fluoro-5-(trifluoromethyl)phenyl)methanol (100 mg, 72.5 µL, 515 mol, Eq: 1) in DCM (2.58 mL) was added p-toluenesulfonic anhydride (185 mg, 567 mol), DIPEA (79.9 mg, 108 µL, 618 µmol) and DMAP (6.29 mg, 51.5 mol). The reaction mixture was stirred for 4 h at 0° C. and for 2 days at room temperature. The reaction mixture was taken up in EtOAc and washed with water and brine. The organic layers were dried over MgSO$_4$ and concentrated in vacuo to give a yellow oil (178 mg) which was used without further purification.

In analogy to B39, and if not specified otherwise, the intermediates shown in the following table were prepared from commercially available benzyl bromides or the prepared tosylate intermediates and the corresponding tert-butyl 3-hydroxyazetidine-1-carboxylate building blocks.

| BB No. | Systematic Name | Starting material | MS, m/z |
| --- | --- | --- | --- |
| BB37 | 3-((2-Chloro-4-(trifluoromethyl)benzyl)oxy)azetidine; trifluoroacetate salt | 1-(Bromomethyl)-2-chloro-4-(trifluoromethyl)benzene | 266.1 [M + H]$^+$ |
| BB38 | 3-((4-(Trifluoromethyl)benzyl)oxy)azetidine; trifluoroacetate salt | 1-(Bromomethyl)-4-(trifluoromethyl)benzene | 232.1 [M + H]$^+$ |
| BB45 | 3-((3-Methoxy-4-(trifluoromethyl)benzyl)oxy)azetidine; trifluoroacetate salt | 4-(Bromomethyl)-2-methoxy-1-(trifluoromethyl)benzene | 262.2 [M + H]$^+$ |
| BB56 | 3-((3-Fluoro-5-(trifluoromethyl)benzyl)oxy)azetidine; trifluoroacetate salt | 3-Fluoro-5-(trifluoromethyl)benzyl 4-methylbenzenesulfonate (BB87) | 250.1 [M + H]$^+$ |
| BB60 | 3-((3-Chloro-4-(trifluoromethyl)benzyl)oxy)azetidine; trifluoroacetate salt | 4-(Bromomethyl)-2-chloro-1-(trifluoromethyl)benzene | 266.1 [M + H]$^+$ |

-continued

| BB No. | Systematic Name | Starting material | MS, m/z |
|---|---|---|---|
| BB62 | 3-((2-Fluoro-4-(trifluoromethyl)benzyl)oxy)-3-(trifluoromethyl)azetidine; trifluoroacetate salt | 1-(Bromomethyl)-2-fluoro-4-(trifluoromethyl)benzene and Tert-butyl 3-hydroxy-3-(trifluoromethyl)azetidine-1-carboxylate (CAS: 398489-42-4) | 318.3 [M + H]+ |
| BB63 | 3-((2-Fluoro-4-(trifluoromethyl)benzyl)oxy)-3-methylazetidine; trifluoroacetate salt | 1-(Bromomethyl)-2-fluoro-4-(trifluoromethyl)benzene and Tert-butyl 3-hydroxy-3-methylazetidine-1-carboxylate (CAS: 1104083-23-9) | 264.1 [M + H]+ |
| BB64 | 3-((2,4-Difluoro-5-(trifluoromethyl)benzyl)oxy)azetidine; trifluoroacetate salt | 1-(Bromomethyl)-2,4-difluoro-5-(trifluoromethyl)benzene | 268.1 [M + H]+ |
| BB65 | 3-((2-Fluoro-5-(trifluoromethyl)benzyl)oxy)azetidine trifluoroacetate salt | 2-(Bromomethyl)-1-fluoro-4-(trifluoromethyl)benzene | 250.1 [M + H]+ |
| BB66 | 3-((2-Fluoro-5-(trifluoromethyl)benzyl)oxy)azetidine; trifluoroacetate salt | 4-(Bromomethyl)-2-fluoro-1-(trifluoromethyl)benzene | 250.1 [M + H]+ |
| BB67 | 3-((2-Methoxy-4-(trifluoromethyl)benzyl)oxy)azetidine; trifluoroacetate salt | 1-(Bromomethyl)-2-methoxy-4-(trifluoromethyl)benzene | 262.2 [M + H]+ |
| BB68 | 3-((4-Chloro-2-(trifluoromethyl)benzyl)oxy)azetidine; trifluoroacetate salt | 1-(Bromomethyl)-4-chloro-2-(trifluoromethyl)benzene | 266.2 [M + H]+ |
| BB88 | 3-[(2,4-dichlorophenyl)methoxy]azetidine | 1-(Bromomethyl)-2,4-dichlorobenzene | 232.1 [M + H]+ |
| BB170 | 3-((3,4-Dichlorobenzyl)oxy)azetidine; 2,2,2-trifluoroacetate | 4-(Bromomethyl)-1,2-dichlorobenzene | 232.1 [M + H]+ |
| BB171 | 3-((2,5-Dichlorobenzyl)oxy)azetidine; 2,2,2-trifluoroacetate | 2-(Bromomethyl)-1,4-dichlorobenzene | 232.1 [M + H]+ |
| BB172 | 3-((3-(Trifluoromethoxy)benzyl)oxy)azetidine; 2,2,2-trifluoroacetate | 3-(Bromomethyl)-trifluoromethoxy-benzene | 248.1 [M + H]+ |
| BB173 | 2-Methyl-3-((4-methyl-3-(trifluoromethyl)benzyl)oxy)azetidine; 2,2,2-trifluoroacetate | tert-Butyl-3-hydroxy-2-methylazetidine-1-carboxylate and 4-(bromomethyl)-1-methyl-2-(trifluoromethyl)benzene | 266.2 [M + H]+ |
| BB178 | 3-(((2-Fluoro-4-(trifluoromethyl)benzyl)oxy)methyl) azetidine; 2,2,2-trifluoroacetate | tert-Butyl 3-(hydroxymethyl)azetidine-1-carboxylate and 1-(Bromomethyl)-2-fluoro-4-(trifluoromethyl)benzene | 264.2 [M + H]+ |
| BB180 | [4-(Azetidin-3-yloxymethyl)-3-fluoro-phenyl]-pentafluoro-☐6-sulfane; 2,2,2-trifluoroacetate | (4-(Bromomethyl)-3-fluorophenyl)pentafluoro-☐6-sulfane | 308.2 [M + H]+ |
| BB185 | 3-((2-Fluoro-4-(trifluoromethyl)benzyl)oxy)-3-(trifluoromethyl)pyrrolidine; 2,2,2-trifluoroacetate | tert-Butyl 3-hydroxy-3-(trifluoromethyl)pyrrolidine-1-carboxylate and 1-(Bromomethyl)-2-fluoro-4-(trifluoromethyl)benzene | 332.2 [M + H]+ |
| BB187 | 3-[[2,4-bis(Trifluoromethyl)phenyl]methoxy]azetidine | 1-(Bromomethyl)-2,4-bis(trifluoromethyl)benzene | 336.2 [M + H]+ |
| BB188 | 3-[[2-Methyl-3-(trifluoromethyl)phenyl]methoxy]azetidine | 1-(Bromomethyl)-2-methyl-3-(trifluoromethyl)benzene | 246.1 [M + H]+ |
| BB189 | 3-[[2-Methyl-4-(trifluoromethoxy)phenyl]methoxy]azetidine | 1-(Bromomethyl)-2-methyl-4-(trifluoromethoxy)benzene | 262.1 [M + H]+ |
| BB190 | 2-Methyl-3-[[2-methyl-4-(trifluoromethoxy)phenyl]methoxy]azetidine | 1-(Bromomethyl)-2-methyl-4-(trifluoromethoxy)benzene and tert-butyl 3-hydroxy-2-methylazetidine-1-carboxylate | 276.2 [M + H]+ |
| BB191 | 2-Methyl-3-[[2-methyl-3-(trifluoromethyl)phenyl]methoxy]azetidine | 1-(Bromomethyl)-2-methyl-3-(trifluoromethyl)benzene and tert-Butyl 3-hydroxy-2-methylazetidine-1-carboxylate | 260.2 [M + H]+ |
| BB207 | 3-[[4-Fluoro-2-(trifluoromethyl)phenyl]methoxy]azetidine; 4-methylbenzenesulfonate | 1-(Chloromethyl)-4-fluoro-2-(trifluoromethyl)benzene (CAS RN 248262-29-5) | 250.2 [M + H]+ |
| BB212 | 3-[[3-Fluoro-4-(trifluoromethoxy)phenyl]methoxy]azetidine; 2,2,2-trifluoroacetate | 4-(Bromomethyl)-2-fluoro-1-(trifluoromethoxy )benzene | Used without purification |

| BB No. | Systematic Name | Starting material | MS, m/z |
|---|---|---|---|
| BB217 | 3-((4-Methyl-3-(trifluoromethyl)benzyl)oxy)azetidine; 2,2,2-trifluoroacetate | 4-(Bromomethyl)-1-methyl-2-(trifluoromethyl)benzene. tBuOK as base | 246.2 [M + H]+ |

In analogy to BB129, intermediates BB12O, BB25 and BB6T of the following table were prepared from the commercially available phen9ols. Where trifluoroacetate salts are indicated, the crude product resulting from concentration of the reaction mixture was used directly without further neutralization or purification.

| BB No. | Systematic Name | Starting material | MS, m/z |
|---|---|---|---|
| BB20 | 3-((2-Fluoro-4-(trifluoromethyl)phenoxy)methyl)azetidine; trifluoroacetate salt | 2-Fluoro-4-(trifluoromethyl)phenol (CAS RN: 77227-78-2) | 250.1 [M + H]+ |
| BB25 | 3-[(2-Chloro-4-fluorophenoxy)methyl]azetidine | 2-Chloro-4-fluorophenol (CAS RN: 1996-41-4) | 216.1 [M + H]+ (purified by RP-HPLC) |
| BB61 | 3-((2-Chloro-4-fluorophenoxy)methyl)-3-fluoroazetidine; trifluoroacetate salt | 2-Chloro-4-fluorophenol (CAS RN: 1996-41-4) and tert-Butyl 3-fluoro-3-(hydroxymethyl)azetidine-1-carboxylate (CAS: 1126650-66-5) | 234.1 [M + H]+ |

In analogy to BB126, intermediates BB2T-BB24 and BB28 of the following table were prepared from the commercially available phenols.

| BB No. | Systematic Name | Starting material | MS, m/z |
|---|---|---|---|
| BB21 | 4-((4-Fluoro-2-(trifluoromethyl)phenoxy)methyl)piperidine; hydrochloride salt | 4-Fluoro-2-(trifluoromethyl)phenol (CAS: 130047-19-7) | 278.1 [M + H]+ |
| BB22 | 4-[[2-Fluoro-4-(trifluoromethyl)phenoxy]methyl]piperidine; hydrochloride salt | 2-Fluoro-4-(trifluoromethyl)phenol (CAS: 77227-78-2) | 278.0 [M + H]+ |
| BB23 | 4-((2-Chloro-4-(trifluoromethyl)phenoxy)methyl)piperidine; hydrochloride salt | 2-Chloro-4-(trifluoromethyl)phenol (CAS: 35852-58-5) | 294.1 [M + H]+ |
| BB24 | 5-Fluoro-2-(piperidin-4-ylmethoxy)benzonitrile; hydrochloride salt | 5-Fluoro-2-hydroxybenzonitrile (CAS: 91407-41-9) | 235.1 [M + H]+ |
| BB28 | 4-[(4-Fluoro-2-methyl-phenoxy)methyl]piperidine; hydrochloride salt | 4-Fluoro-2-methylphenol (CAS: 452-72-2) | 224.0 [M + H]+ |
| BB170 | 3-((3,4-Dichlorobenzyl)oxy)azetidine 2,2,2-trifluoroacetate | 4-(Bromomethyl)-1,2-dichlorobenzene | 232.1 [M + H]+ |
| BB171 | 3-((2,5-Dichlorobenzyl)oxy)azetidine 2,2,2-trifluoroacetate | 2-(Bromomethyl)-1,4-dichlorobenzene | 232.1 [M + H]+ |
| BB172 | 3-((3-(Trifluoromethoxy)benzyl)oxy)azetidine 2,2,2-trifluoroacetate | 3-(Bromomethyl)-trifluoromethoxy-benzene | 248.1 [M + H]+ |
| BB173 | 2-Methyl-3-((4-methyl-3-(trifluoromethyl)benzyl)oxy)azetidine 2,2,2-trifluoroacetate | tert-Butyl-3-hydroxyl-methylazetidine-1-carboxylate and 4-(Bromomethyl)-1-methyl-2-(trifluoromethyl)benzene | 266.2 [M + H]+ |
| BB178 | 3-(((2-Fluoro-4-(trifluoromethyl)benzyl)oxy)methyl)azetidine 2,2,2-trifluoroacetate | tert-Butyl 3-(hydroxymethyl)azetidine-1-carboxylate and 1-(Bromomethyl)-2-fluoro-4-(trifluoromethyl)benzene | 264.2 [M + H]+ |
| BB180 | [4-(Azetidin-3-yloxymethyl)-3-fluoro-phenyl]-pentafluoro-□6-sulfane 2,2,2-trifluoroacetic acid | (4-Bromomethyl)-3-fluorophenyl)pentafluoro-□6-sulfane | 308.2 [M + H]+ |
| BB185 | 3-((2-Fluoro-4-(trifluoromethyl)benzyl)oxy)-3- | tert-Butyl 3-hydroxy-3-(trifluoromethyl)pyrrolidine-1- | 332.2 [M + H]+ |

-continued

| BB No. | Systematic Name | Starting material | MS, m/z |
|---|---|---|---|
| | (trifluoromethyl)pyrrolidine 2,2,2-trifluoroacetate | carboxylate and 1-(Bromomethyl)-2-fluoro-4-(trifluoromethyl)benzene | |
| BB187 | 3-[[2,4-bis(Trifluoromethyl)phenyl]methoxy]azetidine | 1-(Bromomethyl)-2,4-bis(trifluoromethyl)benzene | 336.2 [M + H]+ |
| BB188 | 3-[[2-Methyl-3-(trifluoromethyl)phenyl]methoxy]azetidine | 1-(Bromomethyl)-2-methyl-3-(trifluoromethyl)benzene | 246.1 [M + H]+ |
| BB189 | 3-[[2-Methyl-4-(trifluoromethoxy)phenyl]methoxy]azetidine | 1-(Bromomethyl)-2-methyl-4-(trifluoromethoxy)benzene | 262.1 [M + H]+ |
| BB190 | 2-Methyl-3-[[2-methyl-4-(trifluoromethoxy)phenyl]methoxy]azetidine | 1-(Bromomethyl)-2-methyl-4-(trifluoromethoxy)benzene and tert-butyl 3-hydroxy-2-methylazetidine-1-carboxylate | 276.2 [M + H]+ |
| BB191 | 2-Methyl-3-[[2-methyl-3-(trifluoromethyl)phenyl]methoxy]azetidine | 1-(Bromomethyl)-2-methyl-3-(trifluoromethyl)benzene and tert-Butyl 3-hydroxy-2-methylazetidine-1-carboxylate | 260.2 [M + H]+ |
| BB207 | 3-[[4-Fluoro-2-(trifluoromethyl)phenyl]methoxy]azetidine; 4-methylbenzenesulfonate | 1-(Chloromethyl)-4-fluoro-2-(trifluoromethyl)benzene (CAS RN 248262-29-5) | 250.2 [M + H]+ |
| BB212 | 3-[[3-Fluoro-4-(trifluoromethoxy)phenyl]methoxy]azetidine; 2,2,2-trifluoroacetate | 4-(Bromomethyl)-2-fluoro-1-(trifluoromethoxy)benzene | Used without purification |
| BB217 | 3-((4-Methyl-3-(trifluoromethyl)benzyl)oxy)azetidine; 2,2,2-trifluoroacetate | 4-(Bromomethyl)-1-methyl-2-(trifluoromethyl)benzene. tBuOK as base | 246.2 [M + H]+ |
| BB218 | 3-((2-Fluoro-6-(trifluoromethyl)benzyl)thio)azetidine 2,2,2-trifluoroacetate | tert-Butyl 3-mercaptoazetidine-1-carboxylate and 2-(Bromomethyl)-1-fluoro-3-(trifluoromethyl)benzene | 266.2 [M + H]+ |

Method D1

BB9

4-[2-Chloro-4-(trifluoromethyl)phenoxy]piperidine; trifluoroacetate salt

A mixture of tert-butyl 4-[2-chloro-4-(trifluoromethyl) phenoxy]piperidine-1-carboxylate (750.0 mg, 1.97 mmol) in DCM (20 mL) and TFA (0.76 mL) was stirred at 20° C. for 12 h. The mixture was concentrated. The residue was dissolved in H$_2$O (20 mL) and washed twice with PE:EA=10:1 (20 mL each). The aqueous layer was lyophilized to give the desired product as light yellow solid (716 mg, 1.82 mmol, 87.8%). MS (ESI): m/z=280.1 [M+H]+.

Step a) tert-Butyl 4-[2-chloro-4-(trifluoromethyl) phenoxy]piperidine-1-carboxylate A mixture of 2-chloro-4-(trifluoromethyl)phenol (500 mg, 2.54 mmol), 1-Boc-4-hydroxypiperidine (768 mg, 3.82 mmol) and triphenylphosphine (1334 mg, 5.09 mmol) in THF (10 mL) was stirred at 0° C. until completely dissolved. DIAD (1542 mg, 7.63 mmol) was slowly added dropwise at 0° C. The mixture was stirred at 20° C. for 3 h and then concentrated under vacuum. The residue was purified by prep-HPLC to give the desired compound as light yellow solid (760 mg, 2 mmol, 78.7% yield). MS (ESI): m/z=324.0 [M−56+H]+.

BB57

3-(((2-Fluoro-6-(trifluoromethyl)benzyl)oxy)methyl) azetidine; trifluoroacetate salt To a solution of tert-butyl 3-(((2-fluoro-6-(trifluoromethyl)benzyl)oxy)methyl)azetidine-1-carboxylate (158 mg, 435 µmol) in DCM (1.74 mL) was added TFA (793 mg, 536 µL, 6.96 mmol) and the reaction was stirred at room temperature for 3 h. The reaction mixture was concentrated to give 3-(((2-fluoro-6-(trifluoromethyl)benzyl)oxy)methyl) azetidine; trifluoroacetate salt (202 mg, 434 µmol, 99.7% yield) as a colorless oil. The crude was used without further purification. MS (ESI): m/z=264.1 [M+H]+.

Step a) Tert-butyl 3-(((2-fluoro-4-(trifluoromethyl) benzyl)oxy)methyl)azetidine-1-carboxylate To a solution of tert-butyl 3-(hydroxymethyl)azetidine-1-carboxylate (100 mg, 534 µmol) in dry THF (2.67 mL) was added potassium tert-butoxide 1.65 M solution in THF (340 µL, 561 µmol) and the turbid reaction mixture was stirred at RT for 15 min followed by addition of 1-(bromomethyl)-2-fluoro-6-(trifluoromethyl)benzene (137 mg, 534 µmol). The reaction mixture was then stirred at room temperature for 3 h. The crude reaction was diluted with ethyl acetate and extracted with sat. aq. NaHCO$_3$ solution, the organic phase was collected and the aqueous phase was back-extracted with ethyl acetate. The combined organic phases were dried over sodium sulfate and evaporated down to dryness to yield a clear oil. The crude was immobilized on Isolute and purified by column chromatography eluting with 0 to 30% EtOAc in heptanes to afford tert-butyl 3-(((2-fluoro-6-(trifluoromethyl)benzyl)oxy)methyl)azetidine-1-carboxylate (158 mg, 413 µmol, 77.3% yield) as a colorless oil. MS (ESI): m/z=308.1 [M−56+H]$^+$ Method D2

BB10

4-[[2-Cyclopentyl-4-(trifluoromethyl)phenyl]methyl]piperidine; formic acid salt

A mixture of tert-butyl 4-[[2-cyclopentyl-4-(trifluoromethyl)phenyl]methyl]piperidine-1-carboxylate (440 mg, 0.610 mmol) and 5.0 mL of 4 M HCl in EtOAc in EtOAc (10 mL) was stirred at 20° C. for 12 h. The mixture was concentrated under vacuum. The residue was re-dissolved in H$_2$O (5 mL), washed twice with PE:EA (3:1; 10 mL each) and the layers were separated. The aqueous layer was purified by prep-HPLC to give the desired compound as light yellow solid (124 mg, 0.350 mmol, 65.3% yield). MS (ESI): m/z=312.2 [M+H]$^+$.

Step a) tert-Butyl 4-[[2-cyclopentyl-4-(trifluoromethyl)phenyl]methylene]piperidine-1-carboxylate A solution of tert-butyl 4-[[2-bromo-4-(trifluoromethyl)phenyl]methylene]piperidine-1-carboxylate (500 mg, 1.19 mmol), cyclopentyl bromide (266 mg, 1.78 mmol), Ir(dF(CF$_3$)ppy)$_2$(dtbbpy)PF$_6$ (13.4 mg, 0.010 mmol, CAS RN 870987-63-6), NiCl$_2$·glyme (0.77 mg, 0.060 mmol), dtbbpy (19.2 mg, 0.070 mmol, CAS RN 72914-19-3), TTMSS (296 mg, 1.19 mmol, CAS RN 1873-77-4) and Na$_2$CO$_3$ (252 mg, 2.38 mmol) in DMF (20 mL) was degassed by bubbling argon stream for 20 min. The reaction mixture was irradiated with Blue LED (4×1) at 25° C. for 16 h. The mixture was diluted with H$_2$O and then extracted three times with EtOAc (100 mL each). The combined organic layer was washed with brine, dried over sodium sulfate, filtered and concentrated. The residue was purified by prep-HPLC to give the compound as a colorless oil (460 mg, 1.12 mmol, 53.8%). MS (ESI): m/z=354.1 [M−56+H]$^+$.

Step b) tert-Butyl 4-[[2-cyclopentyl-4-(trifluoromethyl)phenyl]methyl] piperidine-1-carboxylate To a mixture of tert-butyl 4-[[2-cyclopentyl-4-(trifluoromethyl)phenyl]methylene]piperidine-1-carboxylate (460 mg, 0.640 mmol) in EtOAc (10 mL) was added wet Pd/C (40 mg), and then the mixture was stirred at 20° C. for 12 h under H$_2$ (1520 mmHg). The mixture was filtered and the filtrate was concentrated to give the compound as colorless oil (460 mg, 1.12 mmol, 99.5%). MS (ESI): m/z=356.1 [M+H−56]$^+$.

B111

2-(4-Piperidylmethyl)-1,3-benzoxazole; formic acid salt

A solution of 2-aminophenol (1.0 g, 9.16 mmol) and 1-Boc-4-piperidylacetic acid (2.68 g, 11 mmol) in polyphosphoric acid (2.2 g) was stirred at 180° C. for 2 h. The mixture was diluted with a mixture of 12M aqueous NH$_4$OH solution and ice to reach pH>7, and then extracted three times with EtOAc (10 mL each). The combined organic layers were washed with brine, dried over Na$_2$SO$_4$, filtered and concentrated, and the residue was purified by prep-HPLC to give the desired compound as a brown oil (251 mg, 0.960 mmol, 9.7%). MS (ESI): m/z=217.2 [M+H]$^+$.

Method D3

BB13

4-[4-Chloro-3-(4-chlorophenyl)phenoxy]piperidine; hydrochloride salt

A solution of tert-butyl 4-[4-chloro-3-(4-chlorophenyl)phenoxy]piperidine-1-carboxylate (1000 mg, 2.37 mmol) in a 4 M solution of HCl in dioxane (50 mL) was stirred at 20° C. for 12 h. The mixture was concentrated to give the title compound as a white solid (845 mg, 2.35 mmol, 96.2%). MS (ESI): m/z=322.0 [M+H]$^+$.

Step a) tert-Butyl 4-(3-bromo-4-chloro-phenoxy)piperidine-1-carboxylate

A mixture of 3-bromo-4-chlorophenol (1000 mg, 4.82 mmol), 1-Boc-4-hydroxypiperidine (1164 mg, 5.78 mmol) and triphenylphosphine (2529 mg, 9.64 mmol) was stirred in THF (10 mL) until completely dissolved. Then DIAD (1948 mg, 9.64 mmol) was slowly added drop wise at 0° C. The mixture was stirred at 20° C. for 12 h, concentrated and the residue was purified by reversed flash chromatography to give the compound as yellow oil (1300 mg, 3.33 mmol, 69.0%). MS (ESI): m/z=336.0 [M−56+H]$^+$.

Step b) tert-Butyl 4-[4-chloro-3-(4-chlorophenyl)phenoxy]piperidine-1-carboxylate To a solution of tert-butyl 4-(3-bromo-4-chloro-phenoxy)piperidine-1-carboxylate (1150 mg, 2.94 mmol) and 4-chlorophenylboronic acid (506 mg, 3.24 mmol), Na$_2$CO$_3$ (1248 mg, 11.8 mmol) in 1,4-dioxane (20 mL) and H$_2$O (5 mL) was added tetrakis(triphenylphosphine)palladium(0) (340 mg, 0.290 mmol, CAS RN 14221-01-3), and the mixture was stirred at 110° C. under N$_2$ atmosphere for 12 h. The mixture was filtered, the filtrate was concentrated, and the residue was purified by silica gel column chromatography, eluting with a 5-20% EtOAc-PE gradient to give the desired compound as light yellow oil (1100 mg, 2.6 mmol, 88.5%). MS (ESI): m/z=366.1 [M−56+H]$^+$.

BB14

4-[[2-(1H-Pyrazol-4-yl)-4-(trifluoromethyl)phenyl]methyl]piperidine; trifluoroacetate salt To a mixture of tert-butyl 4-[[2-(1-tert-butoxycarbonylpyrazol-4-yl)-4-(trifluoromethyl) phenyl]methyl]piperidine-1-carboxylate (150.0 mg, 0.290 mmol) in DCM (5 mL) was added TFA (1.0 mL). The mixture was stirred at 20° C. for 15 h. The mixture was concentrated under vacuum and then lyophilized to give the title compound as light yellow gum (149 mg, 0.280 mmol, 85.1% yield). MS (ESI): m/z=310.0 [M+H]$^+$.

Step a) tert-Butyl 4-[[2-(1-tert-butoxycarbonylpyrazol-4-yl)-4-(trifluoromethyl)phenyl]methylene]piperidine-1-carboxylate A mixture of tert-butyl 4-[[2-bromo-4-(trifluoromethyl)phenyl]methylene]piperidine-1-carboxylate (600 mg, 1.43 mmol), tert-butyl 4-(4,4,5,5-tetramethyl-1,3-dioxolan-2-yl)

pyrazole-1-carboxylate (846 mg, 2.86 mmol) and $K_2CO_3$ (592 mg, 4.28 mmol) in DMF (10 mL) and $H_2O$ (0.5 mL) was stirred at 80° C. for 12 h. The mixture was poured into $H_2O$ (30 mL) and extracted twice with EtOAc (50 mL each). The combined organic layers were washed with brine (30 mL), dried over $Na_2SO_4$ and filtered. The filtrated was concentrated in vacuum to give the compound as light yellow oil (520 mg, 1.02 mmol, 71.8% yield). MS (ESI): m/z=308.1 $[M+H]^+$.

Step b) tert-Butyl 4-[[2-(1-tert-butoxycarbonylpyrazol-4-yl)-4-(trifluoromethyl) phenyl]methyl]piperidine-1-carboxylate A mixture of tert-butyl 4-[[2-(1-tert-butoxycarbonylpyrazol-4-yl)-4-(trifluoromethyl)phenyl]methylene]piperidine-1-carboxylate (180 mg, 0.350 mmol) and wet Pd/C (18 mg) in EtOAc (10 mL) was stirred at 30° C. for 24 h under $H_2$ atmosphere (~1520 mm Hg). The mixture was filtered and concentrated under vacuum to give the compound as brown oil (150 mg, 0.290 mmol, 83%). MS (ESI): m/z=354.1 $[M-56-100+H]^+$.

BB18

4-[2-(2-Chlorophenyl)ethynyl]piperidine

To a suspension of tert-butyl 4-((2-chlorophenyl)ethynyl) piperidine-1-carboxylate (0.05 g, 0.156 mmol) in MeOH (3 mL) was added 4 M HCl in dioxane (0.391 mL, 1.56 mmol) and the reaction mixture was stirred at room temperature for 2 h. The mixture was evaporated to dryness and the residue triturated in diisopropyl ether, filtered off and further dried under high vacuum to give the title compound as a white solid as the hydrochloride salt (0.02 g, 50%). MS (ESI): m/z=220.1 $[M+H]^+$.

Step a) tert-Butyl 4-[2-(2-chlorophenyl)ethynyl] piperidine-1-carboxylate

In a sealed tube, a mixture of tert-butyl 4-ethynylpiperidine-1-carboxylate (0.1 g, 0.478 mmol, CAS RN 287192-97-6,), 1-bromo-2-chlorobenzene (0.084 mL, 0.717 mmol), copper (I) iodide (0.002 g, 0.009 mmol), TEA (0.666 mL, 4.78 mmol) and bis(triphenylphosphine)palladium(II) chloride (0.027 g, 0.038) in THF (2.8 mL) was degassed for 5 min under Argon. The reaction mixture was then heated to 70° C. and stirred for 4 h. The mixture was filtered off over a pad of Dicalite, washed with EtOAc and the mother liquors were evaporated to dryness. The residue was purified by silica gel flash chromatography, eluting with a gradient of 0-50% EtOAc/n-heptane to give the title compound as a white solid (0.05 g, 33%). MS (ESI): m/z=264.1 $[M-56+H]^+$.

BB48a tert-Butyl 4-[[2-fluoro-4-(trifluoromethyl)phenyl] methyl]piperidine-1-carboxylate A degassed solution of tert-butyl 4-methylenepiperidine-1-carboxylate (4465 mg, 22.6 mmol, CAS RN 159635-49-1) in 9-BBN (45.3 mL, 22.6 mmol) was refluxed for 1 h. After cooling to room temperature, the solution was added into a solution of 4-bromo-3-fluorobenzotrifluoride (5.0 g, 20.6 mmol, CAS RN 40161-54-4), Pd(dppf)$Cl_2$ (1514 mg, 2.06 mmol) and $K_2CO_3$ (5687 mg, 41.1 mmol) in DMF (50 mL) and water (5 mL). The resulting mixture was heated at 80° C. for 5 h. After the mixture was cooled to room temperature and poured into water, the pH was adjusted to 11 with 10% aqueous NaOH solution, and the mixture was extracted with EtOAc. The combined organic extracts were dried with brine and $Na_2SO_4$, filtered, and evaporated to give a residue, which was further purified by column chromatography (silica gel, PE:EtOAc=10:1 to 5:1) to give the compound as light yellow solid (240 mg, 3.2%). MS (ESI): m/z=306 $[M+H-56]^+$.

BB51a

A mixture of tert-butyl 4-[[2-cyclopropyl-4-(trifluoromethyl)phenyl]methylene]piperidine-1-carboxylate (1000 mg, 2.62 mmol) and $PtO_2$ (100 mg, 0.440 mmol) in EtOAc (20 mL) was stirred at 20° C. for 12 h under $H_2$ atmosphere (1520 mmHg). The mixture was filtered and the filtrate concentrated to furnish the compound as light yellow solid (940 mg, 93.5%). MS (ESI): m/z=328.2 $[M+H]^+$.

Step a)
2-Bromo-1-(bromomethyl)-4-(trifluoromethyl)benzene

A mixture of 2-bromo-1-methyl-4-(trifluoromethyl)benzene (5.5 g, 23.0 mmol, CAS RN 128-08-5), benzoyl peroxide (835 mg, 3.45 mmol) and NBS (4.07 g, 23.01 mmol) in $CCl_4$ (50.0 mL, 23.0 mmol) was stirred at 70° C. for 5 h. The mixture was poured into water (20 mL) and extracted twice with DCM (20 mL each). The combined organic layer was washed with brine (20 mL), dried over $Na_2SO_4$, filtered and concentrated in vacuum to give the desired compound as light yellow oil which was used in the next step without further purification (7.1 g, 97%).

Step b) 2-Bromo-1-(diethoxyphosphorylmethyl)-4-(trifluoromethyl)benzene

A mixture of 2-bromo-1-(bromomethyl)-4-(trifluoromethyl)benzene (7.1 g, 22.3 mmol) and triethyl phosphite (30 mL) was stirred at 155° C. for 5 h. The mixture was concentrated in vacuum to remove triethyl phosphite, the residue was diluted with water (100 mL) and extracted three times with EtOAc (100 mL each). The combined organic layers were washed with brine (100 mL), dried over $Na_2SO_4$, filtered and concentrated under vacuum. The residue was purified by column chromatography (PE: EtOAc=100:1 to 10:1) to give the compound as light yellow oil which was used without further purification in the next step (8 g, 95.5%).

Step c) tert-Butyl 4-(2-bromo-4-(trifluoromethyl) benzylidene)piperidine-1-carboxylate To a mixture of 2-bromo-1-(diethoxyphosphorylmethyl)-4-(trifluoromethyl)benzene (6.9 g, 18.4 mmol) in THF (100 mL) was added sodium hydride (2.21 g, 55.2 mmol) at 0° C. The mixture was stirred at 0° C. for 1 h, then 1-Boc-4-piperidone (7.33 g, 36.79 mmol, CAS RN 79099-07-3) was added and the mixture was stirred at 20° C. for 12 h. The mixture was poured into water (100 mL) and extracted three times with EtOAc (100 mL each). The combined organic layers were washed with brine (100 mL), dried over$Na_2SO_4$, filtered and concentrated in vacuum. The residue was purified by column chromatography (PE:EA=100:1 to 50:1) to yield the desired compound as off-white solid (4 g, 51.7%). MS (ESI): m/z=365.9 [M−56+H]$^+$.

Step d) tert-butyl 4-[[2-cyclopropyl-4-(trifluoromethyl)phenyl] methylene]piperidine-1-carboxylate A mixture of tert-butyl 4-[[2-bromo-4-(trifluoromethyl)phenyl]methylene]piperidine-1-carboxylate (2.0 g, 4.76 mmol), cyclopropylboronic acid (818 mg, 9.52 mmol, CAS RN 411235-57-9) and potassium carbonate (1973 mg, 14.3 mmol) in DMF (10 mL) and water (0.5 mL) was stirred at 80° C. under nitrogen atmosphere for 12 h. The mixture was poured into water (50 mL), extracted three times with EtOAc (50 mL each). The combined organic layers were washed with brine (50 mL), dried over Na$_2$SO$_4$ and concentrated in vacuum. The residue was purified by prep-HPLC to give the compound as light yellow oil (1020 mg, 56.2% yield). MS (ESI): m/z=326.0 [M−56+H]$^+$.

BB53a tert-Butyl 3-[(4-chlorophenyl)methoxy]pyrrolidine-1-carboxylate

A solution of N-Boc-3-hydroxypyrrolidine (1.0 g, 5.34 mmol) and 4-chlorobenzyl bromide (1.32 g, 6.41 mmol) in ACN (10 mL) was added potassium carbonate (1.48 g, 10.68 mmol). The mixture was stirred at 80° C. for 15 h. Then the mixture was concentrated and diluted with water and extracted three times with EtOAc (10 mL each). The combined organic layers were concentrated to give the desired compound as colorless oil (326 mg, 19.6% yield) MS (ESI): m/z=256.0 [M−56+H]$^+$.

Method D4

BB70

3-[4-(Trifluoromethyl)phenoxy]azetidine

To a solution of tert-butyl 3-[4-(trifluoromethyl)phenoxy]azetidine-1-carboxylate (500 mg, 1.58 mmol, BB70a) in DCM (3 mL) was added TFA (1.0 mL, 0.950 mmol) at 25° C., the reaction was stirred at this temperature for 12 h. The mixture was concentrated and the residue was purified via prep-HPLC to provide the compound as colorless solid (150 mg, 0.690 mmol, 43.8%). MS (ESI): m/z=218.1 [M+H]$^+$.

BB72a tert-Butyl 4-(4-chloro-3-cyclopropyl-phenoxy)piperidine-1-carboxylate

To a solution of tert-butyl 4-(3-bromo-4-chloro-phenoxy)piperidine-1-carboxylate (500 mg, 1.28 mmol, BB90), potassium carbonate (354 mg, 2.56 mmol) and cyclopropylboronic acid (121 mg, 1.41 mmol) in 1,4-dioxane (5 mL) and water (1 mL) was added [1,1'-bis(diphenylphosphino)ferrocene]dichloro palladium(II) (187.28 mg, 0.260 mmol). The mixture was stirred at 100° C. under nitrogen atmosphere for 12 h. The reaction mixture was filtered and the filtrate was diluted with EtOAc (30 mL), washed with water and then brine, the organic phase was dried over Na$_2$SO$_4$, concentrated. The residue was purified by silica gel column (eluting with a gradient of 5%-10% EtOAc-PE) to give the compound as light yellow oil (220 mg, 48.9%). MS (ESI): m/z=296.1 [M−56+H]$^+$.

BB73a tert-Butyl 4-(4-chloro-3-morpholino-phenoxy)piperidine-1-carboxylate

To a solution of tert-butyl 4-(3-bromo-4-chloro-phenoxy)piperidine-1-carboxylate (500 mg, 1.28 mmol, BB90), cesium carbonate (834 mg, 2.56 mmol), (R)-(+)-2,2'-bis(diphenylphosphino)-1,1'-binaphthalene (159 mg, 0.260 mmol) and morpholine (112 mg, 1.28 mmol) in DMF (10 mL) was added tris(dibenzylideneacetone)dipalladium(0) (187 mg, 0.260 mmol) and the mixture was stirred at 110° C. under nitrogen atmosphere for 12 h. The reaction mixture was filtered, the filtrate was diluted with EtOAc (30 mL), washed with water and then brine, the organic phase was dried over Na$_2$SO$_4$, and concentrated. The residue was purified by silica gel column (eluting with a gradient of 5%-10% EtOAc-PE) to give the desired compound (360 mg, 70.9% yield) as light yellow oil. MS (ESI): m/z=397.1 [M+H]$^+$.

BB74a tert-Butyl 4-[2-methyl-4-(trifluoromethyl)phenoxy]piperidine-1-carboxylate To a solution of tert-butyl 4-[2-bromo-4-(trifluoromethyl)phenoxy]piperidine-1-carboxylate (2.0 g, 4.71 mmol, BB74b) in THF (40 mL) was added lithium methide (11.8 mL, 18.9 mmol) dropwise at −70° C. The mixture was stirred at −70° C. for 1 h and then stirred at 20° C. for 12 h. The mixture was poured into ice water (100 mL) and extracted three times with EtOAc (50 mL each). The combined organic layer was washed with brine (100 mL), dried over Na$_2$SO$_4$ and filtered. The filtrate was concentrated under vacuum to yield the compound as light yellow solid (780 mg, 46%). MS (ESI): m/z=260.1 [M−100+H]$^+$.

BB75a tert-Butyl 4-[2-cyano-4-(trifluoromethyl)phenoxy]piperidine-1-carboxylate

To a solution of zinc cyanide (2214 mg, 18.9 mmol) and tert-butyl 4-[2-bromo-4-(trifluoromethyl)phenoxy]piperidine-1-carboxylate (1600 mg, 3.77 mmol, BB74b) in DMA (30 mL) was added dppf (627 mg, 1.13 mmol), N,N-diisopropylethylamine (1.97 mL, 11.3 mmol), Zinc dust (245 mg, 3.77 mmol) and Pd$_2$(dba)$_3$ (1036 mg, 1.13 mmol) at 20° C., then the mixture was stirred at 140° C. under nitrogen atmosphere for 4 h. The mixture was filtered. The filtrate was poured into water (100 mL) and extracted three times with EtOAc (50 mL each). The combined organic layer was washed with brine (50 mL), dried over Na$_2$SO$_4$ and filtered. The filtrate was concentrated over vacuum to give the title compound as light brown solid (2.3 g, crude). MS (ESI): m/z=315.0 [M−56+H]$^+$.

BB76a tert-Butyl 4-(oxazolo[5,4-c]pyridin-2-ylmethyl)piperidine-1-carboxylate

To a solution of hexachloroethane (2.47 g, 10.4 mmol) in toluene (20 mL) was added triphenylphosphine (3.28 g, 12.5 mmol) and NEt$_3$ (4.65 mL, 33.4 mmol). The mixture was stirred at 80° C. for 5 min, then tert-butyl 4-[2-[(3-hydroxy-4-pyridyl)amino]-2-oxo-ethyl]piperidine-1-carboxylate (1.4 g, 4.17 mmol) was added and stirred at 80° C. for 12 h. The mixture was concentrated to remove toluene, then diluted with water (100 mL) and extracted three times with EtOAc (50 mL each). The combined organic layers were washed with brine, dried over sodium sulfate, filtered and concentrated. The crude was purified by silica gel chromatography (PE:EtOAc=10:1 to 1:0) to give the compound as a yellow oil (814 mg, 21% yield). MS (ESI): m/z=318.1 [M+H]$^+$.

Step a) tert-Butyl 4-[2-[(3-hydroxy-4-pyridyl)amino]-2-oxo-ethyl]piperidine-1-carboxylate A solution of 4-aminopyridin-3-ol (3.0 g, 27.3 mmol) and 1-Boc-4-piperidylacetic acid (7.95 g, 32.7 mmol) in DMF (30 mL) was added HOBt (6.26 g, 40.9 mmol), EDCI (6.34 g, 40.87 mmol) and NEt$_3$ (11.39 mL, 81.74 mmol). The mixture was stirred at 20° C. for 15 h. Then the mixture was concentrated, the residue taken up in water (100 mL), and then extracted three times with EtOAc (20 mL each). The organic phase was washed with brine, dried over Na$_2$SO$_4$ and concentrated. The residue was purified by reversed phase chromatography and lyophilized to give two batches of the desired compound. Batch 1 as colorless solid (1.2 g, 85% purity, 11.1%), and batch 2 as colorless solid (520 mg, 76.7% purity, 4.4% yield). MS (ESI): m/z=336.1[M+H]$^+$ for both batches.

BB77

4-Chloro-3-(2-piperidin-4-ylethynyl)pyridine

Intermediate BB77 was prepared in analogy to BB18, but using 3-bromo-4-chloro-pyridine in step a), to give the title compound as an orange solid. MS (ESI): m/z=221.1 [M+H]$^+$.

BB78

3-Chloro-2-(2-piperidin-4-ylethynyl)pyridine

Intermediate BB78 was prepared in analogy to BB18, but using 2-bromo-3-chloro-pyridine in step a), to give the title compound as a yellow solid. MS (ESI): m/z=221.1 [M+H]$^+$.

BB79

4-[2-(2-Chloro-4-fluorophenyl)ethynyl]piperidine

Intermediate BB79 was prepared in analogy to BB18, but using 1-bromo-2-chloro-4-fluoro-benzene in step a), to give the title compound as a white solid. MS (ESI): m/z=238.1 [M+H]$^+$.

BB80

4-[2-(3-Chlorophenyl)ethynyl]piperidine

Intermediate BB80 was prepared in analogy to BB18, but using 1-bromo-3-chlorobenzene in step a), to give the title compound as a colorless amorphous solid. MS (ESI): m/z=220.2 [M+H]$^+$.

BB81

4-[2-(4-Chlorophenyl)ethynyl]piperidine

Intermediate BB81 was prepared in analogy to BB18, but using 1-bromo-4-chlorobenzene in step a), to give the title compound as a yellow amorphous solid. MS (ESI): m/z=220.2 [M+H]$^+$.

BB82

4-[2-(2-Chloro-4-chlorophenyl)ethynyl]piperidine

Intermediate BB82 was prepared in analogy to BB18, but using 1-bromo-2,4-dichloro-benzene in step a), to give the title compound as a light yellow amorphous solid. MS (ESI): m/z=254.1[M+H]$^+$.

BB83

4-[2-(2-Chlorophenyl)ethynyl]piperidin-4-ol

Intermediate BB83 was prepared in analogy to BB18, but using tert-butyl 4-ethynyl-4-hydroxypiperidine-1-carboxylate (CAS RN 275387-83-2) in step a), to give the title compound as a yellow amorphous solid. MS (ESI): m/z=218.1[M−H$_2$O+H]$^+$.

BB84

3-[2-(2-Chlorophenyl)ethynyl]azetidine

To a solution tert-butyl 3-[2-(2-chlorophenyl)ethynyl]azetidine-1-carboxylate (0.035 g, 0.120 mmol) in DCM (0.6 mL) was added TFA (0.92.4 mL, 1.2 mmol) and the reaction mixture was stirred at room temperature for 2 h. The mixture was diluted with DCM, poured into a saturated aq. NaHCO$_3$ solution and extracted with DCM. The combined organic layers were washed with brine, dried over Na$_2$SO$_4$, filtered, evaporated and further dried on the high vacuum to give the crude title compound (0.02 g, 87%) as a light yellow oil. MS (ESI): m/z=192.0 [M+H]$^+$.

Step a) tert-Butyl 3-[2-(2-chlorophenyl)ethynyl]azetidine-1-carboxylate

The compound was prepared in analogy to intermediate BB18, but using tert-butyl 3-ethynylazetidine-1-carboxylate (CAS RN 287193-01-5) in step a), to give the title compound as a white solid. MS (ESI): m/z=236.1 [M−56+H]$^+$.

BB85

3-[2-(2,4-Dichlorophenyl)ethynyl]azetidine

Intermediate BB85 was prepared in analogy to intermediate BB84, but using 1-bromo-2,4-dichloro-benzene in step a), to give the title compound as a light yellow oil. MS (ESI): m/z=226.1 [M+H]$^+$.

BB86

3-[2-(2-Chloro-4-fluoro-phenyl)ethynyl]azetidine

Intermediate BB86 was prepared in analogy to intermediate BB84, but using 1-bromo-2-chloro-4-fluoro-benzene in step a), to give the title compound as a yellow oil. MS (ESI): m/z=210.1 [M+H]$^+$.

In analogy to BB9a the following building blocks were prepared from the respective building blocks

| BB No. | Systematic Name | Starting materials | MS, m/z |
|---|---|---|---|
| BB54a | tert-Butyl 4-[[2-methyl-4-(trifluoromethyl)phenyl]methyl]piperidine-1-carboxylate | tert-Butyl 4-methylenepiperidine-1-carboxylate 4-Bromo-3-methyl benzotrifluoride | 302.1 [M + H-56]+ |
| BB55a | tert-Butyl 4-[[2-chloro-4-(trifluoromethyl)phenyl]methyl]piperidine-1-carboxylate | tert-Butyl 4-methylenepiperidine-1-carboxylate 4-Bromo-3-chlorobenzotrifluoride | 322.0 [M + H-56]+ |

In analogy to BB15a the following building blocks were prepared from the respective building blocks.

| BB No. | Systematic Name | Starting materials | MS, m/z |
|---|---|---|---|
| BB49a | tert-Butyl 3-[(2-chlorophenyl)methoxy]pyrrolidine-1-carboxylate | 2-Chlorobenzyl bromide N-Boc-3-hydroxypyrrolidine | 256.0 [M-56 + H]+ |
| BB50a | tert-Butyl 3-[(3-chlorophenyl)methoxy]pyrrolidine-1-carboxylate | 3-Chlorobenzyl bromide N-BOC-3-hydroxypyrrolidine | 256.0 [M-56 + H]+ |

In analogy to BB9 step a, the following building blocks were prepared from the respective starting materials.

| BB No. | Systematic Name | Starting materials | MS, m/z |
|---|---|---|---|
| BB47a | tert-Butyl 3-[(2-chlorophenoxy)methyl]pyrrolidine-1-carboxylate | 2-Chlorophenol tert-Butyl 3-(hydroxymethyl)pyrrolidine-1-carboxylate | 256.0 [M-56 + H]+ |
| BB52a | tert-Butyl 3-[(4-chlorophenoxy)methyl]pyrrolidine-1-carboxylate | 4-Chlorophenol tert-Butyl 3-(hydroxymethyl)pyrrolidine-1-carboxylate | 256.0 [M-56 + H]+ |
| BB70a | tert-Butyl 3-[4-(trifluoromethyl)phenoxy]azetidine-1-carboxylate | 4-(Trifluoromethyl)phenol tert-Butyl 3-hydroxyazetidine-1-carboxylate | Used without further purification |
| BB71a | tert-Butyl 4-[4-chloro-3-(trifluoromethyl)phenoxy]piperidine-1-carboxylate | 1-Boc-4-hydroxypiperidine 4-Chloro-3-(trifluoromethyl)phenol | 324.0 [M-56 + H]+ |
| BB74b | tert-Butyl 4-[2-bromo-4-(trifluoromethyl)phenoxy]piperidine-1-carboxylate | 2-Bromo-4-(trifluoromethyl)phenol 1-BOC-4-hydroxypiperidine | 369.9 [M-56 + H]+ |
| BB89a | tert-Butyl 3-[(3-chlorophenoxy)methyl]pyrrolidine-1-carboxylate | 3-Chlorophenol tert-Butyl 3-(hydroxy methyl)pyrrolidine-1-carboxylate | 256.0 [M-56 + H]+ |
| BB90 | tert-Butyl 4-(3-bromo-4-chlorophenoxy) piperidine-1-carboxylate | 3-Bromo-4-chlorophenol 1-BOC-4-hydroxypiperidine | 336.0 [M-56 + H]+ |

Method D5

BB51

4-[[2-Cyclopropyl-4-(trifluoromethyl)phenyl]methyl]piperidine formic acid salt

To a mixture of tert-butyl 4-[[2-cyclopropyl-4-(trifluoromethyl)phenyl]methyl] piperidine-1-carboxylate (940 mg, 2.45 mmol, BB51a) in DCM (10 mL) was added TFA (2.0 mL, 2.45 mmol). The mixture was stirred at 20° C. for 12 h. The mixture was concentrated under vacuum. The residue was purified twice by prep-HPLC to furnish the desired compound as light yellow gum (111 mg, 12.4%). MS (ESI): m/z=284.2 [M+H]+.

Step a)
2-Bromo-1-(bromomethyl)-4-(trifluoromethyl)benzene

A mixture of 2-bromo-1-methyl-4-(trifluoromethyl)benzene (5.5 g, 23.0 mmol, CAS RN 128-08-5), benzoyl peroxide (835 mg, 3.45 mmol) and NBS (4.07 g, 23.0 mmol) in $CCl_4$ (50.0 mL, 23.0 mmol) was stirred at 70° C. for 5 h. The mixture was poured into water (20 mL) and extracted twice with DCM (20 mL each). The combined organic layers were washed with brine (20 mL), dried over $Na_2SO_4$, filtered and concentrated in vacuum to give the compound as light yellow oil (7.1 g, 97%) which was used in the next step without further purification.

Step b) 2-Bromo-1-(diethoxyphosphorylmethyl)-4-(trifluoromethyl)benzene

A mixture of 2-bromo-1-(bromomethyl)-4-(trifluoromethyl)benzene (7.1 g, 22.3 mmol,) and triethyl phosphite (30.0 mL) was stirred at 155° C. for 5 h. The mixture was concentrated in vacuum to remove triethyl phosphite. The residue was diluted with water (100 mL) and extracted three times with EtOAc (100 mL each). The combined organic layers were washed with brine (100 mL), dried over $Na_2SO_4$, filtered and concentrated. The residue was purified by column chromatography (PE:EA=100:1 to 10:1) to give the title compound as light yellow oil (8 g, 21.3 mmol, 95.5%) which was used in the subsequent step without further purification.

Step c) tert-Butyl 4-(2-bromo-4-(trifluoromethyl)benzylidene)piperidine-1-carboxylate A mixture of 2-bromo-1-(diethoxyphosphorylmethyl)-4-(trifluoromethyl)benzene (6.9 g, 18.4 mmol) in THF (100 mL) was added NaH (2.21 g, 55.2 mmol) at 0° C. The mixture was stirred at 0° C. for 1 h, then 1-Boc-4-piperidone (7.33 g, 36.8 mmol, CAS RN 79099-07-3) was added and the mixture was stirred at 20° C. for 12 h. The mixture was poured into water (100 mL) and extracted three times with EtOAc (100 mL each). The combined organic layer was washed with brine (100 mL), dried over $Na_2SO_4$, filtered and concentrated in vacuum. The residue was purified by column chromatography (PE:EA=100:1 to 50:1) to yield the desired compound as off-white solid (4 g, 9.52 mmol, 51.7%). MS (ESI): m/z=365.9 [M−56+H]$^+$.

Step d) tert-Butyl 4-[[2-cyclopropyl-4-(trifluoromethyl)phenyl]methylene]piperidine-1-carboxylate A mixture of tert-butyl 4-[[2-bromo-4-(trifluoromethyl)phenyl]methylene]piperidine-1-carboxylate (2.0 g, 4.76 mmol), cyclopropylboronic acid (818 mg, 9.52 mmol, CAS RN 411235-57-9) and potassium carbonate (1973 mg, 14.3 mmol) in DMF (10 mL) and water (0.5 mL) was stirred at 80° C. for 12 h under nitrogen atmosphere. The mixture was poured into water (50 mL) and extracted three times with EtOAc (50 mL each). The combined organic layers were washed with brine (50 mL), dried over $Na_2SO_4$ and concentrated in vacuum. The residue was purified by prep-HPLC to give the compound as light yellow oil (1020 mg, 56.2% yield) MS (ESI): m/z=326.0 [M−56+H]$^+$.

Step e) tert-Butyl 4-[[2-cyclopropyl-4-(trifluoromethyl)phenyl]methyl]piperidine-1-carboxylate A mixture of tert-butyl 4-[[2-cyclopropyl-4-(trifluoromethyl)phenyl]methylene]piperidine-1-carboxylate (1000 mg, 2.62 mmol) and $PtO_2$ (100 mg, 0.440 mmol) in EtOAc (20 mL) was stirred at 20° C. for 12 h under hydrogen atmosphere (1520 mm Hg). Then the mixture was filtered and the filtrate was concentrated to yield the compound as light yellow solid (940 mg, 93.5% yield). MS (ESI): m/z=328.2 [M+H]$^+$.

Method D6

BB92

N-methyl-N-[4-(trifluoromethyl)phenyl]piperidin-4-amine; trifluoroacetate salt To a solution of tert-butyl 4-[N-methyl-4-(trifluoromethyl)anilino]piperidine-1-carboxylate (150 mg, 0.420 mmol) in DCM (1 mL) was added TFA (0.1 mL) at 0° C. The mixture was stirred at 25° C. for 12 h. The reaction mixture was concentrated in vacuum. The residue was purified by pre-HPLC (in the presence of TFA) to give the desired product as yellow solid (120 mg, 77.0%). MS (ESI): m/z=259.2 [M+H]$^+$.

Step a) tert-Butyl 4-[4-(trifluoromethyl)anilino]piperidine-1-carboxylate

To a solution of p-trifluoromethylaniline (1.17 mL, 9.31 mmol, CAS RN 455-14-1) in DCM (30 mL) was added AcOH (0.560 g, 9.31 mmol) and 1-BOC-4-piperidone (2.78 g, 14.0 mmol, CAS RN 79099-07-3). Then 1M $BH_3$/THF solution (27.9 mL, 27.9 mmol) was added carefully at 0° C. under nitrogen atmosphere. The reaction mixture was stirred at 25° C. for 12 h. The mixture was poured into saturated aqueous $NH_4Cl$ solution (30 mL) and extracted three times with EtOAc. The combined organic layers were washed twice with water $H_2O$, and then brine, dried over $Na_2SO_4$ and concentrated in vacuum to afford yellow residue, which was purified by silica gel column eluting with a gradient of PE:EtOAc (20:1 to 5:1) to give the desired product as white solid (2.0 g, 62.4%). MS (ESI): m/z=289.1 [M−56+H]$^+$.

Step b) tert-Butyl 4-[N-methyl-4-(trifluoromethyl)anilino]piperidine-1-carboxylate To a solution of NaH (52.3 mg, 60.0% wt %, 1.31 mmol) in DMF (5 mL) was added tert-butyl 4-[4-(trifluoromethyl)anilino]piperidine-1-carboxylate (300 mg, 0.870 mmol) at 0° C. under nitrogen atmosphere. The mixture was stirred at 0° C. for 15 min, and then iodomethane (371 mg, 2.61 mmol) was added. The reaction mixture was stirred at 80° C. for 12 hrs. The reaction mixture was poured into water (20 mL) and extracted three times with EtOAc, the combined organic layers were washed twice with water and brine, dried over sodium sulfate and concentrated in vacuum to afford light yellow residue, which was purified by silica gel column eluting with a gradient of PE:EtOAc (20:1 to 5:1) to give the desired product as white solid (160 mg, 51.3%). MS (ESI): m/z=303.1 [M−56+H]$^+$.

BB93

N-methyl-N-(4-(trifluoromethyl)phenyl)azetidin-3-amine (trifluoroacetic acid salt)

The title compound was prepared in analogy to method D6 from tert-butyl 3-[N-methyl-4-(trifluoromethyl)anilino]azetidine-1-carboxylate (48%). MS (ESI): m/z=231.1 [M+H]$^+$.

Step a) tert-Butyl 3-[4-(trifluoromethyl)anilino]azetidine-1-carboxylate

To a solution of p-trifluoromethylaniline (0.780 mL, 6.21 mmol, CAS RN 455-14-1), AcOH (1.86 g, 31.0 mmol) and 1-BOC-3-azetidinone (2.13 g, 12.4 mmol, CAS RN 398489-26-4) in EtOH (10 mL) was added $NaBH_3CN$ (1.95 g, 31.0 mmol) at 25° C. The mixture was stirred at 25° C. for 12 h. The reaction mixture was poured into saturated aqueous $NH_4Cl$ solution (20 mL) and extracted twice with EtOAc. The combined organic layers were washed twice with $H_2O$ and brine, dried over sodium sulfate and concentrated in vacuum to afford yellow residue, which was purified by silica gel column eluting with a gradient of PE:EtOAc (10:1 to 5:1) to give the desired product as white solid (340 mg, 17.3%). MS (ESI): m/z=261.1 [M−56+H]$^+$.

Step b) tert-Butyl 3-[N-methyl-4-(trifluoromethyl)anilino]azetidine-1-carboxylate To a solution of tert-butyl 3-[4-(trifluoromethyl)anilino]azetidine-1-carboxylate (300 mg, 0.950 mmol) in DMF (5 mL) was added NaH (45.5 mg, 60% wt %, 1.14 mmol) at 0° C. The mixture was stirred for 15 min, and then iodomethane (404 mg, 2.85 mmol) was added. The reaction mixture was stirred at 25° C. for 12 h. The reaction mixture was poured into H$_2$O (20 mL) and extracted twice with EtOAc. The combined organic layers were washed three times with H$_2$O and brine, dried over Na$_2$SO$_4$ and concentrated in vacuum to afford yellow residue. The residue was purified by silica gel column eluting with a gradient of PE:EtOAc (10:1 to 5:1) to give the desired product as white solid (310 mg, 98.9%). MS (ESI): m/z=275.2 [M−56+H]$^+$.

Method D7

BB94

N-methyl-N-(piperidin-4-yl)-2-(3-(trifluoromethyl) phenyl)acetamide hydrochloride To a solution of tert-butyl 4-[methyl-[2-[3-(trifluoromethyl)phenyl]acetyl]amino] piperidine-1-carboxylate (0.080 g, 200 μmol) in DCM (1 mL) was added a 2 M HCl solution in diethyl ether (999 μL, 2 mmol). The reaction mixture was stirred at RT overnight and then concentrated in vacuo to afford the title compound (67 mg, 199 μmol) as an off-white solid. MS (ESI): m/z=301.2 [M+H]$^+$.

Step a) tert-Butyl 4-[methyl-[2-[3-(trifluoromethyl) phenyl]acetyl]amino]piperidine-1-carboxylate To a stirred mixture of 2-(3-(trifluoromethyl)phenyl)acetic acid (105 mg, 513 μmol, CAS RN 351-35-9) in DMF (5 mL) was added HATU (195 mg, 513 μmol) and DIPEA (181 mg, 244 μL, 1.4 mmol). After 15 min. stirring, tert-butyl 4-(methylamino)piperidine-1-carboxylate (0.100 g, 467 μmol, CAS RN 147539-41-1) was added and the reaction mixture was stirred at RT for 2 h. The reaction mixture was diluted with DCM and washed with H$_2$O. The org. phase was concentrated to give a crude product which was purified by flash chromatography on a 20 g SiO$_2$ column, using an eluent mixture of n-heptane and EtOAc (0% to 100%) to afford the desired compound as a light yellow oil (85 mg, 213 μmol). MS (ESI): m/z=459.259 [M+CH$_3$CN+NH$_4$]$^+$.

Method D8

BB194

3-(4-Chloro-3-cyclopropylphenoxy)azetidine

To a solution of tert-butyl 3-(4-chloro-3-cyclopropylphenoxy)azetidine-1-carboxylate (0.023 g, 0.057 mmol) in DCM (1 mL) was added TFA (0.088 mL, 1.14 mmol) and the reaction mixture stirred at room temperature for 18 hours. The mixture was diluted with DCM, poured into a sat. aq. NaHCO$_3$ solution and extracted with DCM. The combined organic layers were washed with brine, dried over Na$_2$SO$_4$, filtered and evaporated to dryness to yield the crude title compound (0.007 g, 35%) as a colorless oil. MS (ESI): m/z=224.1 [M+H]$^+$.

Step a) tert-Butyl 3-(3-bromo-4-chlorophenoxy)azetidine-1-carboxylate

In a sealed tube, 3-bromo-4-chlorophenol (0.1 mg, 0.482 mmol) and tert-butyl 3-hydroxyazetidine-1-carboxylate (0.083 g, 0.482 mmol) were dissolved in toluene (1.5 mL). The vial was degassed with argon, then (tributylphosphoranylidene)acetonitrile (CAS RN 157141-27-0, 0.195 mL, 0.723 mmol) was added and the reaction mixture heated to 100° C. for 30 minutes. The mixture was diluted with EtOAc, poured into sat. aq. NaHCO$_3$ solution and the aqueous layer was extracted with EtOAc. The combined organic layers were washed with brine, dried over Na$_2$SO$_4$, filtered and concentrated in vacuo. The residue was purified by silica gel flash chromatography eluting with a 0 to 20% EtOAc/heptane gradient to give the title compound (0.116 g, 53%) as a yellow oil. MS (ESI): m/z=308.1 [M−56+H]$^+$.

Step b) tert-Butyl 3-(4-chloro-3-cyclopropylphenoxy)azetidine-1-carboxylate

In a microwave vial, tert-butyl 3-(3-bromo-4-chlorophenoxy)azetidine-1-carboxylate (0.075 g, 0.165 mmol), cyclopropylboronic acid (0.021 g, 0.248 mmol) and K$_2$CO$_3$ (0.046 g, 0.331 mmol) were mixed in dioxane (1.6 mL). Then, water (0.4 mL) was added followed by bis(triphenylphosphine)palladium (II) chloride (0.012 g, 0.016 mmol) and the reaction mixture heated at 130° C. under microwave irradiation for 1 hour. The reaction mixture was diluted with EtOAc, poured into water and extracted with EtOAc. The organic layers were washed with brine, dried over Na$_2$SO$_4$, filtered and concentrated in vacuo. The residue was purified by silica gel flash chromatography, eluting with a 0 to 10% EtOAc/heptane gradient to give the title compound (0.023 g, 43%) as a colorless oil. MS (ESI): m/z=268.2 [M−56+H]$^+$.

Method D9

BB197

3-(2-Chloro-3-cyclopropylphenoxy)azetidine, trifluoroacetate salt

To a solution of tert-butyl 3-(2-chloro-3-cyclopropylphenoxy)azetidine-1-carboxylate (0.1 g, 0.310 mmol) in DCM (2.5 mL) was added TFA (0.25 mL) and the reaction mixture was stirred at room temperature for 2 hours. The mixture was concentrated in vacuo to give the crude title compound (0.083 g, 80% yield) as a dark brown oil. MS (ESI): m/z=224.6 [M+H]$^+$.

Step a) tert-Butyl 3-(3-bromo-2-chloro-phenoxy) azetidine-1-carboxylate

To a solution of tert-butyl 3-hydroxyazetidine-1-carboxylate (0.5 g, 2.89 mmol) and 3-bromo-2-chloro-phenol (0.5 g, 2.41 mmol) in THF (10 mL) were added PPh$_3$ (0.948 g, 3.62 mmol) followed by diethyl azodicarboxylate (0.47 mL, 3.62 mmol) and the reaction mixture was stirred at room temperature for 12 hours. The mixture was purified by reversed phase HPLC to give the title product (0.4 g, 46%) as a light yellow oil. MS (ESI): m/z=308.3 [M−56+H]$^+$.

Step b) tert-Butyl 3-(2-chloro-3-cyclopropylphenoxy)azetidine-1-carboxylate

In a sealed tube, cyclopropylboronic acid (0.071 g, 0.830 mmol,), tert-butyl 3-(3-bromo-2-chloro-phenoxy)azetidine-1-carboxylate (0.2 g, 0.550 mmol) and Na$_2$CO$_3$ (0.117 g, 1.1 mmol) were mixed in 1,4-dioxane (5 mL) and water (1 mL). Then, Pd(dppf)Cl$_2$ (0.040 g, 0.060 mmol) was added and the mixture was stirred to 110° C. for 12 hours. The mixture was purified by reversed phase HPLC to give the title compound (0.12 g, 67%) as a light yellow oil. MS (ESI): m/z=268.1 [M−56+H]$^+$.

Method D10

BB202

5-(4-Piperidyloxy)-2-(trifluoromethyl)benzonitrile, trifluoroacetate

To a solution of tert-butyl 4-[3-cyano-4-(trifluoromethyl)phenoxy]piperidine-1-carboxylate (0.05 g, 0.140 mmol) in DCM (1.5 mL) was added TFA (0.2 mL) and the reaction mixture stirred at room temperature for 12 hours. The mixture was concentrated in vacuo to give the crude title compound (0.051 g, 98%) as a light brown oil. MS (ESI): m/z=271.6 [M+H]$^+$.

Step a) tert-Butyl 4-[3-bromo-4-(trifluoromethyl)phenoxy]piperidine-1-carboxylate To a solution of 3-bromo-4-(trifluoromethyl)phenol (0.5 g, 2.54 mmol) and 1-Boc-4-hydroxypiperidine (0.512 g, 2.54 mmol) in THF (8.5 mL) were added PPh$_3$ (1 g, 3.82 mmol) followed by diethyl azodicarboxylate (0.665 g, 3.82 mmol) and the reaction mixture was stirred at room temperature for 12 hours. The mixture was purified by silica gel flash chromatography, eluting with with PE:EtOAc 5:1 to give the title compound (0.5 g, 47%) as a light yellow oil. MS (ESI): m/z=370.2 [M−56+H]$^+$.

Step b) tert-Butyl 4-[3-cyano-4-(trifluoromethyl)phenoxy]piperidine-1-carboxylate In a sealed tube, tert-butyl 4-[3-bromo-4-(trifluoromethyl)phenoxy]piperidine-1-carboxylate (0.2 g, 0.470 mmol), Zn(CN)$_2$ (0.111 g, 0.940 mmol), CuI (0.09 g, 0.470 mmol) were mixed in DMF (10 mL). Then, Pd(PPh$_3$)$_4$ (0.109 g, 0.090 mmol) was added and the reaction mixture stirred to 130° C. for 16 hours. The mixture was purified by reversed phase HPLC to give the title product (0.05 g, 29%) as a colorless oil. MS (ESI): m/z=315.5 [M−56+H]$^+$.

Method E

Example 263

(+)-5-[1-[(4aR,8aS)-3-Oxo-4,4a,5,7,8,8a-hexahydropyrido[4,3-b][1,4]oxazine-6-carbonyl]azetidin-3-yl]oxy-2-(trifluoromethyl)benzonitrile

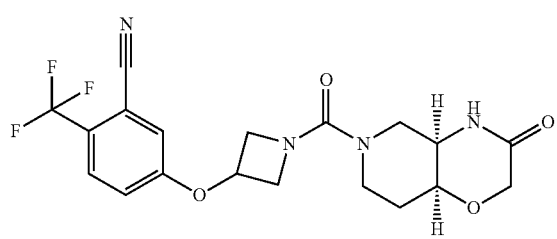 [SMILES: N#Cc1cc(OC2CN(C(=O)N3CC[C@@H]4OCC(=O)N[C@@H]4C3)C2)ccc1C(F)(F)F]

In a sealed tube, (+)-(4aR,8aS)-6-[3-[3-bromo-4-(trifluoromethyl)phenoxy]azetidine-1-carbonyl]-4,4a,5,7,8,8a-hexahydropyrido[4,3-b][1,4]oxazin-3-one (BB 205, 0.2 g, 0.420 mmol), Zn(CN)$_2$ (0.098 g, 0.840 mmol), Zn (0.027 g, 0.420 mmol), dppf (0.232 g, 0.420 mmol), Hünig's base (0.108 g, 0.840 mmol) were mixed in DMA (10 mL) and the mixture was degassed. Then, Pd$_2$(dba)$_3$ (76.59 mg, 0.080 mmol) was added and the reaction mixture was stirred at 130° C. for 16 h. The mixture was purified by reversed phase HPLC to give the title compound (0.055 g, 30%) as a light yellow solid. MS (ESI): m/z=425.3 [M+H]$^+$.

Method F

Example 265

(+)-(4aR,8aS)-6-[3-[3-(2-Azaspiro[3.3]heptan-2-yl)-4-(trifluoromethyl)phenoxy]azetidine-1-carbonyl]-4,4a,5,7,8,8a-hexahydropyrido[4,3-b][1,4]oxazin-3-one

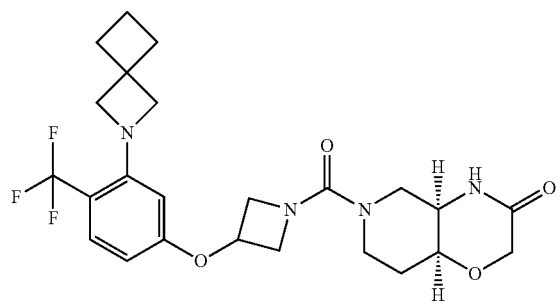 [SMILES: O=C1CO[C@H]2CCN(C(=O)N3CC(Oc4ccc(C(F)(F)F)c(N5CC6(CCC6)C5)c4)C3)C[C@H]2N1]

In a sealed tube, (+)-(4aR,8aS)-6-[3-[3-bromo-4-(trifluoromethyl)phenoxy]azetidine-1-carbonyl]-4,4a,5,7,8,8a-hexahydropyrido[4,3-b][1,4]oxazin-3-one (BB203, 0.2 g, 0.420 mmol), 2-azaspiro[3.3]heptane (CAS RN 665-04-03, 0.117 g, 0.630 mmol), BINAP (0.052 g, 0.080 mmol) and K$_2$CO$_3$ (0.173 g, 1.25 mmol) were mixed in DMF (10 mL) and the mixture was degassed. Then, Pd$_2$(dba)$_3$ (76.59 mg, 0.080 mmol) was added and the reaction mixture was stirred to 110° C. for 16 hours. The reaction mixture was filtered off, the filtrate diluted with water (50 mL) and extracted with EtOAc (3×20 mL). Combined organics were washed with brine, dried over Na$_2$SO$_4$, filtered and concentrated in vacuo. The residue was purified by reversed phase HPLC to give the title compound (0.06 g, 29%) as a white solid. MS (ESI): m/z=495.1 [M+H]$^+$.

Method G

Example 293

(4aR,8aS)-6-(3-(4-Hydroxy-2-(trifluoromethyl)phenethyl)azetidine-1-carbonyl)hexahydro-2H-pyrido[4,3-b][1,4]oxazin-3(4H)-one

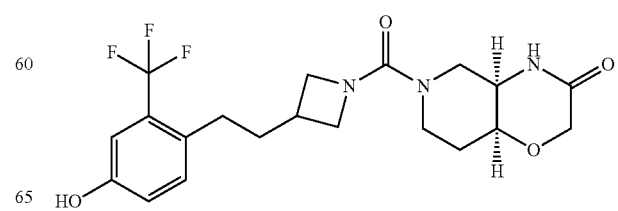

Boron tribromide (11.3 mg, 4.29 μL, 45.3 μmol) was added to an ice cooled solution of (4aR,8aS)-6-(3-(4-methoxy-2-(trifluoromethyl)phenethyl)azetidine-1-carbonyl)hexahydro-2H-pyrido[4,3-b][1,4]oxazin-3(4H)-one (Example 216, 20 mg, 45.3 μmol) in DCM (0.5 mL). The reaction mixture was stirred at ambient temperature for 3 h. A saturated solution of aqueous NaHCO$_3$ was added and the mixture was extracted with AcOEt. The layers were separated, the organic layer was dried over Na$_2$SO$_4$, filtered and the solvent removed under reduced pressure. The crude product was purified by prep. HPLC to give the title compound (19%) as colorless solid. MS (ESI): m/z=427.2 [M+H]$^+$.

The following examples listed in the table below were prepared in analogy to the procedure described for the preparation of Example 265 by using the indicated intermediates and/or commercially available compounds and using the mentioned purification method such as reversed-phase HPLC or silica gel flash chromatography.

| Ex | Systematic Name/Structure | Intermediates | MS, m/z |
|---|---|---|---|
| 266 | (+)-(4aR,8aS)-6-[3-[3-(3-Methylazetidin-1-yl)-4-(trifluoromethyl)phenoxy]azetidine-1-carbonyl]-4,4a,5,7,8,8a-hexahydropyrido[4,3-b][1,4]oxazin-3-one | BB203 BH66 and 3-Methylazetidine hydrochloride (CAS RN 935669-28-6) | 469.2 [M + H]$^+$ |
| 267 | (+)-(4aR,8aS)-6-[3-[3-(3,3-Difluoroazetidin-1-yl)-4-(trifluoromethyl)phenoxy]azetidine-1-carbonyl]-4,4a,5,7,8,8a-hexahydropyrido[4,3-b][1,4]oxazin-3-one | BB203 and Difluoroazetidine hydrochloride (CAS RN 288315-03-7) | 491.2 [M + H]$^+$ |
| 268 | (+)-(4aR,8aS)-6-[3-[3-(3-Fluoro-3-methyl-azetidin-1-yl)-4-(trifluoromethyl)phenoxy]azetidine-1-carbonyl]-4,4a,5,7,8,8a-hexahydropyrido[4,3-b][1,4]oxazin-3-one | BB203 and 3-Fluoro-3-methyl-azetidine hydrochloride (CAS RN 1427379-42-7) | 487.3 [M + H]$^+$ |
| 269 | (+)-(4aR,8aS)-6-[3-[3-(6,6-Difluoro-2-azaspiro[3.3]heptan-2-yl)-4-(trifluoromethyl)phenoxy]azetidine-1-carbonyl]-4,4a,5,7,8,8a-hexahydropyrido[4,3-b][1,4]oxazin-3-one | BB203 and 6,6-Difluoro-2-azaspiro[3.3]heptane (CAS RN 1354952-05-8) | 531.1 [M + H]$^+$ |

| Ex | Systematic Name/Structure | Intermediates | MS, m/z |
|---|---|---|---|
| 270 | 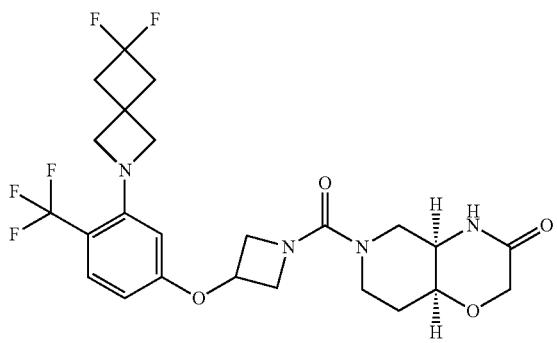 [SMILES: O=C1CO[C@H]2CCN(C(=O)N3CC(Oc4ccc(C(F)(F)F)c(N5CC6(C5)CC(F)(F)C6)c4)C3)C[C@H]2N1]<br>(+)-(4aR,8aS)-6-[3-[3-(5-oxa-2-azaspiro[3.5]nonan-2-yl)-4-(trifluoromethyl)phenoxy]azetidine-1-carbonyl]-4,4a,5,7,8,8a-hexahydropyrido[4,3-b][1,4]oxazin-3-one | BB203 and 5-Oxa-2-azaspiro[3.5]nonane (CAS RN 138387-19-6) | 525.3 [M + H]⁺ |
| 271 | 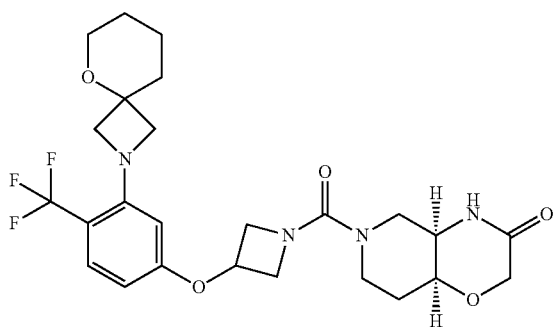 [SMILES: O=C1CO[C@H]2CCN(C(=O)N3CC(Oc4ccc(C(F)(F)F)c(N5CC6(CCCCO6)C5)c4)C3)C[C@H]2N1]<br>(+)-(4aR,8aS)-6-[3-[3-(2-Azaspiro[3.3]heptan-2-yl)-2-chloro-phenoxy]azetidine-1-carbonyl]-4,4a,5,7,8,8a-hexahydropyrido[4,3-b][1,4]oxazin-3-one | Example 258 and 2-Azaspiro[3.3]heptane (CAS RN 665-04-03) | 461.1 [M + H]⁺ |
| 272 | 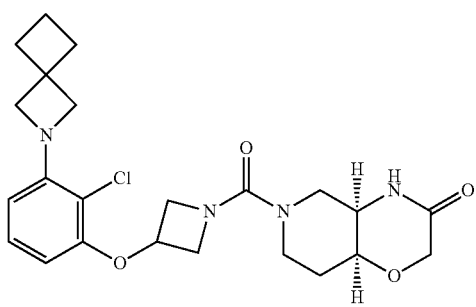 [SMILES: O=C1CO[C@H]2CCN(C(=O)N3CC(Oc4cccc(N5CC6(CCC6)C5)c4Cl)C3)C[C@H]2N1]<br>(+)-(4aR,8aS)-6-[3-[2-Chloro-3-(3-methylazetidin-1-yl)phenoxy]azetidine-1-carbonyl]-4,4a,5,7,8,8a-hexahydropyrido[4,3-b][1,4]oxazin-3-one | Example 258 and 3-Methylazetidine hydrochloride (CAS RN 935669-28-6) | 435.1 [M + H]⁺ |

-continued

| Ex | Systematic Name/Structure | Intermediates | MS, m/z |
|---|---|---|---|
| 273 | (+)-(4aR,8aS)-6-[3-[2-Chloro-3-(3-fluoro-3-methyl-azetidin-1-yl)phenoxy]azetidine-1-carbonyl]-4,4a,5,7,8,8a-hexahydropyrido[4,3-b][1,4]oxazin-3-one | Example 258 and 3-Fluoro-3-methyl-azetidine hydrochloride (CAS RN 1427379-42-7) | 453.2 [M + H]⁺ |
| 274 | (+)-(4aR,8aS)-6-(3-(3-(3-(tert-Butoxy)azetidin-1-yl)-2-chlorophenoxy)azetidine-1-carbonyl)hexahydro-2H-pyrido[4,3-b][1,4]oxazin-3(4H)-one | Example 258 and 3-tert-Butoxyazetidine (CAS RN 1147530-63-9) | 493.2 [M + H]⁺ |
| 275 | (+)-(4aR,8aS)-6-[3-[2-Chloro-3-(5-oxa-2-azaspiro[3.4]octan-2-yl)phenoxy]azetidine-1-carbonyl]-4,4a,5,7,8,8a-hexahydropyrido[4,3-b][1,4]oxazin-3-one | Example 258 and 5-Oxa-2-azaspiro[3.4]octane (CAS RN 145309-24-6) | 477.2 [M + H]⁺ |

| Ex | Systematic Name/Structure | Intermediates | MS, m/z |
|---|---|---|---|
| 276 | (+)-(4aR,8aS)-6-[3-[2-chloro-3-(5-oxa-2-azaspiro[3.5]nonan-2-yl)phenoxy]azetidine-1-carbonyl]-4,4a,5,7,8,8a-hexahydropyrido[4,3-b][1,4]oxazin-3-one | Example 258 and 5-Oxa-2-azaspiro[3.5]nonane (CAS RN 138387-19-6) | 491.2 [M + H]$^+$ |
| 277 | (+)-(4aR,8aS)-6-[3-[3-(2-Azaspiro[3.3]heptan-2-yl)-5-chloro-phenoxy]azetidine-1-carbonyl]-4,4a,5,7,8,8a-hexahydropyrido[4,3-b][1,4]oxazin-3-one | BB204 and 2-Azaspiro[3.3]heptane (CAS RN 665-04-03) | 461.3 [M + H]$^+$ |
| 278 | (+)-(4aR,8aS)-6-[3-(3-Chloro-5-pyrrolidin-1-yl-phenoxy)azetidine-1-carbonyl]-4,4a,5,7,8,8a-hexahydropyrido[4,3-b][1,4]oxazin-3-one | BB204 and Pyrrolidine | 435.3 [M + H]$^+$ |

In analogy to the methods described herein above, the following building blocks were prepared from the respective starting material indicated in the table below.

| BB No. | Systematic Name | Starting material | Method | MS, m/z |
|---|---|---|---|---|
| BB47 | 3-[(2-Chlorophenoxy)methyl]pyrrolidine; hydrochloride salt | tert-Butyl 3-[(2-chlorophenoxy)methyl]pyrrolidine-1-carboxylate BB47a | D3 | 212.1 [M + H]$^+$ |

| BB No. | Systematic Name | Starting material | Method | MS, m/z |
|---|---|---|---|---|
| BB48 | 4-[[2-Fluoro-4-(trifluoromethyl)phenyl]methyl]piperidine; formic acid salt | tert-Butyl 4-[[2-fluoro-4-(trifluoromethyl)phenyl]methyl]piperidine-1-carboxylate BB48a | D2 | 262.1 [M + H]$^+$ |
| BB49 | 3-[(2-Chlorophenyl)methoxy]pyrrolidine; hydrochloride salt | tert-Butyl 3-[(2-chlorophenyl)methoxy]pyrrolidine-1-carboxylate BB49a | D3 | 212.1 [M + H]$^+$ |
| BB50 | 3-[(3-Chlorophenyl)methoxy]pyrrolidine; hydrochloride salt | tert-Butyl 3-[(3-chlorophenyl)methoxy]pyrrolidine-1-carboxylate BB50a | D3 | 212.1 [M + H]$^+$ |
| BB52 | 3-[(4-Chlorophenoxy)methyl]pyrrolidine; hydrochloride salt | tert-Butyl 3-[(4-chlorophenoxy)methyl]pyrrolidine-1-carboxylate BB52a | D3 | 212.1 [M + H]$^+$ |
| BB53 | 3-[(4-Chlorophenyl)methoxy]pyrrolidine formic acid salt | tert-Butyl 3-[(4-chlorophenyl)methoxy]pyrrolidine-1-carboxylate BB53a | D2 | Used without further purification |
| BB54 | 4-[[2-Methyl-4-(trifluoromethyl)phenyl]methyl] piperidine; formic acid salt | tert-Butyl 4-[[2-methyl-4-(trifluoromethyl)phenyl]methyl]piperidine-1-carboxylate BB54a | D2 | 258.2 [M + H]$^+$ |
| BB55 | 4-[[2-Chloro-4-(trifluoromethyl)phenyl]methyl]piperidine; trifluoroacetate salt | tert-Butyl 4-[[2-chloro-4-(trifluoromethyl)phenyl]methyl]piperidine-1-carboxylate BB55a | D1 | 278.0 [M + H]$^+$ |
| BB71 | 4-[4-Chloro-3-(trifluoromethyl)phenoxy]piperidine; hydrochloride salt | tert-Butyl 4-[4-chloro-3-(trifluoromethyl)phenoxy]piperidine-1-carboxylate BB71a | D3 | 280.0 [M + H]$^+$ |
| BB72 | 4-(4-Chloro-3-cyclopropyl-phenoxy) piperidine; trifluoroacetate salt | tert-Butyl 4-(4-chloro-3-cyclopropyl-phenoxy)piperidine-1-carboxylate BB72a | D1 | Used without further purification |
| BB73 | 4-[2-Chloro-5-(4-piperidyloxy) phenyl] morpholine hydrochloride | tert-Butyl 4-(4-chloro-3-morpholino-phenoxy)piperidine-1-carboxylate BB73a | D3 | Used without further purification |
| BB74 | 4-[2-Methyl-4-(trifluoromethyl)phenoxy]piperidine; trifluoroacetate salt | tert-Butyl 4-[2-methyl-4-(trifluoromethyl)phenoxy]piperidine-1-carboxylate BB74a | D1 | 260.2 [M + H]$^+$ |
| BB75 | 2-(4-Piperidyloxy)-5-(trifluoromethyl)benzonitrile | tert-Butyl 4-[2-cyano-4-(trifluoromethyl)phenoxy]piperidine-1-carboxylate BB75a | D4 | 271.1 [M + H]$^+$ |
| BB76 | 2-(4-Piperidylmethyl)oxazolo[5,4-c]pyridine; trifluoroacetate salt | tert-Butyl 4-(oxazolo[5,4-c]pyridin-2-ylmethyl)piperidine-1-carboxylate BB76a | D1 | 218.1 [M + H]$^+$ |
| BB89 | 3-[(3-Chlorophenoxy)methyl]pyrrolidine; hydrochloride salt | tert-Butyl 3-[(3-chlorophenoxy)methyl]pyrrolidine-1-carboxylate BB89a | D3 | 212.1 [M + H]$^+$ |
| BB192 | 4-2-Fluoro-4-(trifluoromethyl)phenoxy]piperidine; hydrochloride salt | tert-Butyl 4-hydroxypiperidine-1-carboxylate | D3 | 264.2 [M + H]$^+$ |
| BB193 | 4-[3-Chloro-4-(trifluoromethyl)phenoxy]piperidine; hydrochloride salt | tert-Butyl 4-[3-chloro-4-(trifluoromethyl)phenoxy]piperidine-1-carboxylate | D3 | 280.1 [M + H]$^+$ |
| BB195 | 4-[2-Chloro-3-(trifluoromethyl)phenoxy]piperidine; hydrochloride salt | tert-Butyl 4-[2-chloro-3-(trifluoromethyl)phenoxy]piperidine-1-carboxylate | D8 | 280.1 [M + H]$^+$ |
| BB196 | 3-(3-Bromo-2-chloro-phenoxy)azetidine; trifluoroacetate salt | tert-Butyl 3-(3-bromo-2-chloro-phenoxy)azetidine-1-carboxylate | D1 | 263.0 [M + H]$^+$ |
| BB198 | 3-[3-Bromo-4-(trifluoromethyl)phenoxy]azetidine; trifluoroacetate salt | tert-Butyl 3-[3-bromo-4-(trifluoromethyl)phenoxy]azetidine-1-carboxylate | D9 | 296.4 [M + H]$^+$ |
| BB199 | 3-[3-Cyclopropyl-4-(trifluoromethyl)phenoxy]azetidine; trifluoroacetate salt | tert-Butyl 3-[3-cyclopropyl-4-(trifluoromethyl)phenoxy]azetidine-1-carboxylate | D9 | 258.1 [M + H]$^+$ |
| BB200 | 3-[3-Chloro-4-(trifluoromethyl)phenoxy]azetidine; trifluoroacetate salt | tert-Butyl 3-[3-chloro-4-(trifluoromethyl)phenoxy]azetidine-1-carboxylate | D1 | 252.5 [M + H]$^+$ |

-continued

| BB No. | Systematic Name | Starting material | Method | MS, m/z |
|---|---|---|---|---|
| BB201 | 3-(3-Bromo-5-chloro-phenoxy)azetidine; trifluoroacetate salt | tert-Butyl 3-(3-bromo-5-chloro-phenoxy)azetidine-1-carboxylate | D1 | 263.9 [M + H]$^+$ |
| BB205 | 3-(3-Bromo-4-chloro-phenoxy)azetidine; trifluoroacetate salt | tert-Butyl 3-(3-bromo-4-chlorophenoxy)azetidine-1-carboxylate | D1 | 263.9 [M + H]$^+$ |

BB91

4-[[2-Pyrrolidin-1-yl-4-(trifluoromethyl)phenyl]methyl]piperidine; formic acid salt A solution of tert-butyl 4-[[2-pyrrolidin-1-yl-4-(trifluoromethyl)phenyl]methyl] piperidine-1-carboxylate (500 mg, 1.21 mmol) in 6 M HCl in MeOH solution (10.0 mL) was stirred at 20° C. for 1 h. The mixture was concentrated under vacuum, purified by reversed phase column to give the title compound as an orange oil (84.4 mg, 21.8% yield). MS (ESI): m/z=313.2 [M+H]$^+$.

Step a) Tert-butyl 4-[[2-pyrrolidin-1-yl-4-(trifluoromethyl)phenyl]methylene]piperidine-1-carboxylate To a solution of tert-butyl 4-[[2-bromo-4-(trifluoromethyl)phenyl]methylene]piperidine-1-carboxylate (800 mg, 1.90 mmol; BB51, step c), pyrrolidine (163 mg, 2.28 mmol), Ruphos (4.25 mg, 0.010 mmol) and potassium tert-butoxide (320 mg, 2.86 mmol) in toluene (15 mL) was added palladium(II) acetate (1.28 mg, 0.010 mmol). The mixture was stirred at 80° C. for 15 h under N$_2$ atmosphere. The mixture was filtered and concentrated under vacuum to remove toluene. The mixture was diluted with H$_2$O (40 mL) and extracted three times with EtOAc (40 mL each). The combined organic layers were washed with brine, dried over Na$_2$SO$_4$, filtered and concentrated. The residue was purified by silica gel chromatography (PE/EtOAc=1:0 to 8:1) to give the compound as light yellow oil (552 mg, 1.34 mmol, 36.7%) MS (ESI): m/z=411.1 [M+H]$^+$.

Step b) Tert-butyl 4-[[2-pyrrolidin-1-yl-4-(trifluoromethyl)phenyl]methyl]piperidine-1-carboxylate To a solution of tert-butyl 4-[[2-pyrrolidin-1-yl-4-(trifluoromethyl)phenyl]methylene]piperidine-1-carboxylate (525 mg, 0.660 mmol) in MeOH (20 mL) was added wet Pd/C (~52 mg) and the mixture was stirred at 20° C. under H$_2$ atmosphere (balloon) for 1 h. The mixture was filtered and concentrated under vacuum to give the desired compound as colorless oil (500 mg) which was used in the next step without further purification.

BB95

3-[2-[2-fluoro-6-(trifluoromethyl)phenyl]ethyl]azetidine 4-methylbenzenesulfonate To an solution of 3-[2-[2-fluoro-6-(trifluoromethyl)phenyl]ethyl]azetidine-1-carboxylate (50 mg, 144 µmol, Eq: 1) in EtOAc (0.8 mL) was added 4-methylbenzenesulfonic acid monohydrate (29.7 mg, 173 µmol, Eq: 1.2) and the mixture was heated at reflux for 1.5 hours. The clear, colorless solution was allowed to cool down to RT. No precipitation occurred. The solution was evaporated to give the desired product as a colorless foam. MS (ESI): m/z=248.1 [M-TsOH+H]$^+$.

Step a) tert-butyl 3-[(E)-2-[2-fluoro-6-(trifluoromethyl)phenyl]ethenyl]azetidine-1-carboxylate To an ice-cold solution of diethyl (2-fluoro-4-(trifluoromethyl)benzyl)phosphonate (300 mg, 955 µmol) in THF (2 mL) was added sodium hydride 55% in mineral oil (41.7 mg, 955 µmol) and the mixture was stirred at this temperature for 30 minutes. To the light brown mixture was added dropwise a solution of tert-butyl 3-formylazetidine-1-carboxylate (177 mg, 955 µmol) in THF (1 mL). This led to an immediate discolouration of the reaction mixture. Stirring was continued for 1 hours at ice-bath temperature followed by stirring at RT for 1.5 hours. The reaction mixture was poured into water and ethyl acetate and the layers were separated. The aqueous layer was extracted twice with ethyl acetate. The organic layers were washed once with brine, dried over MgSO$_4$, filtered, treated with silica gel and evaporated. The compound was purified by silica gel chromatography on a 12 g column using an MPLC system eluting with a gradient of n-heptane:ethyl acetate (100:0 to 25:75) to get the desired compound as a colorless solid (0.108 g; 32.8%). MS (ESI): m/z=290.2 [M−56+H]$^+$.

Step b) tert-butyl 3-[2-[2-fluoro-6-(trifluoromethyl)phenyl]ethyl]azetidine-1-carboxylate To a solution of tert-butyl (E)-3-(2-fluoro-4-(trifluoromethyl)styryl)azetidine-1-carboxylate (105 mg, 304 µmol) in MeOH (1 mL) and Ethyl acetate (1 mL) was added Pd/C 10% (11 mg, 304 µmol) and the mixture was stirred under a hydrogen atmosphere at 1.7 bar and RT for 30 minutes. The suspension was filtered. The filtrate was evaporated to get the desired compound as a colorless oil (0.104 g; 98.5%). MS (ESI): m/z=292.2 [M−56+H]$^+$.

BB96

4-((2-chloro-4-fluorophenoxy)methyl)azepane hydrochloride

To a solution of tert-butyl 4-((2-chloro-4-fluorophenoxy)methyl)azepane-1-carboxylate (620 mg, 1.73 mmol) in DCM (7.5 ml) was added HCl in ether 2M (10 ml, 20 mmol) and the reaction mixture was stirred overnight at rt. The mixture was concentrated in vacuo, the crude material collected as a white solid (490 mg, 1.67 mmol, 96.1%) and used directly on the next step. LC-MS (ESI): m/z: 258.2 [M+H]$^+$ Step a) tert-butyl 4-((2-chloro-4-fluorophenoxy)methyl)azepane-1-carboxylate In a 25 ml four-necked sulphonation flask under argon, tert-butyl 4-(hydroxymethyl)azepane-1-carboxylate (480 mg, 2.09 mmol) was dissolved in THF (10 ml). Subsequently, 2-chloro-4-fluorophenol (337 mg, 251 µl, 2.3 mmol) and triphenylphosphine (604 mg, 2.3 mmol) were added and the clear solution was stirred for 5 min at rt. The mixture was cooled to 0° C. and DEAD (401 mg, 365 µl, 2.3 mmol) was added in portions over 10 min. The mixture was stirred for 1 hr at 0° C., then overnight at rt. The mixture was taken up into EtOAc (50 ml), washed with water (2×25 ml), organic phase washed with 1M NaOH (3×25 ml), brine (20 ml), dried with $Na_2SO_4$, filtered and concentrated in vacuo. Residue was dissolved in n-Heptane/diethylether and the mixture stirred for 30 min, the TPPO precipitate filtered and the crude concentrated in vacuo. The crude material was adsorbed on Isolute® and purified by flash column chromatography (0-30% EtOAc/Heptane) over silica gel (50 g) to afford the desired product (630 mg, 1.76 mmol, 84.1%) as a yellow oil. LC-MS (ESI): m/z: 302.1 $[M-56+H]^+$

BB97

4-[[4-(trifluoromethyl)phenyl]methyl]azepane hydrochloride

To a solution of tert-butyl 4-(4-(trifluoromethyl)benzyl)azepane-1-carboxylate (88 mg, 246 µmol, Eq: 1) in DCM (1.5 ml) was added HCl in ether 2M (3.08 ml, 6.16 mmol) and the reaction mixture was stirred overnight at room temperature. The mixture was concentrated in vacuo, the crude material collected as a white solid (71 mg, 0.24 mmol, 98.2%) and used directly on the next step. LC-MS (ESI): m/z: 258.2 $[M+H]^+$ Step a: Triphenyl(4-(trifluoromethyl)benzyl)phosphonium bromide Triphenylphosphine (1.84 g, 7 mmol) and 1-(bromomethyl)-4-(trifluoromethyl)benzene (1.61 g, 6.74 mmol) were dissolved in xylene (35 ml). The reaction mixture was heated to reflux at 155° C. for 3.5 h and then cooled to room temperature. The precipitated white crystalline solid was collected by filtration, washed with diethyl ether and dried in vacuo. The final compound (3.30 g, 6.58 mmol, 97.7% yield) was obtained as a white powder and directly used on the next step. LC-MS (ESI): m/z: 421.2 $[M+H]^+$ Step b: tert-butyl (E)-4-(4-(trifluoromethyl)benzylidene)azepane-1-carboxylate A suspension of sodium hydride (88.6 mg, 2.22 mmol) in DMF (7.5 ml) was cooled in an ice bath, then triphenyl(4-(trifluoromethyl)benzyl)phosphonium bromide (1.11 g, 2.22 mmol) was added. The suspension was stirred at 0° C. for 5 min. then for 25 min at rt. tert-butyl 4-oxoazepane-1-carboxylate (315 mg, 1.48 mmol) was added and the resulting mixture was stirred at 80° C. for 28 h. The mixture was concentrated in vacuo, diluted with water (50 ml) and EtOAc (40 ml) and extracted EtOAc (3×30 ml). The combined organic fractions were washed with water, 10% LiCl solution, dried with Na2SO4 and concentrated in vacuo. The residual oil was treated with Et2O in order to precipitate the triphenylphosphoxide that was filtered off. The solution was concentrated in vacuo and the residue was purified by flash column chromatography (0-35% EtOAc/Heptane) over silica gel (50 g) to afford the desired product (92 mg, 259 µmol, 17.5% yield) as a yellow oil. LC-MS (ESI): m/z: 300.2 $[M-56+H]^+$ Step c: tert-butyl 4-(4-(trifluoromethyl)benzyl)azepane-1-carboxylate A solution of tert-butyl (E)-4-(4-(trifluoromethyl)benzylidene)azepane-1-carboxylate (90 mg, 253 µmol) was dissolved in MeOH (2.5 ml). The reaction vessel was evacuated and back-filled with argon 5 times. Under argon, Pd—C (13.5 mg, 12.7 µmol) was added and the atmosphere was replaced with hydrogen three times. The reaction was stirred under a hydrogen atmosphere at 1 bar for 24 h. The atmosphere was replaced with argon and the reaction mixture was filtered over a pad of Dicalite. The filter cake was washed with methanol. The filtrate was concentrated in vacuo to give the desired product (89 mg, 249 µmol, 98.3% yield) as a colorless oil which was used without further purification. LC-MS (ESI): m/z: 302.2 $[M-56+H]^+$

BB98

3-((2-Chloro-4-(trifluoromethyl)phenyl)thio)azetidine 2,2,2-trifluoroacetate tert-Butyl 3-((2-chloro-4-(trifluoromethyl)phenyl)thio)azetidine-1-carboxylate (110 mg, 299 µmol) was dissolved in DCM (2 mL) and TFA (273 mg, 184 µL, 2.39 mmol) was added. The reaction mixture was stirred at RT for 3 h. Volatiles were removed in vacuo to yield 110 mg of a light yellow solid (96%). MS (ESI): m/z=268.1 $[M+H]^+$.

Step a) tert-Butyl 3-((2-chloro-4-(trifluoromethyl)phenyl)thio)azetidine-1-carboxylate In a 20 mL glasstube, a solution of 2-chloro-4-(trifluoromethyl)benzenethiol (440 mg, 2.07 mmol) in dry THF (6 mL) was added potassium tert-butoxide 1M solution in THF (2.17 ml, 2.17 mmol) and the yellow reaction mixture was stirred at RT for 15 min followed by addition of tert-butyl 3-bromoazetidine-1-carboxylate (489 mg, 2.07 mmol). The reaction mixture was then stirred at RT for 5 h and over night at 70° C. The crude reaction was diluted with EtOAc and extracted with H2O, the organic phase was collected and the aqueous phase was back-extracted with EtOAc. The combined organic phases were dried over Na2SO4 and evaporated down to dryness. The residue was purified by chromatography ($SiO_2$, n-eptane/EtOAc (0 to 40% over 40 min) yielded the product as a viscous oil (467 mg, 61%). MS (ESI): m/z=312.1 $[M-56]^+$.

BB99

3-((2-Chloro-4-(trifluoromethyl)phenyl)sulfonyl)azetidine 2,2,2-trifluoroacetate tert-Butyl 3-((2-chloro-4-(trifluoromethyl)phenyl)sulfonyl)azetidine-1-carboxylate (100 mg, 250 µmol) was dissolved in DCM and TFA (228 mg, 154 µL, 2 mmol) was added. The reaction mixture was stirred at RT for 8 h. Volatiles were removed in vacuo to yield the desired compound as light yellow solid (102 mg, 98%). MS (ESI): m/z=300.0 $[M+H]^+$.

Step a) tert-Butyl 3-((2-chloro-4-(trifluoromethyl)phenyl)thio)azetidine-1-carboxylate In a 20 mL glasstube, a solution of 2-chloro-4-(trifluoromethyl)benzenethiol (440 mg, 2.07 mmol) in dry THF (6 mL) was added potassium tert-butoxide 1M solution in THF (2.17 mL, 2.17 mmol) and the yellow reaction mixture was stirred at r.t for 15 min followed by addition of tert-butyl 3-bromoazetidine-1-carboxylate (489 mg, 2.07 mmol). The reaction mixture was then stirred at r.t for 5 h and over night at 70° C. The crude reaction was diluted with EtOAc and extracted with H2O, the organic phase was collected and the aqueous phase was back-extracted with EtOAc. The combined organic phases were dried over Na2SO4 and evaporated down to dryness. The residue was purified by column chromatography ($SiO_2$, n-eptane/EtOAc (0 to 40% over 40 min) to yield the desired product as a viscous oil (467 mg, 61%). MS (ESI): m/z=312.1 [M−56+H]$^+$.

Step b) tert-Butyl 3-((2-chloro-4-(trifluoromethyl) phenyl)sulfonyl)azetidine-1-carboxylate mCPBA (347 mg, 1.41 mmol) was added in one portion to a stirred solution of tert-butyl 3-((2-chloro-4-(trifluoromethyl)phenyl)thio)azetidine-1-carboxylate (345 mg, 938 μmol) in DCM (6 mL) in an ice bath. The reaction was stirred at RT for 20 min. The reaction mixture was poured into 5 mL saturated $Na_2CO_3$ solution and extracted twice with DCM (20 mL each). The organic layers were combined, washed with brine, dried over $Na_2SO_4$ and concentrated in vacuo. The crude material was purified by preparative HPLC (YMC-Triart C18, ACN/H2O+0.1% HCOOH) to furnish the product as a white powder (253 mg, 67.5%) MS (ESI): m/z=344.0 [M−56+H]$^+$.

BB100

3-((2-Chloro-4-(trifluoromethyl)phenyl)sulfinyl) azetidine 2,2,2-trifluoroacetate tert-Butyl 3-((2-chloro-4-(trifluoromethyl)phenyl)sulfinyl)azetidine-1-carboxylate (50 mg, 130 μmol) was dissolved in DCM (1.5 mL), TFA (149 mg, 100 μL, 1.3 mmol) was added and the reaction mixture was stirred at RT for 8 h. Volatiles were removed in vacuo to yield the compound as white solid (51 mg, 98%). MS (ESI): m/z=284.1 [M+H]$^+$.

Step a) tert-Butyl 3-((2-chloro-4-(trifluoromethyl) phenyl)thio)azetidine-1-carboxylate The compound was prepared in analogy to BB99, step a, and used in the next step without further purification.

Step b) tert-Butyl 3-((2-chloro-4-(trifluoromethyl) phenyl)sulfinyl)azetidine-1-carboxylate The sulfoxide intermediate was isolated from the the synthesis of the according sulfone building block BB99, step b. The product was obtained as a white lyophilized powder (50 mg, 13.9%) MS (ESI): m/z=328.1 [M−56+H]$^+$.

BB101

3-(((2-Chloro-4-(trifluoromethyl)phenyl)thio) methyl)azetidine 2,2,2-trifluoroacetate To a solution of tert-butyl 3-(((2-chloro-4-(trifluoromethyl)phenyl)thio)methyl)azetidine-1-carboxylate (0.200 g, 524 μmol) in DCM (3 mL) was added TFA (478 mg, 323 μL, 4.19 mmol) and the reaction mixture was stirred at RT for 3 h. Volatiles were removed in vacuo to yield the compound as light yellow oil that was used in the next step without further purification (267 mg). MS (ESI): m/z=282.2 [M+H]$^+$.

Step a) tert-Butyl 3-[[2-chloro-4-(trifluoromethyl) phenyl]sulfanylmethyl]azetidine-1-carboxylate To a solution of 2-chloro-4-(trifluoromethyl)benzenethiol (0.400 g, 1.88 mmol) in dry THF (6 mL) was added potassium tert-butoxide 1M solution in THF (1.98 mL, 1.98 mmol) and the turbid reaction mixture was stirred at RT for 15 min followed by addition of tert-butyl 3-(bromomethyl) azetidine-1-carboxylate (471 mg, 1.88 mmol). The reaction mixture was then stirred at RT for 19 h. The crude reaction was diluted with EtOAc and extracted with aq. 1 M $NaHCO_3$ solution, the organic phase was collected and the aqueous phase was back-extracted with EtOAc. The combined organic phases were dried over $Na_2SO_4$ and evaporated down to dryness to yield the crude product which was used in the next step without further purification (762 mg). MS (ESI): m/z=326.1 [M−56+H]$^+$.

BB102

3-((2-Fluoro-6-(trifluoromethyl)benzyl)sulfonyl) azetidine 2,2,2-trifluoroacetate tert-Butyl 3-((2-fluoro-6-(trifluoromethyl)phenyl)methylsulfonyl)azetidine-1-carboxylate (0.047 g, 118 μmol) was dissolved in DCM (0.5 mL) and TFA (108 mg, 72.9 μL, 946 μmol) was added. The reaction mixture was stirred at RT for 2 h. Volatiles were removed in vacuo to yield the compound as a yellow oil (56 mg) that was used in the next step without further purification. MS (ESI): m/z=298.2 [M+H]$^+$.

Step a) tert-Butyl 3-((2-fluoro-6-(trifluoromethyl) benzyl)thio)azetidine-1-carboxylate To a solution of tert-butyl 3-mercaptoazetidine-1-carboxylate (0.400 g, 2.11 mmol) in dry THF (5 mL) was added potassium tert-butoxide 1M solution in THF (2.22 mL, 2.22 mmol) and the reaction mixture was stirred at RT for 15 min followed by addition of 2-(bromomethyl)-1-fluoro-3-(trifluoromethyl)benzene (CAS RN 239087-08-2). The reaction mixture was then stirred at RT for 14 h. The crude reaction was diluted with EtOAc and extracted with aq. 1 M $NaHCO_3$ solution, the organic phase was collected and the aqueous phase was back-extracted with EtOAc. The combined organic phases were dried over $NaSO_4$ and evaporated down to dryness to yield the crude product (805 mg) which was used in the next step without further purification. MS (ESI): m/z=310.2 [M−56+H]$^+$.

Step b) tert-Butyl 3-[[2-fluoro-6-(trifluoromethyl) phenyl]methylsulfonyl]azetidine-1-carboxylate 3-Chlorobenzoperoxoic acid (283 mg, 1.64 mmol) was added in portion to a stirred solution of tert-butyl 3-((2-fluoro-6-(trifluoromethyl)benzyl)thio)azetidine-1-carboxylate (0.300 g, 821 μmol) in DCM (5 mL) in an ice bath. The reaction mixture was stirred at RT for 15 min and poured into 5 mL saturated aqueous $NaHCO_3$ solution and extracted twice with DCM (10 mL each). The organic layers were combined, washed with brine, dried over Na2SO4 and concentrated in vacuo. The crude material was purified by flash column chromatography (silica gel, 20 g, 0% to 100%

EtOAc in n-heptane) to furnish the desired product as a colorless oil (47 mg, 15%). MS (ESI): m/z=415.1 [M+NH$_4$]$^+$.

BB103

3-((2-Fluoro-6-(trifluoromethyl)benzyl)sulfinyl)azetidine 2,2,2-trifluoroacetate tert-Butyl 3-[[2-fluoro-6-(trifluoromethyl)phenyl]methylsulfinyl]azetidine-1-carboxylate (0.086 g, 225 µmol) was dissolved in DCM (1 mL) and TFA (206 mg, 139 µL, 1.8 mmol) was added. The reaction mixture was stirred at RT for 2 h. Volatiles were removed in vacuo to yield the compound as a yellow oil (93 mg) that was used in the next step without further purification. MS (ESI): m/z=282.2 [M+H]$^+$.

Step a) tert-Butyl 3-[[2-fluoro-6-(trifluoromethyl)phenyl]methylsulfinyl]azetidine-1-carboxylate The sulfoxide intermediate was isolated from the synthesis of BB102, step b, as a colorless oil (86 mg, 28%). MS (ESI): m/z=404.1 [M+Na]$^+$.

BB104

3-(((2-Chloro-4-(trifluoromethyl)phenyl)sulfonyl)methyl)azetidine 2,2,2-trifluoroacetate tert-Butyl 3-(((2-chloro-4-(trifluoromethyl)phenyl)sulfonyl)methyl)azetidine-1-carboxylate (0.145 g, 350 µmol) was dissolved in DCM (2 mL) and TFA (320 mg, 216 µL, 2.8 mmol) was added. The reaction mixture was stirred at RT for 2 h. Volatiles were removed in vacuo to yield the compound as a yellow oil (181 mg) that was used in the next step without further purification. MS (ESI): m/z=314.1 [M+H]$^+$.

Step a) tert-Butyl 3-(((2-chloro-4-(trifluoromethyl)phenyl)sulfonyl)methyl)azetidine-1-carboxylate 3-Chlorobenzoperoxoic acid (352 mg, 1.57 mmol) was added in portions to a stirred solution of tert-butyl 3-(((2-chloro-4-(trifluoromethyl)phenyl)thio)methyl)azetidine-1-carboxylate (BB101, step a) (0.300 g, 786 µmol) in DCM (5 mL) in an ice bath. The reaction mixture was stirred at RT for 15 min and poured into 5 mL saturated aqueous NaHCO$_3$ solution and extracted twice with DCM (10 mL each). The organic layers were combined, washed with brine, dried over Na$_2$SO$_4$ and concentrated in vacuo. The crude material was purified by flash chromatography (silica gel, 20 g, 0% to 100% EtOAc in n-heptane) to provide the desired product as a colorless oil (145 mg, 45%). MS (ESI): m/z=314.0 [M−56+H]$^+$.

BB105

3-(((2-Chloro-4-(trifluoromethyl)phenyl)sulfinyl)methyl)azetidine 2,2,2-trifluoroacetate tert-Butyl 3-(((2-chloro-4-(trifluoromethyl)phenyl)sulfinyl)methyl)azetidine-1-carboxylate (0.086 g, 216 µmol) was dissolved in DCM (1 mL) and TFA (197 mg, 133 µL, 1.73 mmol) was added. The reaction mixture was stirred at RT for 2 h. Volatiles were removed in vacuo to yield the compound as a yellow oil (99 mg) that was used in the next step without further purification. MS (ESI): m/z=298.1 [M+H]$^+$.

Step a) tert-Butyl 3-(((2-chloro-4-(trifluoromethyl)phenyl)sulfinyl)methyl)azetidine-1-carboxylate The sulfoxide intermediate was isolated from the synthesis of BB104, step a. The desired product was obtained as a yellow oil (80 mg, 25.6%). MS (ESI): m/z=398.1 [M+H]$^+$.

BB106

3-((2-Fluoro-4-(trifluoromethyl)benzyl)thio)azetidine 2,2,2-trifluoroacetate To a solution of tert-butyl 3-((2-fluoro-4-(trifluoromethyl)benzyl)thio)azetidine-1-carboxylate (0.282 g, 772 µmol) in DCM (3 mL) was added TFA (880 mg, 595 µL, 7.72 mmol) and the reaction mixture was stirred at RT for 3 h. Volatiles were removed in vacuo to yield the desired compound as a colorless oil (302 mg) that was used in the next step without further purification. MS (ESI): m/z=266.2 [M+H]$^+$.

Step a) tert-Butyl 3-[[2-fluoro-4-(trifluoromethyl)phenyl]methylsulfanyl]azetidine-1-carboxylate To a solution of tert-butyl 3-mercaptoazetidine-1-carboxylate (0.200 g, 1.06 mmol) in dry THF (2 mL) was added potassium tert-butoxide 1M solution in THF (1.11 mL, 1.11 mmol) and the reaction mixture was stirred at RT for 15 m followed by addition of 1-(bromomethyl)-2-fluoro-4-(trifluoromethyl)benzene (272 mg, 1.06 mmol, CAS RN 239087-07-1). The reaction mixture was then stirred at RT for 14 h. The crude reaction was diluted with EtOAc and extracted with aq. 1 M NaHCO$_3$ solution, the organic phase was collected and the aqueous phase was back-extracted with EtOAc. The combined organic phases were dried over NaSO$_4$ and evaporated down to dryness and purified by flash chromatography (silica gel, 20 g, 000 to 80% EtOAc in n-heptane) to furnish the desired product as a colorless oil (288 mg, 75%). MS (ESI): m/z=310.2 [M−56+H].

In analogy to BB184, the following intermediates were prepared from the respective commercially available starting materials.

| BB No. | Systematic Name | Starting material | MS, m/z |
| --- | --- | --- | --- |
| BB107 | 3-[2-(2,6-Dichlorophenyl)ethynyl]azetidine | 1,3-Dichloro-2-iodobenzene | 226.1 [M + H]$^+$ |
| BB108 | 3-[2-[2-Fluoro-4-(trifluoromethyl)phenyl]ethynyl]azetidine | 1-Bromo-2-fluoro-4-(trifluoromethyl)benzene | 244.2 [M + H]$^+$ |
| BB109 | 3-[2-(2,6-Difluorophenyl)ethynyl]azetidine | 1,3-Difluoro-2-iodobenzene | 194.2 [M + H]$^+$ |
| BB110 | 3-[2-[3-Chloro-4-(trifluoromethyl)phenyl]ethynyl]azetidine | 4-Bromo-2-chloro-1-(trifluoromethyl)benzene | 260.2 [M + H]$^+$ |
| BB111 | 3-[2-(2-Chloro-6-fluoro-phenyl)ethynyl]azetidine | 2-Bromo-1-chloro-3-fluorobenzene | 210.1 [M + H]$^+$ |
| BB112 | 3-[2-(2-Chloro-4-cyclopropyl-phenyl)ethynyl]azetidine | 1-Bromo-2-chloro-4-cyclopropylbenzene | 232.2 [M + H]$^+$ |

-continued

| BB No. | Systematic Name | Starting material | MS, m/z |
|---|---|---|---|
| BB113 | 3-[2-(2-Methoxyphenyl)ethynyl]azetidine | 1-Bromo-2-methoxybenzene | 188.2 [M + H]+ |
| BB114 | 3-[2-[4-Chloro-2-(trifluoromethyl)phenyl]ethynyl]azetidine | 4-Chloro-1-iodo-2-(trifluoromethyl)benzene | 260.1 [M + H]+ |
| BB115 | 3-[2-(3-Chlorophenyl)ethynyl]azetidine | 1-Bromo-3-chlorobenzene | 192.1 [M + H]+ |
| BB116 | 3-[2-[4-(Trifluoromethoxy)phenyl]ethynyl]azetidine | 1-bromo-4-(Trifluoromethoxy)benzene | 242.2 [M + H]+ |
| BB117 | 3-[2-[4-(Trifluoromethyl)phenyl]ethynyl]azetidine | 1-Bromo-4-(trifluoromethyl)benzene | 226.2 [M + H]+ |
| BB118 | 3-[2-(3-Fluoro-2-methyl-phenyl)ethynyl]azetidine | 1-Bromo-3-fluoro-2-methylbenzene | 190.2 [M + H]+ |
| BB119 | 3-[2-(2,6-Dimethylphenyl)ethynyl]azetidine | 2-Iodo-1,3-dimethylbenzene | 186.2 [M + H]+ |
| BB120 | 3-[2-[2-(Trifluoromethoxy)phenyl]ethynyl]azetidine | 1-Bromo-2-(trifluoromethoxy)benzene | 242.2 [M + H]+ |
| BB121 | 3-[2-(2-Bromophenyl)ethynyl]azetidine | 1-Bromo-2-iodobenzene | 236.1 [M + H]+ |
| BB122 | 3-[2-(2-Chloro-3-fluoro-phenyl)ethynyl]azetidine | 1-Bromo-2-chloro-3-fluorobenzene | 210.1 [M + H]+ |
| BB123 | 3-[2-(o-Tolyl)ethynyl]azetidine | 1-Bromo-2-methylbenzene | 172.2 [M + H]+ |
| BB124 | 3-[2-(4-Chloro-2-fluoro-phenyl)ethynyl]azetidine | 4-Chloro-2-fluoro-1-iodobenzene | 210.1 [M + H]+ |
| BB125 | 3-[2-[2-(Difluoromethoxy)phenyl]ethynyl]azetidine | 1-(Difluoromethoxy)-2-iodobenzene | 224.2 [M + H]+ |
| BB126 | 2-[2-(Azetidin-3-yl)ethynyl]-3-chloro-benzonitrile | 2-Bromo-3-chlorobenzonitrile | 217.2 [M + H]+ |
| BB127 | 3-[2-[4-(Difluoromethoxy)phenyl]ethynyl]azetidine | 1-(Difluoromethoxy)-4-iodobenzene | 224.2 [M + H]+ |
| BB128 | 1-[4-[2-(Azetidin-3-yl)ethynyl]phenyl]cyclopropanecarbonitrile | 1-(4-Bromophenyl)cyclopropane-1-carbonitrile | 223.2 [M + H]+ |
| BB129 | 3-[2-(4-Cyclopropylphenyl)prop-1-ynyl]azetidine | 1-Bromo-4-cyclopropyl-benzene | 198.2 [M + H]+ |
| BB130 | 1-[4-[2-(Azetidin-3-yl)ethynyl]phenyl]cyclopropanol | 1-(4-Bromophenyl)cyclopropanol | 214.2 [M + H]+ |
| BB131 | 3-[2-(3-Methoxyphenyl)ethynyl]azetidine | 1-Iodo-3-methoxybenzene | 188.2 [M + H]+ |
| BB132 | 3-[2-[2-(Difluoromethyl)phenyl]ethynyl]azetidine | 1-Bromo-2-(difluoromethyl)benzene | 208.2 [M + H]+ |
| BB133 | 3-[2-(3-Methoxy-2-methyl-phenyl)ethynyl]azetidine | 1-Iodo-3-methoxy-2-methylbenzene | 202.2 [M + H]+ |
| BB134 | 3-[2-(2-Chloro-6-methyl-phenyl)ethynyl]azetidine | 1-Chloro-2-iodo-3-methylbenzene | 206.1 [M + H]+ |
| BB135 | 3-[2-(2-Chloro-5-fluoro-phenyl)ethynyl]azetidine | 2-Bromo-1-chloro-4-fluorobenzene | 210.1 [M + H]+ |
| BB136 | 3-[2-(4-Methylsulfonylphenyl)ethynyl]azetidine | 1-Bromo-4-methylsulfonyl-benzene | 236.2 [M + H]+ |
| BB137 | 3-[2-(5-Chloro-2-thienyl)ethynyl]azetidine | 2-Bromo-5-chlorothiophene | 198.1 [M + H]+ |
| BB138 | 3-[2-(5-Chloro-3-thienyl)ethynyl]azetidine | 4-Bromo-2-chlorothiophene | 198.1 [M + H]+ |
| BB139 | 3-[2-[2-Chloro-6-fluoro-4-(trifluoromethyl)phenyl]ethynyl]azetidine | 2-Bromo-1-chloro-3-fluoro-5-(trifluoromethyl)benzene | 278.1 [M + H]+ |
| BB140 | 3-[2-(2-Chlorophenyl)ethynyl]azetidin-3-ol | Chloro-2-iodobenzene and tert-butyl 3-ethynyl-3-hydroxyazetidine-1-carboxylate (CAS RN 1259034-35-9) | 208.1 [M + H]+ |
| BB141 | 3-[2-[2-(Methoxymethyl)phenyl]ethynyl]azetidine | 1-Iodo-2-(methoxymethyl)benzene | 202.2 [M + H]+ |
| BB142 | 3-[2-[2-Chloro-4-(trifluoromethyl)phenyl]ethynyl]azetidine | 2-Chloro-1-iodo-4-(trifluoromethyl)benzene | 260.2 [M + H]+ |

In analogy to BB 18, the following intermediates were prepared from the respective commercially available starting materials.

| BB No. | Systematic Name | Starting material | MS, m/z |
|---|---|---|---|
| BB143 | 4-[2-[2-(Trifluoromethyl)phenyl]ethynyl]piperidine | 1-Bromo-2-(trifluoromethyl)benzene | 254.3 [M + H]+ |

-continued

| BB No. | Systematic Name | Starting material | MS, m/z |
|---|---|---|---|
| BB144 | 4-[2-(2-Methoxyphenyl)ethynyl]piperidine | 1-Bromo-2-methoxybenzene | 216.3 [M + H]$^+$ |
| BB145 | 4-[2-(o-Tolyl)ethynyl]piperidine | 1-Bromo-2-methylbenzene | 200.3 [M + H]$^+$ |
| BB146 | 4-[2-(2,6-Dimethylphenyl)ethynyl]piperidine | 2-Iodo-1,3-dimethylbenzene | 214.3 [M + H]$^+$ |
| BB147 | 4-[2-(2,4-Dichlorophenyl)ethynyl]-4-methyl-piperidine | Bromo-2,4-dichlorobenzene and tert-Butyl 4-ethynyl-4-methylpiperidine-1-carboxylate (CAS RN 1363383-17-8) | 268.2 [M + H]$^+$ |
| BB148 | 4-[2-(2-Chloro-4-fluoro-phenyl)ethynyl]-4-methyl-piperidine | 2-Chloro-4-fluoro-1-iodobenzene and tert-Butyl 4-ethynyl-4-methylpiperidine-1-carboxylate (CAS RN 1363383-17-8) | 252.2 [M + H]$^+$ |

BB149

1-[2-(Azetidin-3-yl)ethynyl]cyclopentanol hydrochloride

To a solution of tert-butyl 3-[2-(1-hydroxycyclopentyl)ethynyl]azetidine-1-carboxylate (0.02 g, 0.075 mmol) in dioxane (0.5 mL) was added 4 M HCl in dioxane (0.094 mL, 0.377 mmol) and the reaction mixture was stirred at RT for 18 h. The mixture was evaporated to dryness and the residue triturated in diisopropyl ether, filtered off and further dried under high vacuum to give the title compound as a white solid as the hydrochloride salt (0.013 g, 87%). MS (ESI): m/z=166.1 [M+H]$^+$.

Step a) tert-Butyl 3-[2-(1-hydroxycyclopentyl)ethynyl]azetidine-1-carboxylate

To a solution of tert-butyl 3-ethynylazetidine-1-carboxylate (0.2 g, 1.1 mmol) in THF (6.5 mL) at −78° C. was added nBuLi (0.759 mL, 1.21 mmol) dropwise and the reaction mixture was stirred at this temperature for 1 h. Then, cyclopentanone (0.107 mL, 1.21 mmol) in THF (3 mL) was added dropwise to the mixture which was stirred at −78° C. for 2 h. The mixture was allowed to warm up to 0° C., poured into a sat. NH$_4$OH aqueous solution and extracted with EtOAc. The combined organic layers were washed with brine, dried over Na$_2$SO$_4$, filtered and evaporated. The residue was purified by silica gel flash chromatography, eluting with a gradient of EtOAc n-heptane (0 to 100%) to yield the title compound as a light yellow oil (0.020 g, 7%). MS (ESI): m/z=192.2 [M−56−18+H]$^+$.

BB150

4-[3-Pyrazol-1-yl-5-(trifluoromethyl)phenoxy]piperidine formate

A mixture of tert-butyl 4-[3-pyrazol-1-yl-5-(trifluoromethyl)phenoxy]piperidine-1-carboxylate (400.0 mg, 0.970 mmol) and TFA (1.0 mL, 0.970 mmol) in DCM (10 mL) was stirred at 20° C. for 12 h. The mixture was purified by prep-HPLC (ACN and water containing 0.225% v/v FA) to give the desired product (300 mg, 94.4%) as colorless gum. MS (ESI): m/z=312.1 [M+H]$^+$.

Step a: tert-Butyl 4-[3-bromo-5-(trifluoromethyl)phenoxy]piperidine-1-carboxylate To a solution of 3-bromo-5-(trifluoromethyl)phenol (2.0 g, 8.3 mmol), 1-BOC-4-hydroxypiperidine (1.84 g, 9.13 mmol, CAS RN 106-52-5) and PPh$_3$ (2.61 g, 9.96 mmol) in THF (32.6 mL) was added diisopropyl azodicarboxylate (1.96 mL, 9.96 mmol) and the mixture was stirred at 20° C. for 15 h. The mixture was concentrated under vacuum. The residue was purified by prep-HPLC (ACN and water containing 0.225% v/v FA) and concentrated under vacuum to give the desired product (2.6 g, 73.9% yield) as light yellow oil. MS (ESI): m/z=367.9 [M−56+H]$^+$.

Step b) tert-Butyl 4-[3-pyrazol-1-yl-5-(trifluoromethyl)phenoxy]piperidine-1-carboxylate A mixture of tert-butyl 4-[3-bromo-5-(trifluoromethyl)phenoxy]piperidine-1-carboxylate (500.0 mg, 1.18 mmol), pyrazole (160.47 mg, 2.36 mmol), CuI (22.37 mg, 0.120 mmol), cesium carbonate (1152 mg, 3.54 mmol) and N,N′-dimethylethylenediamine (519.15 mg, 5.89 mmol) in DMF (5 mL) was stirred at 110° C. for 12 h. The mixture was poured into H$_2$O water (30 mL) and extracted three times with EtOAc (50 mL). The combined organic layer was washed with ammonia (10 mL), brine (50 mL), dried over Na$_2$SO$_4$ and filtered. The filtrate was concentrated under vacuum to give the desired product (400 mg, 82.5% yield) as light yellow oil. MS (ESI): m/z=356.2 [M−56+H]$^+$.

BB151

4-[[2-(2,2,2-Trifluoroethoxy)-4-(trifluoromethyl)phenyl]methyl]piperidine

A mixture of 4-[[2-(2,2,2-trifluoroethoxy)-4-(trifluoromethyl)phenyl]methylene]piperidine (250.0 mg, 0.740 mmol) and Pd/C (50.0 mg, wt. 10%) in THF (10 mL) was stirred at 20° C. for 12 h under H$_2$ (1520 mmHg). The mixture was filtered and concentrated under vacuum to give the desired compound (240 mg, 95.4%) as light brown gum. MS (ESI): m/z=342.1 [M+H]$^+$.

Step a) tert-Butyl 4-(p-tolylsulfonylhydrazono)piperidine-1-carboxylate

To a solution of 4-methylbenzenesulfonhydrazide (9.35 g, 50.19 mmol, CAS RN 1576-35-8) in MeOH (100 mL) was added 1-BOC-4-piperidone (10.0 g, 50.19 mmol, CAS RN 17502-28-8) and the mixture was stirred at 25° C. for 12 h. The mixture was concentrated to give the desired product (18.4 g, 99.8%) as off-white solid. MS (ESI): m/z=368.2 [M+H]+.

Step b) 2-(2,2,2-Trifluoroethoxy)-4-(trifluoromethyl)benzaldehyde

A mixture of NaH (187.39 mg, 60% dispersion in mineral oil, 4.68 mmol,) in 2,2,2-trifluoroethanol (16.67 mL, 228.74 mmol, CAS RN75-89-8) was stirred at 0° C. The cooling bath was removed and the mixture was stirred at 20° C. for 2 h, and then 2-fluoro-4-(trifluoromethyl)benzaldehyde (1.0 g, 5.21 mmol, CAS RN 763-93-9) was added and the mixture was stirred at 20° C. for 12 h. The mixture was poured into H2O (30 mL) and extracted twice with EtOAc (30 mL each). The combined organic layers were washed with brine (30 mL), dried over $Na_2SO_4$ and filtered. The filtrate was concentrated under vacuum to give the desired product (1.2 g, 84.7%) as light yellow solid. $^1$H NMR (400 MHz, DMSO-d6) δ 10.44-10.34 (m, 1H), 7.93 (d, J=8.1 Hz, 1H), 7.75 (s, 1H), 7.55 (d, J=8.1 Hz, 1H), 5.11 (q, J=8.7 Hz, 2H).

Step c) tert-Butyl 4-[2-(2,2,2-trifluoroethoxy)-4-(trifluoromethyl)benzoyl]piperidine-1-carboxylate A mixture of 2-(2,2,2-trifluoroethoxy)-4-(trifluoromethyl)benzaldehyde (1000.0 mg, 3.67 mmol), tert-butyl 4-(p-tolylsulfonylhydrazono)piperidine-1-carboxylate (1350.3 mg, 3.67 mmol) and cesium carbonate (1795.9 mg, 5.51 mmol) in 1,4-dioxane (30 mL) was stirred at 110° C. for 12 h under $N_2$ atmosphere. The mixture was poured into H2O (50 mL) and extracted three times with EtOAc (50 mL each). The combined organic layers were washed with brine (50 mL), dried over $Na_2SO_4$ and filtered. The filtrate was concentrated under vacuum and the residue was purified by prep-HPLC (MeCN and water containing 0.225% v/v FA) to give the desired product (980 mg, 58.6%) as light yellow gum. MS (ESI): m/z=400.1 [M−56+H]+.

Step d) tert-Butyl 4-[hydroxy-[2-(2,2,2-trifluoroethoxy)-4-(trifluoromethyl)phenyl]methyl]piperidine-1-carboxylate To a solution of tert-butyl 4-[2-(2,2,2-trifluoroethoxy)-4-(trifluoromethyl)benzoyl]piperidine-1-carboxylate (900.0 mg, 1.98 mmol) in MeOH (45 mL) was added $NaBH_4$ (149.54 mg, 3.95 mmol) at 0° C. and the mixture was stirred at 20° C. for 12 h. The mixture was purified by prep-HPLC (MeCN and water containing 0.225% v/v FA) (650 mg, 71.9%) as light yellow oil. MS (ESI): m/z=384.0 [M−56−OH+H]+.

Step e) 4-[[2-(2,2,2-Trifuoroethoxy)-4-(trifluoromethyl)phenyl]methylene]piperidine A mixture of tert-butyl 4-[hydroxy-[2-(2,2,2-trifluoroethoxy)-4-(trifluoromethyl)phenyl]methyl]piperidine-1-carboxylate (400.0 mg, 0.870 mmol) and MsOH (840.43 mg, 8.74 mmol) in DCM (4 mL) was stirred at 40° C. for 24 h. The mixture was poured into saturated aqueous $Na_2CO_3$ solution (5 mL) and extracted three times with EtOAc (10 mL each). The combined organic layers were washed with brine (10 mL), dried over $Na_2SO_4$ and filtered. The filtrate was concentrated under vacuum to give the desired compound as light yellow oil (260 mg, 76.2%). MS (ESI): m/z=340.1 [M+H]+.

BB152

4-[3-(1,2,4-Triazol-1-yl)-5-(trifluoromethyl)phenoxy]piperidine trifluoroacetate To a mixture of tert-butyl 4-[3-(1,2,4-triazol-1-yl)-5-(trifluoromethyl)phenoxy]piperidine-1-carboxylate (240.0 mg, 0.580 mmol) in DCM (10 mL) was added TFA (1.0 mL). The mixture was stirred at 20° C. for 12 h and then concentrated under vacuum to give 4-[3-(1,2,4-triazol-1-yl)-5-(trifluoromethyl)phenoxy]piperidine 2,2,2-trifluoroacetic acid salt (240 mg, 96.7%) as light yellow gum. MS (ESI): m/z=313.1 [M+H]+.

Step a) tert-Butyl 4-[3-(1,2,4-triazol-1-yl)-5-(trifluoromethyl)phenoxy]piperidine-1-carboxylate A mixture of tert-butyl 4-[3-bromo-5-(trifluoromethyl)phenoxy]piperidine-1-carboxylate (500.0 mg, 1.18 mmol, BB98, intermediate a), 1,2,4-triazole (162.8 mg, 2.36 mmol) and CuI (22.37 mg, 0.120 mmol) in DMF (5 mL) was stirred at 110° C. for 12 h. The mixture was poured into H2O (20 mL) and extracted three times with EtOAc (30 mL each). The combined organic layers were washed with ammonia (20 mL), brine (20 mL, three times), dried over $Na_2SO_4$ and filtered. The filtrate was concentrated under vacuum and the residue was purified by column chromatography (PE:EA=50:1~3:1) to give the desired product (240 mg, 49.4%) as light yellow solid. MS (ESI): m/z=357.1 [M−56+H]+.

BB153

3-[4-Chloro-3-(trifluoromethyl)phenoxy]azetidine trifluoroacetate

To a solution of tert-butyl 3-[4-chloro-3-(trifluoromethyl)phenoxy]azetidine-1-carboxylate (300.0 mg, 0.530 mmol) in DCM (7.5 mL) was added TFA (1.04 mL) at 0° C. and the mixture was stirred at 20° C. for 2 h. The mixture was concentrated to give the title compound as yellow oil (280 mg, 97%). MS (ESI): m/z=252.0 [M+H]+.

Step a) tert-Butyl 3-[4-chloro-3-(trifluoromethyl)phenoxy]azetidine-1-carboxylate To a solution of 2-chloro-5-hydroxybenzotrifluoride (1 g, 5.1 mmol CAS RN 6294-93-5), tert-butyl 3-hydroxyazetidine-1-carboxylate (0.97 g, 5.6 mmol CAS RN 141699-55-0) and triphenylphosphine (1.6 g, 6.11 mmol) in THF (20 mL) was added diisopropyl azodicarboxylate (1.2 mL, 6.11 mmol) and the mixture was stirred at 20° C. for 15 h. The mixture was concentrated and purified by reversed phase chromatography (MeCN and water containing 0.225% v/v FA) to give the title compound (820 mg, 28.7%) as brown solid. MS (ESI): m/z=295.9 [M−56+H]+.

BB154

4-(4-Chloro-3-pyrazol-1-yl-phenoxy)piperidine trifluoroacetate

To a solution of tert-butyl 4-(4-chloro-3-pyrazol-1-yl-phenoxy)piperidine-1-carboxylate (260.0 mg, 0.690 mmol)

in DCM (5.38 mL) was added TFA (1.34 mL, 17.46 mmol) at 0° C. and the mixture was stirred at 20° C. for 1 h. The mixture was concentrated to give the title compound as an orange oil (250 mg, 92.7 yield). MS (ESI): m/z=278.1 [M+H]$^+$.

Step a) tert-Butyl 4-(3-bromo-4-chloro-phenoxy) piperidine-1-carboxylate

To a solution of 1-BOC-4-hydroxypiperidine (2.04 g, 10.12 mmol, CAS RN 106-52-5), 3-bromo-4-chlorophenol (2.0 g, 9.64 mmol, CAS RN 2402-82-6) and triphenylphosphine (3.03 g, 11.57 mmol) in THF (50 mL) was added diisopropyl azodicarboxylate (2.28 mL, 11.57 mmol) and the mixture was stirred at 20° C. for 15 h. Then the mixture was concentrated and the residue was purified by reversed flash chromatography (MeCN and water containing 0.1% v/v FA) to give the desired product (2.8 g, 74.3%) as light yellow oil. MS (ESI): m/z=335.9 [M−56+H].

Step b) tert-Butyl 4-(4-chloro-3-pyrazol-1-yl-phenoxy)piperidine-1-carboxylate

To a mixture of tert-butyl 4-(3-bromo-4-chloro-phenoxy)piperidine-1-carboxylate (1.0 g, 2.56 mmol), pyrazole (139.4 mg, 2.05 mmol), cesium carbonate (2501.8 mg, 7.68 mmol) and 1,10-phenanthroline (225.49 mg, 2.56 mmol) in DMF (20 mL) was added CuI (48.59 mg, 0.260 mmol) and the mixture was stirred at 110° C. for 12 h under N$_2$ atmosphere. The mixture was concentrated, diluted with H2O (20 mL) and extracted three times with EtOAc (10 mL). The combined organic layers were concentrated and the residue purified by reversed phase chromatography (ACN and water containing 0.1% v/v FA) to give the desired product (265 mg, 22.5%, 82% purity) as yellow oil. MS (ESI): m/z=378.1 [M+H]$^+$.

BB155

4-[5-(4-Piperidyloxy)-2-(trifluoromethyl)phenyl] morpholine trifluoroacetate

To a solution of tert-butyl 4-[3-morpholino-4-(trifluoromethyl)phenoxy]piperidine-1-carboxylate (400.0 mg, 0.93 mmol) in DCM (3 mL) was added TFA (1.0 mL) and the reaction mixture was stirred at 25° C. for 12 h. The reaction was concentrated in vacuum to provide the crude product (300 mg) as yellow oil, which was used in next step without further purification. MS (ESI): m/z=331.2 [M+H]$^+$.

Step a) tert-Butyl 4-(3-bromo-4-(trifluoromethyl) phenoxy)piperidine-1-carboxylate To a solution of 3-bromo-4-(trifluoromethyl)phenol (500.0 mg, 2.54 mmol, CAS RN1214385-56-4) and 1-BOC-4-hydroxypiperidine (512 mg, 2.54 mmol, CAS RN 106-52-5) in THF (8.5 mL) was added PPh3 (1000.9 mg, 3.82 mmol) and diethyl azodicarboxylate (664.53 mg, 3.82 mmol) and the mixture was stirred at 25° C. for 12 h. The mixture was purified by silica gel chromatography using PE:EA=5:1 as eluant to provide the desired product (503 mg, 46.6% yield) as light yellow oil. MS (ESI): m/z=369.2 [M−56+H].

Step b) tert-Butyl 4-(3-morpholino-4-(trifluoromethyl)phenoxy)piperidine-1-carboxylate A mixture of tert-butyl 4-[3-bromo-4-(trifluoromethyl)phenoxy]piperidine-1-carboxylate (500.0 mg, 1.18 mmol), morpholine (154 mg, 1.77 mmol, CAS RN 110-91-8), (R)-(+)-2,2'-bis(diphenylphosphino)-1,1'-binaphthalene (146.77 mg, 0.24 mmol, CAS RN 76189-55-4), cesium carbonate (1.15 g, 3.54 mmol) and tris(dibenzylideneacetone)dipalladium(0) (172.47 mg, 0.240 mmol, CAS RN 76971-72-7) in DMF (10 mL) was stirred at 110° C. for 12 h. The mixture was poured into H2O and extracted three times with EtOAc. The combined organic layers were washed with brine, dried over Na2SO4 and filtered. The filtrate was concentrated under vacuum and the residue was purified by column chromatography (gradient of EtOAc in PE 5% to 33%) to give the desired product (480 mg, 94.6%) as light yellow solid. MS (ESI): m/z=431.1 [M+H]$^+$.

BB156

4-(4-Chloro-3-(1,2,4-triazol-1-yl)phenoxy)piperidine trifluoroacetate

To a solution of tert-butyl 4-[4-chloro-3-(1,2,4-triazol-1-yl)phenoxy]piperidine-1-carboxylate (196.0 mg, 0.520 mmol) in DCM (5 mL) was added TFA (1.01 mL, 13.13 mmol) at 0° C. and the mixture was stirred at 20° C. for 1 h. The mixture was concentrated to give the title compound (178 mg, 87.6%) as brown oil. MS (ESI): m/z=279.1 [M+H]$^+$.

Step a) tert-Butyl 4-[4-chloro-3-(1,2,4-triazol-1-yl) phenoxy]piperidine-1-carboxylate A mixture of tert-butyl 4-(3-bromo-4-chloro-phenoxy) piperidine-1-carboxylate (500.0 mg, 1.28 mmol, BB102, intermediate a), 1,2,4-triazole (176.8 mg, 2.56 mmol), CuI (24.3 mg, 0.130 mmol) and cesium carbonate (1250.9 mg, 3.84 mmol) and dimethyl glycine (1.0 mL, 1.28 mmol) in DMF (10 mL) was stirred at 120° C. for 12 h. The mixture was concentrated to remove the DMF, diluted with H2O (50 mL) and extracted three times with EtOAc (20 mL each). The combined organic layers were evaporated and the residue purified by reverse phase flash chromatography (ACN and water containing 0.1% v/v FA) to give the title compound (196 mg, 37.1%) as colorless oil. MS (ESI): m/z=323.0 [M−56+H]$^+$.

BB157

4-[3-Cyclopropyl-4-(trifluoromethyl)phenoxy]piperidine trifluoroacetate

To a mixture of tert-butyl 4-[3-cyclopropyl-4-(trifluoromethyl)phenoxy]piperidine-1-carboxylate (360.0 mg, 0.930 mmol) in DCM (18 mL) was added TFA (1.8 mL). The mixture was stirred at 25° C. for 12 h. The mixture was concentrated under vacuum to provide the desired compound as light yellow gum (370 mg, 99.2%). MS (ESI): m/z=286.2 [M+H]$^+$.

Step a) tert-Butyl 4-[3-cyclopropyl-4-(trifluoromethyl)phenoxy]piperidine-1-carboxylate A mixture of tert-butyl 4-[3-bromo-4-(trifluoromethyl) phenoxy]piperidine-1-carboxylate (500.0 mg, 1.18 mmol, BB103, intermediate b), cyclopropylboronic acid (151.86 mg, 1.77 mmol), Na2CO3 (374.74 mg, 3.54 mmol) and Pd(PPh3)4 (13.6 mg, 0.010 mmol) in 1,4-dioxane (10 mL) and H2O (1 mL) was stirred at 95° C. for 12 h. The mixture was poured into H2O (50 mL) and extracted three times with EtOAc (50 mL each). The combined organic layers were washed with brine (50 mL), dried over Na2SO4 and filtered. The filtrate was concentrated under vacuum and purified by column chromatography (PE:EtOAc=20:1~5:1) to give the desired product (380 mg, 83.7%) as colorless gum. MS (ESI): m/z=330.1 [M−56+H]$^+$.

BB158

4-[3-Pyrazol-1-yl-4-(trifluoromethyl)phenoxy]piperidine trifluoroacetate

To a solution of tert-butyl 4-[3-pyrazol-1-yl-4-(trifluoromethyl)phenoxy]piperidine-1-carboxylate (180.0 mg, 0.440 mmol) in DCM (5 mL) was added TFA (0.5 mL). The mixture was stirred at 25° C. for 12 h and then concentrated under vacuum to give the desired product (180 mg, 96.7%) as light yellow gum. MS (ESI): m/z=312.1 [M+H]$^+$.

Step a) tert-Butyl 4-[3-pyrazol-1-yl-4-(trifluoromethyl)phenoxy]piperidine-1-carboxylate A mixture of tert-butyl 4-[3-bromo-4-(trifluoromethyl)phenoxy]piperidine-1-carboxylate (500.0 mg, 1.18 mmol, BB103, intermediate b), pyrazole (120.35 mg, 1.77 mmol), CuI (22.37 mg, 0.120 mmol), N,N'-dimethylethylenediamine (519.45 mg, 5.89 mmol) and Cs2CO3 (767.99 mg, 2.36 mmol) in DMF (10 mL) was stirred at 110° C. for 12 h. The mixture was poured into H2O (30 mL) and extracted three times with EtOAc (50 mL each). The combined organic layers were washed with ammonia (20 mL), brine (50 mL), dried over Na$_2$SO$_4$ and filtered. The filtrate was concentrated and the crude product was purified by prep-TLC (PE:EA=5:1) to give the desired product (190 mg, 39.2%) as colorless oil. MS (ESI): m/z=356.1 [M−56+H]$^+$.

BB159

4-[[2,6-Difluoro-4-(trifluoromethyl)phenyl]methyl]piperidine trifluoroacetate

To a solution of tert-butyl 4-[[2,6-difluoro-4-(trifluoromethyl)phenyl]methyl]piperidine-1-carboxylate (70.0 mg, 0.180 mmol) in DCM (1 mL) was added TFA (0.2 mL) and the mixture was stirred at 20° C. for 1 h. The mixture was concentrated to give the title compound (50 mg, 68.9%) as brown oil. MS (ESI): m/z=280.1 [M+H]$^+$.

Step a) 2-(Diethoxyphosphorylmethyl)-1,3-difluoro-5-(trifluoromethyl)benzene

A solution of 2-(bromomethyl)-1,3-difluoro-5-(trifluoromethyl)benzene (1.29 mL, 3.27 mmol, CAS RN 493038-91-8) in triethyl phosphite (5.44 g, 32.73 mmol) was stirred at 160° C. for 5 h. The mixture was concentrated under vacuum to provide the title compound (600 mg, 55.2%; colorless oil) which was used in the next step without further purification.

Step b) tert-Butyl 4-[[2,6-difluoro-4-(trifluoromethyl)phenyl]methylene]piperidine-1-carboxylate A mixture of 2-(diethoxyphosphorylmethyl)-1,3-difluoro-5-(trifluoromethyl)benzene (400.0 mg, 1.2 mmol) in THF (4 mL) was added to sodium hydride (144.49 mg, 3.61 mmol) in THF (4 mL) at 0° C. The mixture was stirred at 0° C. for 1 h, and then 1-BOC-4-piperidone (479.83 mg, 2.41 mmol, CAS RN 79099-07-3) was added to the above mixture. The mixture was stirred at 20° C. for 12 h. The mixture was poured into H2O (50 mL) and extracted three times with EtOAc (20 mL each). The combined organic layers were washed with brine, dried over Na2SO4, filtered and concentrated under vacuum. The residue was purified by column chromatography (PE:EA=1:0 to 2:1) to give the title compound (100 mg, 22.0%) as colorless oil. MS (ESI): m/z=322.0 [M−56+H]$^+$.

Step c) tert-Butyl 4-[[2,6-difluoro-4-(trifluoromethyl)phenyl]methyl]piperidine-1-carboxylate To a solution of tert-butyl 4-[[2,6-difluoro-4-(trifluoromethyl)phenyl]methylene]piperidine-1-carboxylate (100.0 mg, 0.270 mmol) in MeOH (8 mL) was added Pd/C (10.0 mg, wt. 10%). The mixture was stirred at 20° C. for 1 h under H2 atmosphere, then filtered and concentrated to give the title compound as colorless oil (70 mg, 69.6%). MS (ESI): m/z=324.1[M−56+H]$^+$.

BB160

4-[4-Chloro-3-(4-chlorophenyl)-2-fluoro-phenoxy]piperidine trifluoroacetate

To a mixture of tert-butyl 4-[4-chloro-3-(4-chlorophenyl)-2-fluoro-phenoxy]piperidine-1-carboxylate (145.0 mg, 0.330 mmol) in DCM (10 mL) was added TFA (1.0 mL). The mixture was stirred at 20° C. for 5 h. The mixture was concentrated under vacuum to give the desired product (149 mg, 99.6%) as light brown gum. MS (ESI): m/z=340.1 [M+H]$^+$.

Step a) 1-Chloro-2-(4-chlorophenyl)-3-fluoro-4-methoxy-benzene

A mixture of 4-bromochlorobenzene (1.41 g, 7.34 mmol, CAS RN 106-39-8), (6-chloro-2-fluoro-3-methoxy-phenyl)boronic acid (1.0 g, 4.89 mmol, CAS RN 867333-04-8) and K$_2$CO$_3$ (2.03 g, 14.68 mmol) in 1,4-dioxane (15 mL) and H2O (1.5 mL) was stirred under N2 atmosphere at 110° C. for 1 h in a microwave oven. The mixture was poured into H2O (20 mL) and extracted three times with EtOAc (20 mL each). The combined organic layers were washed with brine (20 mL), dried over Na2SO4 and filtered. The filtrate was concentrated under vacuum and the residue was purified by column chromatography using PE as eluant to give the desired product (110 mg, 8.3%) as colorless oil which was used in the next step without further purification.

Step b) 4-chloro-3-(4-chlorophenyl)-2-fluoro-phenol

To a mixture of 1-chloro-2-(4-chlorophenyl)-3-fluoro-4-methoxy-benzene (215.0 mg, 0.790 mmol) in DCM (7 mL) was added a solution of BBr3 (993.36 mg, 3.97 mmol) in DCM (7 mL) drop wise at −78° C. The mixture was stirred at 20° C. for 12 h. The reaction was quenched by adding MeOH (1 mL) followed by water (10 mL), and the mixture was extracted three times with DCM (10 mL each). The combined organic layers were washed with brine (10 mL), dried over Na2SO4 and filtered. The filtrate was concentrated under vacuum to give the desired product (120 mg, 57.5%) as light brown solid which was used in the next step without further purification.

Step c) tert-Butyl 4-[4-chloro-3-(4-chlorophenyl)-2-fluoro-phenoxy]piperidine-1-carboxylate A mixture of 4-chloro-3-(4-chlorophenyl)-2-fluoro-phenol (120.0 mg, 0.470 mmol), 1-BOC-4-hydroxypiperidine (187.88 mg, 0.930 mmol, CAS RN 106-52-5), PPh3 (244.85 mg, 0.930 mmol) and DIAD (0.18 mL, 0.930 mmol) in THF (12 mL) was stirred at 20° C. for 12 h. The mixture was poured into H2O and extracted three times with EtOAc. The combined organic layer was washed with brine, dried over Na2SO4 and filtered. The filtrate was concentrated under vacuum and the residue purified by column chromatography (PE:EA=1:0~20:1) to give the desired product as light yellow gum (150 mg, 73%). MS (ESI): m/z=384.0 [M−56+H]$^+$.

BB161

3-[2-Chloro-4-(Trifluoromethyl)phenoxy]azetidine trifluoroacetate

To a solution of tert-butyl 3-[2-chloro-4-(trifluoromethyl)phenoxy]azetidine-1-carboxylate (400.0 mg, 1.14 mmol) in DCM (10 mL) was added TFA (2.0 mL) at 20° C. After stirring for 2 h the mixture was concentrated to give the crude product (410 mg, 98.6%) as light yellow oil which was used in the next step without further purification.

Step a) tert-Butyl 3-[2-chloro-4-(trifluoromethyl)phenoxy]azetidine-1-carboxylate To a solution of 2-chloro-4-(trifluoromethyl)phenol (1000.0 mg, 5.09 mmol, CAS RN 35852-58-5) and tert-butyl 3-hydroxyazetidine-1-carboxylate (1057.5 mg, 6.11 mmol, CAS RN 141699-55-0) in THF (20 mL) was added PPh3 (1999.49 mg, 7.63 mmol) and diethyl azodicarboxylate (1329.05 mg, 7.63 mmol), the mixture was stirred at 25° C. for 12 h. The reaction mixture solution was evaporated in vacuum, the residue was purified by reverse-phase flash flash (0.1% v/v FA) to afford the desired product (800 mg, 2.27 mmol, 44.7% yield) as light yellow oil. MS (ESI): m/z=296.0 [M−56+H]$^+$.

BB162

3-((2-Fluoro-6-(trifluoromethyl)benzyl)oxy)azetidine trifluoroacetate

To a solution of tert-butyl 3-[[2-fluoro-6-(trifluoromethyl)phenyl]methoxy]azetidine-1-carboxylate (400.0 mg, 1.15 mmol) in dry DCM (10 mL) was added TFA (2.0 mL) at 25° C. and the mixture was stirred at 25° C. for 12 h. The solvent was stripped off and the residue was dried under vacuum to afford the desired compound as yellow oil (300 mg, 22%). MS (ESI): m/z=250.0 [M+H]$^+$.

Step a) tert-Butyl 3-[[2-fluoro-6-(trifluoromethyl)phenyl]methoxy]azetidine-1-carboxylate To a solution of 2-fluoro-6-(trifluoromethyl)benzyl bromide (1000.0 mg, 3.89 mmol, CAS RN 239087-08-2) and tert-butyl 3-hydroxyazetidine-1-carboxylate (673.92 mg, 3.89 mmol, CAS RN 141699-55-0) in dry THF (10 mL) at 25° C., was added t-BuOK (5.84 mL, 5.84 mmol; 1.0 M in dry THF) and the mixture was stirred at 25° C. for 12 h. The mixture was poured into H2O (10 mL) and extracted three times with EA (20 mL each). The combined organic layers were combined, dried over anhydrous Na2SO4 and filtered. The filtrate was concentrated under reduced pressure, purified by flash chromatography on silica gel (gradient PE:EA=10:1 to 2:8) to give the title compound as colorless oil (1100 mg, 80.9%). MS (ESI): m/z=294.0 [M−56+H]$^+$.

BB163

3-[2-(2-Fluoro-4-methyl-phenyl)ethyl]azetidine trifluoroacetate

To a solution of tert-butyl 3-[2-(2-fluoro-4-methyl-phenyl)ethyl]azetidine-1-carboxylate (350.0 mg, 1.19 mmol) in dry DCM (10 mL) at 25° C., was added TFA (1.0 mL, 1.19 mmol) and the mixture was stirred at 25° C. for 12 h. The reaction mixture was concentrated by reduced pressure and the residue was dried in vacuum to provide the desired compound as colorless oil (260 mg, 70.9%). MS (ESI): m/z=194.0 [M+H]$^+$.

Step a) tert-Butyl 3-(2-trimethylsilylethynyl)azetidine-1-carboxylate

To a solution of trimethylsilylacetylene (9.97 g, 101.55 mmol, CAS RN 1066-54-2) in dry THF (200 mL) at 25° C., was added i-PrMgCl (48.57 mL, 97.14 mmol; 1.0 M in dry THF) and the mixture was stirred at 25° C. for 15 mins. Then a solution of 1-BOC-3-iodoazetidine (25.0 g, 88.3 mmol, CAS RN 254454-54-1) was added followed by FeCl2 (0.34 g, 2.65 mmol) in dry DMF (606 mL) and the mixture was stirred at 25° C. for 12 hrs. The mixture was poured into saturated aq. NH4Cl solution (200 mL) and extracted three times with EtOAc (150 mL each). The organic layers were combined, dried with anhydrous Na2SO4, filtered and the filtrate was concentrated under reduced pressure. The residue was purified by flash chromatography on silica gel (PE:EA=20:1 to 10:1) to give the desired product as black oil (18 g, 80.4%). 1H NMR (400 MHz, CHLOROFORM-d) δ=4.11 (t, J=8.4 Hz, 2H), 3.92 (dd, J=6.5, 8.1 Hz, 2H), 3.51-3.17 (m, 1H), 1.44 (s, 10H), 0.16 (s, 9H).

Step b) tert-Butyl 3-ethynylazetidine-1-carboxylate

To a solution of tert-butyl 3-(2-trimethylsilylethynyl)azetidine-1-carboxylate (6243 mg, 24.64 mmol) in dry MeOH (40 mL) was added potassium carbonate (1700 mg, 12.32 mmol) at 25° C. and the reaction mixture was stirred at 25° C. for 2 h. The mixture was filtered, the filtrate was poured into saturated aq. NH4Cl solution (100 mL) and extracted with EA (100 mL three times). The combined organic layers were dried with anhydrous Na2SO4, filtered and the filtrate concentrated under reduced pressure. The residue was purified by flash chromatography on silica gel (PE:EA=50:1 to 15:1) to afford the title compound as light yellow oil (4100 mg, 91.8%). 1H NMR (400 MHz, CHLOROFORM-d) δ=4.16-4.11 (m, 2H), 3.93 (dd, J=6.5, 8.2 Hz, 2H), 3.37-3.20 (m, 1H), 2.28 (d, J=2.4 Hz, 1H), 1.43 (s, 9H).

Step c) tert-Butyl 3-[2-(2-fluoro-4-methyl-phenyl)ethynyl]azetidine-1-carboxylate To a solution of tert-butyl 3-ethynylazetidine-1-carboxylate (1000.0 mg, 5.52 mmol) and 4-bromo-3-fluorotoluene (1251.58 mg, 6.62 mmol, CAS RN 452-74-4) in dry THF (20 mL) were added Pd(PPh3)4 (530.63 mg, 0.460 mmol), CuI (87.83 mg, 0.460 mmol) and TEA (4644.2 mg, 46.0 mmol) at 25° C. The mixture was purged with N2 for 1 min and then stirred at 60° C. under N2 atmosphere for 12 h. The mixture was poured into saturated aq. NH4Cl solution (50 mL) and extracted three times with EtOAc (30 mL each). The combined organic layers were dried with anhydrous Na$_2$SO$_4$, filtered, the filtrate was concentrated under reduced pressure. The residue was purified by flash chromatography on silica gel (PE:EA=20:1 to 10:1) to provide the desired compound as colorless oil (650 mg, 40.7%). 1H NMR (400 MHz, CHLOROFORM-d) δ=7.33-7.28 (m, 1H), 6.94-6.85 (m, 2H), 4.26-4.19 (m, 2H), 4.05 (dd, J=6.4, 8.1 Hz, 2H), 3.66-3.49 (m, 1H), 2.36 (s, 3H), 1.46 (s, 9H).

Step d) tert-Butyl 3-[2-(2-fluoro-4-methyl-phenyl)ethyl]azetidine-1-carboxylate

Batch a: To a solution of tert-butyl 3-[2-(2-fluoro-4-methyl-phenyl)ethynyl]azetidine-1-carboxylate (50.0 mg, 0.170 mmol, 1 eq) in EtOAc (5 mL) was added Pd/C (50.0 mg, wt. 10%) at 25° C. The mixture was stirred at 40° C. under a balloon of hydrogen gas for 12 h. LCMS analysis found 79.8% of desired product.

Batch b: To a solution of tert-butyl 3-[2-(2-fluoro-4-methyl-phenyl)ethynyl]azetidine-1-carboxylate (500.0 mg, 1.73 mmol) in EtOAc (10 mL) was added Pd/C (250.0 mg, wt. 10%) at 25° C. and the mixture was stirred at 40° C. under a balloon of hydrogen gas for 6 h. LCMS found 80.4% of desired product. Batch a and b were combined, the reaction mixture was filtered through a pad of celite, the filtrate was concentrated under reduced pressure and the residue was dried in vacuum to give the compound as colorless oil (350 mg, 69.0%). MS (ESI): m/z=238.1 [M−56+H]$^+$.

BB164

3-[2-[4-Methoxy-2-(trifluoromethyl)phenyl]ethyl]azetidine trifluoroacetate

To a solution of tert-butyl 3-[2-(2-fluoro-4-methyl-phenyl)ethyl]azetidine-1-carboxylate (180.0 mg, 0.5 mmol) in dry DCM (10 mL) was added TFA (1.0 mL, 1.19 mmol) at 25° C. and the mixture was stirred at 25° C. for 12 h. The reaction mixture was concentrated under reduced pressure and the residue was dried in vacuum to give the title compound (150 mg, 80.2%) as colorless oil. MS (ESI): m/z=260.1 [M+H]$^+$.

Step a) tert-Butyl 3-[2-[4-methoxy-2-(trifluoromethyl)phenyl]ethynyl]azetidine-1-carboxylate To a solution of tert-butyl 3-ethynylazetidine-1-carboxylate (800.0 mg, 4.41 mmol, BB111, intermediate b) and 3-trifluoromethyl-4-bromoanisole (1350.9 mg, 5.3 mmol, CAS RN 400-72-6) in dry THF (30 mL) at 25° C., was added Pd(PPh$_3$)$_4$ (509.41 mg, 0.440 mmol), CuI (84.31 mg, 0.440 mmol) and TEA (4458.42 mg, 44.14 mmol). The mixture was purged with N$_2$ for 1 min and then stirred at 60° C. under N$_2$ atmosphere for 12 h. The mixture was poured into saturated aq. NH$_4$Cl solution (100 mL) and extracted three times with EtOAc (50 mL each). The organic layers were combined, dried with anhydrous Na$_2$SO$_4$, filtered, the filtrate was concentrated with reduced pressure. The residue was purified by flash chromatography on silica gel (PE:EA=20:1 to 10:1) to provide the product as colorless oil (160 mg, 8.2%). MS (ESI): m/z=300.1 [M−56+H]$^+$.

Step b) tert-Butyl 3-[2-[4-methoxy-2-(trifluoromethyl)phenyl]ethyl]azetidine-1-carboxylate To a solution of tert-butyl 3-[2-(2-fluoro-4-methyl-phenyl)ethynyl]azetidine-1-carboxylate (230.0 mg, 0.65 mmol) in EtOAc (10 mL) at 25° C., was added Pd/C (150.0 mg, wt. 10%), the mixture was stirred at 40° C. under a balloon of H$_2$ (about 15 psi) for 12 h. The reaction mixture was filtered through a pad of celite and the filtrate was concentrated under reduced pressure. The residue was dried under vacuum to furnish the desired compound as colorless oil (180 mg, 77.4%). MS (ESI): m/z=304.1 [M−56+H]$^+$.

BB165

3-[[4-Methyl-2-(trifluoromethyl)phenyl]methoxy]azetidine trifluoroacetate

To a solution of tert-butyl 3-[[4-methyl-2-(trifluoromethyl)phenyl]methoxy]azetidine-1-carboxylate (130.0 mg, 0.380 mmol) in DCM (6.5 mL) was added TFA (1.3 mL, 16.87 mmol) and the reaction was stirred at 20° C. After 12 h the mixture was evaporated to give the desired crude product as light brown oil (130 mg, 96.1%). MS (ESI): m/z=246.5 [M+H]$^+$.

Step a)
4-Bromo-1-(Bromomethyl)-2-(trifluoromethyl)benzene

The solution of 5-bromo-2-methylbenzotrifluoride (2000 mg, 8.37 mmol, CAS RN 86845-27-4), N-bromosuccinimide (1489 mg, 8.37 mmol, CAS RN 128-08-5) and benzoyl peroxide (101.34 mg, 0.420 mmol, CAS RN 2685-64-5) in carbon tetrachloride (30 mL) was stirred at 90° C. for 12 h. The mixture was evaporated and the residue was purified by silica gel column chromatography (100% PE) to give the desired product as light brown oil (690 mg, 25.9%) which was used in the next step without further purification.

Step b) tert-Butyl 3-[[4-bromo-2-(Trifluoromethyl)phenyl]methoxy]azetidine-1-carboxylate To a solution of tert-butyl 3-hydroxyazetidine-1-carboxylate (337.5 mg, 1.95 mmol, CAS RN 22214-30-8) in THF (9 mL) was added t-BuOK (1.95 mL, 1.95 mmol), then 4-bromo-1-(bromomethyl)-2-(trifluoromethyl) benzene (590.0 mg, 1.86 mmol) was added and the mixture was stirred at 20° C. for 12 h. The mixture was poured into aq. NH$_4$Cl solution (200 mL) and extracted three times with EtOAc (50 mL). The combined organic layers were washed with brine, dried over Na$_2$SO$_4$ and concentrated. The residue was purified by prep-HPLC (ACN and water containing 0.225% v/v FA) to give the desired product as light brown oil (300 mg, 39.4%). MS (ESI): m/z=356.3 [M−56+H]$^+$.

Step c) tert-Butyl 3-[[4-Methyl-2-(trifluoromethyl)phenyl]methoxy]azetidine-1-carboxylate To a solution of tert-butyl 3-[[4-bromo-2-(trifluoromethyl)phenyl]methoxy]azetidine-1-carboxylate (250.0 mg, 0.610 mmol), trimethylboroxine (114.8 mg, 0.910 mmol), K$_2$CO$_3$ (168.5 mg, 1.22 mmol) in 1,4-dioxane (10 mL) and H2O (2.5 mL) was added Pd(dppf)Cl$_2$ (89.18 mg, 0.120 mmol). The reaction was stirred at 100° C. for 12 h. The mixture was filtered, concentrated, and the residue was purified by reversed flash chromatography (ACN and water containing 0.1% v/v FA) to give the desired product as light brown oil (146 mg, 69.4%). MS (ESI): m/z=290.4 [M−56+H]$^+$.

BB166

3-[2-[2-Methoxy-6-(trifluoromethyl)phenyl]ethyl] azetidine trifluoroacetate

To a solution of tert-butyl 3-[2-[2-methoxy-6-(trifluoromethyl)phenyl]ethyl]azetidine-1-carboxylate (300.0 mg, 0.830 mmol) in DCM (5 mL), TFA (1.0 mL) was added and stirred at 25° C. for 1 h. The reaction mixture was evaporated under reduced pressure to give the desired product (300 mg, 96.3%) as colorless oil. MS (ESI): m/z=260.1 [M+H]$^+$.

Step a) tert-Butyl 3-[2-[2-methoxy-6-(trifluoromethyl)phenyl]ethynyl]azetidine-1-carboxylate To a solution of tert-butyl 3-ethynylazetidine-1-carboxylate (710.6 mg, 3.92 mmol, B111, intermediate b) and 2-bromo-1-methoxy-3-(trifluoromethyl)benzene (500.0 mg, 1.96 mmol) in dry DMSO (17.5 mL) at 25° C., was added Pd(PPh$_3$)$_2$Cl$_2$ (137.6 mg, 0.200 mmol) and Cs$_2$CO$_3$ (1278 mg, 3.92 mmol). The mixture was purged with N$_2$ for 1 min and then stirred at 110° C. under N$_2$ atmosphere for 12 h. The mixture was filtered, the filtrate was concentrated and the residue was purified by silica gel (PE:EtOAc=20:1) to give the desired product as light yellow oil (600 mg, 86.1%) that was used in the next step without further purification.

Step b) tert-Butyl 3-[2-[2-methoxy-6-(trifluoromethyl) phenyl] ethynyl] azetidine-1-carboxylate To a solution of tert-butyl 3-[2-[2-methoxy-6-(trifluoromethyl)phenyl]ethynyl]azetidine-1-carboxylate (400.0 mg, 1.13 mmol) in EtOAc (20 mL), wet Pd/C (50 mg, 10 wt. %) was added. The mixture was purged with H$_2$ 3 times and then stirred at 40° C. under H$_2$ atmosphere (balloon) for 12 h. The mixture was filtered and the filtrate was concentrated to give the desired product as light yellow oil (300 mg, 74.2% yield) which was used in the next step without further purification.

BB167

3-[2-[4-Methyl-2-(trifluoromethyl)phenyl]ethyl] azetidine trifluoroacetate

To a solution of tert-butyl 3-[2-[4-methyl-2-(trifluoromethyl)phenyl]ethyl]azetidine-1-carboxylate (100.0 mg, 0.290 mmol) in DCM (4 mL) was added TFA (0.5 mL) and the mixture was stirred at 20° C. for 12 h. The reaction mixture was evaporated under reduced pressure to give the desired product as yellow oil (98 mg, 94.2%). MS (ESI): m/z=244.1 [M+H]$^+$.

Step a) tert-Butyl 3-[2-[4-methyl-2-(trifluoromethyl) phenyl]ethynyl]azetidine-1-carboxylate To a solution of tert-butyl 3-ethynylazetidine-1-carboxylate (606.6 mg, 3.35 mmol) and 2-bromo-5-methylbenzotrifluoride (400.0 mg, 1.67 mmol) in dry DMSO (14.9 mL) at 25° C., was added Pd(PPh$_3$)$_2$Cl$_2$ (117.46 mg, 0.170 mmol) and Cs$_2$CO$_3$ (1091 mg, 3.35 mmol). The mixture was purged with N$_2$ for 1 min and then stirred at 110° C. under N$_2$ atmosphere for 12 h. The reaction mixture was poured into H2O and extracted with EtOAc. The organic layer was evaporated and the residue was purified by silica gel column chromatography (PE:EtOAc=20:1) to give the desired compound as a yellow oil (390 mg, 68.7% yield). MS (ESI): m/z=284.1 [M−56+H]$^+$.

Step b) tert-Butyl 3-[2-[4-methyl-2-(trifluoromethyl)phenyl]ethyl]azetidine-1-carboxylate To a solution of tert-butyl 3-[2-[4-methyl-2-(trifluoromethyl)phenyl]ethynyl]azetidine-1-carboxylate (390.0 mg, 1.15 mmol) in EtOAc (19.5 mL), wet Pd/C (150 mg, 10 wt. %) was added, the mixture was purged 3 times with H$_2$ and stirred at 40° C. under H$_2$ atmosphere (balloon) for 12 h. The mixture was filtered and the filtrate was concentrated to give the desired product as light yellow oil (295 mg, 72.9% yield). MS (ESI): m/z=288.1 [M−56+H]$^+$.

BB168

1-[2-[2-(Azetidin-3-yl)ethyl]-5-(trifluoromethyl) phenyl]ethanone trifluoroacetate To a solution of tert-butyl 3-[2-[2-acetyl-4-(trifluoromethyl)phenyl]ethyl]azetidine-1-carboxylate (50.0 mg, 0.130 mmol) in DCM (1 mL) was added TFA (0.2 mL) and the solution was stirred at 20° C. for 12 h. The mixture was concentrated to give the desired product as light brown oil (50 mg, 96.4% yield). MS (ESI): m/z=272.1 [M+H]$^+$.

Step a) 2-Bromo-1-(bromomethyl)-4-(trifluoromethyl)benzene

To a solution of [2-bromo-4-(trifluoromethyl)phenyl]methanol (500.0 mg, 1.96 mmol, CAS RN 497959-33-8) and PPh3 (770.5 mg, 2.94 mmol) in THF (10 mL) was added carbon tetrabromide (975.3 mg, 2.94 mmol), and the mixture was stirred at 25° C. for 12 h. The reaction was concentrated in vacuum and the residue was purified by silica gel column chromatography (PE:EA=0:1~20:1) to yield the desired product as colorless oil (600 mg, 96.3% yield). $^1$H NMR (400 MHz, CHLOROFORM-d) δ=7.78 (s, 1H), 7.55-7.46 (m, 2H), 4.53 (s, 2H).

Step b) 2-Bromo-1-(diethoxyphosphorylmethyl)-4-(trifluoromethyl)benzene

A solution of 2-bromo-1-(bromomethyl)-4-(trifluoromethyl)benzene (600.0 mg, 1.89 mmol) in triethyl phosphite (3136 mg, 18.87 mmol) was stirred at 160° C. for 5 h. The mixture was concentrated at 100° C. under reduced pressure to remove most of the triethyl phosphite to give the crude product (700 mg) as light yellow oil. MS (ESI): m/z=375.2 [M+H]$^+$.

Step c) tert-Butyl 3-[(E)-2-[2-bromo-4-(trifluoromethyl)phenyl]vinyl]azetidine-1-carboxylate A mixture of 2-bromo-1-(diethoxyphosphorylmethyl)-4-(trifluoromethyl)benzene (600.0 mg, 1.6 mmol) in THF (10 mL) was added to another suspension of NaH (191.9 mg, 4.8 mmol, 60% dispersion in mineral oil) in THF (10 mL) at 0° C. The mixture was stirred at 0° C. for 1 h. Then tert-butyl 3-formylazetidine-1-carboxylate (296.3 mg, 1.6 mmol) was added and the mixture was stirred at 20° C. for 11 h. The reaction mixture was poured into aq. NH$_4$Cl solution (100 mL) and extracted three times with EtOAc (50 mL each). The combined organic layers were washed with brine (100 mL), dried over $Na_2SO_4$, filtered and concentrated. The residue was purified by silica gel column chromatography (PE:EtOAc=20:1) to give the desired product as light yellow oil (450 mg, 69.3%). MS (ESI): m/z=352.0 [M56+H]$^+$. $^1$H NMR (400 MHz, CHLOROFORM-d) δ=7.74 (d, J=0.8 Hz, 1H), 7.58-7.51 (m, 1H), 7.49-7.41 (m, 1H), 6.71 (d, J=15.8 Hz, 1H), 6.36 (dd, J=8.4, 15.8 Hz, 1H), 4.13 (t, J=8.5 Hz, 2H), 3.78 (dd, J=5.8, 8.6 Hz, 2H), 3.44-3.31 (m, 1H), 1.39 (s, 9H).

Step d) tert-Butyl 3-[(E)-2-[2-acetyl-4-(trifluoromethyl)phenyl]vinyl]azetidine-1-carboxylate A solution of tributyl(1-ethoxyvinyl)tin (426.7 mg, 1.18 mmol), tert-butyl 3-[(E)-2-[2-bromo-4-(trifluoromethyl)phenyl]vinyl]azetidine-1-carboxylate (400.0 mg, 0.980 mmol) and $Pd(Ph_3P)_2Cl_2$ (138.2 mg, 0.200 mmol) in THF (16 mL) was stirred at 80° C. under $N_2$ atmosphere for 4 h. The mixture was cooled down to room temperature and aq. KF solution (10 mL) was added. The mixture was stirred for 10 mins, extracted three times with EtOAc (20 mL each) and the combined organic layers were concentrated. The residue was dissolved in THF (20 mL) and aq. HCl (0.6 N, 20 mL) was added. The mixture was stirred at 20° C. for 0.5 h, extracted three times with EtOAc (20 mL each) and the combined organic layers were concentrated. The residue was purified by silica gel column chromatography (PE:EtOAc=20:1) to give the desired product (280 mg, 77% yield) as light yellow oil. MS (ESI): m/z=314.1 [M−56+H]$^+$.

Step e) tert-Butyl 3-[2-[2-acetyl-4-(trifluoromethyl)phenyl]ethyl]azetidine-1-carboxylate To a solution of tert-butyl 3-[(E)-2-[2-acetyl-4-(trifluoromethyl)phenyl]vinyl]azetidine-1-carboxylate (50.0 mg, 0.140 mmol) in EtOAc (5 mL) was added wet Pd/C (20.0 mg, 10 wt. %) and the mixture was stirred at 20° C. under $H_2$ (balloon) atmosphere for 12 h. The reaction was then warmed up to 50° C. and stirred for another 12 h. The mixture was filtered and the filtrate was concentrated to give the desired product (50 mg, 99.5%) as light yellow oil. MS (ESI): m/z=316.2 [M−56+H]$^+$.

BB169

3-[2-[2-Bromo-4-(trifluoromethyl)phenyl]ethyl]azetidine trifluoroacetate

To a solution of tert-butyl 3-[2-[2-bromo-4-(trifluoromethyl)phenyl]ethyl]azetidine-1-carboxylate (400.0 mg, 0.980 mmol) in DCM (10 mL) was added TFA (1.0 mL) and the mixture was stirred at 20° C. for 12 h. The reaction mixture was evaporated under reduced pressure to give the desired product (413 mg, 99.8% yield) as yellow oil. MS (ESI): m/z=308.1 [M+H]$^+$.

Step a) tert-Butyl 3-[2-[2-bromo-4-(trifluoromethyl)phenyl]ethyl]azetidine-1-carboxylate To a suspension of tert-butyl 3-[(E)-2-[2-bromo-4-(trifluoromethyl) phenyl]vinyl]azetidine-1-carboxylate (600.0 mg, 1.48 mmol, BB116, intermediate c) and MgO (118.1 mg, 2.95 mmol) in EtOAc (20 mL) was added Pd/C (300.0 mg, 10 wt. %), the mixture was stirred at 25° C. under $H_2$ atmosphere (balloon) for 1 h. The reaction mixture was filtered and the filtrate was evaporated under reduced pressure to give the desired product (500 mg, 82.9%) as light yellow oil. MS (ESI): m/z=352.0 [M−56+H]$^+$.

BB174

2-(Azetidin-3-ylmethoxy)-5-(trifluoromethyl)pyridine 2,2,2-trifluoroacetate

Synthesis of BB174 was performed in analogy to BB57, starting from tert-butyl 3-(hydroxymethyl)azetidine-1-carboxylate and 2-bromo-5-(trifluoromethyl)pyridine. MS (ESI): m/z=233.1 [M+H]$^+$.

BB175

3-Methyl-5-[[rac-(3R,4R)-3-methyl-4-piperidyl]methoxy]-2-(trifluoromethyl)pyridine dihydrochloride tert-Butyl (rac-3R,4R)-3-methyl-4-(((5-methyl-6-(trifluoromethyl)pyridin-3-yl)oxy)methyl)piperidine-1-carboxylate (198 mg, 510 μmol) was dissolved in DCM (2 mL) and HCl 2M in ether (1.53 mL, 3.06 mmol) was added. The reaction mixture was stirred at RT for 8 h. The reaction mixture was concentrated in vacuo to yield 180 mg of desired product as white solid (98%) MS (ESI): m/z=289.3 [M+H]$^+$.

a) tert-Butyl (rac-3R,4R)-4-(hydroxymethyl)-3-methylpiperidine-1-carboxylate

To a stirred solution of cis-N—BOC-3-methylpiperidine-4-carboxylic acid methyl ester (2 g, 7.77 mmol) in THF (10 ml) was added lithium borohydride (5.83 mL, 11.7 mmol) at 2-5° C. The reaction mixture was then heated at reflux for 3 h and then cooled to 2-5° C. Water was added and the aqueous layer was extracted twice with EtOAc (30 mL each). The organic layer was washed with water, $NaHCO_3$ and brine, the layers were separated, and the organics dried over $Na_2SO_4$ and concentrated in vacuum. Purification by flash chromatography (gradient of EtOAc in n-heptane, 0 to 65%) provided the product as a colorless oil (930 mg, 50%). MS (ESI): m/z=174.1 [M−56+H]$^+$.

b) tert-Butyl (rac-3R,4R)-3-methyl-4-(((5-methyl-6-(trifluoromethyl)pyridin-3-yl)oxy)methyl)piperidine-1-carboxylate tert-butyl (3R,4R)-4-(hydroxymethyl)-3-methylpiperidine-1-carboxylate (239 mg, 1.04 mmol) was dissolved in DMF (4.17 mL) and NaH in mineral oil (60%, 45.8 mg, 1.15 mmol) was added at RT. The reaction was stirred for 20 min, then 5-bromo-3-methyl-2-(trifluoromethyl)pyridine (250 mg, 167 μL, 1.04 mmol) was added and stirring continued for 12 h at RT. The reaction was quenched with 10 mL sat. $NH_4Cl$ solution and extracted three times with water/EtOAc. The organic phases were combined and dried over $MgSO_4$ and the solvent was removed in vacuo. Flash chromatography (gradient of EtOAc in n-heptane, 0 to 50%) yielded the product as white solid (148 mg, 49%). MS (ESI): m/z=333.2 [M−56+H]$^+$.

BB176

3-((2-Fluoro-4-(trifluoromethyl)benzyl)oxy)-2-methylazetidine 2,2,2-trifluoroacetate To a solution of tert-butyl 3-((2-fluoro-4-(trifluoromethyl)benzyl)oxy)-2-methylazetidine-1-carboxylate (0.265 g, 729

μmol) in DCM (4 mL) was added TFA (832 mg, 562 μL, 7.29 mmol). The resultant reaction mixture was stirred at RT for 1 h. The reaction mixture was concentrated to give the title compound as a colorless oil. The crude product was used without further purification. MS (ESI): m/z=264.2 [M+H]$^+$.

Step a) [2-Fluoro-4-(trifluoromethyl)phenyl]methyl methanesulfonate

To an ice-cold solution of (2-fluoro-4-(trifluoromethyl) phenyl)methanol (840 mg, 4.33 mmol) and triethylamine (1.31 g, 1.81 mL, 13 mmol) in DCM (8 mL) was added dropwise methanesulfonyl chloride (496 mg, 337 μL, 4.33 mmol) and the mixture was stirred at 0° C. for 1 h. The reaction mixture was poured on saturated aqueous NaHCO$_3$ solution (10 mL) and DCM (20 mL) and the layers were separated. The aqueous layer was extracted once with DCM (20 mL). The organic layers were washed once with brine, dried over MgSO$_4$, filtered and evaporated to yield the desired compound as a yellow oil (1.13 g, 96%).

Step b) tert-Butyl 3-[[2-fluoro-4-(trifluoromethyl) phenyl]methoxy]-2-methyl-azetidine-1-carboxylate To an ice-cold solution of tert-butyl 3-hydroxy-2-methylazetidine-1-carboxylate (250 mg, 1.34 mmol) in DMF (3 mL) was added NaH (60% in mineral oil, 58.7 mg, 1.47 mmol) in portions and the mixture was stirred at ice-bath temperature for 5 min followed by stirring at RT for 40 min. A solution of 2-fluoro-4-(trifluoromethyl)benzyl methanesulfonate (436 mg, 1.6 mmol) in DMF (1 mL) was added dropwise to the mixture at RT. Stirring of the slurry was continued at RT for 16 h. The reaction mixture was poured on saturated aqueous NH$_4$Cl solution (10 mL) and EtOAc (20 mL) and the layers were separated. The aqueous layer was extracted once with EtOAc (50 mL). The organic layers were washed twice with water, dried over Na$_2$SO$_4$, filtered, and concentrated. The crude compound was purified by silica gel chromatography (gradient of n-heptane:EtOAc 100:0 to 0:100) to get tert-butyl 3-[[2-fluoro-4-(trifluoromethyl)phenyl]methoxy]-2-methyl-azetidine-1-carboxylate as a colorless oil (0.265 g, 54.6% yield). MS (ESI): m/z=308.2 [M−56+H]$^+$.

BB 177

2-(Azetidin-3-ylmethoxy)-4,5-bis(trifluoromethyl) pyridine 2,2,2-trifluoroacetate Synthesis of BB177 was performed in analogy to BB57, starting from tert-butyl 3-(hydroxymethyl)azetidine-1-carboxylate and 2-chloro-4,5-bis(trifluoromethyl)pyridine. MS (ESI): m/z=301.2 [M+H]$^+$.

BB179

3-((4-Chloro-2-phenoxybenzyl)oxy)azetidine 2,2,2-trifluoroacetate

Synthesis of BB179 was done in analogy to BB39, starting from tert-butyl 3-hydroxyazetidine-1-carboxylate and 1-(bromomethyl)-4-chloro-2-phenoxybenzene (synthesis described below). MS (ESI): m/z=290.2 [M+H]$^+$.

1-(Bromomethyl)-4-chloro-2-phenoxybenzene i) In a 10 mL round-bottomed flask, methyl 4-chloro-2-phenoxybenzoate (547 mg, 2.08 mmol) was diluted in toluene (3.82 mL) and the reaction mixture was cooled in an ice bath. Sodium bis(2-methoxyethoxy)aluminum hydride 70% in toluene (649 mg, 637 μL, 2.25 mmol) was added dropwise slowly at max. 15° C. to give a light yellow solution. The reaction mixture was stirred at r.t. for 30 min. The crude reaction mixture, containing the product (4-chloro-2-phenoxyphenyl)methanol was used directly in the next step.

ii) In a 25 mL round-bottomed flask, hydrobromic acid 48% in H$_2$O (6.49 g, 4.35 mL, 38.5 mmol) was cooled in an ice bath. Then 4-chloro-2-phenoxyphenyl)methanol (crude, 488 mg, 2.08 mmol) was added dropwise slowly and the mixture was stirred at 50° C. for 2 h. Hydrobromic acid 48% in H$_2$O (6.25 g, 2.18 mL, 19.25 mmol) was added and the mixture was stirred at 60° C. for 1 h, then cooled to RT. The aqueous phase was separated, the organic phase was washed four times with H$_2$O and evaporated. The crude material was purified by flash column chromatography (gradient 0% to 25% EtOAc in hexanes) and was used in the next step without further purification. Yield: 85%.

BB 181

3-((1-(2,4-Dichlorophenyl)cyclopropyl)methoxy) azetidine 2,2,2-trifluoroacetate To a solution of tert-Butyl 3-((1-(2,4-dichlorophenyl) cyclopropyl)methoxy)azetidine-1-carboxylate (165 mg, 443 μmol) in DCM (2 mL) was added TFA (202 mg, 137 μL, 1.77 mmol) and the reaction stirred at RT for 8 h. The mixture was concentrated in vacuo (azeotrop with toluene, EtOAc and n-heptane) to provide the compound as a colorless oil (170 mg, 99%). MS (ESI): m/z=272.2 [M+H]$^+$.

Step a) 1-(2,4-Dichlorophenyl)cyclopropyl)methanol

In a 50 mL three-necked flask, 1-(2,4-dichlorophenyl) cyclopropane-1-carboxylic acid (1 g, 4.33 mmol) was combined with THF (20 mL) to give a colorless solution. At 0° C., borane tetrahydrofuran complex solution 1.0 M in THF (6.49 mL, 6.49 mmol) was added dropwise over a period of 15 min. The reaction was stirred at RT for 2 h. MeOH (2 mL) was added dropwise followed by 1M aq. HCl solution and stirred for 30 min. The reaction mixture was extracted twice with EtOAc (40 mL each) and the organic layers were washed with 10% aq Na$_2$CO$_3$ solution (40 mL) followed by brine (40 mL). The organic fractions were combined and dried over Na$_2$SO$_4$ and concentrated in vacuo. The crude material was purified by flash column chromatography (gradient EtOAc in n-heptane, 0% to 30%) to yield the compound as colorless oil (90%) MS (ESI): m/z=201.0 [M−16+H]$^+$.

Step b) 1-(2,4-Dichlorophenyl)cyclopropyl]methyl methanesulfonate

To an ice-cold solution of (1-(2,4-dichlorophenyl)cyclopropyl)methanol (350 mg, 1.61 mmol) and TEA (326 mg, 449 μL, 3.22 mmol) in DCM (6 mL) was added dropwise methanesulfonyl chloride (185 mg, 126 μL, 1.61 mmol) and the mixture was stirred at 0° C. for 1 h, then at RT overnight. The reaction mixture was poured on saturated aqueous NaHCO$_3$ solution (10 mL) and DCM (10 mL) and the layers were separated. The aqueous layer was extracted once with DCM (10 mL). The organic layers were washed with brine, dried over MgSO$_4$, filtered and evaporated to furnish the desired intermediate mesylate compound as a yellow oil (435 mg, 91%). MS (ESI): m/z=201.0 [M−mesyl+H]$^+$.

Step c) tert-Butyl 3-((1-(2,4-dichlorophenyl)cyclopropyl)methoxy)azetidine-1-carboxylate To an ice-cold solution of tert-butyl 3-hydroxyazetidine-1-carboxylate (220 mg, 1.27 mmol) in DMF (4 mL) was added sodium hydride in mineral oil (60%, 61 mg, 1.52 mmol) in portions and the mixture was stirred at ice-bath temperature for 5 min followed by stirring at RT for 40 min. A solution of 1-(2,4-dichlorophenyl)cyclopropyl)methyl methanesulfonate (431 mg, 1.46 mmol) was dissolved in DMF (1 mL) and added dropwise to the mixture at RT. Stirring of the slurry was continued at RT for 16 h, then at 55° C. for 2.5 h. The reaction mixture was poured on saturated aqueous NH$_4$Cl solution (10 mL) and EtOAc (20 mL) and the layers were separated. The aqueous layer was extracted once with EtOAc (50 mL). The organic layers were washed twice with water, dried over MgSO$_4$, filtered and evaporated. Flash Chromatography (gradient of EtOAc in n-heptane 0 to 40%) yielded the product as colorless oil (165 mg, 35%) MS (ESI): m/z=316.2 [M−56+H]$^+$.

BB182

2-((Azetidin-3-yloxy)methyl)-6-(4-fluorophenoxy)-4-(trifluoromethyl)pyridine 4-methylbenzenesulfonate Tert-butyl 3-((6-(4-fluorophenoxy)-4-(trifluoromethyl)pyridin-2-yl)methoxy)azetidine-1-carboxylate (150 mg, 339 μmol) was dissolved under argon in EtOAc (2 mL), p-toluenesulfonic acid monohydrate (77.4 mg, 407 μmol) was added and the mixture was stirred at RT for 5 min, then for 80° C. 3 h at and at RT over night. The reaction mixture was evaporated to provide the compound as 180 mg of a yellow oil which was used in the next step without further purification. MS (ESI): m/z=343.2 [M+H]$^+$.

Step a) tert-Butyl 3-((6-bromo-4-(trifluoromethyl)pyridin-2-yl)methoxy)azetidine-1-carboxylate To a solution of tert-butyl 3-hydroxyazetidine-1-carboxylate (272 mg, 1.57 mmol) in dry THF (8 mL) was added potassium tert-butoxide 1M in THF (1.57 mL, 1.57 mmol) and the turbid reaction mixture was stirred at RT for 30 min. 2-Bromo-6-(bromomethyl)-4-(trifluoromethyl)pyridine (500 mg, 1.57 mmol) was added at 0-2° C. and the reaction stirred at 0-2° C. for 20 min. The reaction mixture was then stirred at RT for 16 h. The reaction mixture was diluted with EtOAc, extracted with water, the organic phase was collected and the aqueous phase was back-extracted with EtOAc. The combined organic layers were dried over sodium sulfate and evaporated down to dryness. The crude material was purified by flash column chromatography (gradient of EtOAc in n-heptane, 0% to 40%) to provide the product as light yellow oil (41%) MS (ESI): m/z=355.1 [M−56+H]$^+$.

Step b) tert-Butyl 3-[[6-(4-fluorophenoxy)-4-(trifluoromethyl)-2-pyridyl]methoxy]azetidine-1-carboxylate tert-Butyl 3-((6-bromo-4-(trifluoromethyl)pyridin-2-yl)methoxy)azetidine-1-carboxylate (260 mg, 632 μmol) and 4-fluorophenol (70.9 mg, 632 μmol) were dissolved in DMF (2 mL), then K$_2$CO$_3$ (131 mg, 948 μmol) was added and the mixture was stirred at 80° for 30 h. The reaction mixture was evaporated under vacuum and the residue was dissolved in EtOAc and extracted with water and brine. The organic layers were dried over MgSO$_4$, filtered and the solvent was removed under vacuum. The residue was purified by flash chromatography (gradient of EtOAc in n-heptane, 0 to 30%) to yield the product as a light yellow oil (93%). MS (ESI): m/z=443.4 [M+H]$^+$.

BB183

6-((Azetidin-3-yloxy)methyl)-2-(4-fluorophenoxy)-3-(trifluoromethyl)pyridine 4-methylbenzenesulfonate tert-Butyl 3-((6-(4-fluorophenoxy)-5-(trifluoromethyl)pyridin-2-yl)methoxy)azetidine-1-carboxylate (170 mg, 384 μmol) was dissolved under argon atmosphere in EtOAc (2.27 mL) and p-toluenesulfonic acid monohydrate (87.7 mg, 461 μmol) was added. The reaction was stirred at RT for 5 min, then at 80° C. for 3 h and stirred at RT over night. The reaction mixture was evaporated under reduced pressure to dryness to provide the desired product as light yellow oil (89%) MS (ESI): m/z=343.2 [M+H]$^+$.

Step a) Methyl 6-(4-fluorophenoxy)-5-(trifluoromethyl)picolinate

Methyl 6-chloro-5-(trifluoromethyl)picolinate (800 mg, 3.34 mmol), 4-fluorophenol (412 mg, 3.67 mmol) and K$_2$CO$_3$ (692 mg, 5.01 mmol) were dissolved in DMF (6 mL) and stirred at 80° C. for 6 h. The reaction mixture was cooled to RT and extracted three times with water (20 mL each), twice with EtOAc (30 mL each), brine (20 mL), dried over MgSO$_4$, filtered and evaporated in vacuo. The crude residue was purified by flash column chromatography (gradient of EtOAc in n-heptane, 0 to 50%) to provide the product as white solid (67%). MS (ESI): m/z=316.1 [M+H]$^+$.

Step b) (6-(4-Fluorophenoxy)-5-(trifluoromethyl)pyridin-2-yl)methanol

To a stirred solution of methyl 6-(4-fluorophenoxy)-5-(trifluoromethyl)picolinate (705 mg, 2.24 mmol) in THF (8 mL) was added lithium borohydride 2M in THF (1.34 mL, 2.68 mmol) at 2-5° C. The reaction mixture was stirred at RT for 3 h and then cooled to 2-4° C. and quenched with 10 mL water (slowly added). The aqueous layer was extracted twice with EtOAc (30 mL each) and the combined organic layers were washed with water, 10 mL NaHCO$_3$ solution and 10 mL brine. The organic layer was dried over Na$_2$SO$_4$ and concentrated in vacuum. Purification by flash column chromatography (gradient of EtOAc in n-heptane, 0 to 50%) yielded the product as a colorless solid (95%). MS (ESI): m/z=288.2 [M+H]$^+$.

Step c) 6-(Bromomethyl)-2-(4-fluorophenoxy)-3-(trifluoromethyl)pyridine

To a solution of (6-(4-fluorophenoxy)-5-(trifluoromethyl)pyridin-2-yl)methanol (330 mg, 1.15 mmol) in dry DCM (5 mL) was added tetrabromomethane (457 mg, 1.38 mmol). The mixture was cooled to 0-3° C. and over 10 min triphenylphosphine (392 mg, 1.49 mmol) in 1 mL dry DCM was added. The mixture was stirred 1 hr at 2-4° C., then 20 mL DCM and silica gel was added. The solvent was removed in vacuo and the residue subjected to column flash chromatography (gradient of EtOAC in n-heptane, 0 to 40%) to yield the desired product as a colorless oil (94%). MS (ESI): m/z=350.0 [M+H]$^+$.

Step d) tert-Butyl 3-((6-(4-fluorophenoxy)-5-(trifluoromethyl)pyridin-2-yl)methoxy)azetidine-1-carboxylate To a solution of tert-butyl 3-hydroxyazetidine-1-carboxylate (183 mg, 1.06 mmol) in dry THF (5 mL) was added potassium tert-butoxide 1M in THF (1.11 mL, 1.11 mmol) and the reaction mixture was stirred at RT for 15 min. Then, 6-(bromomethyl)-2-(4-fluorophenoxy)-3-(trifluoromethyl) pyridine (370 mg, 1.06 mmol) was added. The reaction mixture was stirred at RT for 1 h and then diluted with EtOAc and extracted with 1M aq. NaHCO$_3$solution. The organic phase was collected and the aqueous phase was back-extracted with EtOAc. The combined organic phases were dried over sodium sulfate and evaporated down to dryness. The residue was purified by column flash chromatography (gradient of EtOAc in n-heptane, 0 to 30%) to furnish the product as a colorless oil (34%). MS (ESI): m/z=387.2 [M−56+H]$^+$.

BB184

2-((Azetidin-3-yloxy)methyl)-4-(4-fluorophenyl) thiazole 2,2,2-trifluoroacetate

To a solution of tert-butyl 3-((4-(4-fluorophenyl)thiazol-2-yl)methoxy)azetidine-1-carboxylate (150 mg, 412 µmol) in dry DCM (1.5 mL) under argon atmosphere was added TFA (282 mg, 190 µL, 2.47 mmol) and the solution was stirred at RT for 8 h. The reaction mixture was concentrated in vacuo (azeotrop with toluene, EtOAc and heptane) to yield the desired product as a yellow solid (98%). MS (ESI): m/z=265.2 [M+H]$^+$.

Step a) (4-(4-Fluorophenyl)thiazol-2-yl)methanol

To a stirred solution of ethyl 4-(4-fluorophenyl)thiazole-2-carboxylate (835 mg, 3.32 mmol) in dry THF (10 mL) was added lithium borohydride 2M in THF (1.99 mL, 3.99 mmol) at 2-5° C. The reaction mixture was stirred at RT for 3 h, then cooled to 2-4° C. and quenched with water (10 mL slowly added). The aqueous layer was extracted twice with EtOAc (30 mL each) and the organic layers were washed with water, 10 mL NaHCO$_3$ solution and 10 mL brine. The combined organic layers were dried over Na$_2$SO$_4$ and concentrated in vacuum. The residue was purified by column flash chromatography (gradient of EtOAc in n-heptane, 0 to 60%) to yield the desired product as a white solid (94%) MS (ESI): m/z=210.1 [M+H]$^+$.

Step b) 2-(Bromomethyl)-4-(4-fluorophenyl)thiazole

To a solution of (4-(4-fluorophenyl)thiazol-2-yl)methanol (400 mg, 1.91 mmol) in dry DCM (7 mL) was added tetrabromomethane (761 mg, 2.29 mmol), the solution was cooled to 0-3° C. and triphenylphosphine (652 mg, 2.49 mmol) in 1 mL dry DCM was added over 10 min. The mixture was stirred at 2-4° C. for 1 h, then 20 mL DCM were added. The reaction mixture was extracted with water, saturated NH$_4$Cl solution and brine. The organic phase was dryed over MgSO$_4$, filtered and evaporated. The residue was purified by flash chromatography (gradient of EtOAc in n-heptane, 0 to 40%) to provide 480 mg of the title compound as a light yellow oil (83%). MS (ESI): m/z=273.9 [M+H]$^+$.

Step c) tert-Butyl 3-((4-(4-fluorophenyl)thiazol-2-yl)methoxy)azetidine-1-carboxylate To a solution of tert-butyl 3-hydroxyazetidine-1-carboxylate (293 mg, 1.69 mmol) in dry THF (6 mL) was added potassium tert-butoxide 1M in THF (1.77 mL, 1.77 mmol) and the reaction mixture was stirred at RT for 15 min. After cooling down to 2-4° C. 2-(bromomethyl)-4-(4-fluorophenyl)thiazole (460 mg, 1.69 mmol) in 1 mL THF was added. The reaction mixture was stirred at RT for 1 h, diluted with EtOAc and extracted with 1M aq. NaHCO$_3$ solution. The organic phase was collected and the aqueous phase was back-extracted with EtOAc. The combined organic phases were dried over Na$_2$SO$_4$ and evaporated down to dryness. The residue was purified by column flash chromatography (gradient of EtOAc in n-heptane, 0 to 40%) to furnish the desired product as a light yellow solid (89%). MS (ESI): m/z=365.2 [M+H]$^+$.

BB186 rac-(2R,3S)-3-(2-Bromo-5-(trifluoromethyl)phenoxy)-2-methylpyrrolidine 2,2,2-trifluoroacetate To a solution of rac-tert-butyl (2R,3S)-3-(2-bromo-5-(trifluoromethyl)phenoxy)-2-methylpyrrolidine-1-carboxylate (225 mg, 530 µmol) in dry DCM (2 mL) under argon atmosphere was added TFA (242 mg, 163 µL, 2.12 mmol) and the solution was stirred at RT over night. The reaction mixture was concentrated in vacuo to dryness (azeotrop with n-heptane) to provide 233 mg of the title compound as a colorless oil (97%). MS (ESI): m/z=324.1 [M+H]$^+$.

Step a) rac-tert-Butyl (2R,3S)-3-(2-bromo-5-(trifluoromethyl)phenoxy)-2-methylpyrrolidine-1-carboxylate To a solution of rac-tert-butyl (2R,3S)-3-hydroxy-2-methylpyrrolidine-1-carboxylate (CAS: 1807941-04-3, 150 mg, 745 µmol) in dry THF (4 mL) under argon atmosphere was added potassium tert-butoxide 1M in THF (783 µL, 783 µmol). The mixture was stirred at RT for 15 min, then cooled down to 2-4° C. and a solution of 1-bromo-2-fluoro-4-(trifluoromethyl)benzene (181 mg, 745 µmol) in 0.5 mL dry THF was added slowly. The mixture was stirred at RT for 2 h and then extracted with EtOAc and aqueous 5% NaHCO3solution followed by water and brine. The organic phase was dried over MgSO$_4$, filtered off and evaporated to dryness. The residue was purified by column flash chromatography (gradient of EtOAc in n-heptane, 0 to 40%) to yield the product as light yellow oil (71%). MS (ESI): m/z=368 [M−56+H]$^+$.

The following intermediates were synthesized from 4-nitrophenyl (4aR,8aS)-3-oxohexahydro-2H-pyrido[4,3-b][1,4]oxazine-6(5H)-carboxylate (BB7a) and the suitable building blocks in analogy to the reaction methods described herein.

| BB No. | Building block(s) | MS, m/z | Method |
|---|---|---|---|
| BB203 | BB198 | 480.1 [M + H]$^+$ | A10 without DMAP |

| BB No. | Building block(s) | MS, m/z | Method |
|---|---|---|---|
| BB204 | BB201 | 445.1 [M + H]+ | A10 without DMAP |

BB206

3-[2-[2-Fluoro-4-(trifluoromethyl)phenyl]ethyl]azetidine; 4-methylbenzenesulfonic acid The compound was prepared in analogy to BB95 from tert-butyl 3-(2-fluoro-4-(trifluoromethyl)phenethyl)azetidine-1-carboxylate and 4-methylbenzenesulfonic acid monohydrate. Upon cooling a suspension formed which was filtered. The filter cake was washed with a small volume of EtOAc to provide the desired product as a colorless solid (71.6%). MS (ESI): m/z=248.2 [M+H]+.

Step a) Diethyl (2-fluoro-4-(trifluoromethyl)benzyl)phosphonate

The compound was prepared in analogy to BB159, step a, from 1-(bromomethyl)-2-fluoro-4-(trifluoromethyl)benzene and triethyl phosphite. Colorless oil (83.4%). MS (ESI): m/z=315.2 [M+H]+.

Step b) tert-Butyl 3-[(E)-2-[2-fluoro-4-(trifluoromethyl)phenyl]vinyl]azetidine-1-carboxylate The compound was prepared in analogy to BB95, step a, from diethyl (2-fluoro-4-(trifluoromethyl)benzyl)phosphonate and tert-butyl 3-formylazetidine-1-carboxylate to yield the compound as a colorless oil (69.9%). MS (ESI): m/z=290.1 [M−56+H]+.

Step c) tert-Butyl 3-[2-[2-fluoro-4-(trifluoromethyl)phenyl]ethyl]azetidine-1-carboxylate The compound was prepared in analogy to BB95, step b, from tert-butyl 3-[(E)-2-[2-fluoro-4-(trifluoromethyl)phenyl]vinyl]azetidine-1-carboxylate. Colorless oil (92.0%). MS (ESI): m/z=292.2 [M−56+H]+.

BB208

3-[2,2-Difluoro-2-[4-(trifluoromethyl)phenyl]ethyl]azetidine; 4-methylbenzenesulfonic acid The compound was prepared in analogy to BB95 from tert-butyl 3-(2,2-difluoro-2-(4-(trifluoromethyl)phenyl)ethyl)azetidine-1-carboxylate and 4-methylbenzenesulfonic acid monohydrate and using the material isolated from the filtrate after evaporation, which was used without further purification (30%). MS (ESI): m/z=266.2 [M+H]+.

Step a) tert-Butyl 3-[2-[methoxy(methyl)amino]-2-oxo-ethyl]azetidine-1-carboxylate To a suspension of 2-(1-(tert-butoxycarbonyl)azetidin-3-yl)acetic acid (2 g, 9.29 mmol) and HATU (3.89 g, 10.2 mmol) in DCM (65 mL) was added DIPEA (2.64 g, 3.57 mL, 20.4 mmol) and the mixture was stirred at RT for 30 min before N,O-dimethylhydroxylamine hydrochloride (906 mg, 9.29 mmol) was added. Stirring was continued at RT overnight. The reaction mixture was poured on saturated aqueous NH4Cl solution and EtOAc and the layers were separated. The aqueous layer was extracted twice with EtOAc. The organic layers were washed twice with water, dried over MgSO4, filtered, treated with silica gel and evaporated. The compound was purified by silica gel chromatography on a 25 g column using an MPLC system eluting with a gradient of n-heptane:EtOAc (100:0 to 0:100) to furnish the desired compound as a colorless oil (100%) which was used in the next step without further purification. MS (ESI): m/z=203.2 [M−56+H]+.

Step b) tert-Butyl 3-[2-oxo-2-[4-(trifluoromethyl)phenyl]ethyl]azetidine-1-carboxylate To an ice-cold solution of tert-butyl 3-(2-(methoxy(methyl)amino)-2-oxoethyl)azetidine-1-carboxylate (0.8 g, 3.1 mmol) in THF (5 mL) in an argon-flushed and heat-dried 2-neck flask was added dropwise a turbid solution of (4-(trifluoromethyl)phenyl)magnesium bromide 2.22 M in THF (1.95 mL, 4.34 mmol). The brown solution was stirred in an ice-bath for 2.5 h allowing the temperature to rise to RT. The reaction mixture was poured on saturated aqueous NH4Cl solution and EtOAc and the layers were separated. The aqueous layer was extracted twice with EtOAc. The organic layers were dried over MgSO4, filtered, treated with silica gel and evaporated. The compound was purified by silica gel chromatography on a 25 g column using an MPLC system eluting with a gradient of n-heptane:EtOAc (100:0 to 0:100) to provide the desired compound as a colorless solid (25.9%). MS (ESI): m/z=342.3 [M−H]−.

Step c) tert-Butyl 3-[2,2-difluoro-2-[4-(trifluoromethyl)phenyl]ethyl]azetidine-1-carboxylate To a solution of tert-butyl 3-(2-oxo-2-(4-(trifluoromethyl)phenyl)ethyl)azetidine-1-carboxylate (50 mg, 146 µmol) in toluene (0.3 mL) under argon was added bis(2-methoxyethyl)aminosulphur trifluoride (50% solution in THF, 387 mg, 379 µL, 874 µmol) and the mixture was stirred at 80° C. for 19 h. The dark mixture was allowed to cool down and another batch of bis(2-methoxyethyl)aminosulphur trifluoride (50% solution in THF, 387 mg, 379 µL, 874 µmol) was added. Heating was continued at 80° C. for another 4 h. The reaction mixture was poured on saturated aqueous NaHCO3 solution and EtOAc and the layers were separated. The aqueous layer was extracted twice with EtOAc. The organic layers were dried over MgSO4, filtered, treated with silica gel and evaporated. The compound was purified by silica gel chromatography on a 4 g column using an MPLC system eluting with a gradient of n-heptane:EtOAc (100:0 to 50:50) to yield the desired compound as a light brown oil (45.1%). MS (ESI): m/z=266.1 [M+H]+.

BB209

3-[2-Fluoro-5-(trifluoromethyl)phenoxy]pyrrolidine; 4-methylbenzenesulfonic acid The compound was prepared in analogy to BB95 from tert-butyl 3-[2-fluoro-5-(trifluoromethyl)phenoxy]pyrrolidine-1-carboxylate. Colorless oil which was used in the next step without further purification. MS (ESI): m/z=250.1 [M+H]+.

Step a) tert-Butyl 3-[2-fluoro-5-(trifluoromethyl)phenoxy]pyrrolidine-1-carboxylate To a solution of 2-fluoro-5-(trifluoromethyl)phenol (321 mg, 1.78 mmol), tert-butyl 3-hydroxypyrrolidine-1-carboxylate (334 mg, 1.78 mmol; CAS RN: 103057-44-9) and triphenylphosphine (467 mg, 1.78 mmol) in THF (5 mL) was added (E)-diazene-1,2-diylbis(piperidin-1-ylmethanone) (450 mg, 1.78 mmol, CAS RN 10465-81-3) in portions and the mixture was stirred at RT for 40 h. Silica gel was added to the suspension and it was evaporated. The compound was purified by silica gel chromatography on a 24 g column using an MPLC (ISCO) system eluting with a gradient of n-heptane:EtOAc (100:0 to 75:25) to provide the desired compound as a colorless oil (8.3%) which was used in the next step without further purification. MS (ESI): m/z=294.1 [M−56+H]$^+$.

BB210

3-[2-Chloro-5-(trifluoromethyl)phenoxy]pyrrolidine; 4-methylbenzenesulfonic acid The compound was prepared in analogy to BB95 from tert-butyl 3-[2-chloro-5-(trifluoromethyl)phenoxy]pyrrolidine-1-carboxylate. Colorless oil. MS (ESI): m/z=266.1 [M+H]$^+$.

Step a) tert-Butyl 3-[2-chloro-5-(trifluoromethyl)phenoxy]pyrrolidine-1-carboxylate The compound was prepared in analogy to BB209, step a, from 2-chloro-5-(trifluoromethyl)phenol and tert-butyl 3-hydroxypyrrolidine-1-carboxylate. Colorless solid which was used after chromatography without further purification. MS (ESI): m/z=310.1 [M−56+H]$^+$.

BB211

3-[(E)-2-(2-fluoro-4-methyl-phenyl)vinyl]azetidine; 4-methylbenzenesulfonic acid The compound was prepared in analogy to BB95 from tert-butyl 3-[(E)-2-(2-fluoro-4-methyl-phenyl)vinyl]azetidine-1-carboxylate and 4-methylbenzenesulfonic acid monohydrate. Colorless solid (87%). MS (ESI): m/z=192.2 [M+H]$^+$.

Step a) 1-(Diethoxyphosphorylmethyl)-2-fluoro-4-methyl-benzene

The compound was prepared in analogy to BB206, step a, from 1-(bromomethyl)-2-fluoro-4-methylbenzene and triethyl phosphite followed by silica gel chromatography on a 40 g column using an MPLC (ISCO) system eluting with a gradient of n-heptane:EtOAc (100:0 to 0:100). Colorless liquid (85%). MS (ESI): m/z=261.1 [M+H]$^+$.

Step b) tert-Butyl 3-[(E)-2-(2-fluoro-4-methyl-phenyl)vinyl]azetidine-1-carboxylate The compound was prepared in analogy to example BB206, step b, from tert-butyl 3-formylazetidine-1-carboxylate and 1-(diethoxyphosphorylmethyl)-2-fluoro-4-methyl-benzene. Colorless oil (7%). MS (ESI): m/z=236.2 [M−56+H]$^+$.

The invention claimed is:
1. A compound of formula (I):

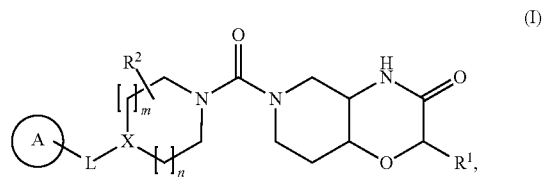

or a pharmaceutically acceptable salt thereof,
wherein:
(i) X is C—R$^3$; m is 0; n is selected from 0, 1 and 2; L is selected from —(CH$_2$)$_p$—, —O—, —OCH$_2$—, —CH$_2$OCH$_2$—, —CF$_2$CH$_2$—, —CH═CH—, —(CR$^{16}$R$^{17}$)$_q$—CH$_2$O—, and —CH$_2$CF$_2$—; and A is C$_6$-C$_{14}$-aryl substituted with R$^4$, R$^5$, and R$^6$; or A is 5- to 14-membered heteroaryl substituted with R$^7$, R$^8$, and R$^9$; or A is 3- to 14-membered heterocycloalkyl substituted with R$^{10}$, R$^{11}$, and R$^{12}$; or
(ii) X is C—R$^3$; m is 1; n is selected from 0, 1 and 2; L is selected from —O—, —OCH$_2$—, —CH$_2$OCH$_2$—, —CF$_2$CH$_2$—, —CH═CH—, —(CR$^{16}$R$^{17}$)$_q$—CH$_2$O—, and —CH$_2$CF$_2$—; and A is C$_6$-C$_{14}$-aryl substituted with R$^4$, R$^5$, and R$^6$; or A is 5- to 14-membered heteroaryl substituted with R$^7$, R$^8$, and R$^9$; or A is 3- to 14-membered heterocycloalkyl substituted with R$^{10}$, R$^{11}$, and R$^{12}$; or
(iii) X is C—R$^3$; m is 1; n is selected from 0, 1 and 2; L is —(CH$_2$)$_p$—; and A is 5- to 14-membered heteroaryl substituted with R$^7$, R$^8$, and R$^9$; or A is 3- to 14-membered heterocycloalkyl substituted with R$^{10}$, R$^{11}$, and R$^{12}$; or
(iv) X is N; m is 1; n is 1 or 2; L is —(CH$_2$)$_p$— or —CF$_2$CH$_2$—; and A is C$_6$-C$_{14}$-aryl substituted with R$^4$, R$^5$, and R$^6$; or A is 5- to 14-membered heteroaryl substituted with R$^7$, R$^8$, and R$^9$; or A is 3- to 14-membered heterocycloalkyl substituted with R$^{10}$, R$^{11}$, and R$^{12}$;
p is selected from 1, 2, and 3;
q is 0 or 1;
R$^1$ is hydrogen or C$_{1-6}$-alkyl;
R$^2$ is selected from hydrogen, C$_{1-6}$-alkyl, and hydroxy-C$_{1-6}$-alkyl;
R$^3$ is selected from hydrogen, halogen, hydroxy, C$_{1-6}$-alkoxy, C$_{1-6}$-alkyl, and halo-C$_{1-6}$-alkyl;
each of R$^4$, R$^5$, R$^6$, R$^7$, R$^8$, R$^9$, R$^{10}$, R$^{11}$ and R$^{12}$ is independently selected from hydrogen, halogen, cyano, hydroxy, C$_{1-6}$-alkyl, halo-C$_{1-6}$-alkyl, hydroxy-C$_{1-6}$-alkyl, C$_{1-6}$-alkanoyl, halo-C$_{1-5}$-alkyl-CH(OH)—, C$_{1-6}$-alkoxy, halo-C$_{1-6}$-alkoxy, SF$_5$, CH$_3$SO$_2$, C$_{3-10}$-cycloalkyl, C$_{3-10}$-cycloalkyl substituted with R$^{13}$, 3- to 14-membered heterocycloalkyl, 3- to 14-membered heterocycloalkyl substituted with R$^{14}$ and R$^{15}$, 5- to 14-membered heteroaryl, C$_6$-C$_{14}$-aryl, C$_6$-C$_{14}$-aryloxy, halo-C$_6$-C$_{14}$-aryl, and halo-C$_6$-C$_{14}$-aryloxy;
each of R$^{13}$, R$^{14}$, and R$^{15}$ is independently selected from C$_{1-6}$-alkyl, C$_{1-6}$-alkoxy, halo-C$_{1-6}$-alkyl, halo-C$_{1-6}$-alkoxy, halogen, and hydroxy; and
R$^{16}$ and R$^{17}$, taken together with the carbon atom to which they are attached, form a C$_{3-10}$-cycloalkyl.
2. The compound of claim 1, or a pharmaceutically acceptable salt thereof, wherein the compound of formula (I) is a compound of formula (Ia):

(Ia)

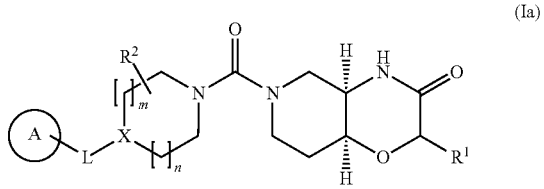

wherein A, L, X, m, n, R$^1$, and R$^2$ are as defined in claim 1.

3. The compound of claim 1, or a pharmaceutically acceptable salt thereof, wherein the compound of formula (I) is a compound of formula (Ib):

(Ib)

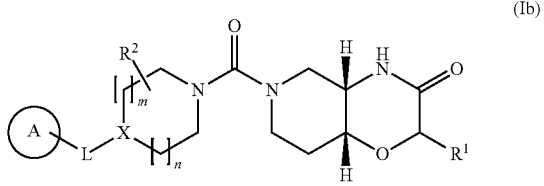

wherein A, L, X, m, n, R$^1$, and R$^2$ are as defined in claim 1.

4. The compound of claim 1, or a pharmaceutically acceptable salt thereof, wherein:
X is C—R$^3$; m is 0; n is selected from 0, 1, and 2; and L is selected from —(CH$_2$)$_p$—, —O—, —OCH$_2$—, —CF$_2$CH$_2$—, —CH═CH—, —(CR$^{16}$R$^{17}$)$_q$—CH$_2$O—, and —CH$_2$OCH$_2$—; or
X is N; m and n are both 1; and L is —(CH$_2$)$_p$—; and p is 1 or 2;
R$^2$ is hydrogen or C$_{1-6}$-alkyl; and
R$^3$ is selected from hydrogen, halogen, C$_{1-6}$-alkyl and halo-C$_{1-6}$-alkyl.

5. The compound of claim 1, or a pharmaceutically acceptable salt thereof, wherein:
X is C—R$^3$;
m and n are both 0, or m and n are both 1;
L is selected from —(CH$_2$)$_p$—, —O—, —OCH$_2$— and —CH$_2$O—;
p is 2;
R$^2$ is hydrogen or C$_{1-6}$-alkyl; and
R$^3$ is selected from hydrogen, halogen and C$_{1-6}$-alkyl.

6. The compound of claim 1, or a pharmaceutically acceptable salt thereof, wherein:
R$^4$ is selected from hydrogen, halogen, hydroxy, cyano, C$_{1-6}$-alkyl, C$_{1-6}$-alkanoyl, SF$_5$, C$_{1-6}$-alkoxy, halo-C$_{1-6}$-alkoxy, halo-C$_{1-6}$-alkyl, C$_{3-10}$-cycloalkyl, 3- to 14-membered heterocycloalkyl, 3- to 14-membered heterocycloalkyl substituted with R$^{14}$ and R$^{15}$, 5- to 14-membered heteroaryl, C$_6$-C$_{14}$-aryloxy, and halo-C$_6$-C$_{14}$-aryl;
R$^5$ is selected from hydrogen, cyano, halogen, C$_{1-6}$-alkyl, halo-C$_{1-6}$-alkyl, C$_{1-6}$-alkoxy, 3-to 14-membered heterocycloalkyl, C$_{3-10}$-cycloalkyl, 5- to 14-membered heteroaryl, and halo-C$_6$-C$_{14}$-aryl;
R$^6$ is hydrogen or halogen;
R$^7$ is selected from hydrogen, C$_{1-6}$-alkyl, C$_6$-C$_{14}$-aryl, halo-C$_6$-C$_{14}$-aryl, halo-C$_6$-C$_{14}$-aryloxy, and halo-C$_{1-6}$-alkyl;
R$^8$ is selected from hydrogen, halogen, C$_{1-6}$-alkyl, and halo-C$_{1-6}$-alkyl;
R$^9$ is hydrogen;
R$^{10}$ is halogen;
R$^{11}$ is halogen;
R$^{12}$ is hydrogen;
R$^{14}$ is selected from C$_{1-6}$-alkyl, C$_{1-6}$-alkoxy, and halogen; and
R$^{15}$ is hydrogen or halogen.

7. The compound of claim 1, or a pharmaceutically acceptable salt thereof, wherein:
A is selected from:
(i) C$_6$-C$_{14}$-aryl substituted with R$^4$, R$^5$ and R$^6$; and
(ii) 5- to 14-membered heteroaryl substituted with R$^7$, R$^8$ and R$^9$;
R$^4$ is selected from halogen, SF$_5$, C$_{1-6}$-alkyl, C$_{1-6}$-alkoxy, halo-C$_{1-6}$-alkoxy, halo-C$_{1-6}$-alkyl, C$_{3-10}$-cycloalkyl, and 3- to 14-membered heterocycloalkyl;
R$^5$ is selected from hydrogen, cyano, halogen, C$_{1-6}$-alkyl, halo-C$_{1-6}$-alkyl, 3- to 14-membered heterocycloalkyl, C$_{3-10}$-cycloalkyl and halo-C$_6$-C$_{14}$-aryl;
R$^6$ is hydrogen;
R$^7$ is C$_{1-6}$-alkyl or halo-C$_{1-6}$-alkyl;
R$^8$ is hydrogen or halo-C$_{1-6}$-alkyl; and
R$^9$ is hydrogen.

8. The compound of claim 7, or a pharmaceutically acceptable salt thereof, wherein:
X is C—R$^3$;
m and n are both 1;
L is selected from —(CH$_2$)$_p$—, —O—, —OCH$_2$—, and —CH$_2$O—;
p is 1 or 2; and
R$^1$ is hydrogen.

9. The compound of claim 1, or a pharmaceutically acceptable salt thereof, wherein:
A is selected from:
(i) phenyl substituted with R$^4$, R$^5$, and R$^6$;
(ii) oxazolyl substituted with R$^7$, R$^8$, and R$^9$; and
(iii) pyridyl substituted with R$^7$, R$^8$, and R$^9$;
R$^4$ is selected from chloro, SF$_5$, methyl, methoxy, —OCF$_3$, —CF$_3$, cyclopropyl, and 2-azaspiro[3.3]heptan-2-yl;
R$^5$ is selected from hydrogen, cyano, fluoro, chloro, methyl, —CF$_3$, pyrrolidinyl, cyclopentyl, cyclopropyl and chlorophenyl;
R$^6$ is hydrogen;
R$^7$ is tert-butyl or —CF$_3$;
R$^8$ is hydrogen or —CF$_3$; and
R$^9$ is hydrogen.

10. The compound of claim 9, or a pharmaceutically acceptable salt thereof, wherein:
X is C—R$^3$;
m and n are both 1;
L is selected from —O—, —OCH$_2$— and —CH$_2$O—;
R$^1$ is hydrogen;
A is phenyl substituted with R$^4$, R$^5$, and R$^6$;
R$^4$ is selected from chloro, SF$_5$, methyl, methoxy, —OCF$_3$, and —CF$_3$;
R$^5$ is selected from hydrogen, cyano, fluoro, chloro, methyl, —CF$_3$; and
R$^6$ is hydrogen.

11. The compound of claim 9, or a pharmaceutically acceptable salt thereof, wherein:
X is C—R$^3$;
m and n are both 0;
L is selected from —(CH$_2$)$_p$—, —O—, —OCH$_2$— and —CH$_2$O—;
A is phenyl substituted with R$^4$, R$^5$, and R$^6$;
p is 1 or 2;

R¹ is hydrogen;
R⁴ is selected from chloro, SF₅, methyl, methoxy, —OCF₃, and —CF₃;
R⁵ is selected from hydrogen, cyano, fluoro, chloro, methyl, —CF₃; and
R⁶ is hydrogen.

12. The compound of claim 1, or a pharmaceutically acceptable salt thereof, wherein:
X is C—R³;
m and n are both 0;
L is selected from —(CH₂)ₚ—, —O—, —OCH₂—, —CH=CH—, and —(CR¹⁶R¹⁷)_q—CH₂O—;
A is phenyl substituted with R⁴, R⁵, and R⁶;
p is 1 or 2;
q is 0;
R¹ is hydrogen or C₁₋₆-alkyl;
R² is selected from hydrogen, C₁₋₆-alkyl, and hydroxy-C₁₋₆-alkyl;
R³ is hydrogen
R⁴ is selected from halogen, SF₅, C₁₋₆-alkyl, C₁₋₆-alkoxy, halo-C₁₋₆-alkoxy, halo-C₁₋₆-alkyl, C₃₋₁₀-cycloalkyl, and 3- to 14-membered heterocycloalkyl;
R⁵ is selected from hydrogen, cyano, halogen, C₁₋₆-alkyl, halo-C₁₋₆-alkyl, 3- to 14-membered heterocycloalkyl, C₃₋₁₀-cycloalkyl and halo-C₆₋₁₄-aryl; and
R⁶ is hydrogen.

13. The compound of claim 1, wherein the compound is:
(+)-(4aR,8aS)-6-(4-((4-(tert-Butyl)oxazol-2-yl)methyl) piperidine-1-carbonyl)hexahydro-2H-pyrido[4,3-b][1, 4]oxazin-3(4H)-one;
(+)-(4aR,8aS)-6-(4-((2-Chloro-4-fluorophenoxy)methyl) piperidine-1-carbonyl)hexahydro-2H-pyrido[4,3-b][1, 4]oxazin-3(4H)-one;
rac-(4aR,8aS)-6-(3-((2-Fluoro-4-(trifluoromethyl)benzyl)oxy)azetidine-1-carbonyl)hexahydro-2H-pyrido[4, 3-b][1,4]oxazin-3(4H)-one;
(+)-(4aR,8aS)-6-(3-((2-Chloro-4-fluorobenzyl)oxy)azetidine-1-carbonyl)hexahydro-2H-pyrido[4,3-b][1,4] oxazin-3(4H)-one;
(−)-(4aR,8aS)-6-(3-((2-Chloro-4-fluorobenzyl)oxy)azetidine-1-carbonyl)hexahydro-2H-pyrido[4,3-b][1,4] oxazin-3(4H)-one;
(+)-(4aR,8aS)-6-(3-((2-Fluoro-4-(trifluoromethyl)benzyl)oxy)azetidine-1-carbonyl)hexahydro-2H-pyrido[4, 3-b][1,4]oxazin-3(4H)-one;
(−)-(4aR,8aS)-6-(3-((2-Fluoro-4-(trifluoromethyl)benzyl)oxy)azetidine-1-carbonyl)hexahydro-2H-pyrido[4, 3-b][1,4]oxazin-3(4H)-one;
(+)-(4aR,8aS)-6-(4-(2-Chloro-4-(trifluoromethyl)phenoxy)piperidine-1-carbonyl)hexahydro-2H-pyrido[4, 3-b][1,4]oxazin-3(4H)-one;
(−)-(4aR,8aS)-6-(4-(2-Chloro-4-(trifluoromethyl)phenoxy)piperidine-1-carbonyl)hexahydro-2H-pyrido[4, 3-b][1,4]oxazin-3(4H)-one;
(+)-(4aR,8aS)-6-(4-(3-(Trifluoromethyl)phenoxy)piperidine-1-carbonyl)hexahydro-2H-pyrido[4,3-b][1,4] oxazin-3(4H)-one;
(−)-(4aR,8aS)-6-(4-(3-(Trifluoromethyl)phenoxy)piperidine-i-carbonyl)hexahydro-2H-pyrido[4,3-b][1,4] oxazin-3(4H)-one;
(+)-(4aR,8aS)-6-[4-[[2-Chloro-4-(trifluoromethoxy)phenoxy]methyl]piperidine-1-carbonyl]-4,4a,5,7,8,8a-hexahydropyrido[4,3-b][1,4]oxazin-3-one;
(−)-(4aR,8aS)-6-[4-[[2-Chloro-4-(trifluoromethoxy)phenoxy]methyl]piperidine-1-carbonyl]-4,4a,5,7,8,8a-hexahydropyrido[4,3-b][1,4]oxazin-3-one;
(+)-(4aR,8aS)-6-(3-((2-Fluoro-4-(trifluoromethyl)phenoxy)methyl)azetidine-1-carbonyl)hexahydro-2H-pyrido[4,3-b][1,4]oxazin-3(4H)-one;
(−)-(4aR,8aS)-6-(3-((2-Fluoro-4-(trifluoromethyl)phenoxy)methyl)azetidine-1-carbonyl)hexahydro-2H-pyrido[4,3-b][1,4]oxazin-3(4H)-one;
(+)-(4aR,8aS)-6-(4-((4-Chloro-2-fluorophenoxy)methyl) piperidine-1-carbonyl)hexahydro-2H-pyrido[4,3-b][1, 4]oxazin-3(4H)-one;
(−)-(4aR,8aS)-6-(4-((4-Chloro-2-fluorophenoxy)methyl) piperidine-1-carbonyl)hexahydro-2H-pyrido[4,3-b][1, 4]oxazin-3(4H)-one;
(+)-(4aR,8aS)-6-(4-((4-Fluoro-2-(trifluoromethyl)phenoxy)methyl)piperidine-1-carbonyl)hexahydro-2H-pyrido[4,3-b][1,4]oxazin-3(4H)-one;
(−)-(4aR,8aS)-6-(4-((4-Fluoro-2-(trifluoromethyl)phenoxy)methyl)piperidine-1-carbonyl)hexahydro-2H-pyrido[4,3-b][1,4]oxazin-3(4H)-one;
(+)-(4aR,8aS)-6-(4-((2-Fluoro-4-(trifluoromethyl)phenoxy)methyl)piperidine-1-carbonyl)hexahydro-2H-pyrido[4,3-b][1,4]oxazin-3(4H)-one;
(−)-(4aR,8aS)-6-(4-((2-Fluoro-4-(trifluoromethyl)phenoxy)methyl)piperidine-1-carbonyl)hexahydro-2H-pyrido[4,3-b][1,4]oxazin-3(4H)-one;
(+)-(4aR,8aS)-6-(4-((2-Chloro-4-(trifluoromethyl)phenoxy)methyl)piperidine-1-carbonyl)hexahydro-2H-pyrido[4,3-b][1,4]oxazin-3(4H)-one;
(−)-(4aR,8aS)-6-(4-((2-Chloro-4-(trifluoromethyl)phenoxy)methyl)piperidine-1-carbonyl)hexahydro-2H-pyrido[4,3-b][1,4]oxazin-3(4H)-one;
(+)-3-Chloro-4-((1-((4aR,8aS)-3-oxooctahydro-2H-pyrido[4,3-b][1,4]oxazine-6-carbonyl)piperidin-4-yl) methoxy)benzonitrile;
(−)-3-Chloro-4-((1-((4aR,8aS)-3-oxooctahydro-2H-pyrido[4,3-b][1,4]oxazine-6-carbonyl)piperidin-4-yl) methoxy)benzonitrile;
(+)-(4aR,8aS)-6-(3-((2-Chloro-4-(trifluoromethyl)phenoxy)methyl)azetidine-1-carbonyl)hexahydro-2H-pyrido[4,3-b][1,4]oxazin-3(4H)-one;
(−)-(4aR,8aS)-6-(3-((2-Chloro-4-(trifluoromethyl)phenoxy)methyl)azetidine-1-carbonyl)hexahydro-2H-pyrido[4,3-b][1,4]oxazin-3(4H)-one;
(+)-(4aR,8aS)-6-(4-((2-Chloro-4-fluorophenoxy) methyl)-4-fluoropiperidine-1-carbonyl)hexahydro-2H-pyrido[4,3-b][1,4]oxazin-3(4H)-one;
(−)-(4aR,8aS)-6-(4-((2-Chloro-4-fluorophenoxy) methyl)-4-fluoropiperidine-1-carbonyl)hexahydro-2H-pyrido[4,3-b][1,4]oxazin-3(4H)-one;
(+)-(4aR,8aS)-6-(4-((4',6-Dichloro-[1,1'-biphenyl]-3-yl) oxy)piperidine-1-carbonyl)hexahydro-2H-pyrido[4,3-b][1,4]oxazin-3(4H)-one;
(−)-(4aR,8aS)-6-(4-((4',6-Dichloro-[1,1'-biphenyl]-3-yl) oxy)piperidine-1-carbonyl)hexahydro-2H-pyrido[4,3-b][1,4]oxazin-3(4H)-one;
(+)-(4aR,8aS)-6-(cis-4-((2-Chloro-4-fluorophenoxy) methyl)-3-methylpiperidine-1-carbonyl)hexahydro-2H-pyrido[4,3-b][1,4]oxazin-3(4H)-one;
(−)-(4aR,8aS)-6-(cis-4-((2-Chloro-4-fluorophenoxy) methyl)-3-methylpiperidine-1-carbonyl)hexahydro-2H-pyrido[4,3-b][1,4]oxazin-3(4H)-one;
(+)-(4aR,8aS)-6-(3-((2-Chloro-4-(trifluoromethyl)benzyl)oxy)azetidine-1-carbonyl)hexahydro-2H-pyrido[4, 3-b][1,4]oxazin-3(4H)-one;
(−)-(4aR,8aS)-6-(3-((2-Chloro-4-(trifluoromethyl)benzyl)oxy)azetidine-1-carbonyl)hexahydro-2H-pyrido[4, 3-b][1,4]oxazin-3(4H)-one;

(+)-(4aR,8aS)-6-(3-((2-Fluoro-4-(trifluoromethoxy)benzyl)oxy)azetidine-1-carbonyl)hexahydro-2H-pyrido[4,3-b][1,4]oxazin-3(4H)-one;
(−)-(4aR,8aS)-6-(3-((2-Fluoro-4-(trifluoromethoxy)benzyl)oxy)azetidine-1-carbonyl)hexahydro-2H-pyrido[4,3-b][1,4]oxazin-3(4H)-one;
(+)-(4aR,8aS)-6-(4-((2-Chloro-4-fluorophenoxy)methyl)-4-methylpiperidine-1-carbonyl)hexahydro-2H-pyrido[4,3-b][1,4]oxazin-3(4H)-one;
(−)-(4aR,8aS)-6-(4-((2-Chloro-4-fluorophenoxy)methyl)-4-methylpiperidine-1-carbonyl)hexahydro-2H-pyrido[4,3-b][1,4]oxazin-3(4H)-one;
(4aR,8aS)-6-[3-[(2,4-Dichlorophenyl)methoxy]azetidine-1-carbonyl]-4,4a,5,7,8,8a-hexahydropyrido[4,3-b][1,4]oxazin-3-one;
(4aR,8aS)-6-[3-[[3-Chloro-4-(trifluoromethyl)phenyl]methoxy]azetidine-1-carbonyl]-4,4a,5,7,8,8a-hexahydropyrido[4,3-b][1,4]oxazin-3-one;
(4aR,8aS)-6-[3-[[2-Fluoro-5-(trifluoromethyl)phenyl]methoxy]azetidine-1-carbonyl]-4,4a,5,7,8,8a-hexahydropyrido[4,3-b][1,4]oxazin-3-one;
(4aR,8aS)-6-[3-[2-[2-Fluoro-6-(trifluoromethyl)phenyl]ethyl]azetidine-1-carbonyl]-4,4a,5,7,8,8a-hexahydropyrido[4,3-b][1,4]oxazin-3-one;
(4aR,8aS)-6-(3-(2-fluoro-4-(trifluoromethyl)phenethyl)azetidine-1-carbonyl)hexahydro-2H-pyrido[4,3-b][1,4]oxazin-3(4H)-one;
6-(3-((2,4-bis(trifluoromethyl)benzyl)oxy)azetidine-1-carbonyl)hexahydro-2H-pyrido[4,3-b][1,4]oxazin-3(4H)-one;
(4aR,8aS)-6-[4-[3-chloro-4-(trifluoromethyl)phenoxy]piperidine-1-carbonyl]-4,4a,5,7,8,8a-hexahydropyrido[4,3-b][1,4]oxazin-3-one;
(4aR,8aS)-6-(3-methyl-4-(((5-methyl-6-(trifluoromethyl)pyridin-3-yl)oxy)methyl)piperidine-1-carbonyl)hexahydro-2H-pyrido[4,3-b][1,4]oxazin-3(4H)-one;
(4aR,8aS)-6-(3-((3,4-dichlorobenzyl)oxy)azetidine-1-carbonyl)hexahydro-2H-pyrido[4,3-b][1,4]oxazin-3(4H)-one;
(4aR,8aS)-6-(3-((2,5-dichlorobenzyl)oxy)azetidine-1-carbonyl)hexahydro-2H-pyrido[4,3-b][1,4]oxazin-3(4H)-one;
rac-(4aR,8aS)-6-(2-methyl-3-((4-methyl-3-(trifluoromethyl)benzyl)oxy)azetidine-1-carbonyl)hexahydro-2H-pyrido[4,3-b][1,4]oxazin-3(4H)-one;
(4aR,8aS)-6-(3-(((4,5-bis(trifluoromethyl)pyridin-2-yl)oxy)methyl)azetidine-1-carbonyl)hexahydro-2H-pyrido[4,3-b][1,4]oxazin-3(4H)-one;
rac-(4aR,8aS)-6-(3-((2-fluoro-4-(trifluoromethyl)benzyl)oxy)-2-methylazetidine-1-carbonyl)hexahydro-2H-pyrido[4,3-b][1,4]oxazin-3(4H)-one;
(4aR,8aS)-6-(3-((2-fluoro-4-(pentafluoro-16-sulfanyl)benzyl)oxy)azetidine-1-carbonyl)hexahydro-2H-pyrido[4,3-b][1,4]oxazin-3(4H)-one;
(4aR,8aS)-6-(3-((4-methyl-2-(trifluoromethoxy)benzyl)oxy)azetidine-1-carbonyl)hexahydro-2H-pyrido[4,3-b][1,4]oxazin-3(4H)-one;
(4aR,8aS)-6-[4-[3-cyclopropyl-4-(trifluoromethyl)phenoxy]piperidine-1-carbonyl]-4,4a,5,7,8,8a-hexahydropyrido[4,3-b][1,4]oxazin-3-one;
(4aR,8aS)-6-[3-2-(2-fluoro-4-methyl-phenyl)ethyl]azetidine-1-carbonyl]-4,4a,5,7,8,8a-hexahydropyrido[4,3-b][1,4]oxazin-3-one;
(4aR,8aS)-6-[3-[2-[4-methoxy-2-(trifluoromethyl)phenyl]ethyl]azetidine-1-carbonyl]-4,4a,5,7,8,8a-hexahydropyrido[4,3-b][1,4]oxazin-3-one;
(4aR,8aS)-6-[3-[3-(2-azaspiro[3.3]heptan-2-yl)-4-(trifluoromethyl)phenoxy]azetidine-1-carbonyl]-4,4a,5,7,8,8a-hexahydropyrido[4,3-b][1,4]oxazin-3-one;
(4aR,8aS)-6-[3-[2-[4-methyl-2-(trifluoromethyl)phenyl]ethyl]azetidine-1-carbonyl]-4,4a,5,7,8,8a-hexahydropyrido[4,3-b][1,4]oxazin-3-one;
(4aR,8aS)-6-(3-((4-methyl-3-(trifluoromethyl)benzyl)oxy)azetidine-1-carbonyl)hexahydro-2H-pyrido[4,3-b][1,4]oxazin-3(4H)-one;
(4aR,8aS)-6-(3-((2-methyl-3-(trifluoromethyl)benzyl)oxy)azetidine-1-carbonyl)hexahydro-2H-pyrido[4,3-b][1,4]oxazin-3(4H)-one;
rac-(4aR,8aS)-6-[2-methyl-3-[[2-methyl-4-(trifluoromethoxy)phenyl]methoxy]azetidine-1-carbonyl]-4,4a,5,7,8,8a-hexahydropyrido[4,3-b][1,4]oxazin-3-one;
rac-(4aR,8aS)-6-[2-methyl-3-[[2-methyl-3-(trifluoromethyl)phenyl]methoxy]azetidine-1-carbonyl]-4,4a,5,7,8,8a-hexahydropyrido[4,3-b][1,4]oxazin-3-one;
(4aR,8aS)-6-[3-(4-chloro-3-cyclopropylphenoxy)azetidine-1-carbonyl]-4,4,5,7,8,8a-hexahydropyrido[4,3-b][1,4]oxazin-3-one;
(4aR,8aS)-6-[4-[2-chloro-3-(trifluoromethyl)phenoxy]piperidine-1-carbonyl]-4,4a,5,7,8,8a-hexahydropyrido[4,3-b][1,4]oxazin-3-one;
(4aR,8aS)-6-[3-(2-chloro-3-cyclopropyl-phenoxy)azetidine-1-carbonyl]-4,4a,5,7,8,8a-hexahydropyrido[4,3-b][1,4]oxazin-3-one;
(4aR,8aS)-6-[3-[3-(2-azaspiro[3.3]heptan-2-yl)-2-chlorophenoxy]azetidine-1-carbonyl]-4,4a,5,7,8,8a-hexahydropyrido[4,3-b][1,4]oxazin-3-one;
(4aR,8aS)-6-[3-[2-chloro-3-(5-oxa-2-azaspiro[3.5]nonan-2-yl)phenoxy]azetidine-1-carbonyl]-4,4a,5,7,8,8a-hexahydropyrido[4,3-b][1,4]oxazin-3-one;
(4aR,8aS)-6-[3-[(E)-2-(2-fluoro-4-methyl-phenyl)vinyl]azetidine-1-carbonyl]-4,4a,5,7,8,8a-hexahydropyrido[4,3-b][1,4]oxazin-3-one;
(4aR,8aS)-6-(3-((E)-2-fluoro-6-(trifluoromethyl)styryl)azetidine-1-carbonyl)hexahydro-2H-pyrido[4,3-b][1,4]oxazin-3(4H)-one; or
(4aR,8aS)-6-(3-((4-methyl-3-(trifluoromethyl)benzyl)oxy)azetidine-1-carbonyl)hexahydro-2H-pyrido[4,3-b][1,4]oxazin-3(4H)-one, or a pharmaceutically acceptable salt thereof.

14. A pharmaceutical composition, comprising a compound of claim 1, or a pharmaceutically acceptable salt thereof, and a therapeutically inert carrier.

15. A pharmaceutical composition, comprising a compound of claim 13, or a pharmaceutically acceptable salt thereof, and a therapeutically inert carrier.

16. A process of manufacturing a compound of claim 1, or a pharmaceutically acceptable salt thereof, the process comprising:

reacting a first amine of formula 1, wherein $R^1$ is as described in claim 1:

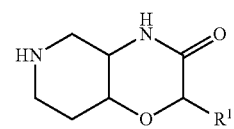

1 with a second amine 2, wherein A, L, m, n, X and $R^2$ are as described in claim 1:

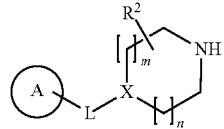

in the presence of a base and a urea forming reagent,
to form said compound of claim 1, or a pharmaceutically acceptable salt thereof.

17. A method for the treatment of a condition in a human, comprising administering an effective amount of a compound of claim 1, or a pharmaceutically acceptable salt thereof, to the human, wherein the condition is a neurodegenerative disease.

18. The method of claim 17, wherein the condition is multiple sclerosis, Alzheimer's disease, Parkinson's disease, or amyotrophic lateral sclerosis.

19. A method for the treatment of a condition in a human, comprising administering an effective amount of a compound of claim 13, or a pharmaceutically acceptable salt thereof, to the human, wherein the condition is a neurodegenerative disease.

20. The method of claim 19, wherein the condition is multiple sclerosis, Alzheimer's disease, Parkinson's disease, or amyotrophic lateral sclerosis.

* * * * *